US012636011B2

(12) United States Patent
Huitema et al.

(10) Patent No.: US 12,636,011 B2
(45) Date of Patent: May 26, 2026

(54) FASTENER CARTRIDGE COMPRISING NON-UNIFORM FASTENERS

(71) Applicant: Cilag GmbH International, Zug (CH)

(72) Inventors: Thomas W. Huitema, West Chester, OH (US); Kevin R. Doll, West Chester, OH (US); Frederick E. Shelton, IV, Hillsboro, OH (US); Emily A Schellin, Cincinnati, OH (US); Jason L. Harris, Lebanon, OH (US); Geoffrey C. Hueil, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 19/029,178

(22) Filed: Jan. 17, 2025

(65) Prior Publication Data

US 2025/0235212 A1      Jul. 24, 2025

Related U.S. Application Data

(63) Continuation of application No. 18/436,831, filed on Feb. 8, 2024, now Pat. No. 12,369,914, which is a
(Continued)

(51) Int. Cl.
*A61B 17/068*      (2006.01)
*A61B 17/064*      (2006.01)
(Continued)

(52) U.S. Cl.
CPC ........ *A61B 17/105* (2013.01); *A61B 17/0644* (2013.01); *A61B 17/068* (2013.01);
(Continued)

(58) Field of Classification Search
CPC ... A61B 17/105; A61B 17/068; A61B 17/072; A61B 90/03
See application file for complete search history.

(56) References Cited

U.S. PATENT DOCUMENTS

| | | |
|---|---|---|
| 5,258,009 A | 11/1993 | Conners |
| 5,630,540 A | 5/1997 | Blewett |

(Continued)

FOREIGN PATENT DOCUMENTS

JP      2011200665 A      10/2011

*Primary Examiner* — Nathaniel C Chukwurah
(74) *Attorney, Agent, or Firm* — Lempia Summerfield Katz LLC

(57) ABSTRACT

A fastener cartridge can comprise fastener cavities arranged in longitudinal rows. A first fastener having a first configuration and a second fastener having a second configuration can be stored within a longitudinal row. First fasteners having a first configuration can be stored within a first longitudinal row and second fasteners having a second configuration can be stored within a second longitudinal row. Each first fastener can have a proximal leg, or leg portion, extending at a first proximal angle and a distal leg, or leg portion, extending at a first distal angle and each second fastener can have a proximal leg, or leg portion, extending at a second proximal angle and a distal leg, or leg portion, extending at a second distal angle. The first proximal angle can be different than the second proximal angle and/or the first distal angle can be different than the second distal angle.

20 Claims, 85 Drawing Sheets

Related U.S. Application Data continuation of application No. 17/476,700, filed on Sep. 16, 2021, now Pat. No. 11,974,746, which is a continuation of application No. 16/388,952, filed on Apr. 19, 2019, now Pat. No. 11,266,409, which is a continuation of application No. 14/319,008, filed on Jun. 30, 2014, now Pat. No. 10,299,792.

(60) Provisional application No. 61/980,270, filed on Apr. 16, 2014.

(51) Int. Cl.

| | |
|---|---|
| *A61B 17/072* | (2006.01) |
| *A61B 17/10* | (2006.01) |
| *A61B 90/00* | (2016.01) |
| *G06F 11/14* | (2006.01) |
| *A61B 17/00* | (2006.01) |
| *A61B 90/30* | (2016.01) |

(52) U.S. Cl.

CPC .. *A61B 17/07207* (2013.01); *A61B 17/07292* (2013.01); *A61B 90/03* (2016.02); *G06F 11/1425* (2013.01); *A61B 2017/00057* (2013.01); *A61B 2017/00115* (2013.01); *A61B 2017/00398* (2013.01); *A61B 2017/0046* (2013.01); *A61B 2017/00734* (2013.01); *A61B 2017/07235* (2013.01); *A61B 2017/07242* (2013.01); *A61B 2017/07257* (2013.01); *A61B 2017/07264* (2013.01); *A61B 2017/07271* (2013.01); *A61B 2017/07278* (2013.01); *A61B 2090/034* (2016.02); *A61B 2090/038* (2016.02); *A61B 2090/0801* (2016.02); *A61B 2090/0807* (2016.02); *A61B 2090/0811* (2016.02); *A61B 2090/306* (2016.02); *A61B 2090/309* (2016.02)

(56) References Cited

U.S. PATENT DOCUMENTS

| | | | |
|---|---|---|---|
| 7,401,721 B2 | 7/2008 | Holsten et al. | |
| 7,618,427 B2 | 11/2009 | Ortiz et al. | |
| 7,635,074 B2 | 12/2009 | Olson et al. | |
| 7,669,746 B2 * | 3/2010 | Shelton, IV | A61B 17/0682 227/176.1 |
| 7,673,780 B2 * | 3/2010 | Shelton, IV | A61B 17/07207 227/181.1 |
| 8,561,870 B2 | 10/2013 | Baxter, III et al. | |
| 8,613,384 B2 | 12/2013 | Pastorelli et al. | |
| 8,733,613 B2 | 5/2014 | Huitema et al. | |
| 9,050,084 B2 | 6/2015 | Schmid et al. | |
| 9,265,500 B2 | 2/2016 | Sorrentino et al. | |
| 9,332,974 B2 | 5/2016 | Henderson et al. | |
| 9,554,796 B2 | 1/2017 | Kostrzewski | |
| 9,713,468 B2 | 7/2017 | Harris et al. | |
| 9,833,241 B2 | 12/2017 | Huitema et al. | |
| 9,844,369 B2 | 12/2017 | Huitema et al. | |
| 9,877,721 B2 | 1/2018 | Schellin et al. | |
| 10,010,324 B2 | 7/2018 | Huitema et al. | |
| 10,194,904 B2 | 2/2019 | Viola et al. | |
| 10,213,204 B2 | 2/2019 | Aranyi et al. | |
| 10,299,792 B2 | 5/2019 | Huitema et al. | |
| 10,470,768 B2 | 11/2019 | Harris et al. | |
| 10,517,594 B2 | 12/2019 | Shelton, IV et al. | |
| 10,542,988 B2 | 1/2020 | Schellin et al. | |
| 10,561,422 B2 | 2/2020 | Schellin et al. | |
| 11,185,330 B2 | 11/2021 | Huitema et al. | |
| 11,298,134 B2 | 4/2022 | Huitema et al. | |
| 11,382,625 B2 | 7/2022 | Huitema et al. | |
| 11,382,627 B2 | 7/2022 | Huitema et al. | |
| 11,517,315 B2 | 12/2022 | Huitema et al. | |
| 11,596,406 B2 | 3/2023 | Huitema et al. | |
| 11,717,294 B2 | 8/2023 | Huitema et al. | |
| 11,963,678 B2 | 4/2024 | Huitema et al. | |
| 2002/0138086 A1 | 9/2002 | Sixto et al. | |
| 2005/0230453 A1 | 10/2005 | Viola | |
| 2006/0180633 A1 | 8/2006 | Emmons | |
| 2009/0255974 A1 | 10/2009 | Viola | |
| 2010/0065605 A1 * | 3/2010 | Shelton, VI | A61B 17/07207 227/176.1 |
| 2010/0089974 A1 * | 4/2010 | Shelton, IV | A61B 17/07207 227/180.1 |
| 2010/0133317 A1 * | 6/2010 | Shelton, IV | A61B 17/07207 606/167 |
| 2010/0191262 A1 | 7/2010 | Harris et al. | |
| 2010/0256675 A1 | 10/2010 | Romans | |
| 2012/0074198 A1 * | 3/2012 | Huitema | A61B 17/0682 227/176.1 |
| 2013/0037596 A1 * | 2/2013 | Bear | A61B 17/07207 227/176.1 |
| 2013/0153641 A1 | 6/2013 | Shelton, IV et al. | |
| 2013/0256380 A1 | 10/2013 | Schmid et al. | |
| 2015/0297223 A1 | 10/2015 | Huitema et al. | |
| 2015/0297225 A1 | 10/2015 | Huitema et al. | |
| 2019/0029682 A1 | 1/2019 | Huitema et al. | |

* cited by examiner

415

415

415

FASTENER CARTRIDGE COMPRISING NON-UNIFORM FASTENERS

CROSS-REFERENCE TO RELATED APPLICATIONS

This application is a continuation application claiming priority under 35 U.S.C. § 120 to U.S. patent application Ser. No. 18/436,831, entitled FASTENER CARTRIDGE COMPRISING NON-UNIFORM FASTENERS, filed Feb. 8, 2024, now U.S. Patent Application Publication No. 2024/0260963, which is a continuation application claiming priority under 35 U.S.C. § 120 to U.S. patent application Ser. No. 17/476,700 entitled ANVIL FOR USE WITH A SURGICAL STAPLING ASSEMBLY, filed Sep. 16, 2021, which issued on May 7, 2024 as U.S. Pat. No. 11,974,746, which is a continuation application claiming priority under 35 U.S.C. § 120 to U.S. patent application Ser. No. 16/388,952, entitled FASTENER CARTRIDGE COMPRISING NON-UNIFORM FASTENERS, filed Apr. 19, 2019, which issued on Mar. 8, 2022 as U.S. Pat. No. 11,266,409, which is a continuation application claiming priority under 35 U.S.C. § 120 to U.S. patent application Ser. No. 14/319,008, entitled FASTENER CARTRIDGE COMPRISING NON-UNIFORM FASTENERS, filed Jun. 30, 2014, which issued on May 28, 2019 as U.S. Pat. No. 10,299,792, which claims the benefit under 35 U.S.C. § 119 (e) to U.S. Provisional Patent Application Ser. No. 61/980,270, entitled FASTENING INSTRUMENTS AND FASTENING CARTRIDGES FOR USE THEREWITH, filed Apr. 16, 2014, which are hereby incorporated by reference herein in their respective entireties.

BACKGROUND

The present invention relates to stapling instruments and, in various embodiments, to a surgical stapling instrument for producing one or more rows of staples.

A stapling instrument can include a pair of cooperating elongate jaw members, wherein each jaw member can be adapted to be inserted into a patient and positioned relative to tissue that is to be stapled and/or incised. In various embodiments, one of the jaw members can support a staple cartridge with at least two laterally spaced rows of staples contained therein, and the other jaw member can support an anvil with staple-forming pockets aligned with the rows of staples in the staple cartridge. Generally, the stapling instrument can further include a pusher bar and a knife blade which are slidable relative to the jaw members to sequentially eject the staples from the staple cartridge via camming surfaces on the pusher bar and/or camming surfaces on a wedge sled that is pushed by the pusher bar. In at least one embodiment, the camming surfaces can be configured to activate a plurality of staple drivers carried by the cartridge and associated with the staples in order to push the staples against the anvil and form laterally spaced rows of deformed staples in the tissue gripped between the jaw members. In at least one embodiment, the knife blade can trail the camming surfaces and cut the tissue along a line between the staple rows. Examples of such stapling instruments are disclosed in U.S. Pat. No. 7,794,475, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, the entire disclosure of which is hereby incorporated by reference herein.

The foregoing discussion is intended only to illustrate various aspects of the related art in the field of the invention at the time, and should not be taken as a disavowal of claim scope.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows:

3

Figure 15:
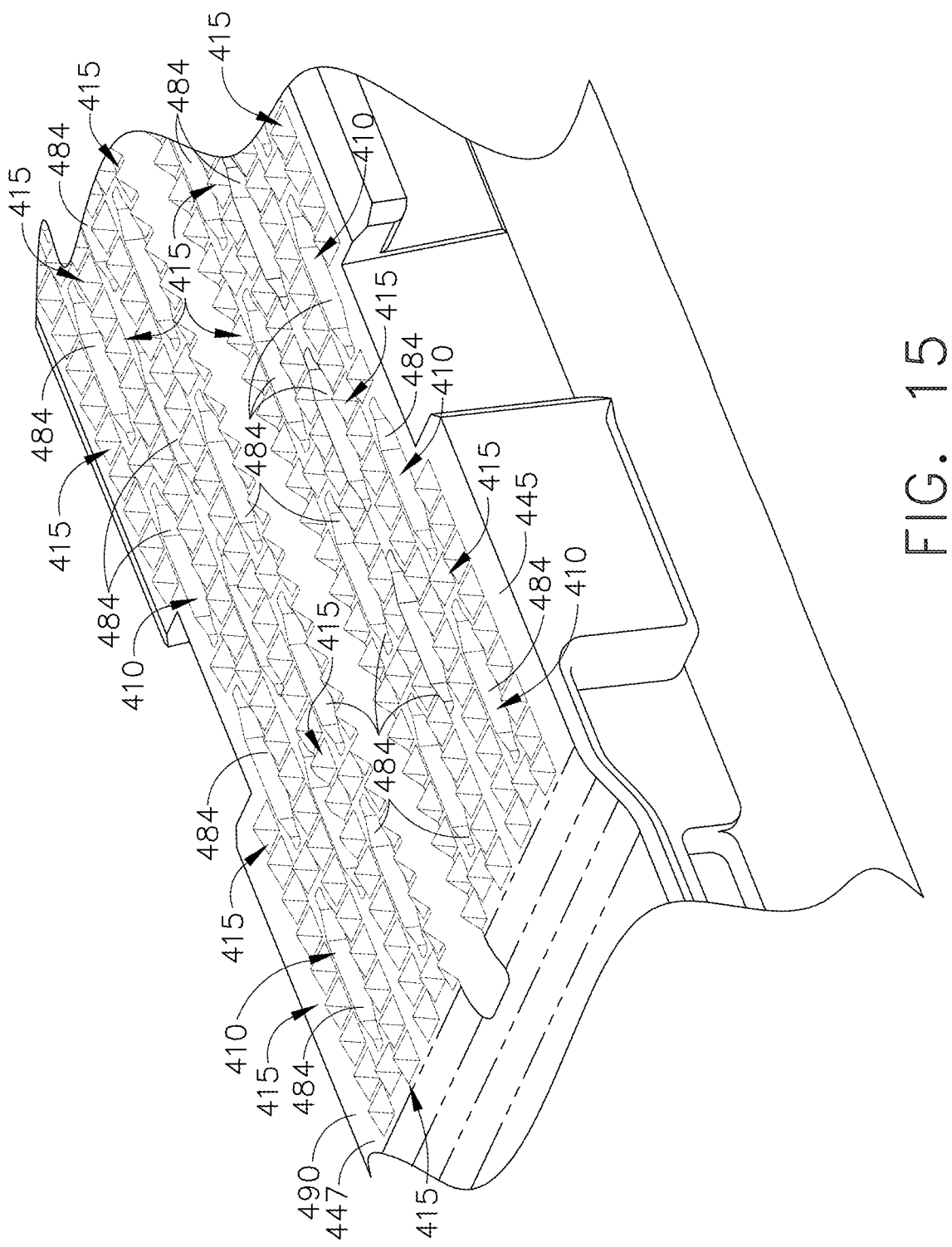
FIG. 15 is a partial perspective view of a staple cartridge in accordance with at least one alternative embodiment comprising a plurality of knurled ridges extending from a cartridge body.
Figure 15A:
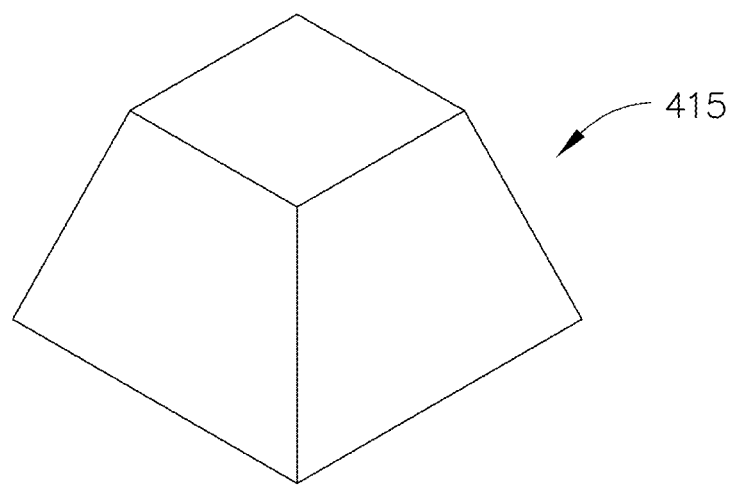
FIG. 15A is a perspective view of a pyramidal knurl in accordance with at least one embodiment.
Figure 15B:
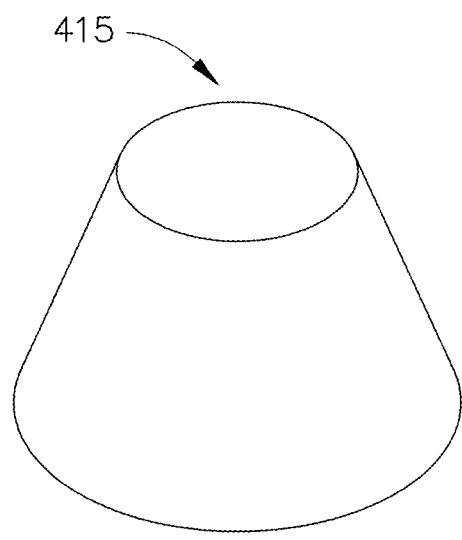
FIG. 15B is a perspective view of a frustoconical knurl in accordance with at least one embodiment.
Figure 15C:
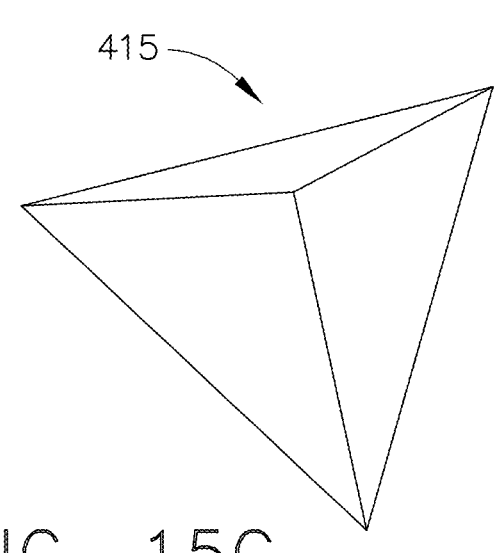
Figure 16:
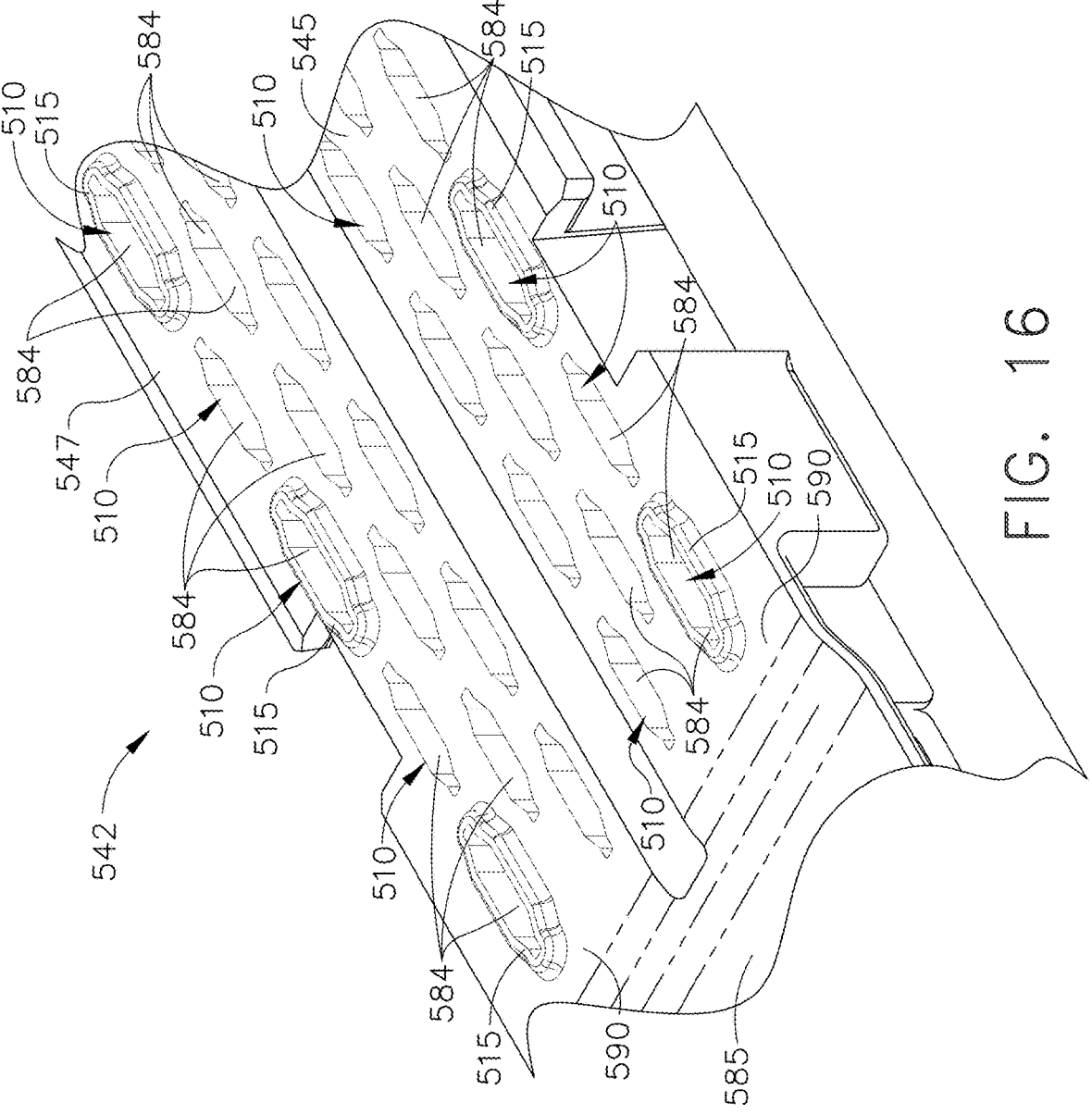
Figure 16A:
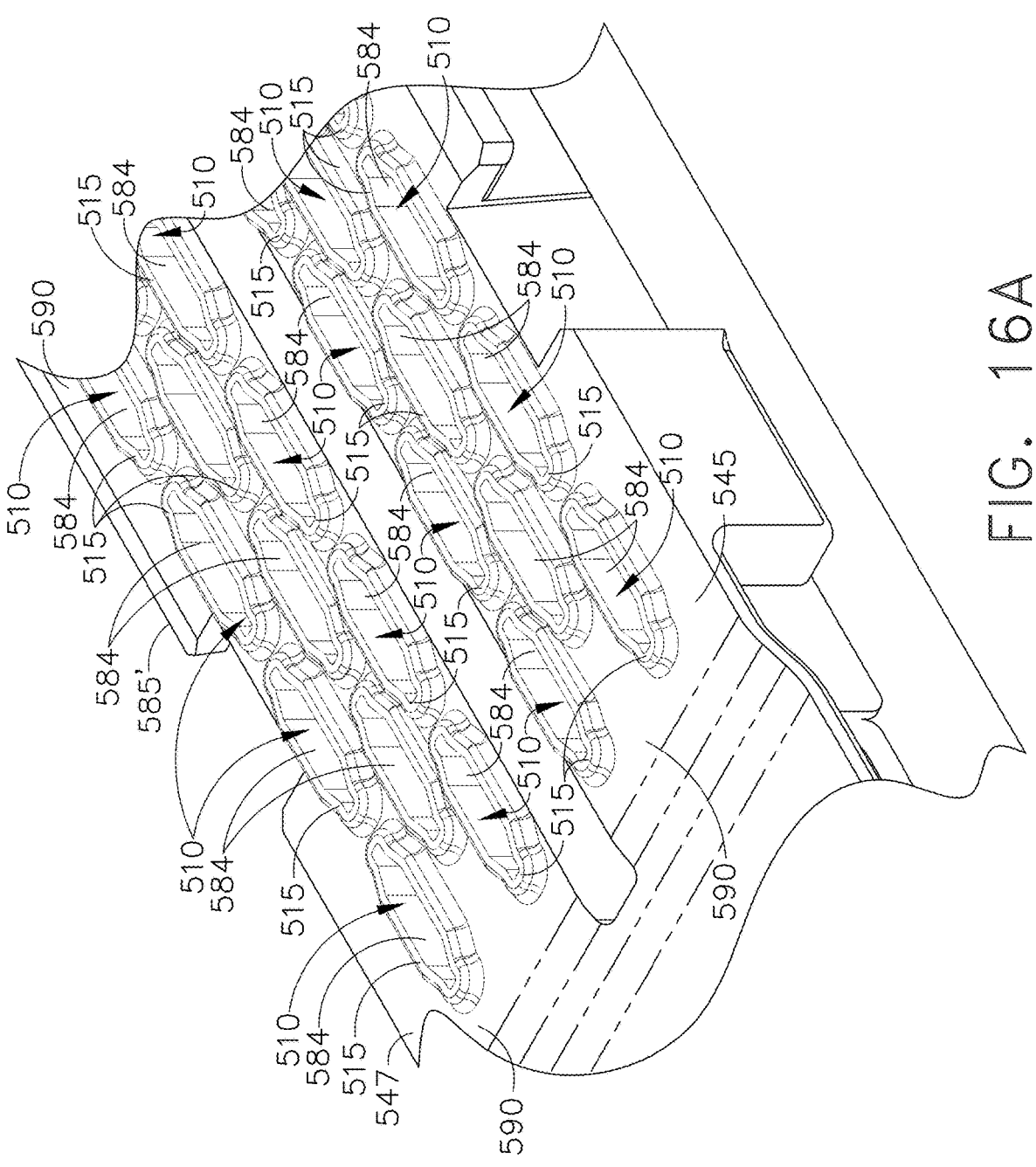
Figure 17:
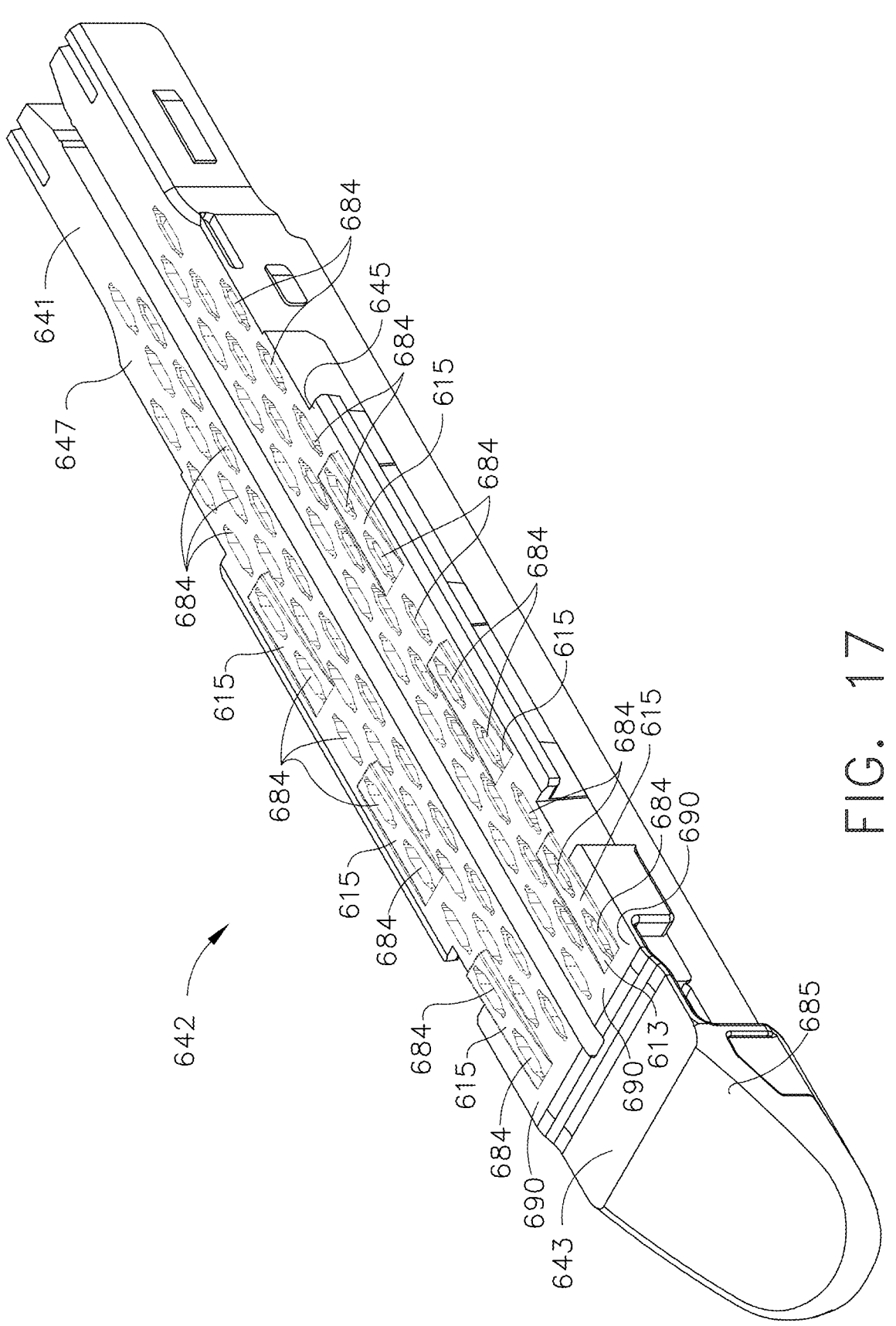
Figure 18:
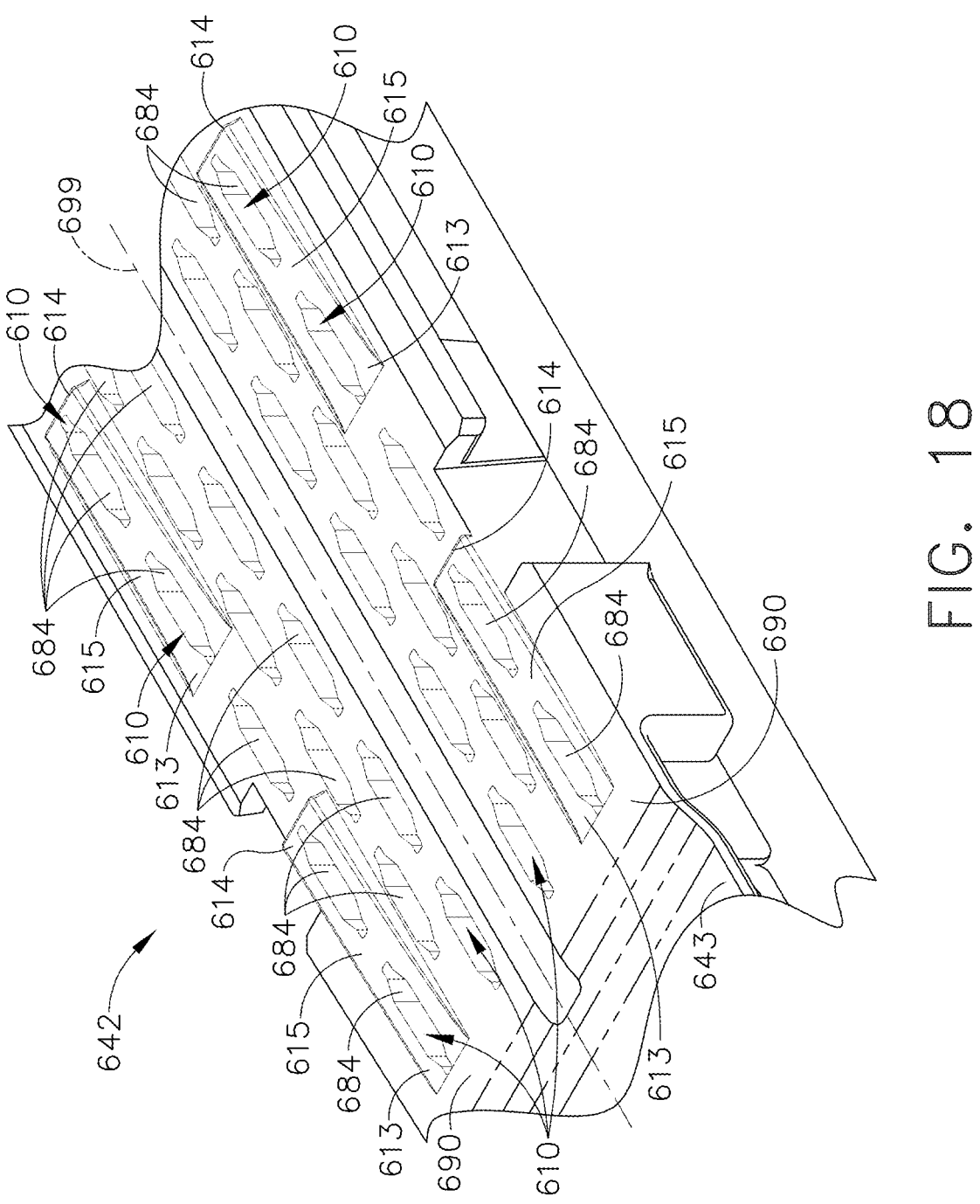
Figure 19:
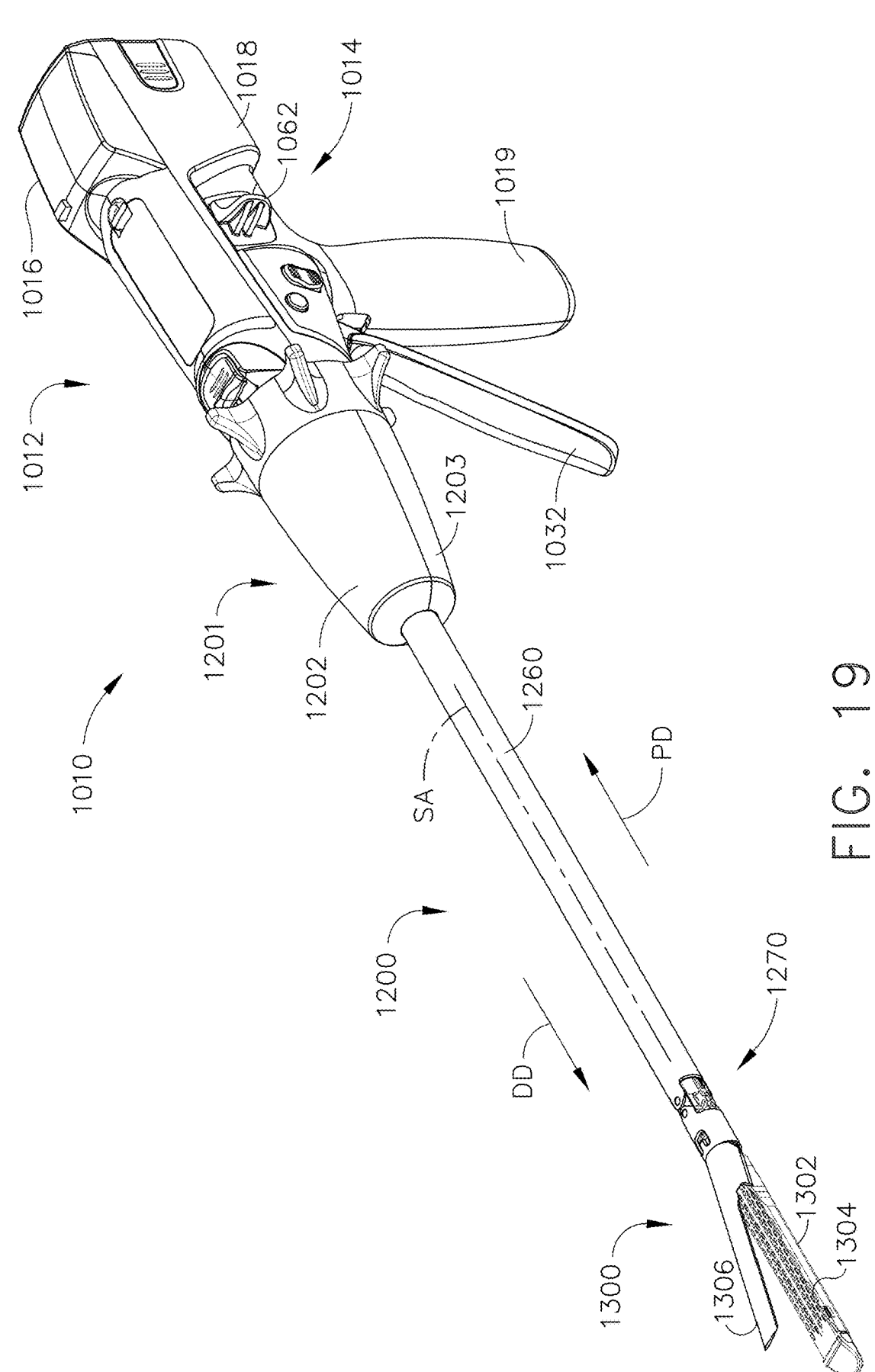
Figure 20:
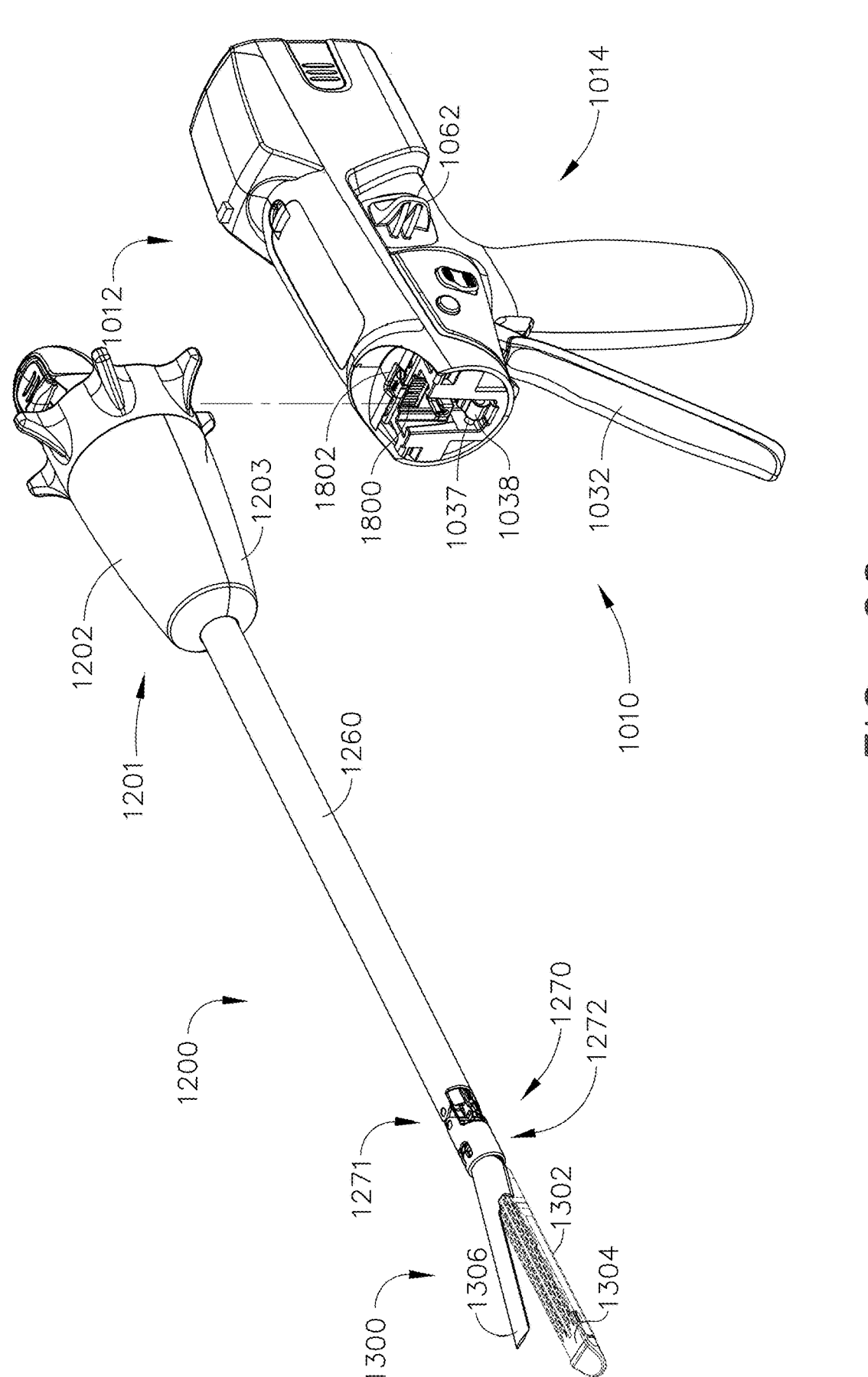
Figure 21:
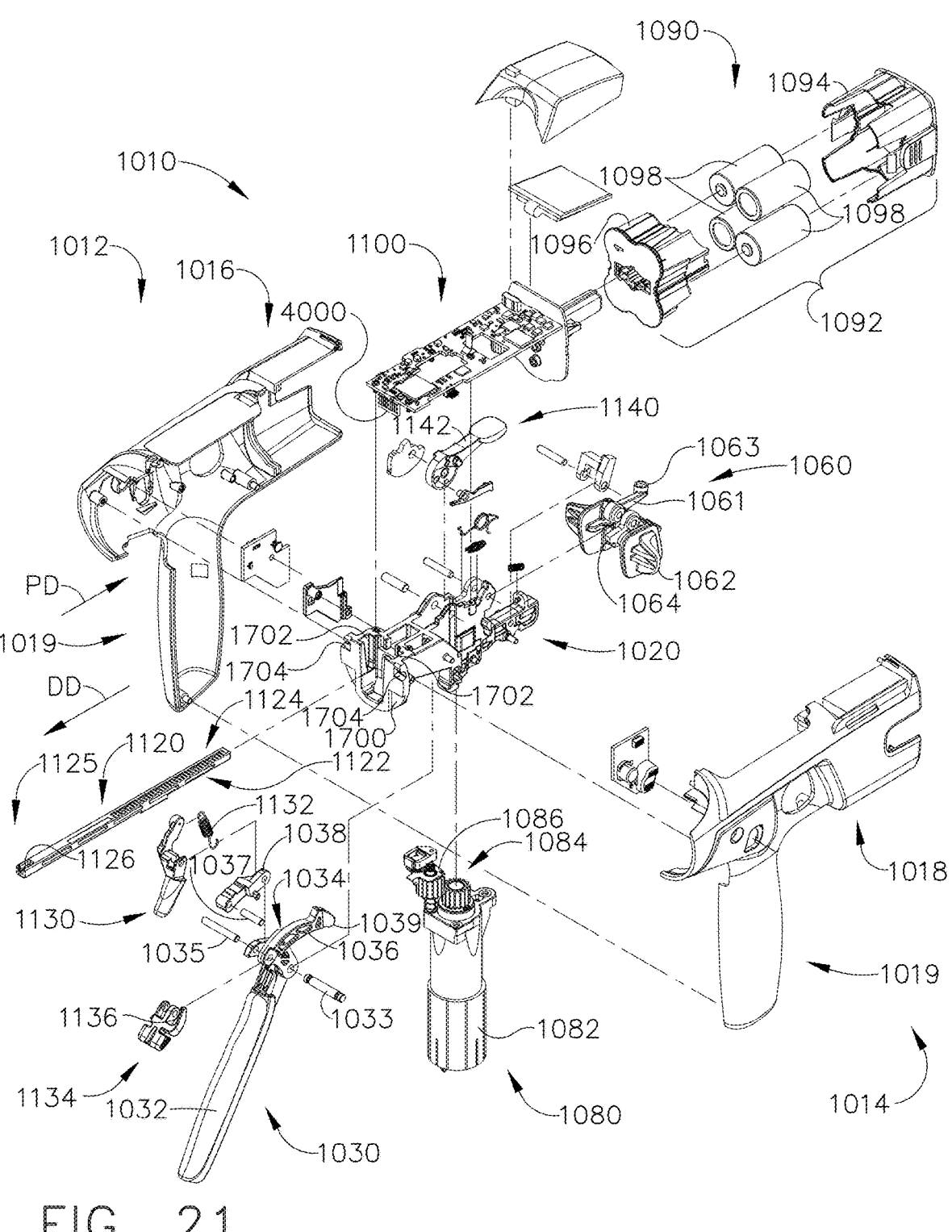
Figure 22:
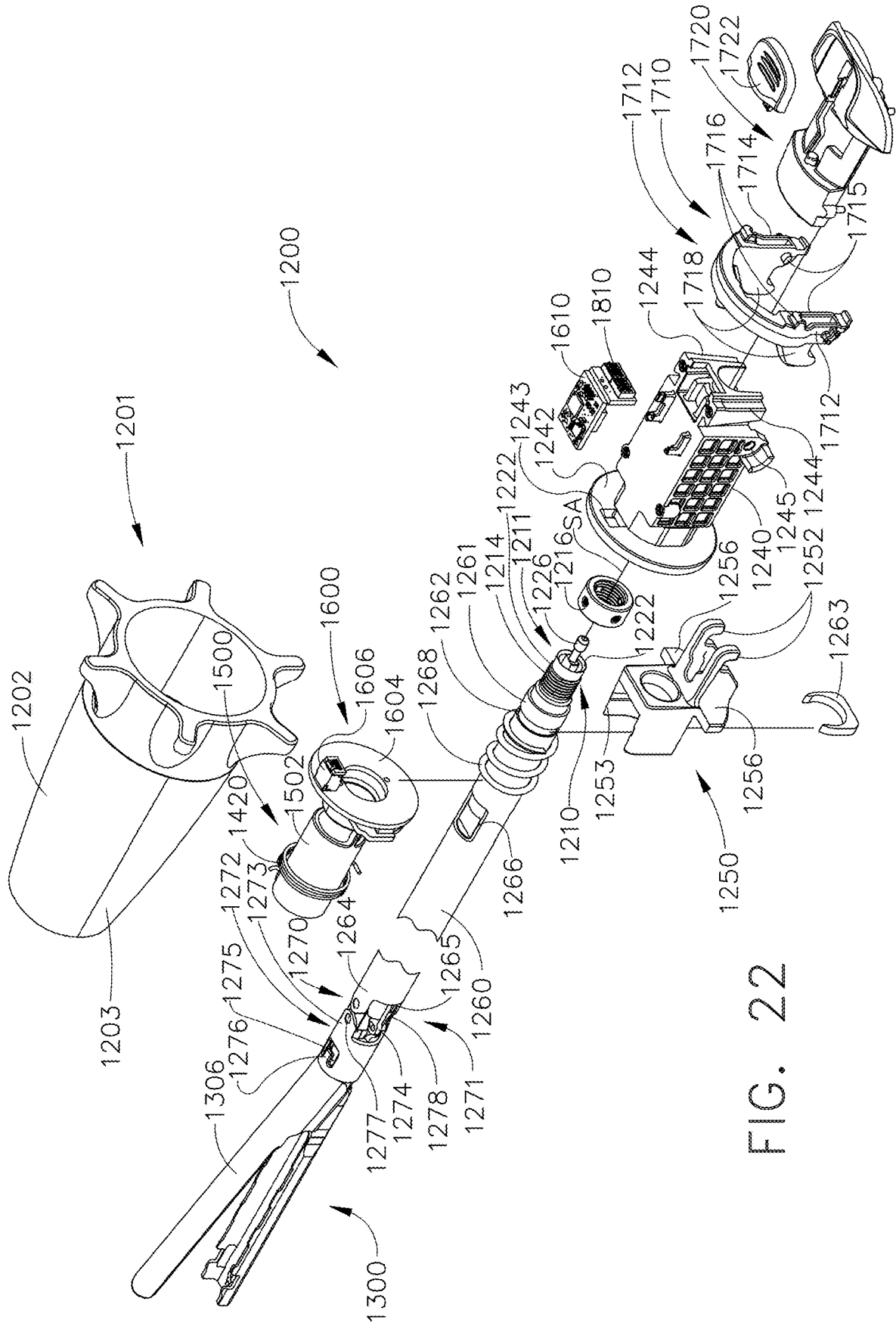
Figure 23:
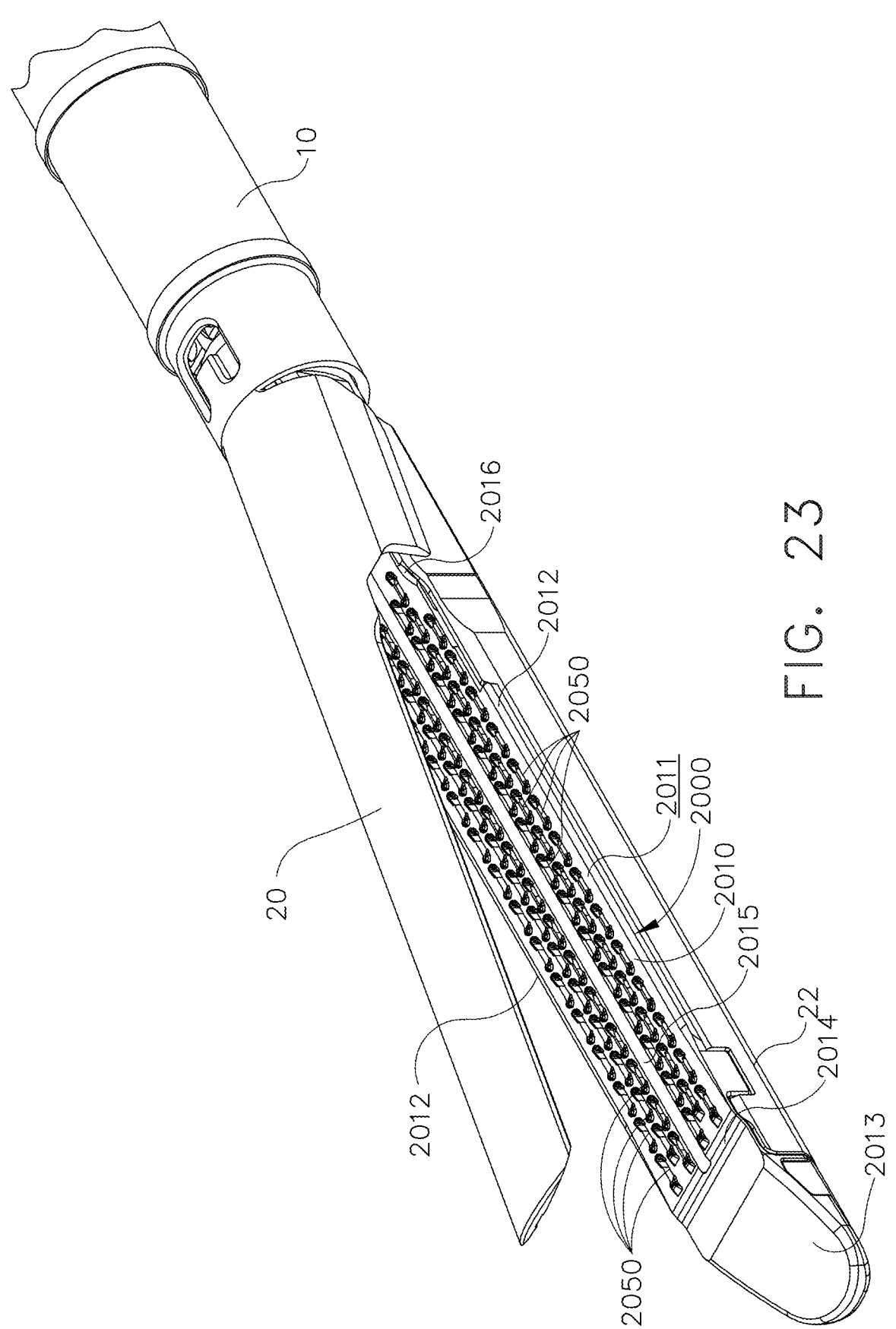
Figure 24:
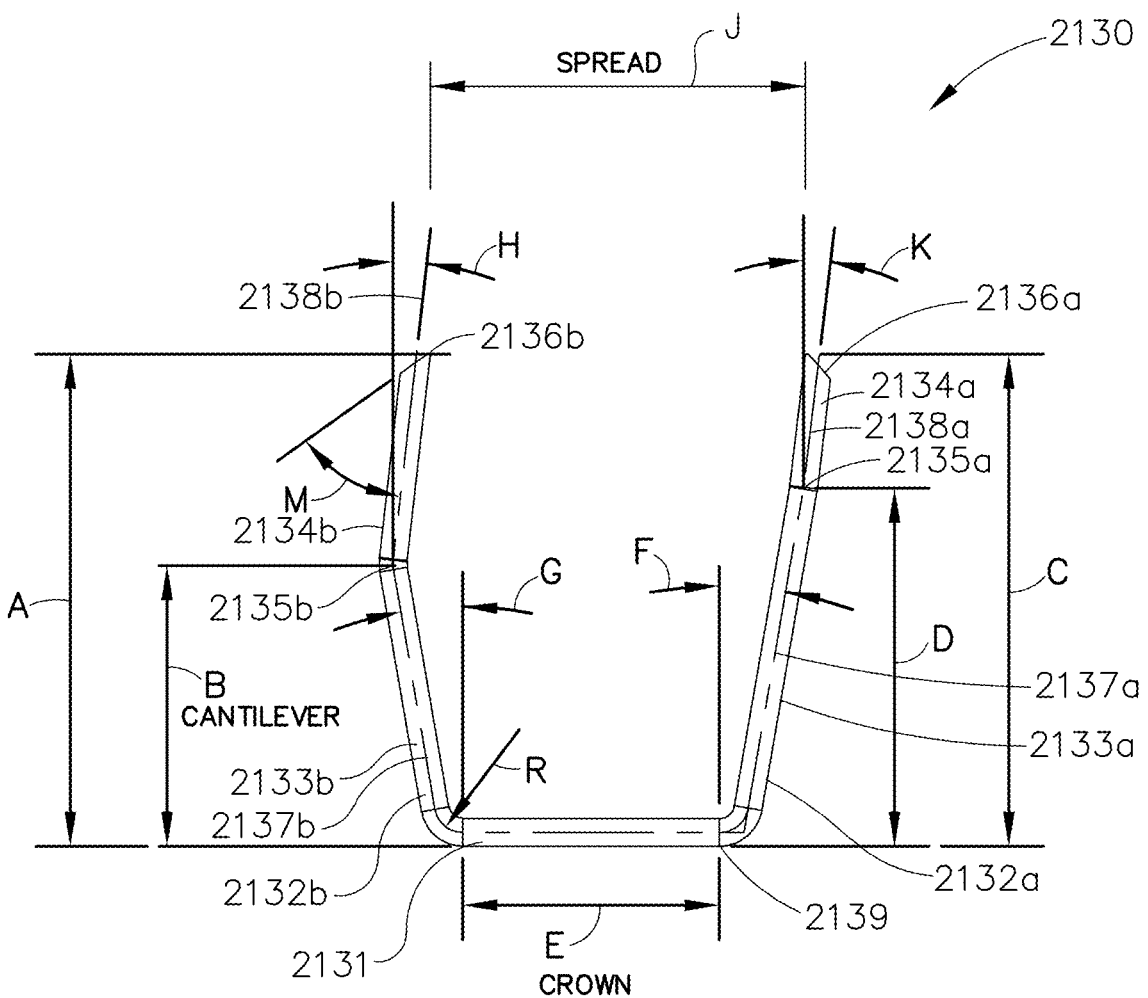
Figure 25:
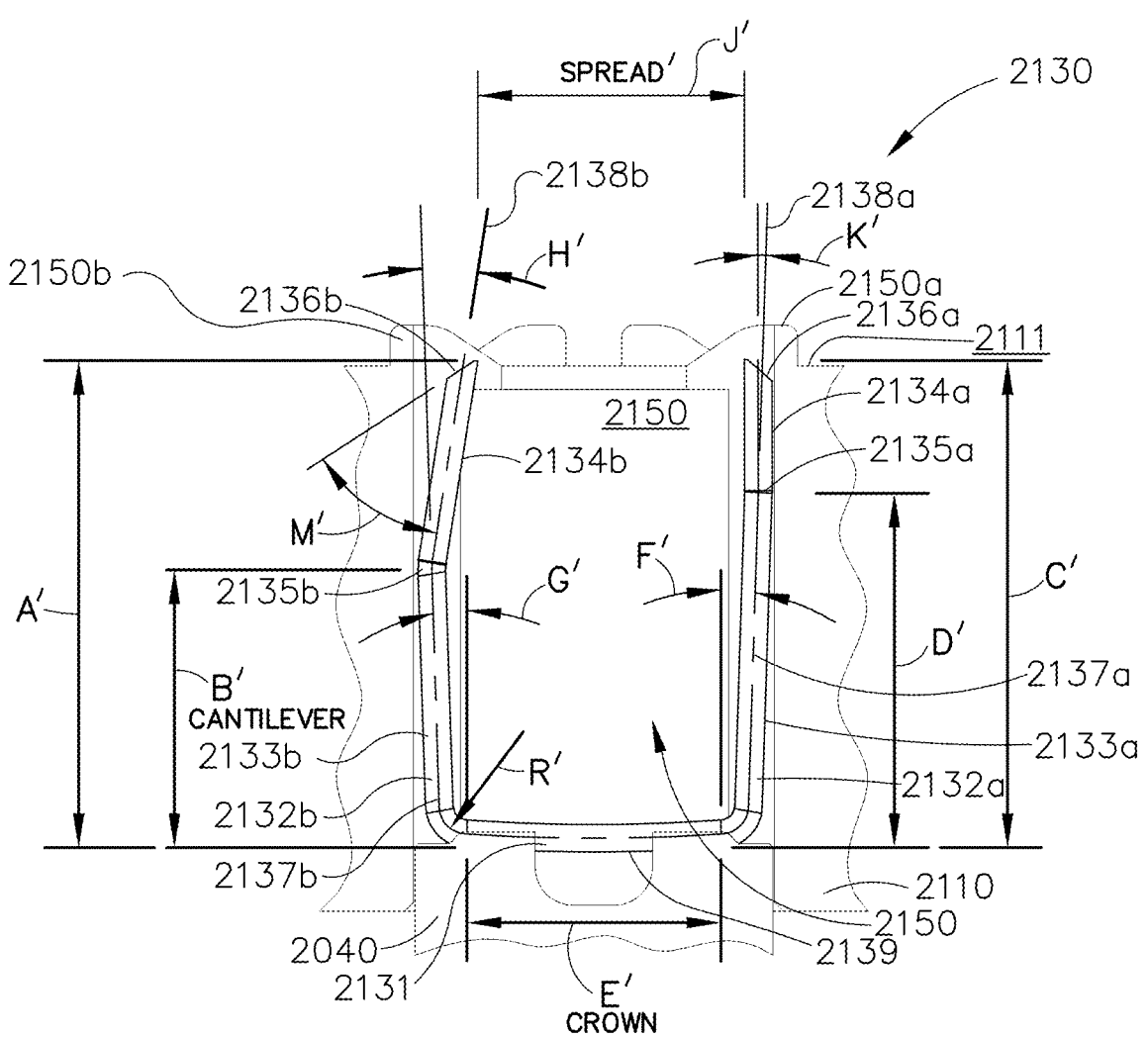
Figures 26, 27:
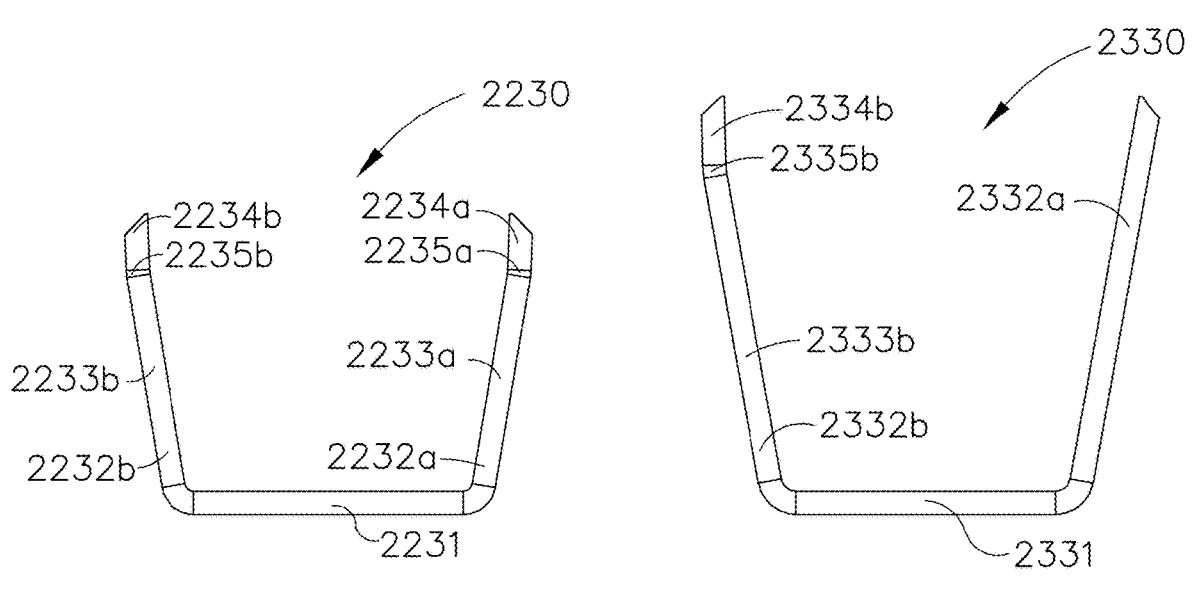
Figures 28, 29:
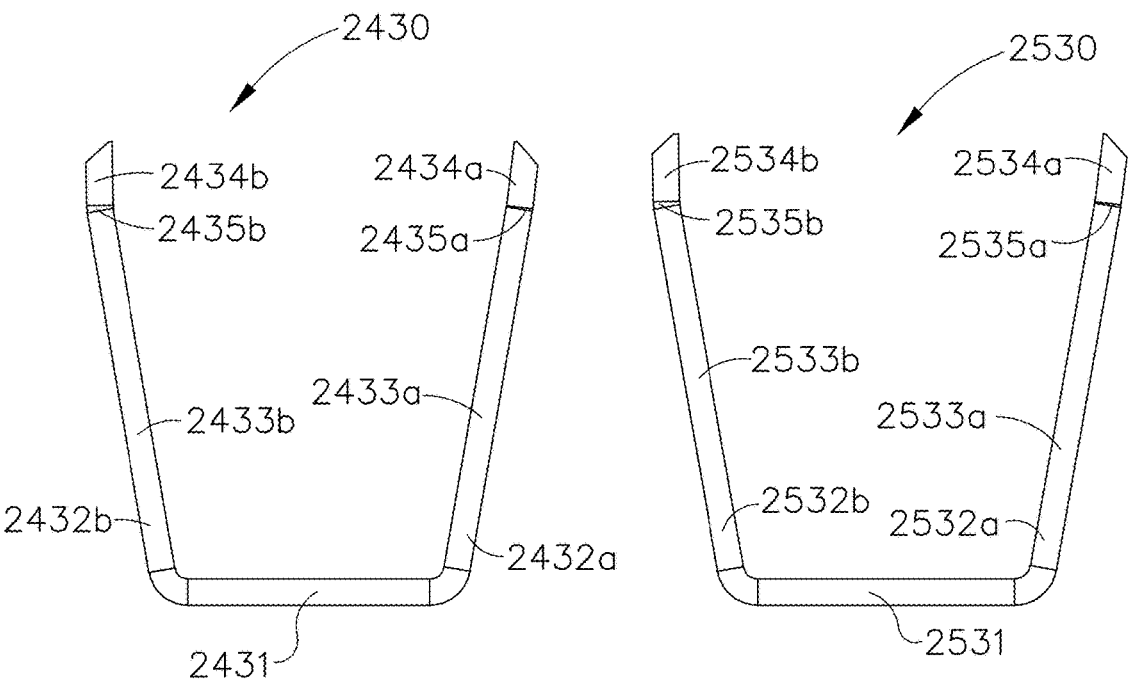
Figure 30:
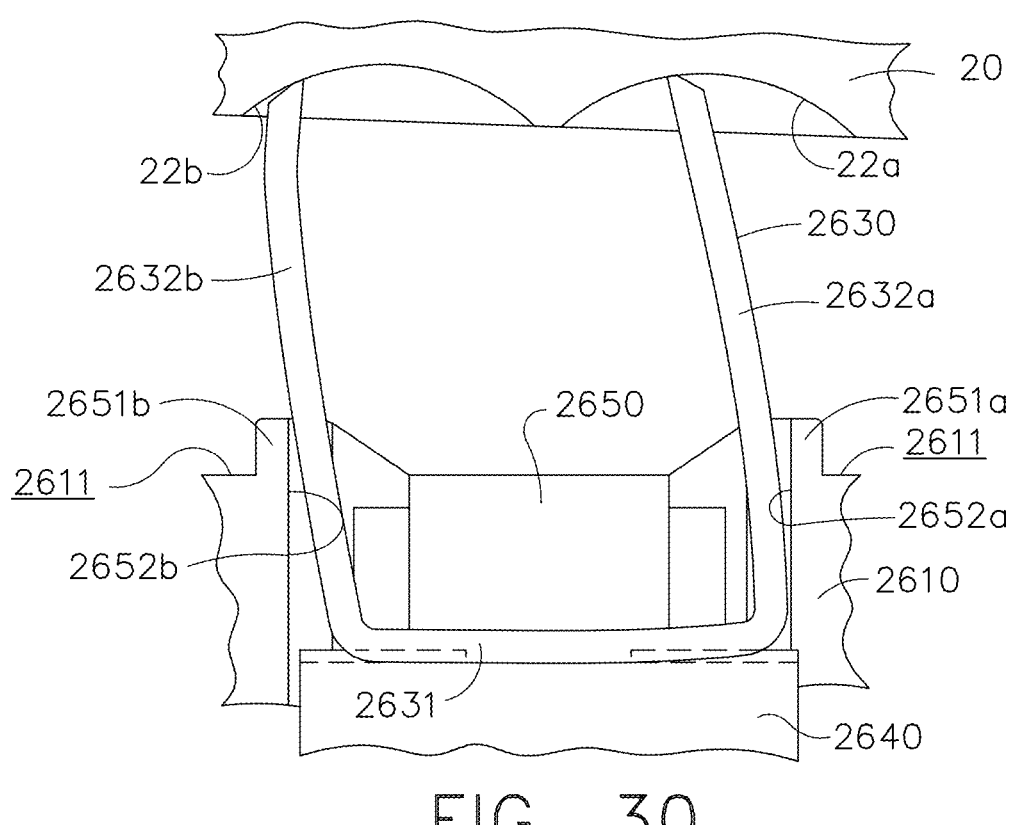
Figure 31:
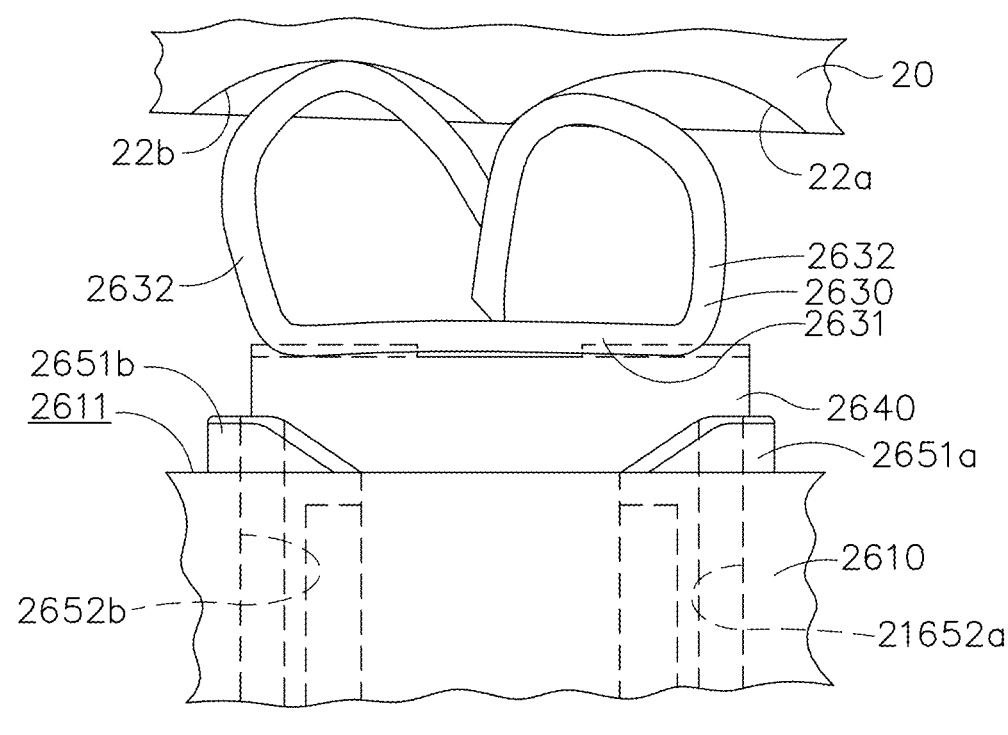
Figure 32:
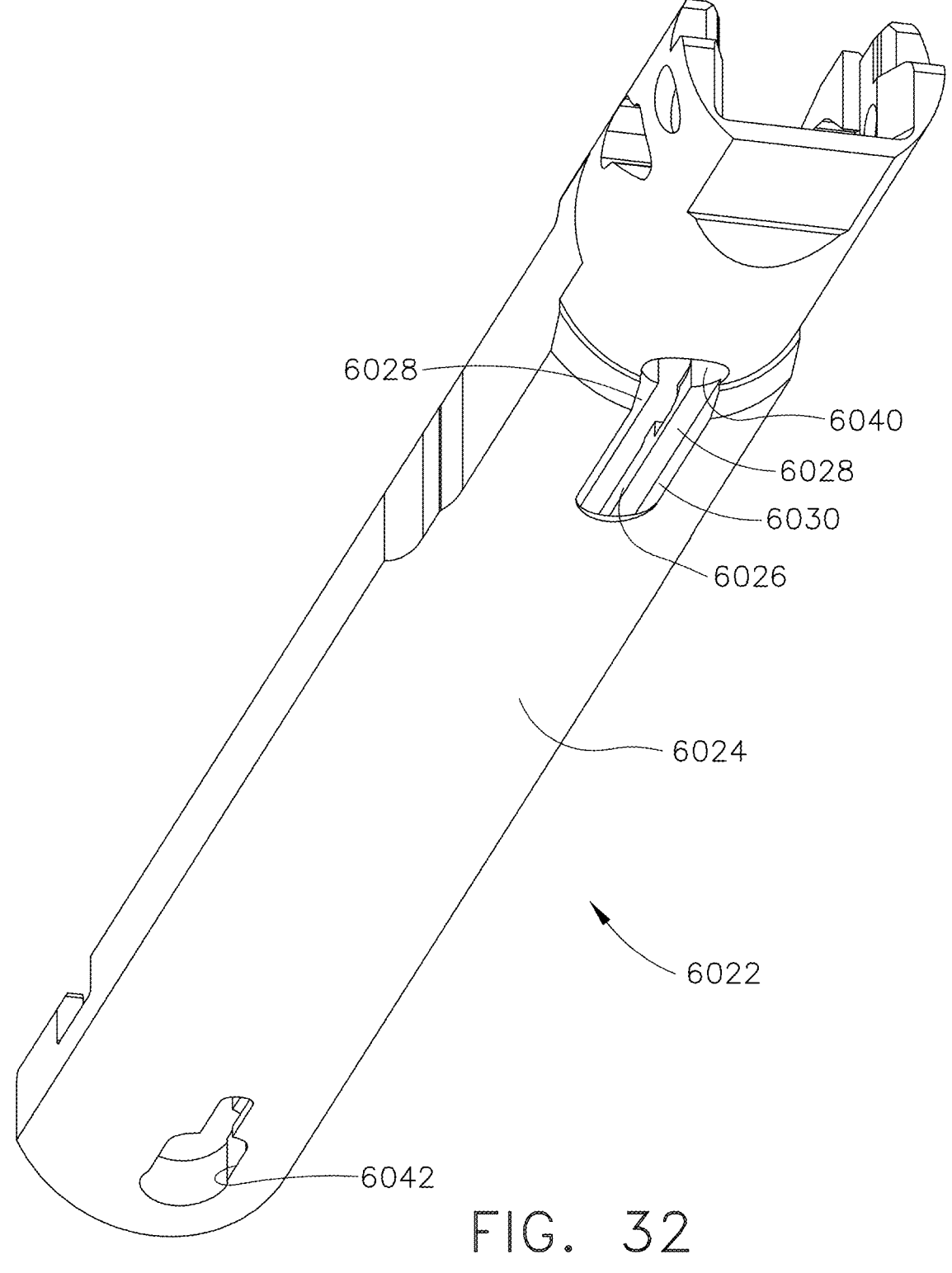
Figure 33:
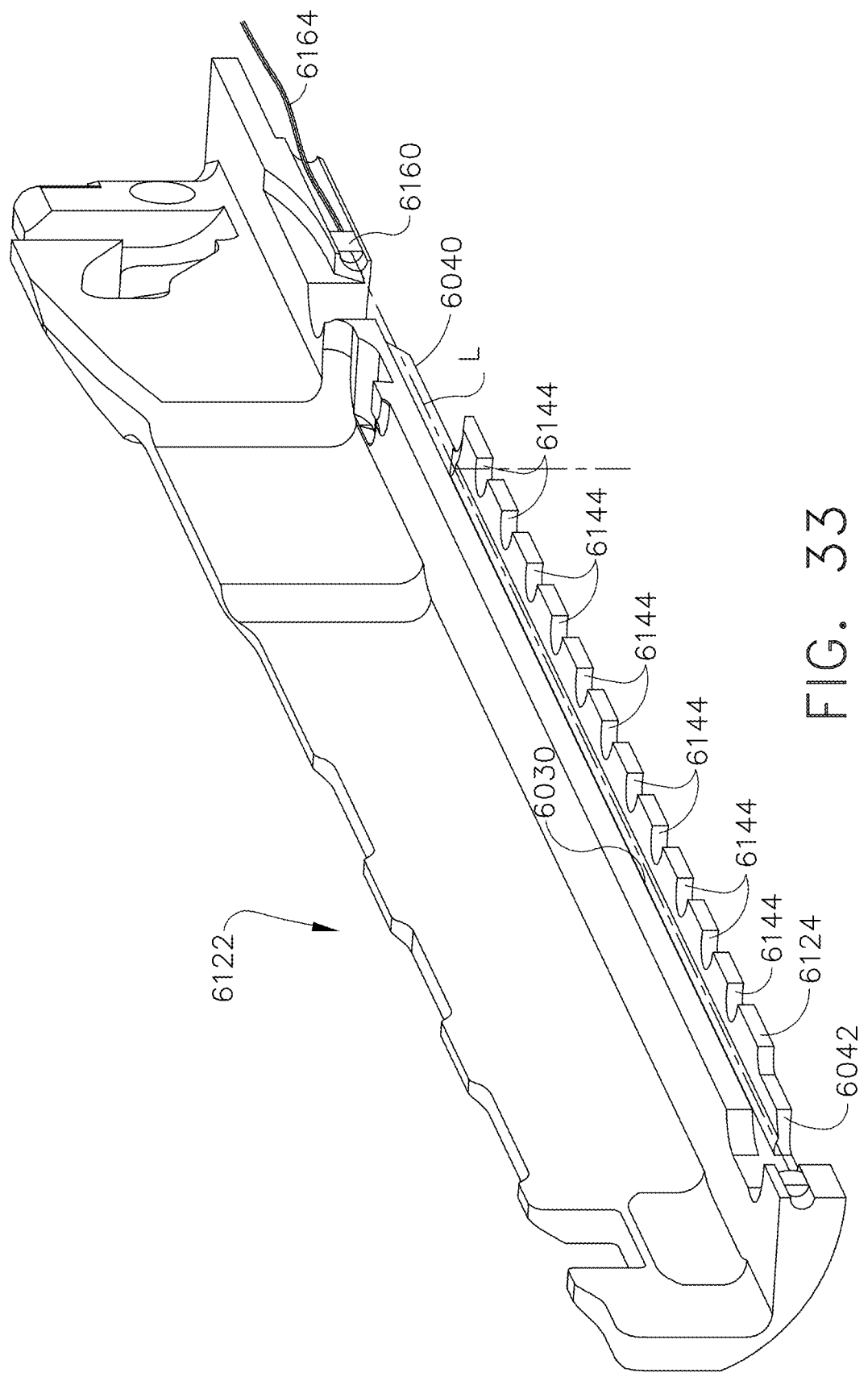
Figure 34:
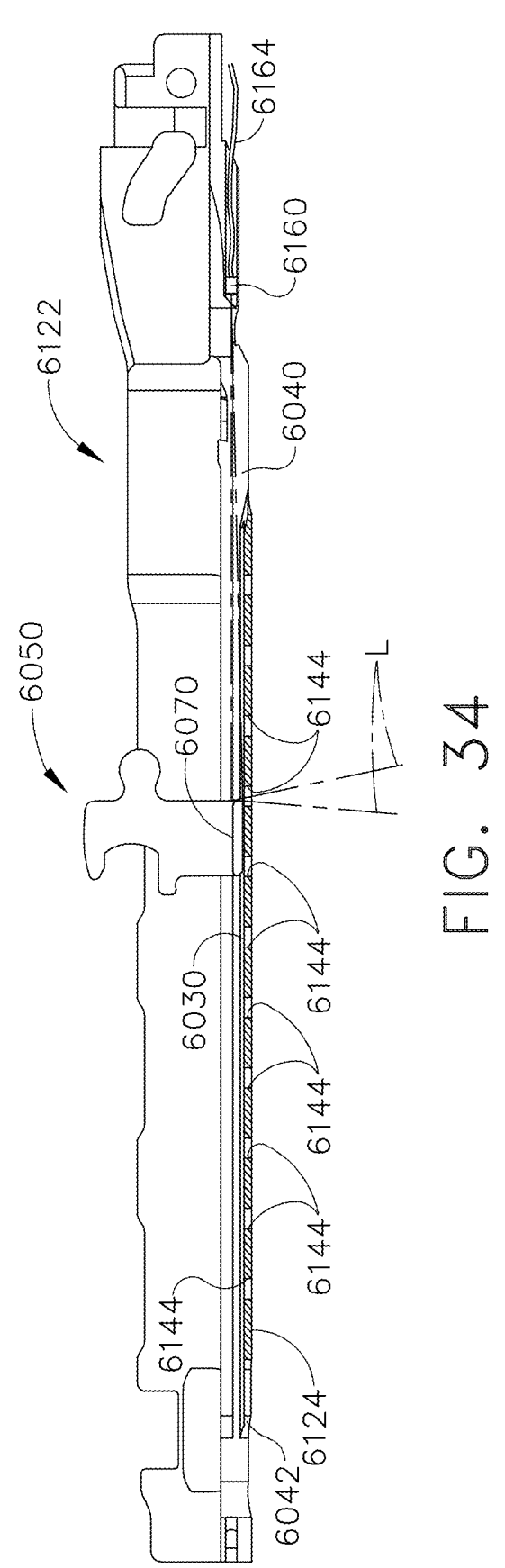
Figure 35:
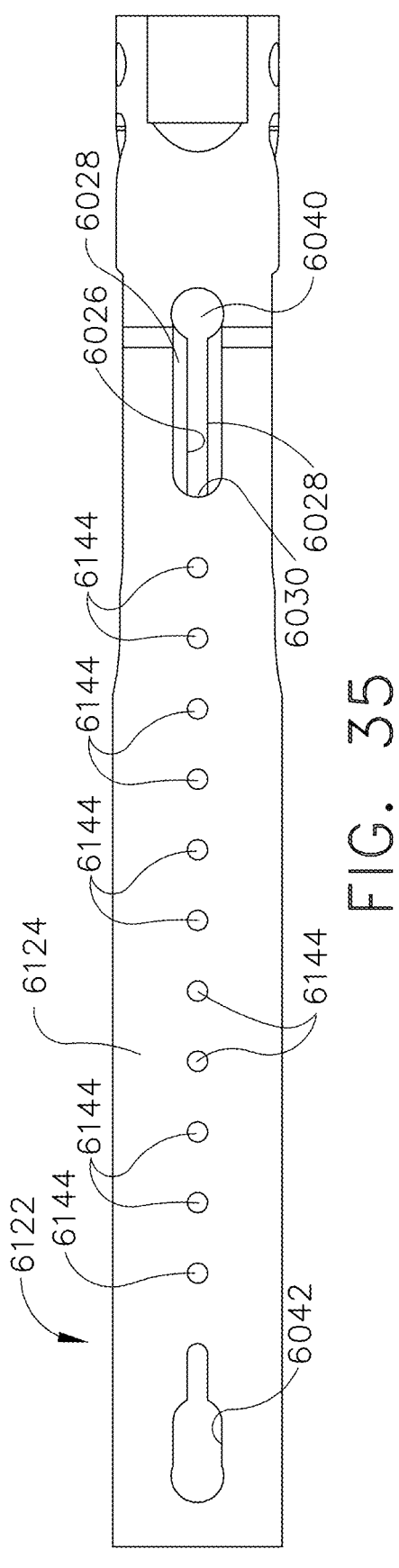
Figures 36, 37:
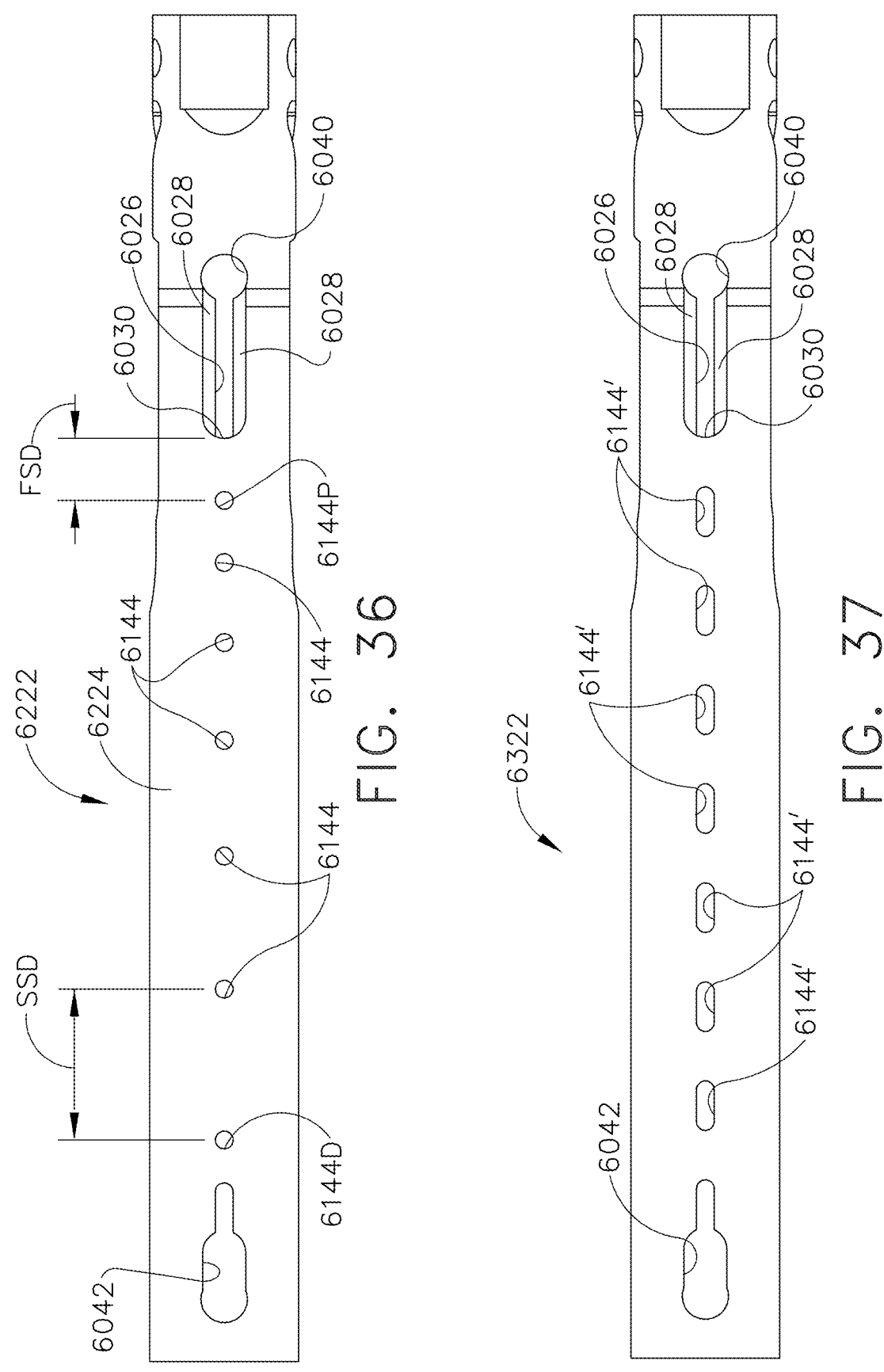
Figures 38, 39:
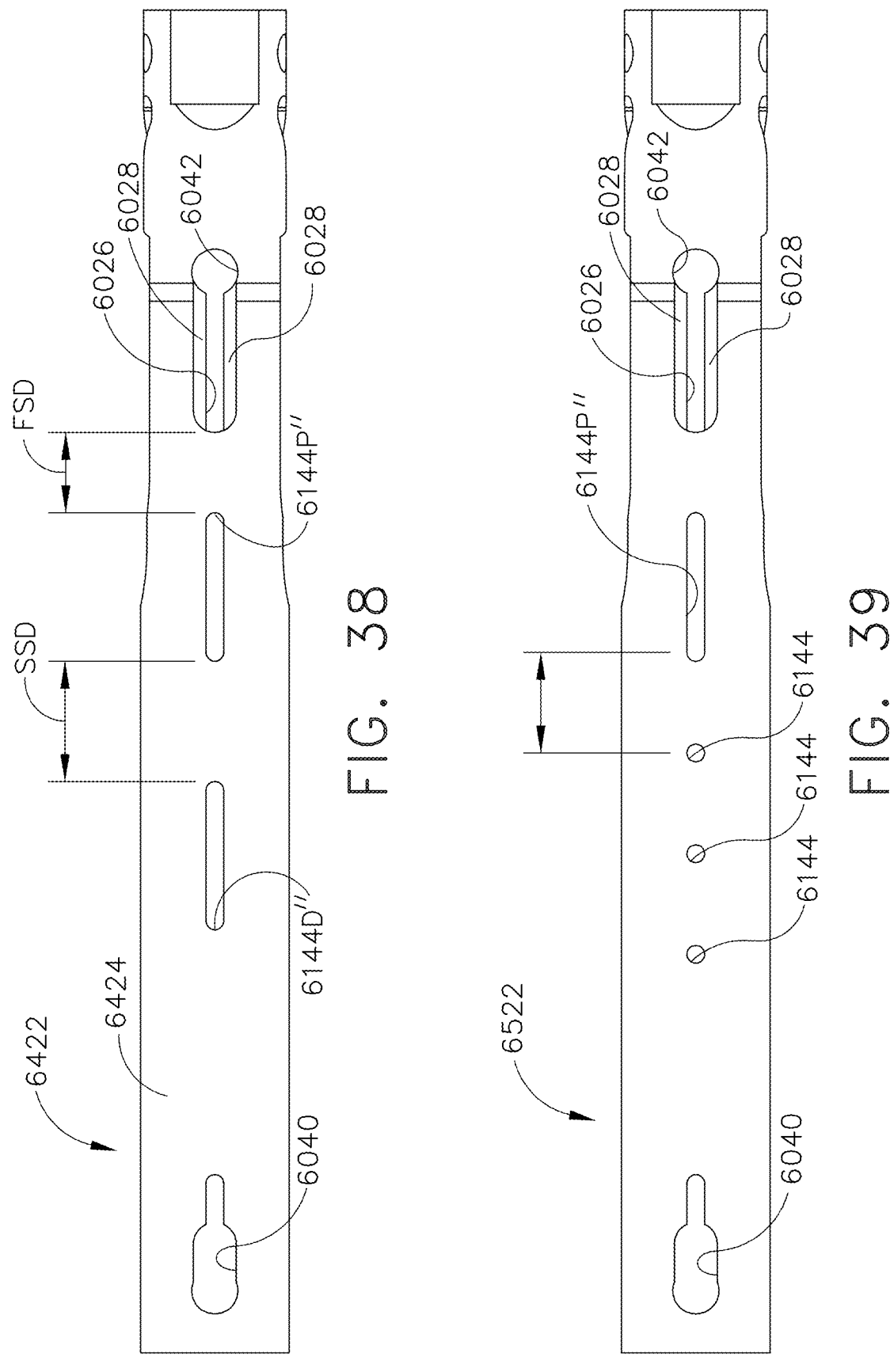
Figures 40, 41:
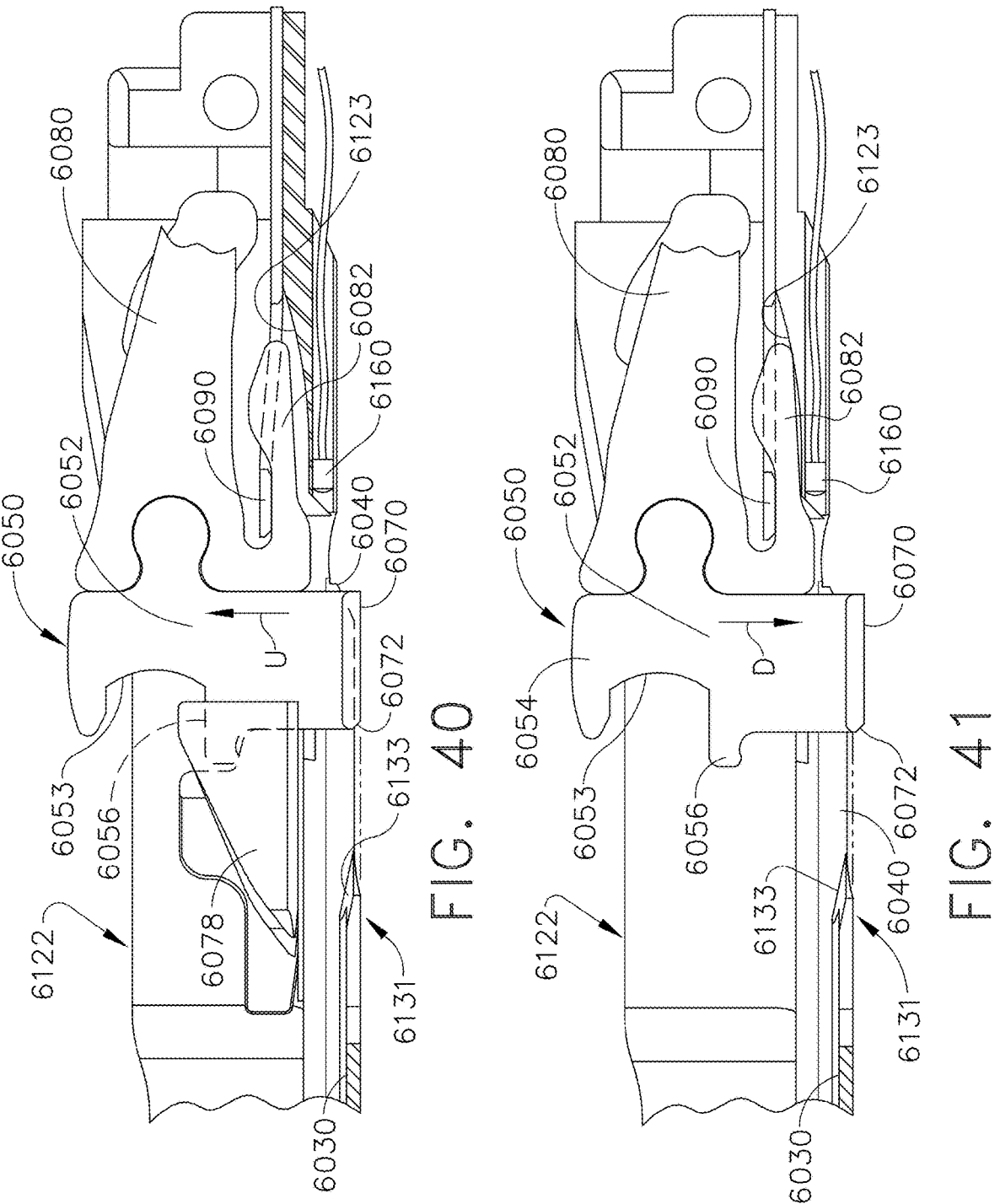

FIG. 15C is a perspective view of a triangular knurl in accordance with at least one embodiment;

FIG. 16 is a partial perspective view of a staple cartridge in accordance with at least one alternative embodiment comprising a plurality of ridges entirely surrounding staple cavity openings defined in a cartridge body;

FIG. 16A is a partial perspective view of a staple cartridge in accordance with at least one alternative embodiment comprising a plurality of ridges entirely surrounding staple cavity openings defined in a cartridge body;

FIG. 17 is a perspective view of a staple cartridge in accordance with at least one alternative embodiment comprising a plurality of longitudinal ridges extending from a cartridge body;

FIG. 18 is a detail view of the staple cartridge of FIG. 17;

FIG. 19 is a perspective view of a surgical instrument that has an interchangeable shaft assembly operably coupled thereto;

FIG. 20 is an exploded assembly view of the interchangeable shaft assembly and surgical instrument of FIG. 19;

FIG. 21 is an exploded assembly view of a portion of the surgical instrument of FIGS. 19 and 20;

FIG. 22 is another exploded assembly view showing portions of the interchangeable shaft assembly and surgical instrument of FIGS. 19-21;

FIG. 23 is a perspective view of a staple cartridge positioned in an end effector of a surgical instrument in accordance with at least one embodiment, wherein the staple cartridge comprises a plurality of ridges extending from a cartridge body of the staple cartridge;

FIG. 24 is an elevational view of a staple in accordance with at least one embodiment;

FIG. 25 is an elevational view of the staple of FIG. 24 positioned within a staple cavity in a staple cartridge;

FIG. 26 is an elevational view of a staple in accordance with at least one embodiment;

FIG. 27 is an elevational view of an asymmetrical staple in accordance with at least one embodiment;

FIG. 28 is an elevational view of another asymmetrical staple in accordance with at least one embodiment;

FIG. 29 is an elevational view of another asymmetrical staple in accordance with at least one embodiment;

FIG. 30 is an elevational view of a staple illustrated in a partially deformed condition;

FIG. 31 is an elevational view of the staple of FIG. 30 in a fully deformed condition;

FIG. 32 is a bottom perspective view of an elongate channel;

FIG. 33 is a cross-sectional perspective view of another elongate channel;

FIG. 34 is another cross-sectional view of the elongate channel of FIG. 33 with a cutting head diagrammatically shown therein;

FIG. 35 is a bottom view of the elongate channel of FIGS. 33 and 34;

FIG. 36 is a bottom view of another elongate channel;

FIG. 37 is a bottom view of another elongate channel;

FIG. 38 is a bottom view of another elongate channel;

FIG. 39 is a bottom view of another elongate channel;

FIG. 40 is a partial side view of an elongate channel and cutting head with the elongate channel shown in cross-section and portions of the surgical staple cartridge omitted for clarity and with the cutting head in an unlocked position and ready for firing;

FIG. 41 is another partial side view of the elongate channel and cutting head of FIG. 40 with the cutting head biased in a locked position;

4

Figure 42:
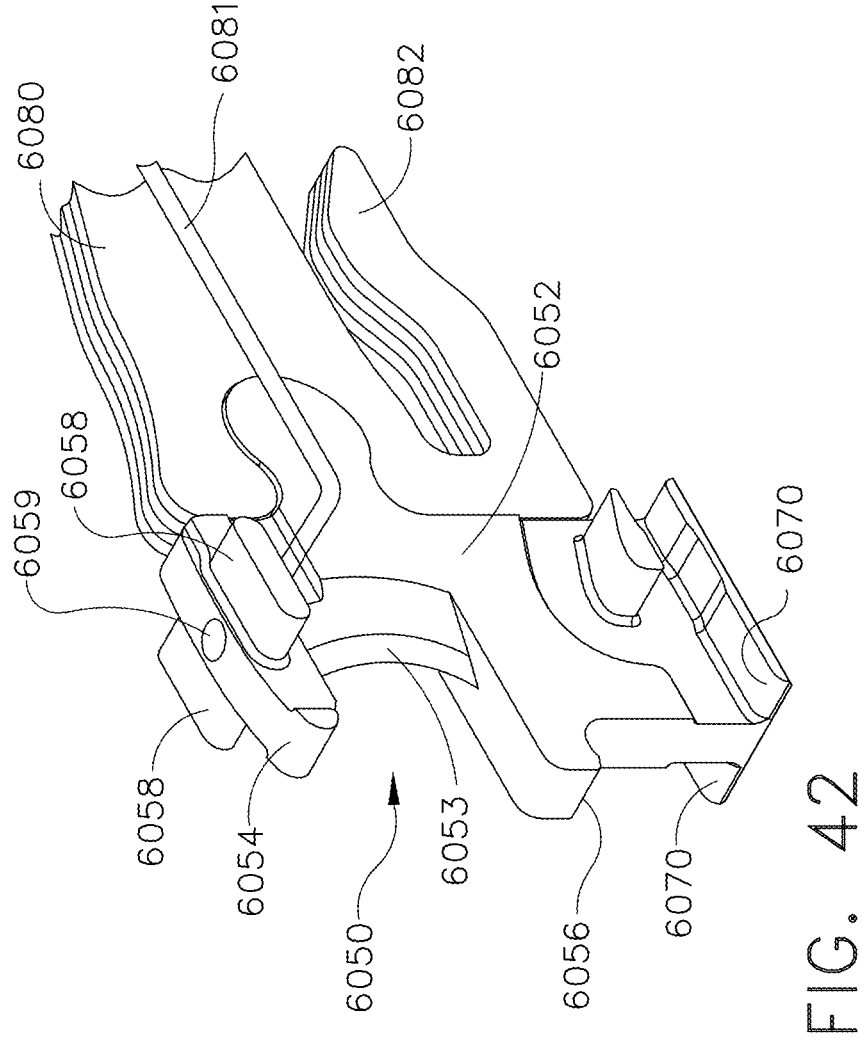
Figures 43, 44:
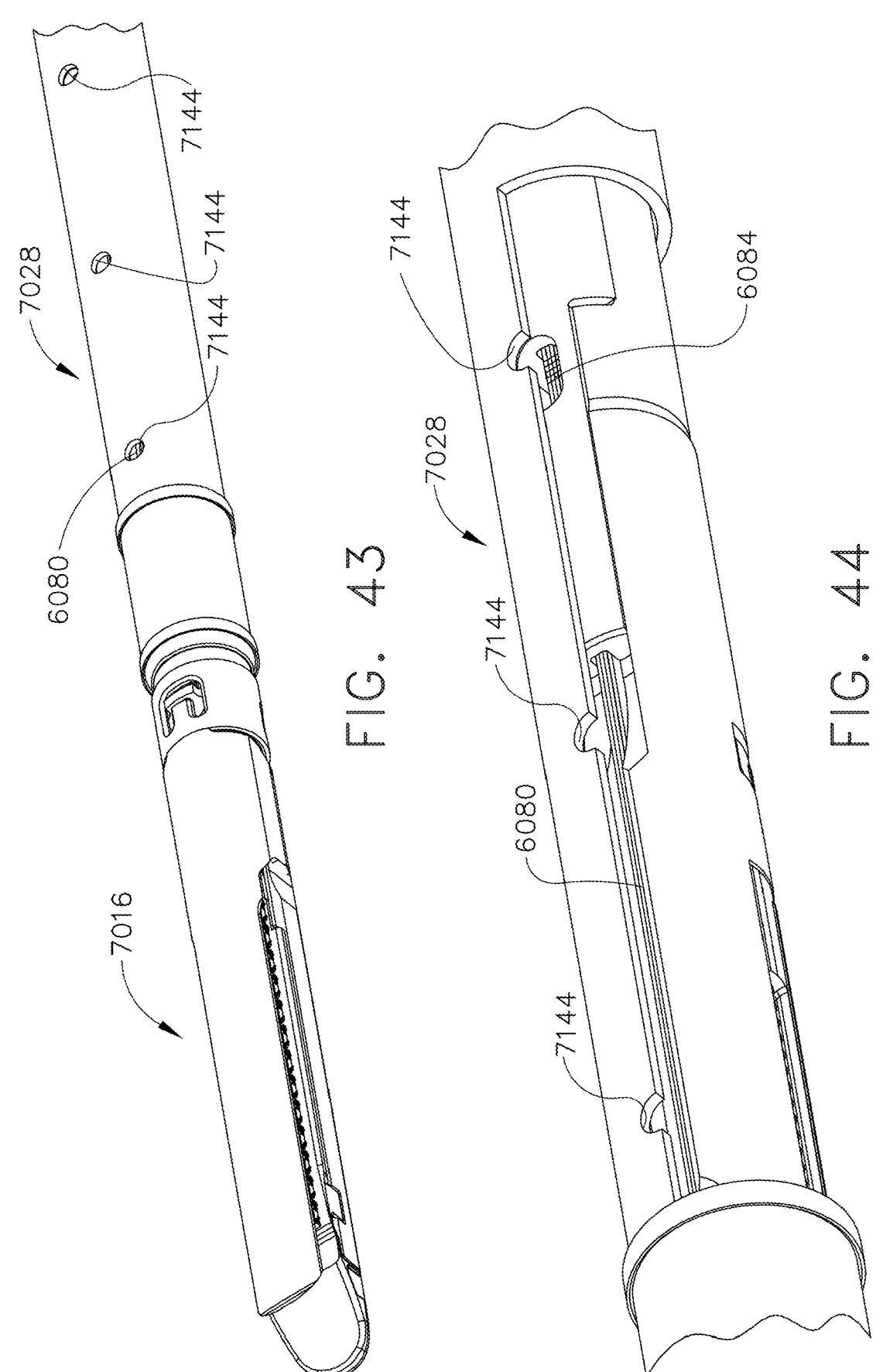
Figure 45:
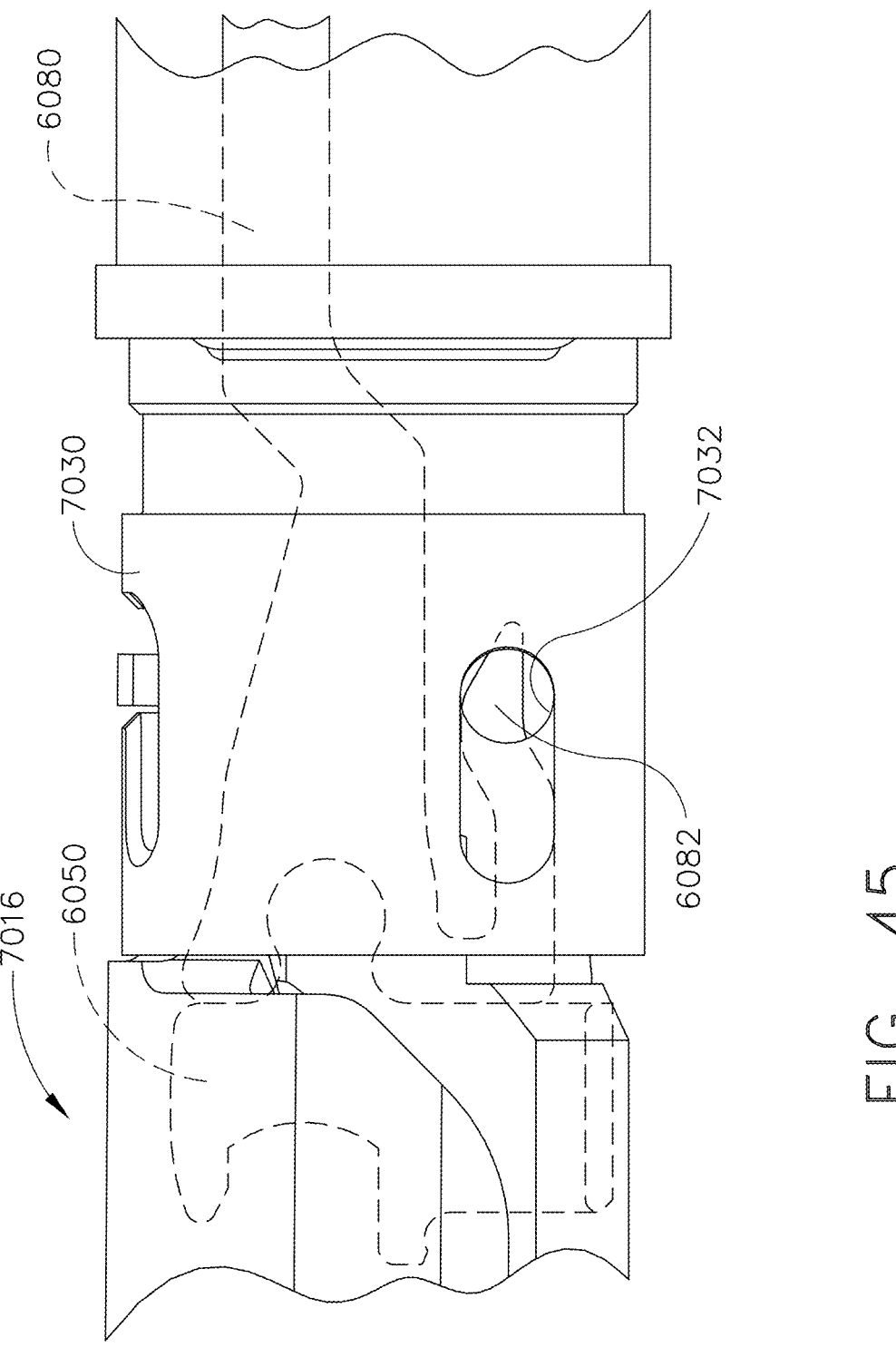
Figures 46, 47, 48:
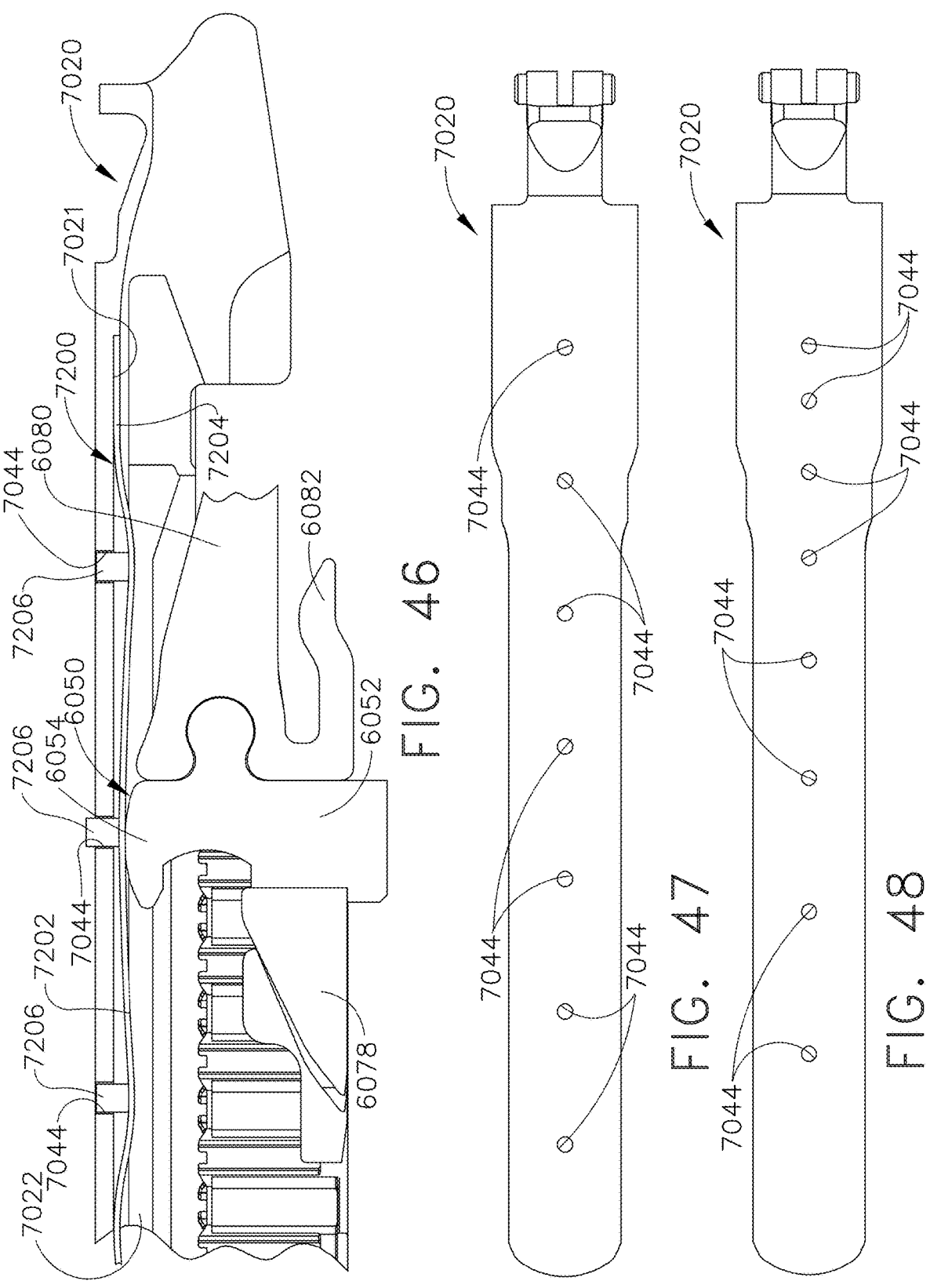
Figure 49:
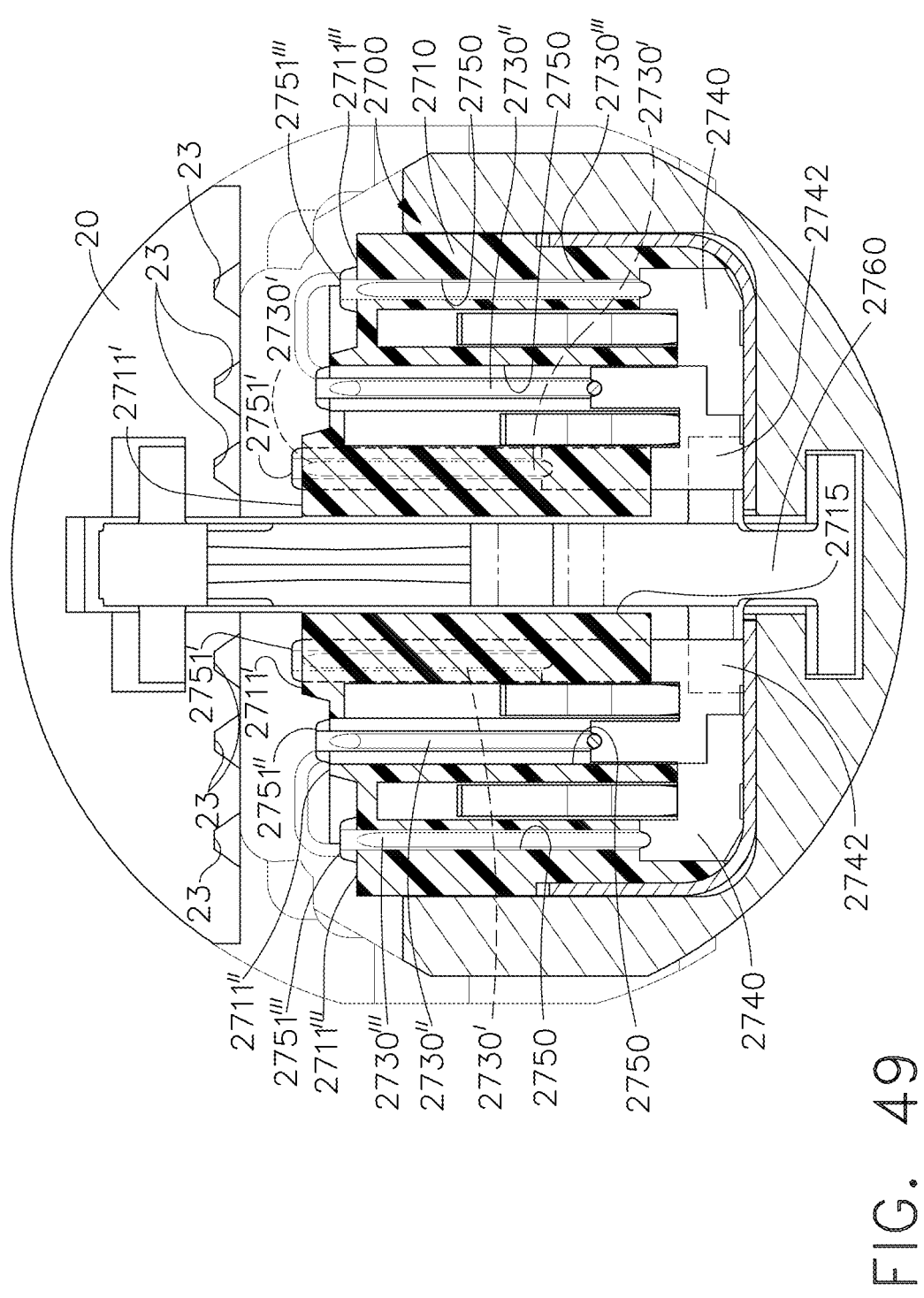
Figure 49A:
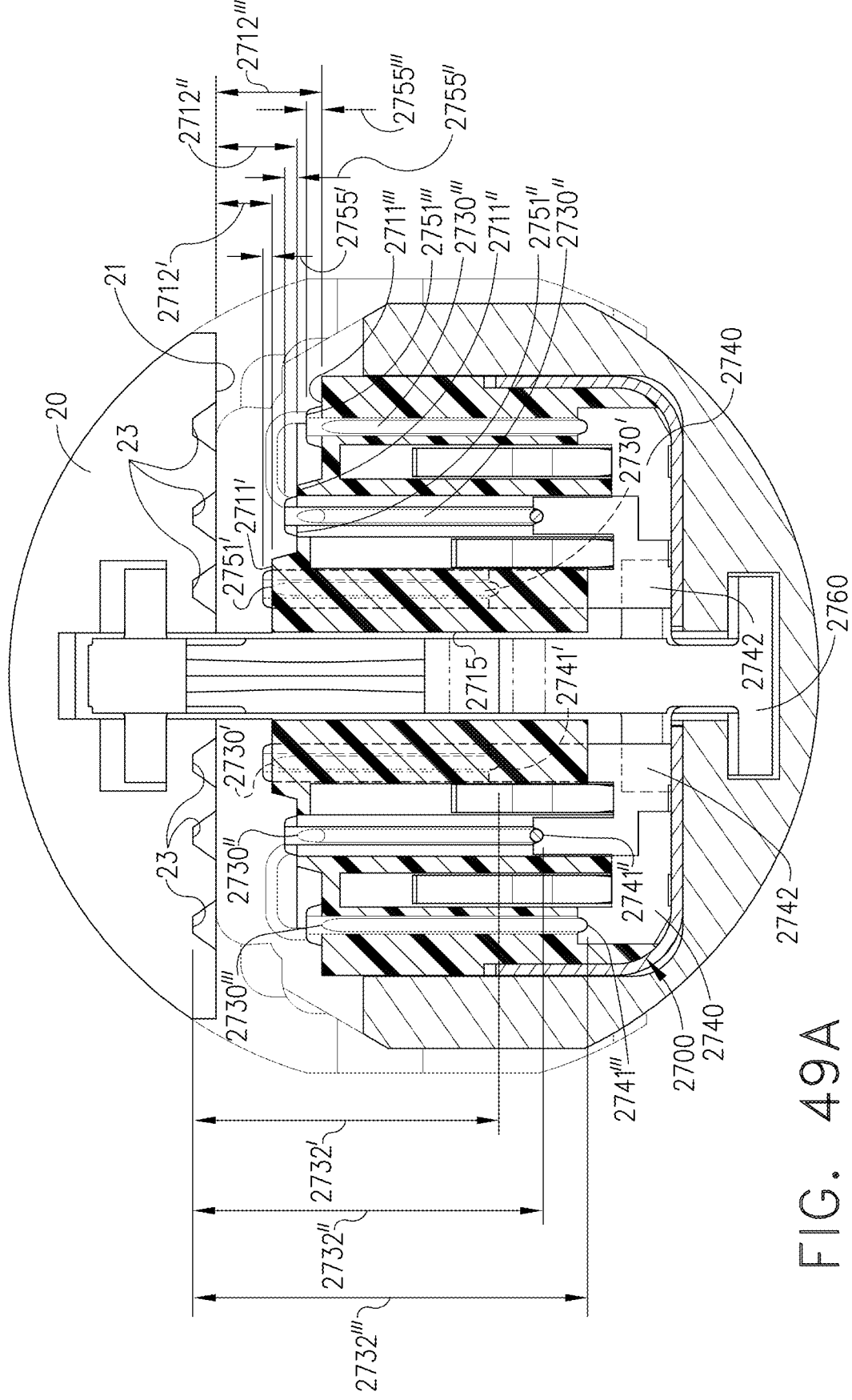
Figure 50:
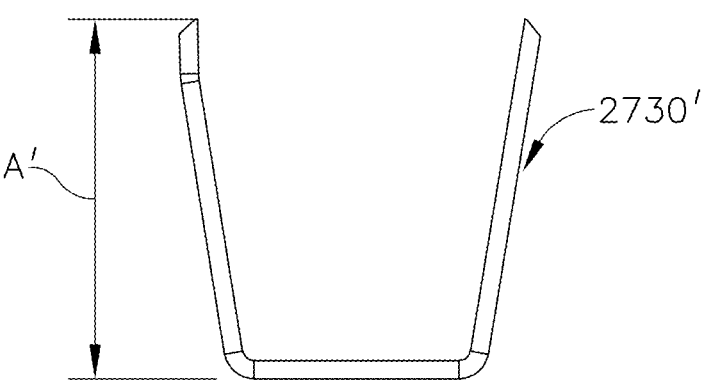
Figure 51:
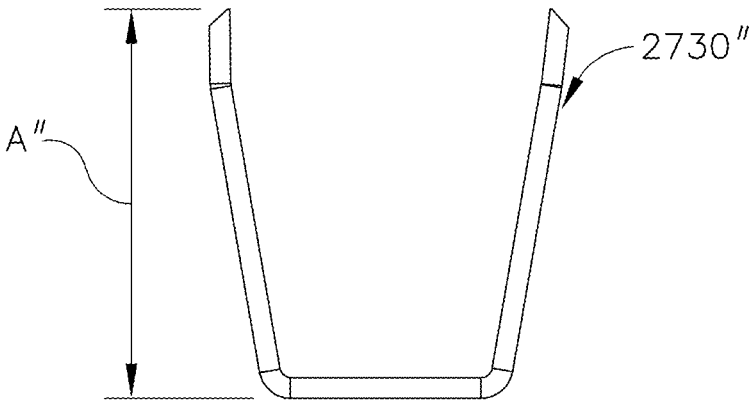
Figure 52:
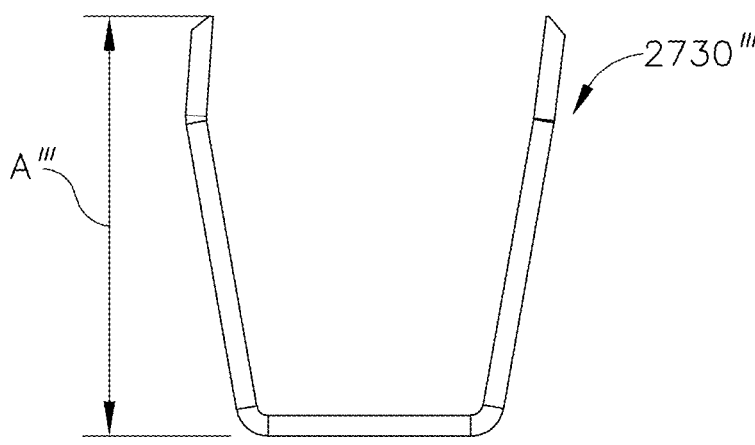
Figure 53:
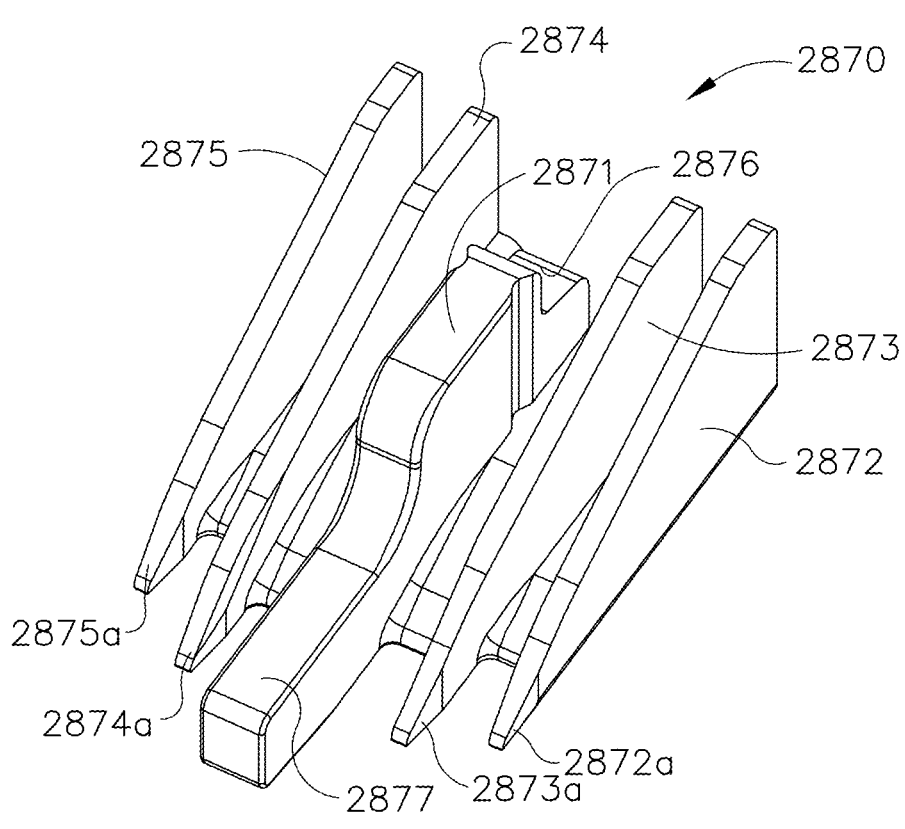
Figure 54:
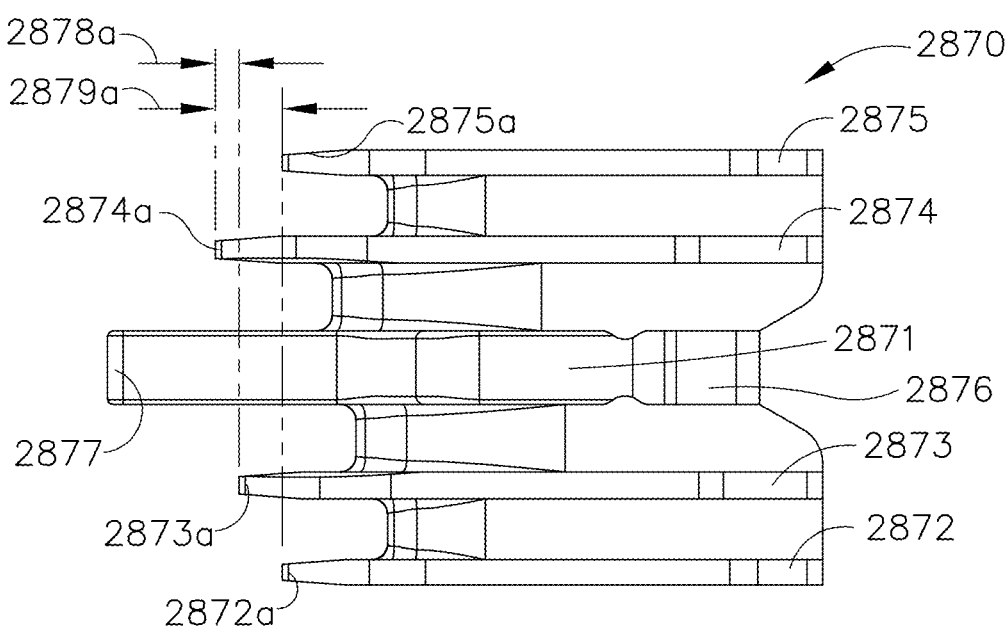
Figure 54A:
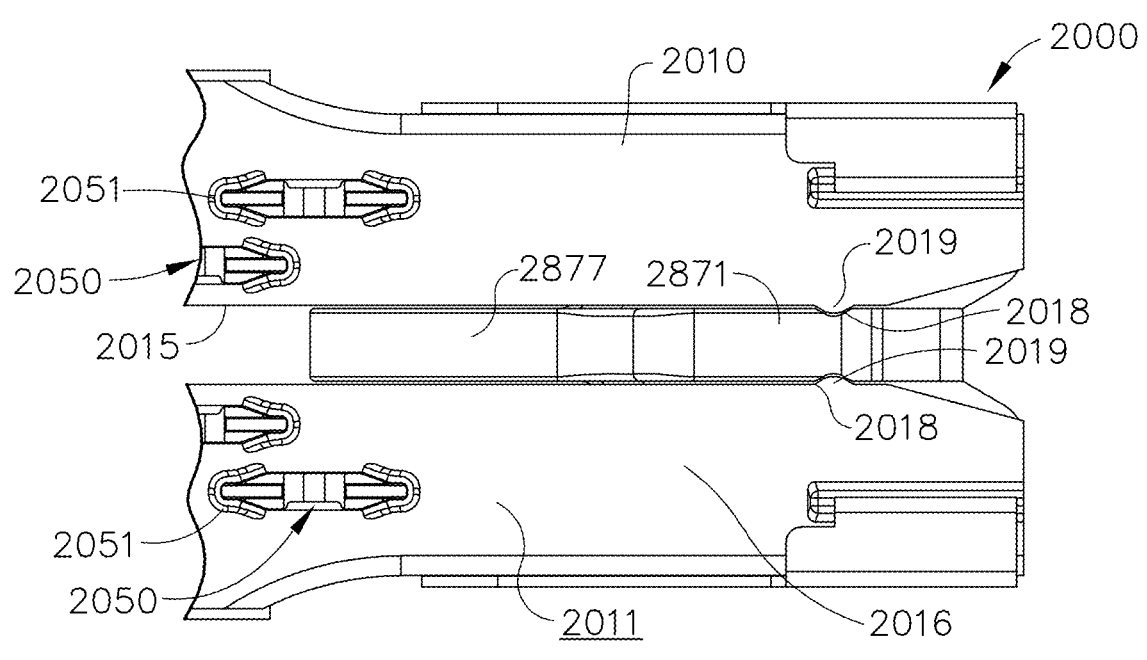
Figure 54B:
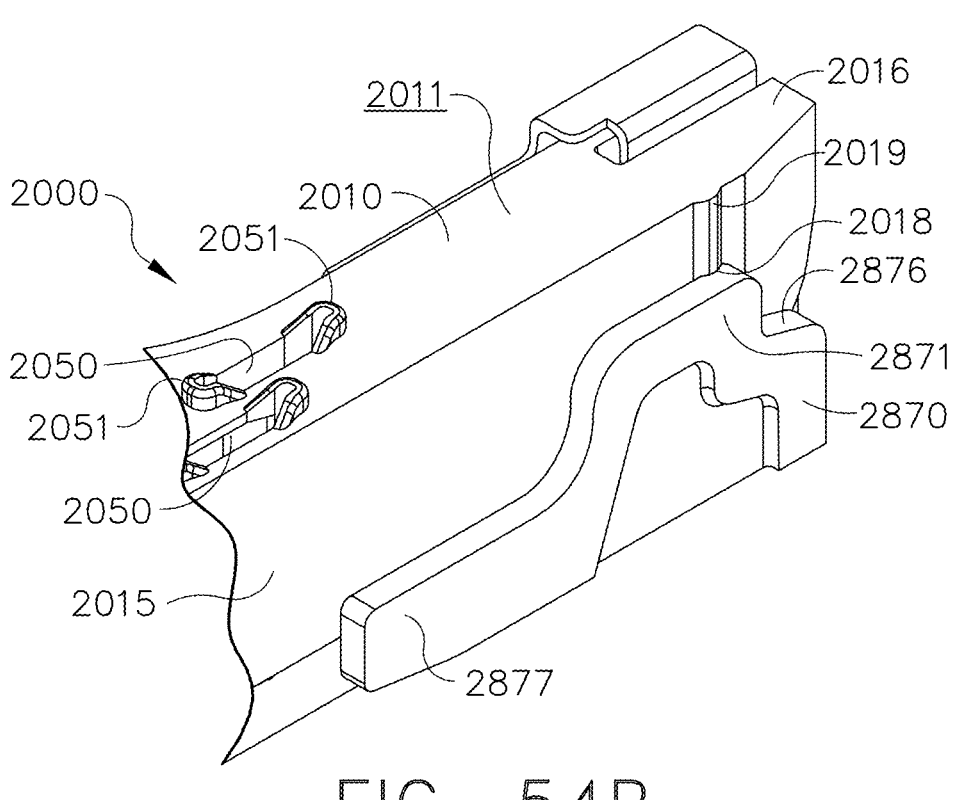
Figure 54C:
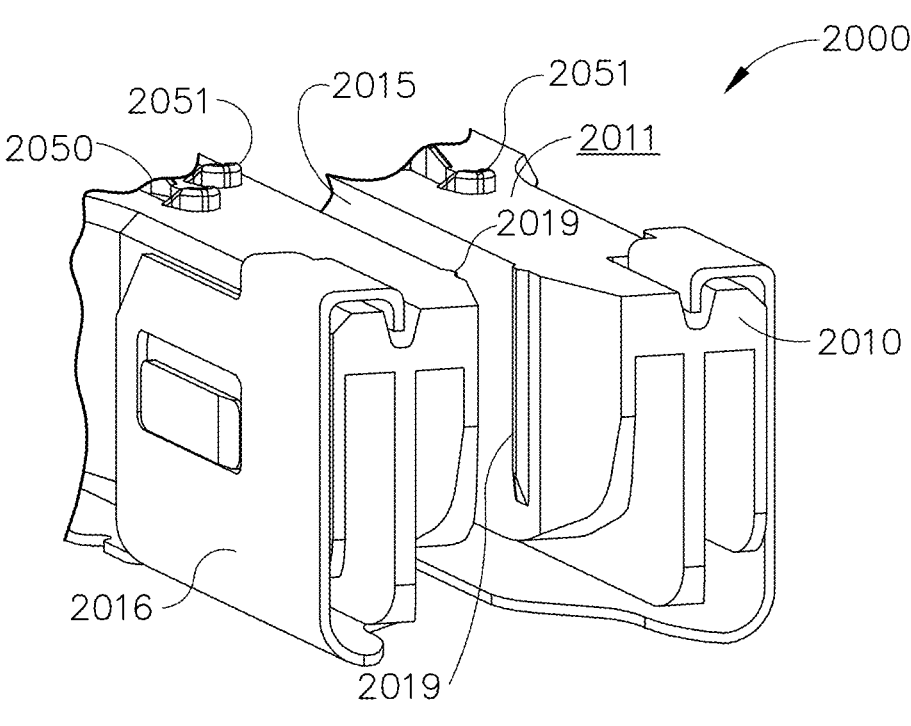
Figure 54D:
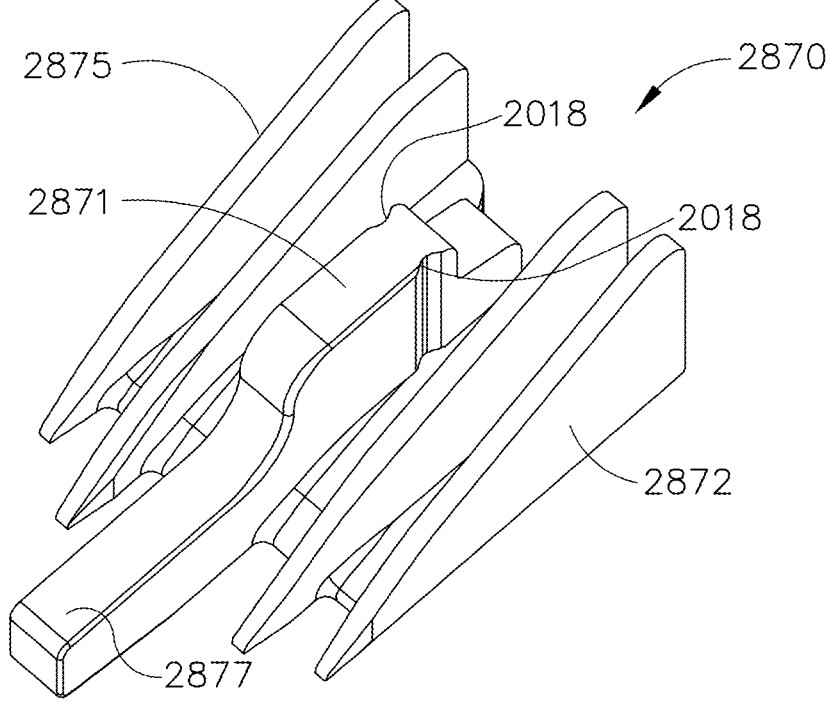
Figure 55:
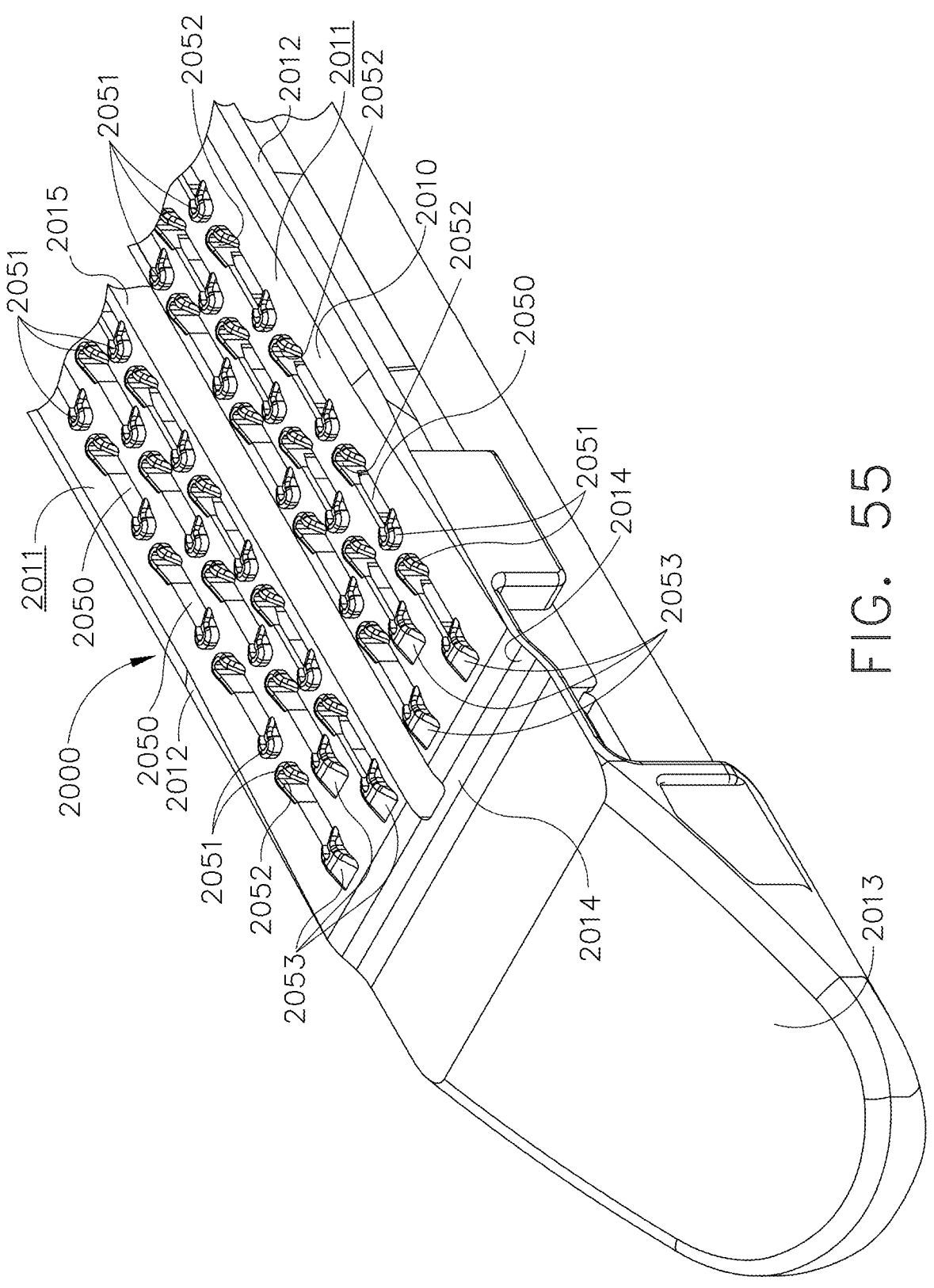
Figure 55A:
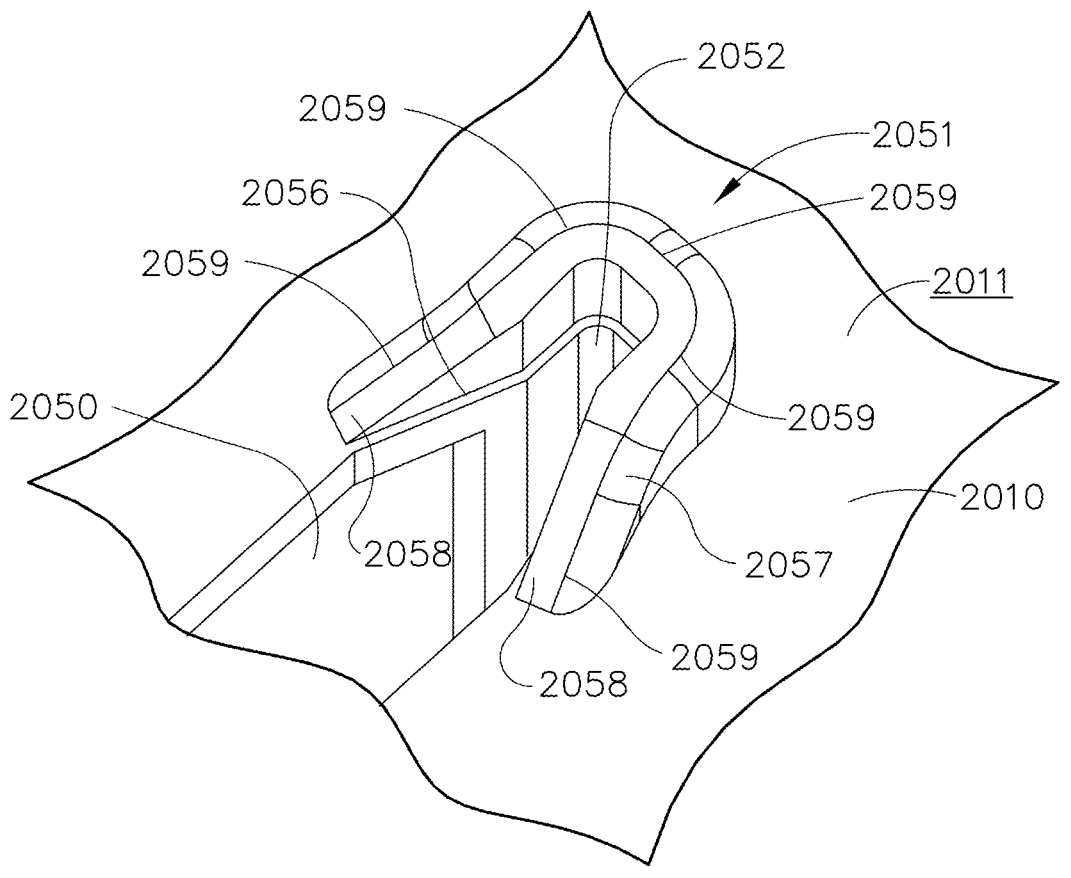
Figure 56:
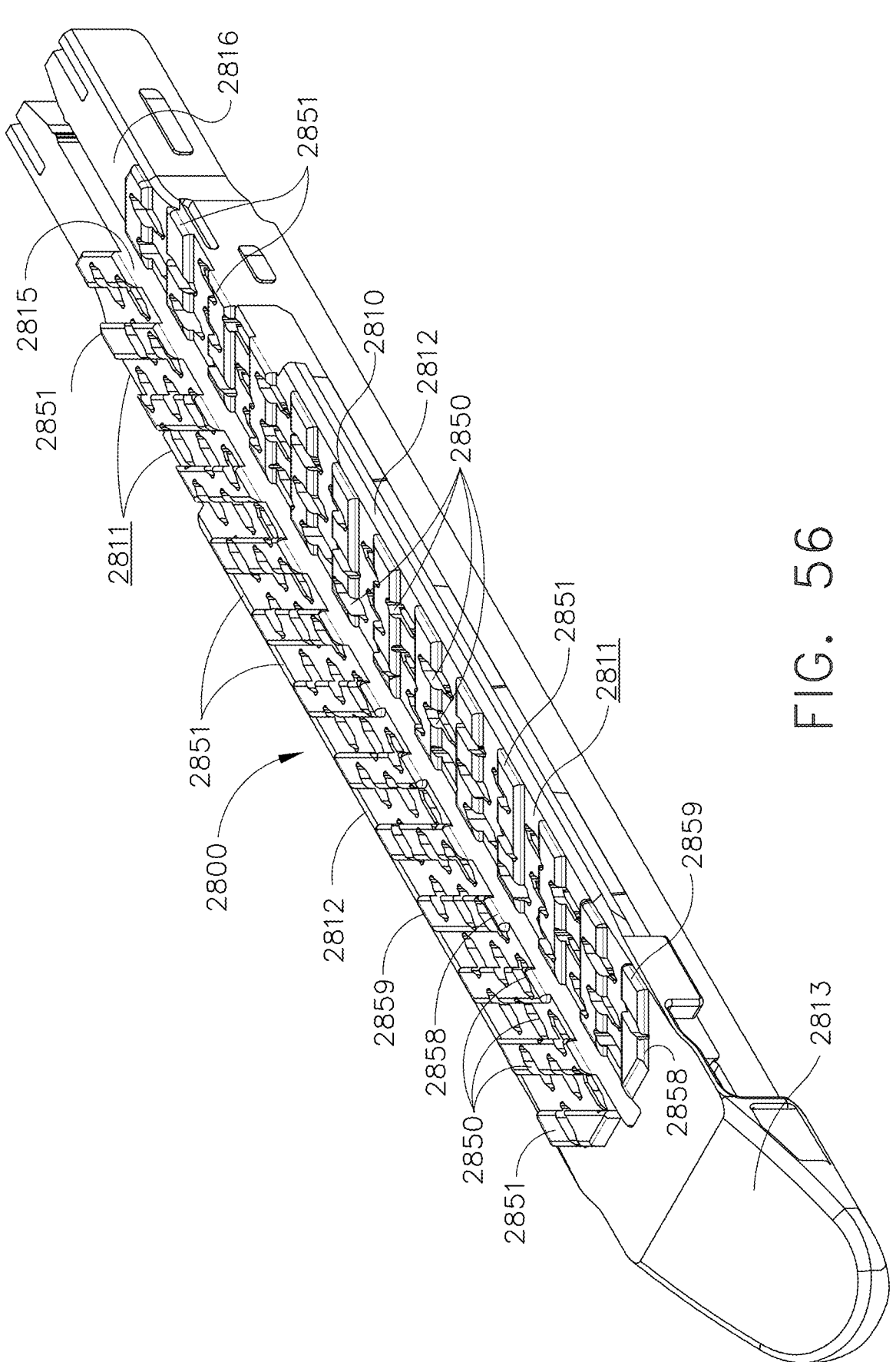
Figure 57:
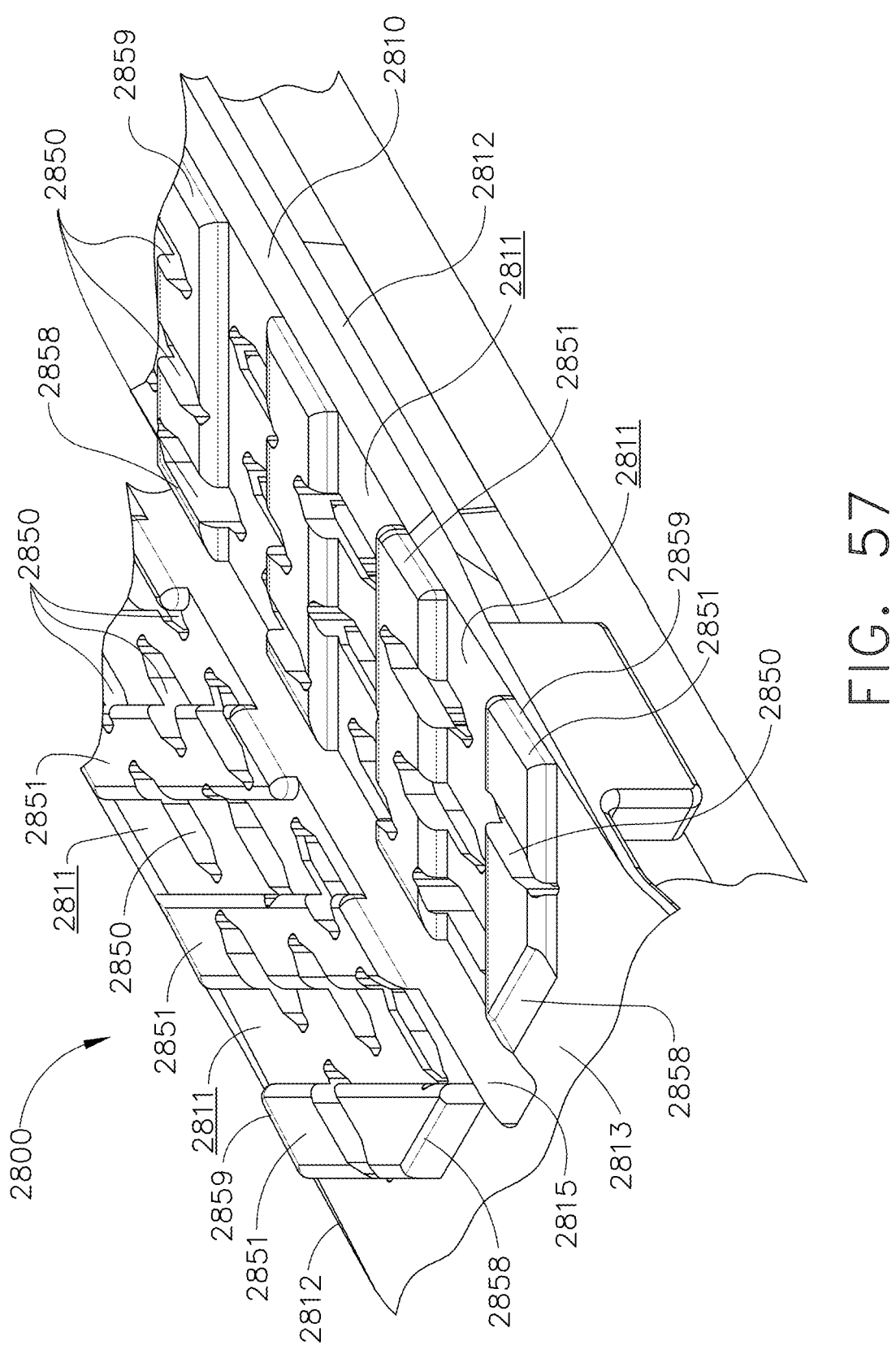
Figure 58:
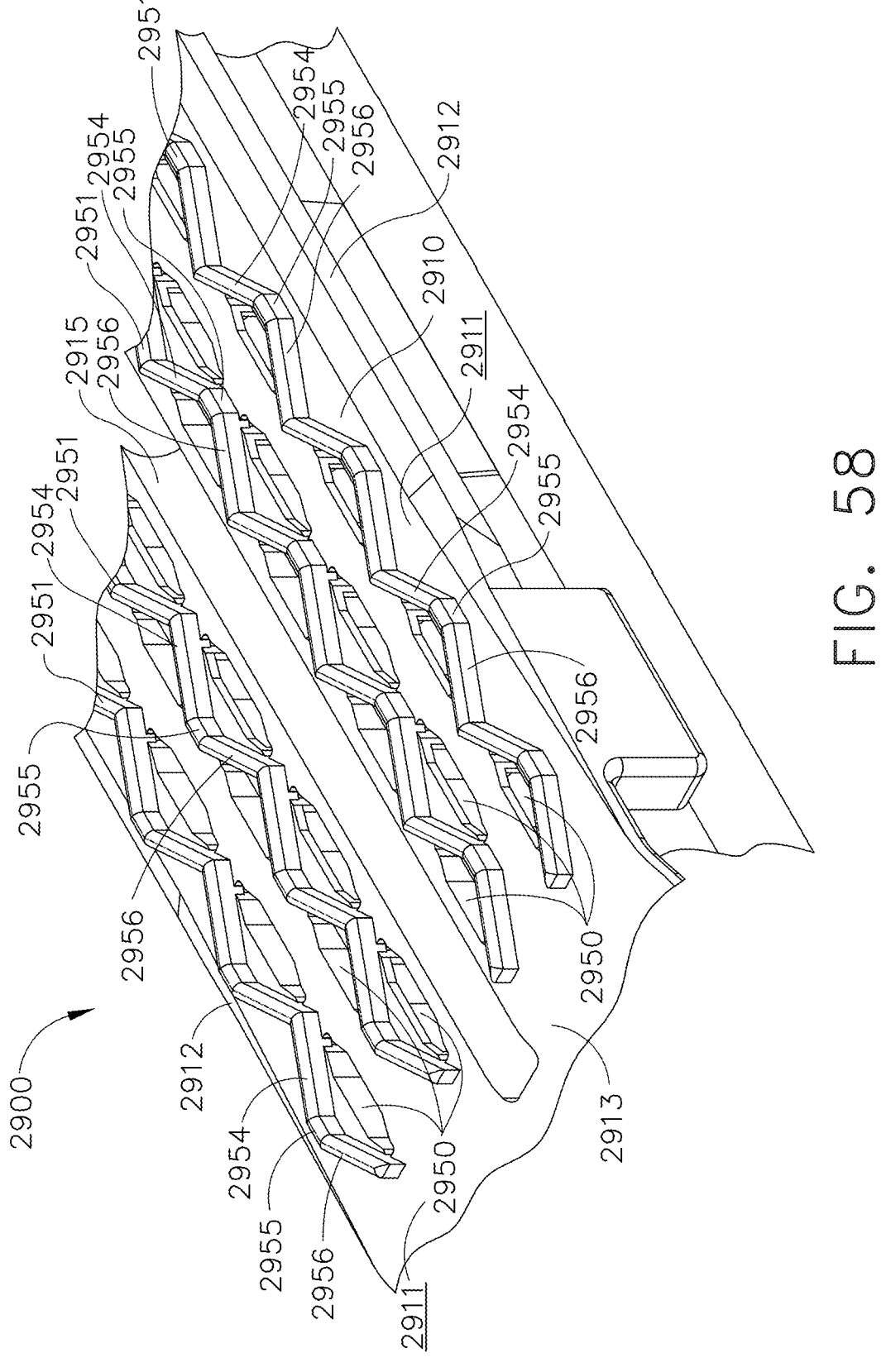
Figures 59, 60:
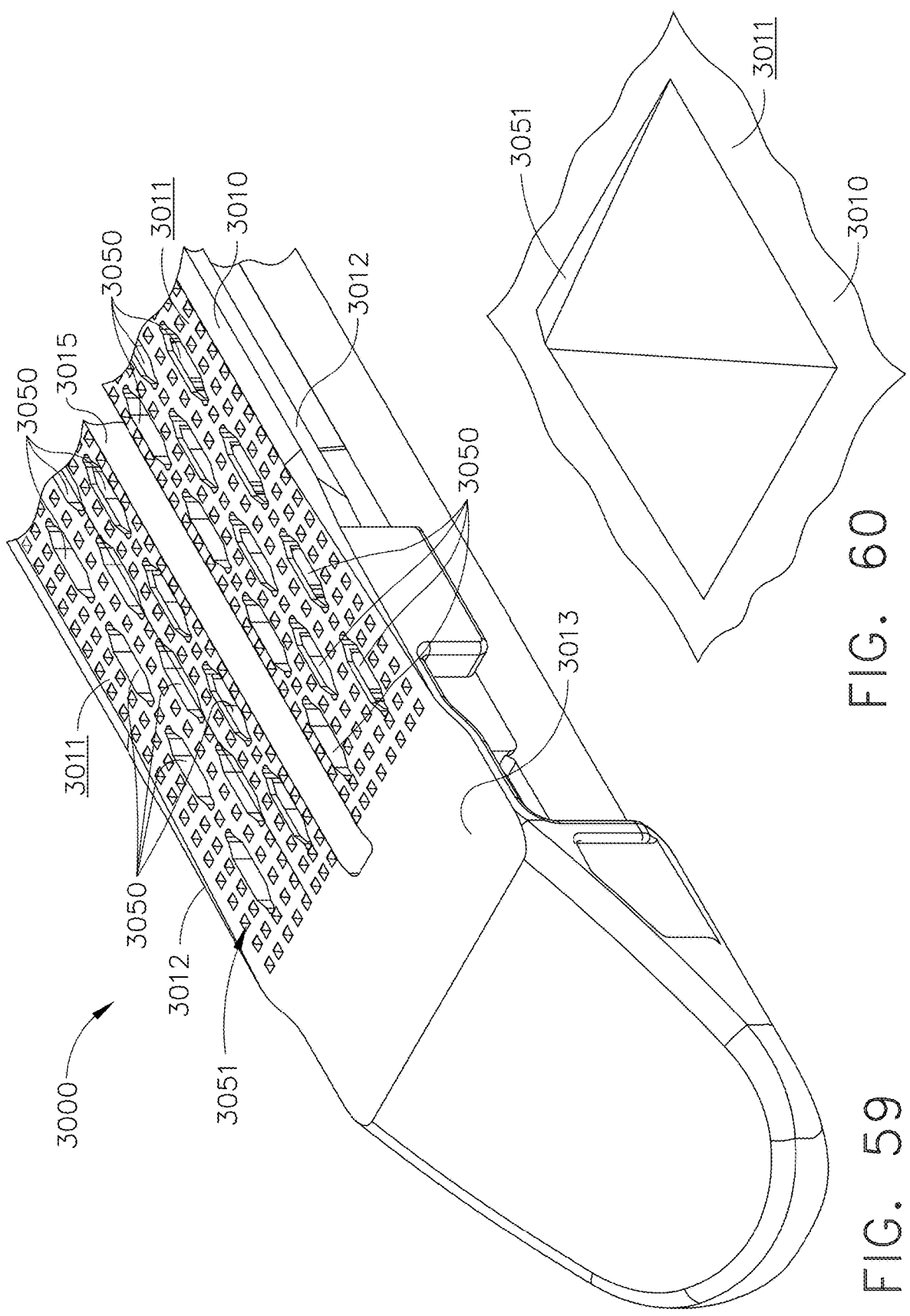
Figures 61, 62:
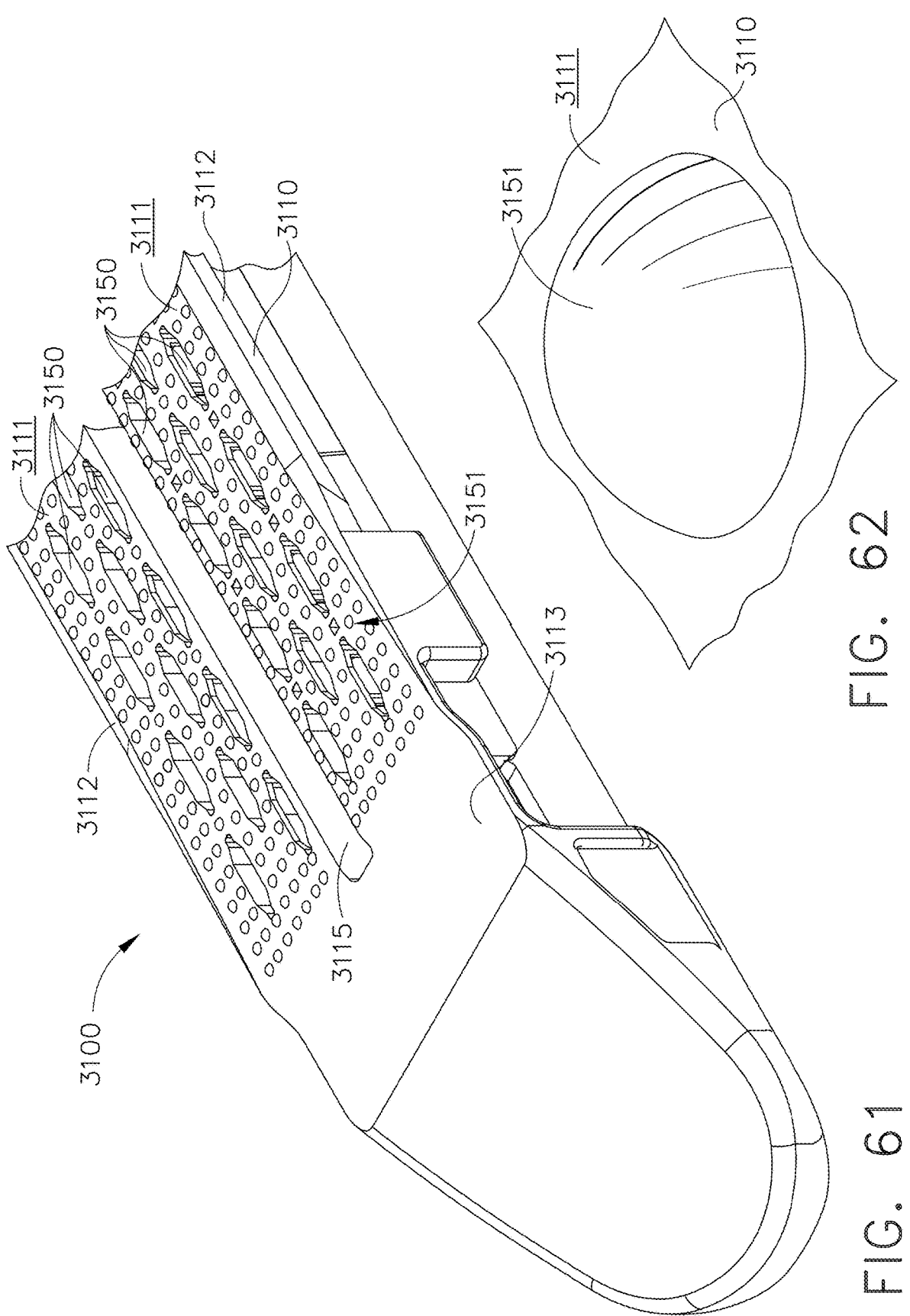
Figure 63:
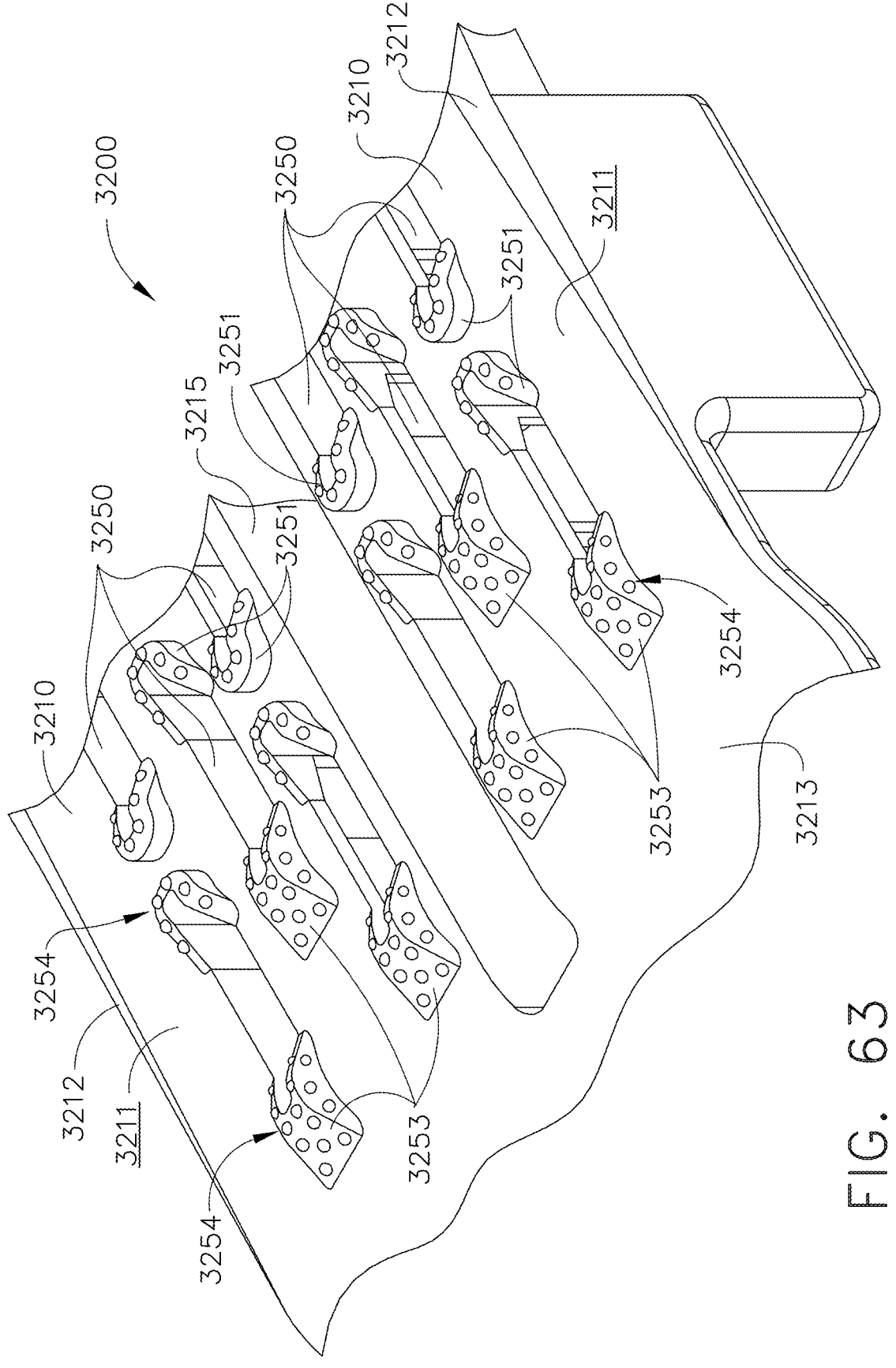
Figures 64, 65:
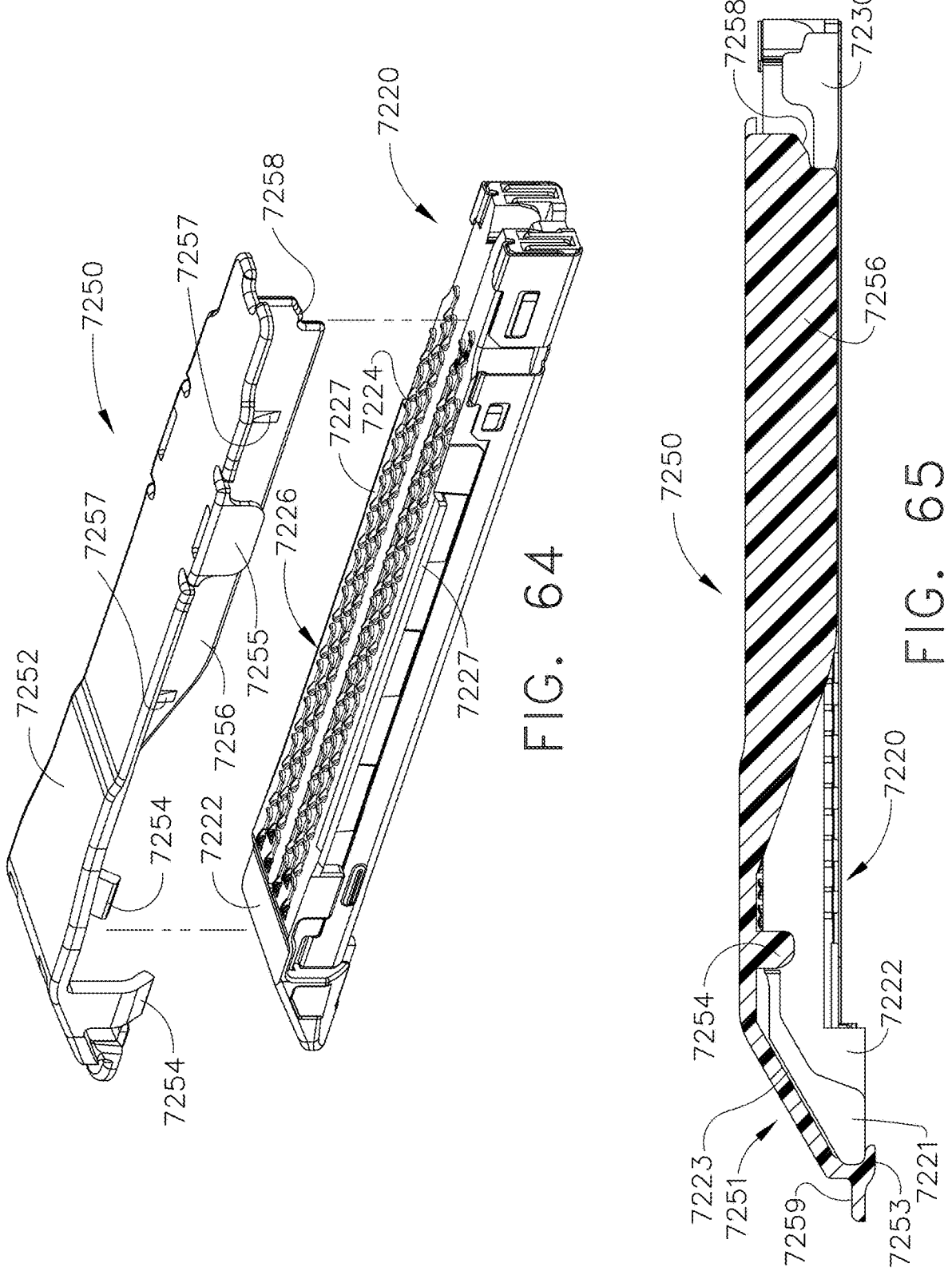
Figure 66:
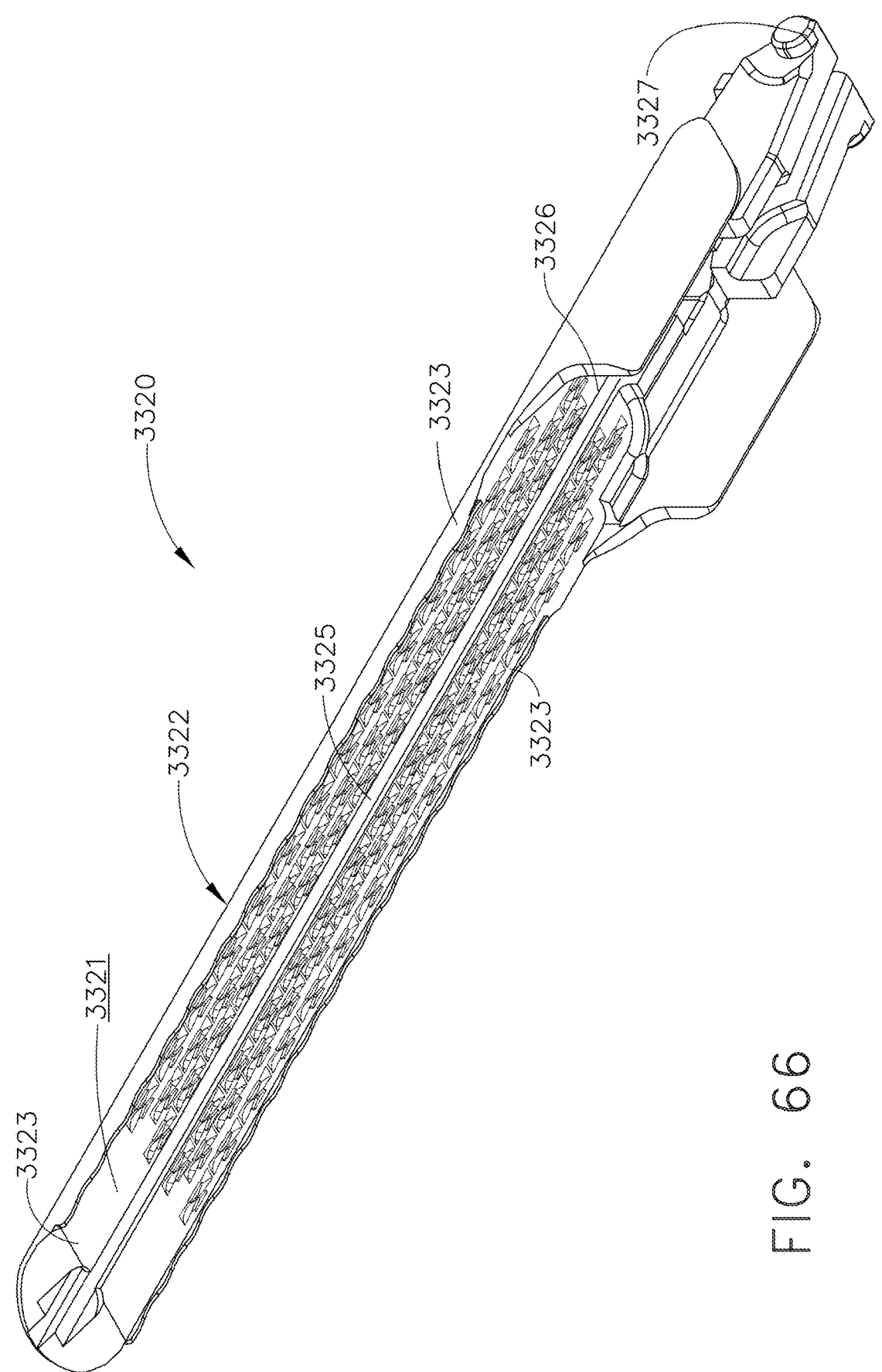
Figure 67:
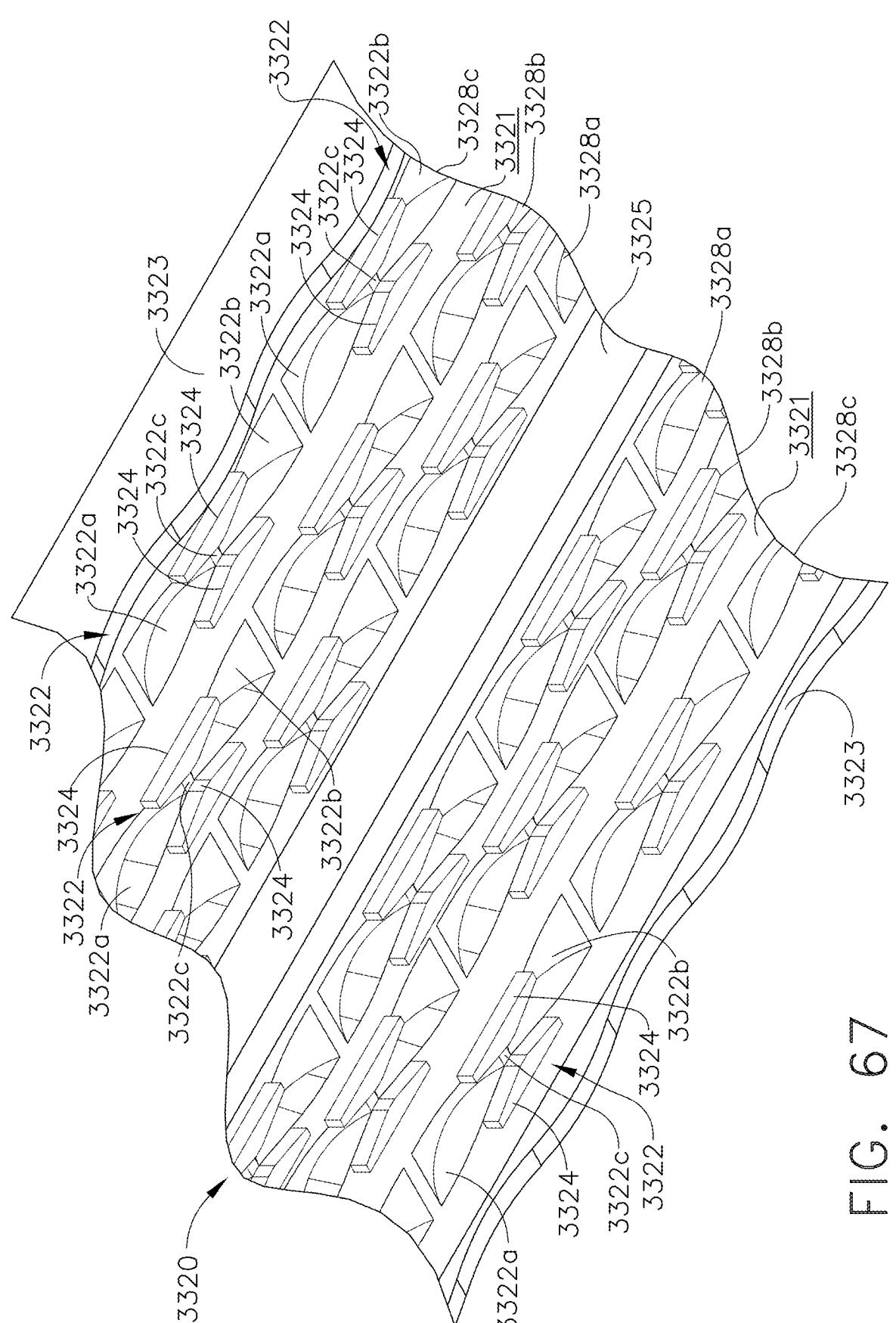
Figure 68:
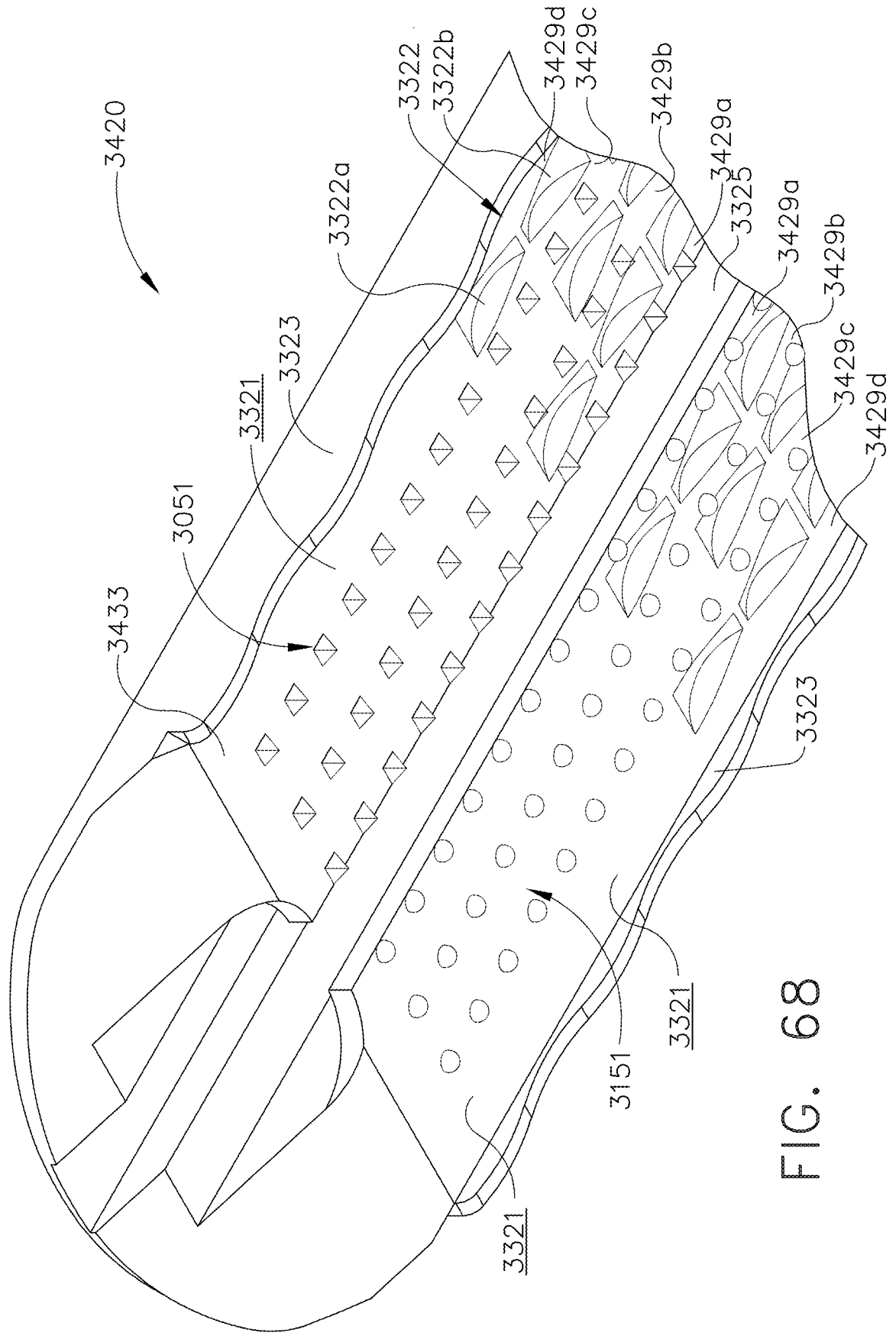
Figure 69:
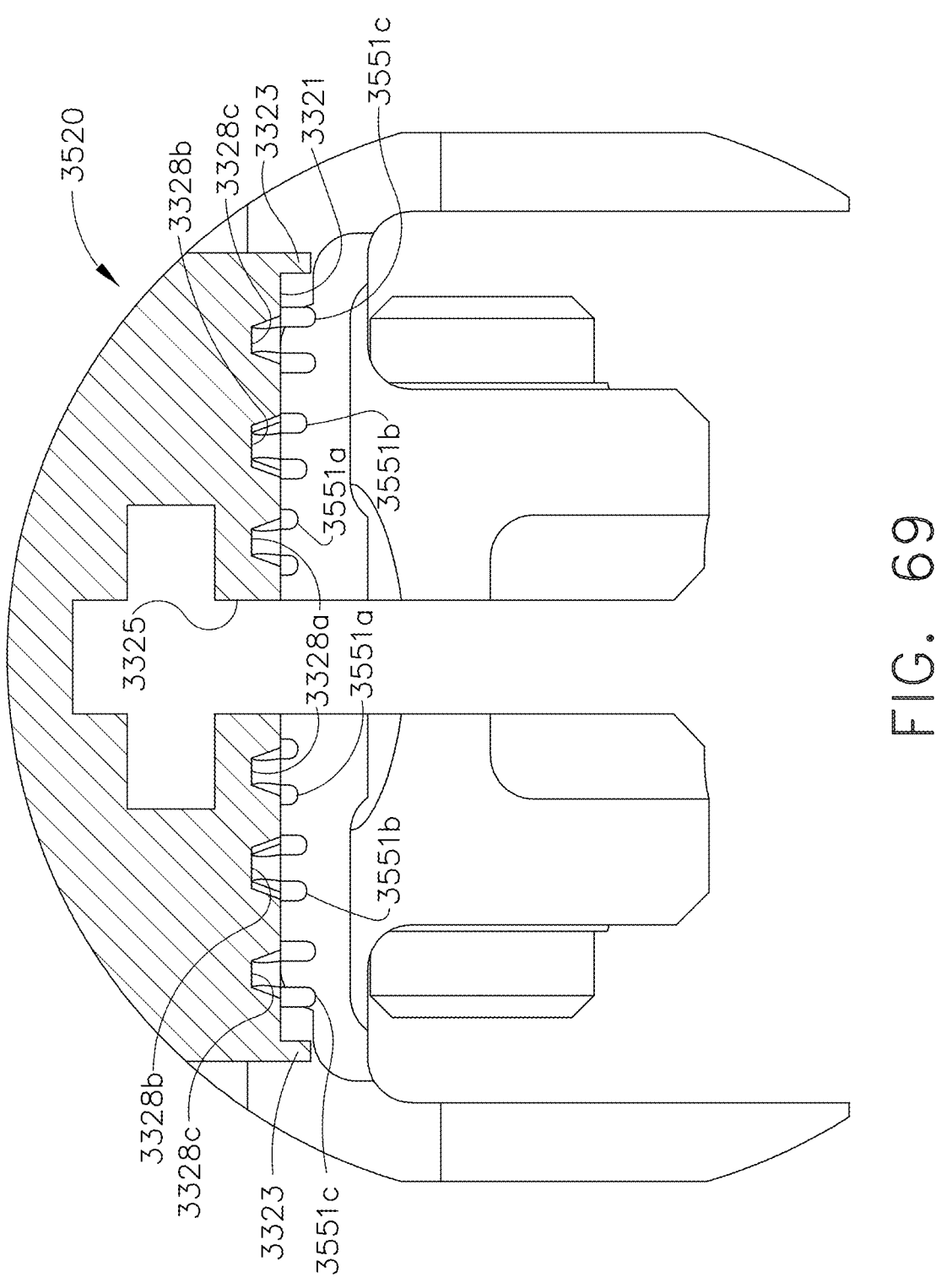
Figure 70:
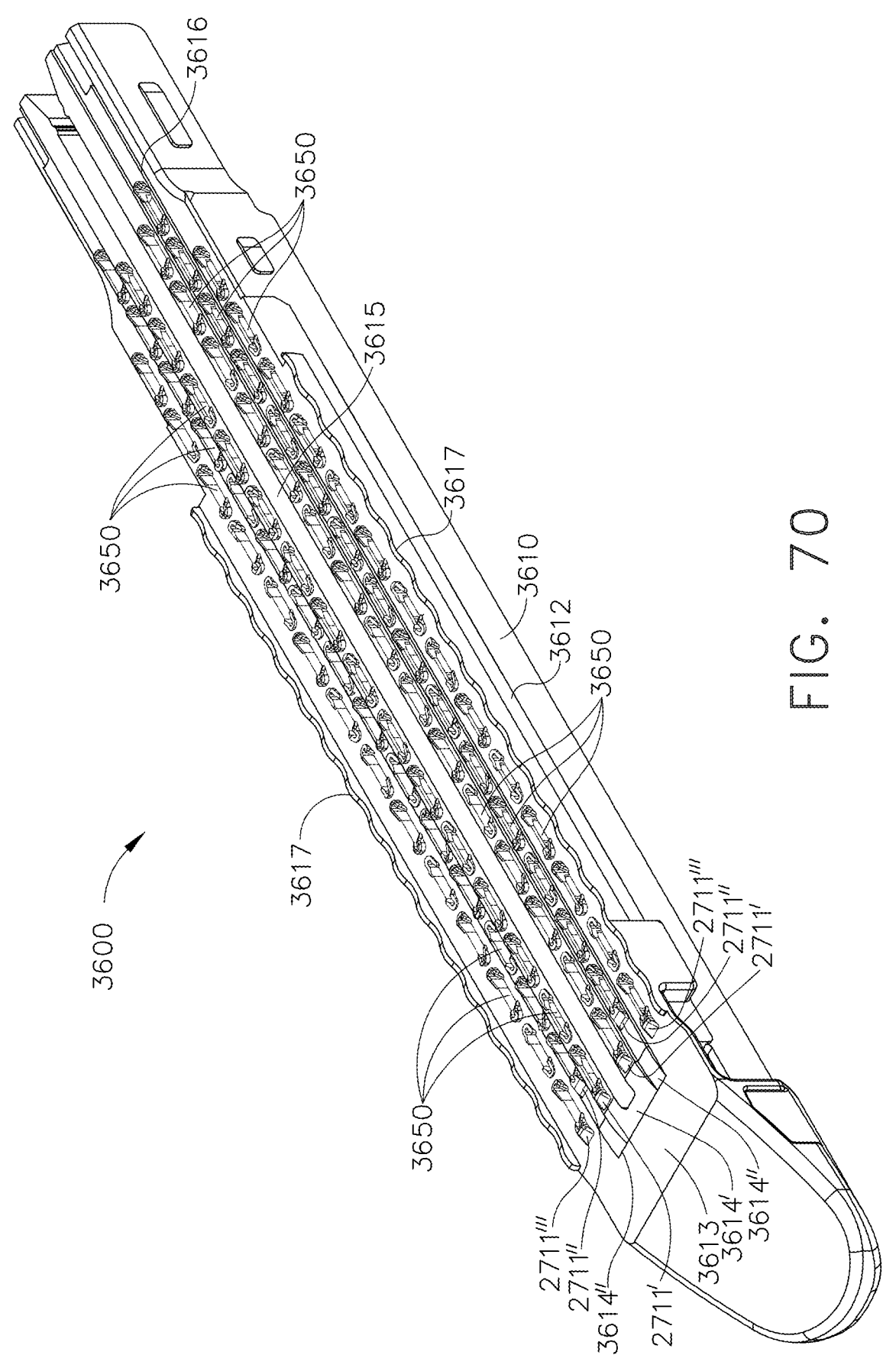
Figure 71:
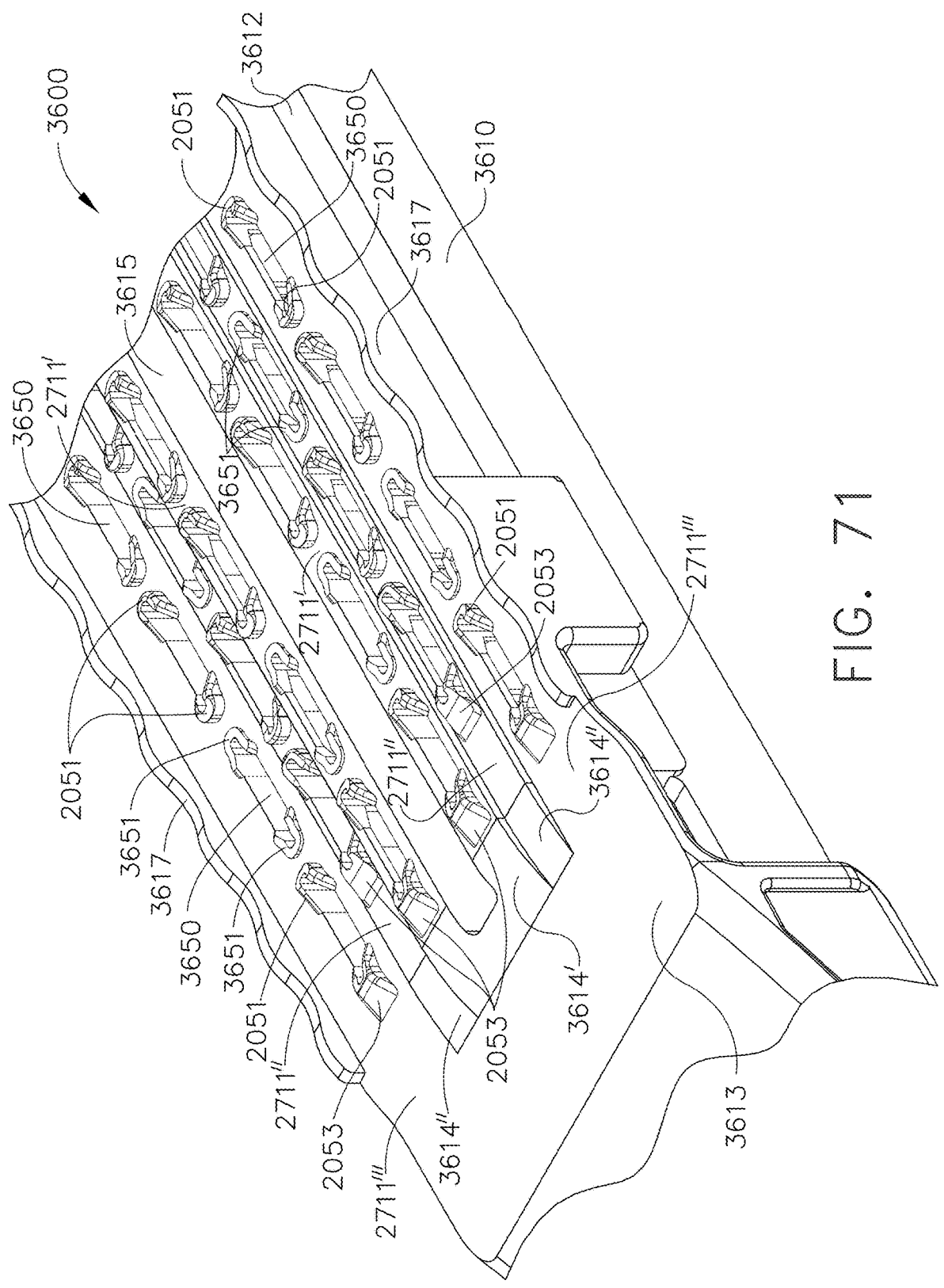
Figure 72:
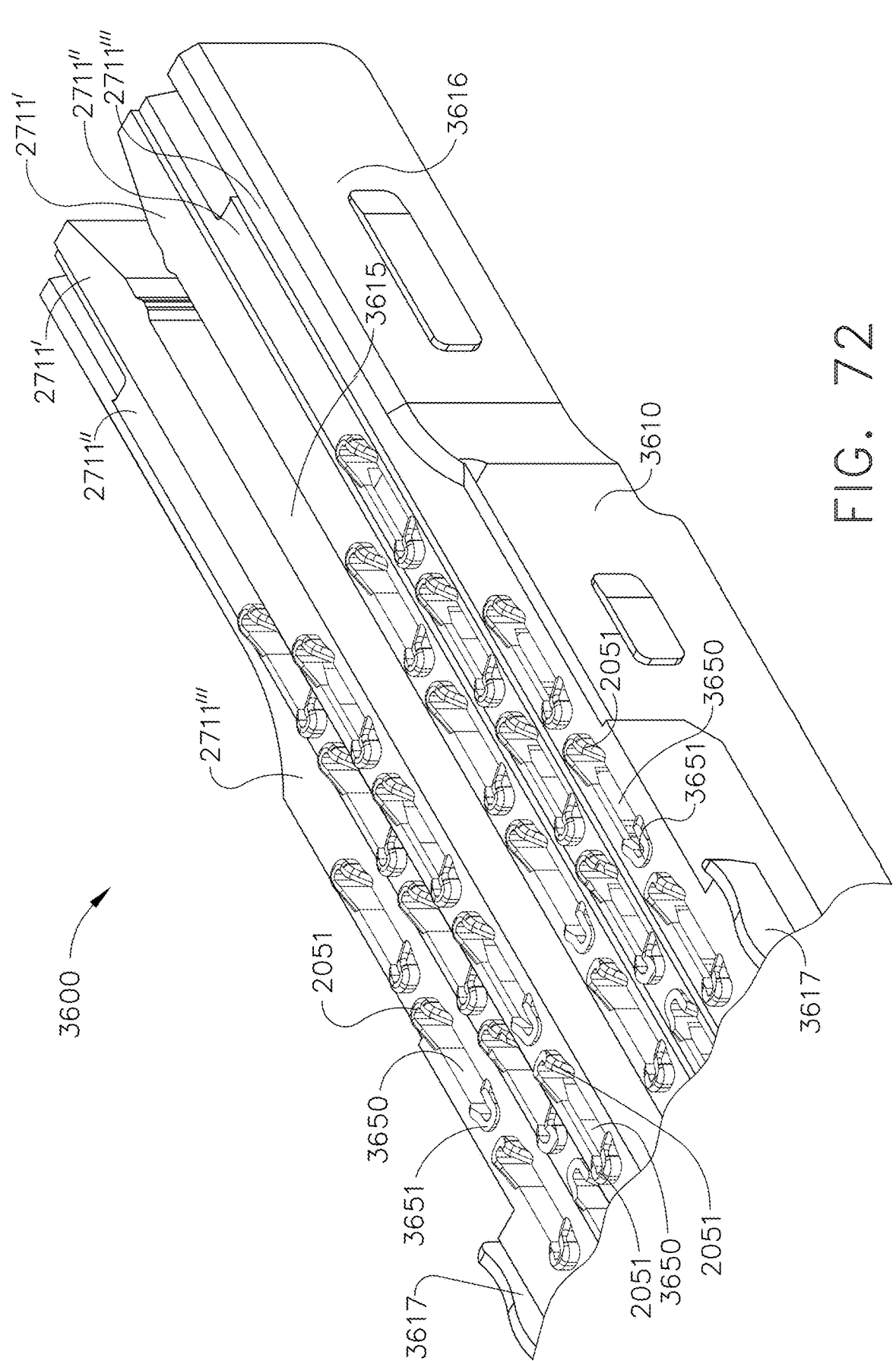
Figure 73:
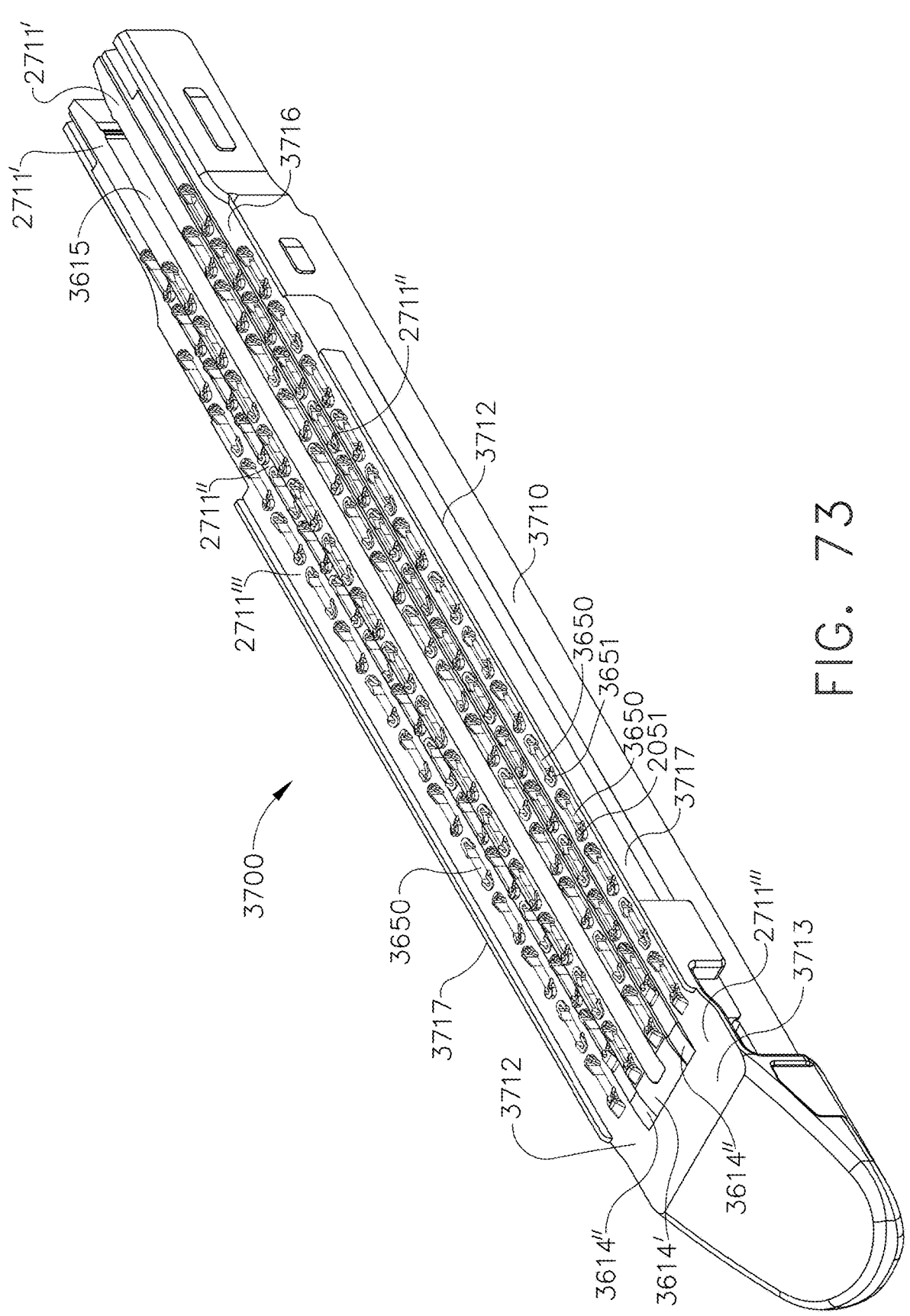
Figure 74:
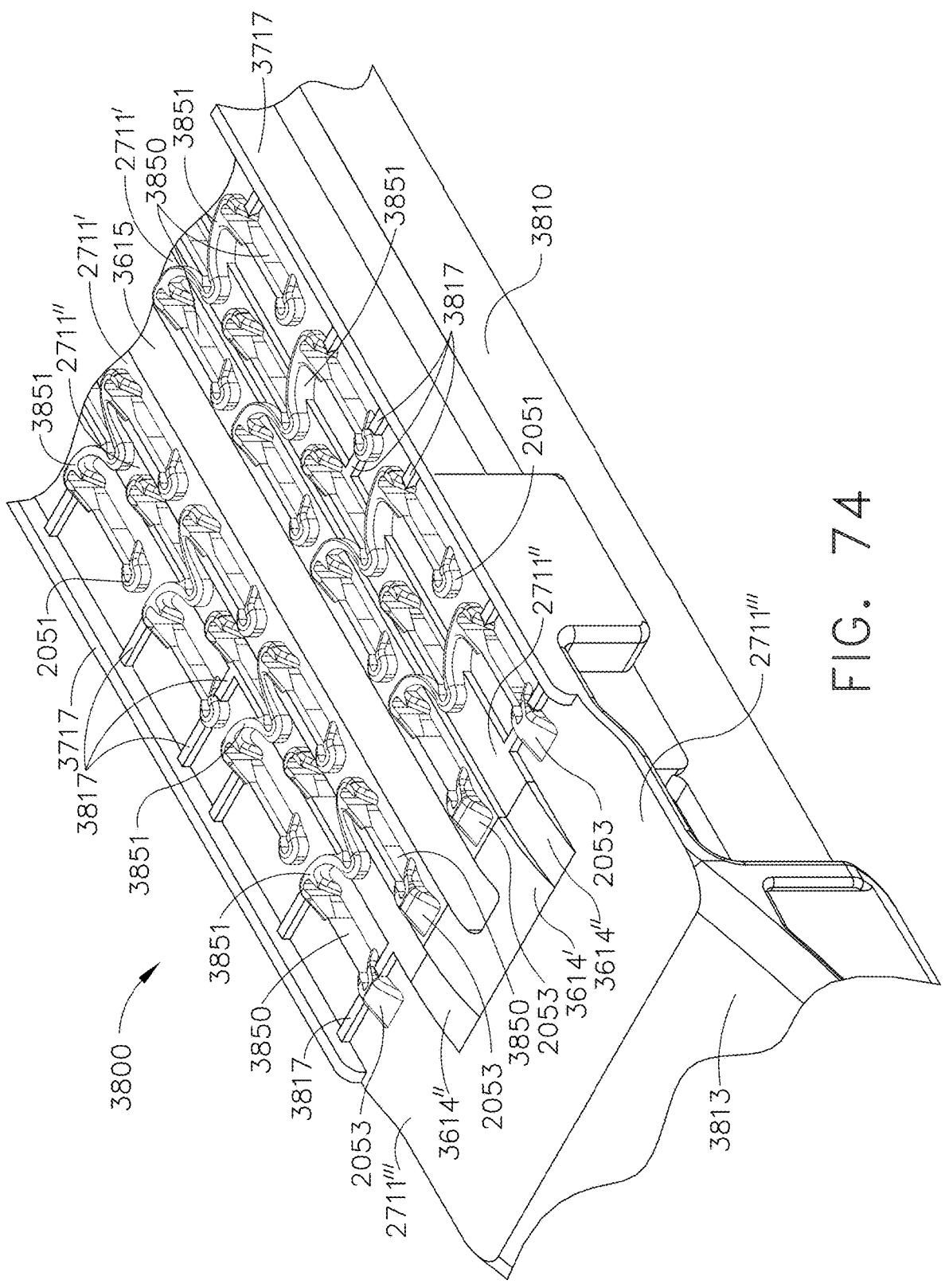
Figure 75:
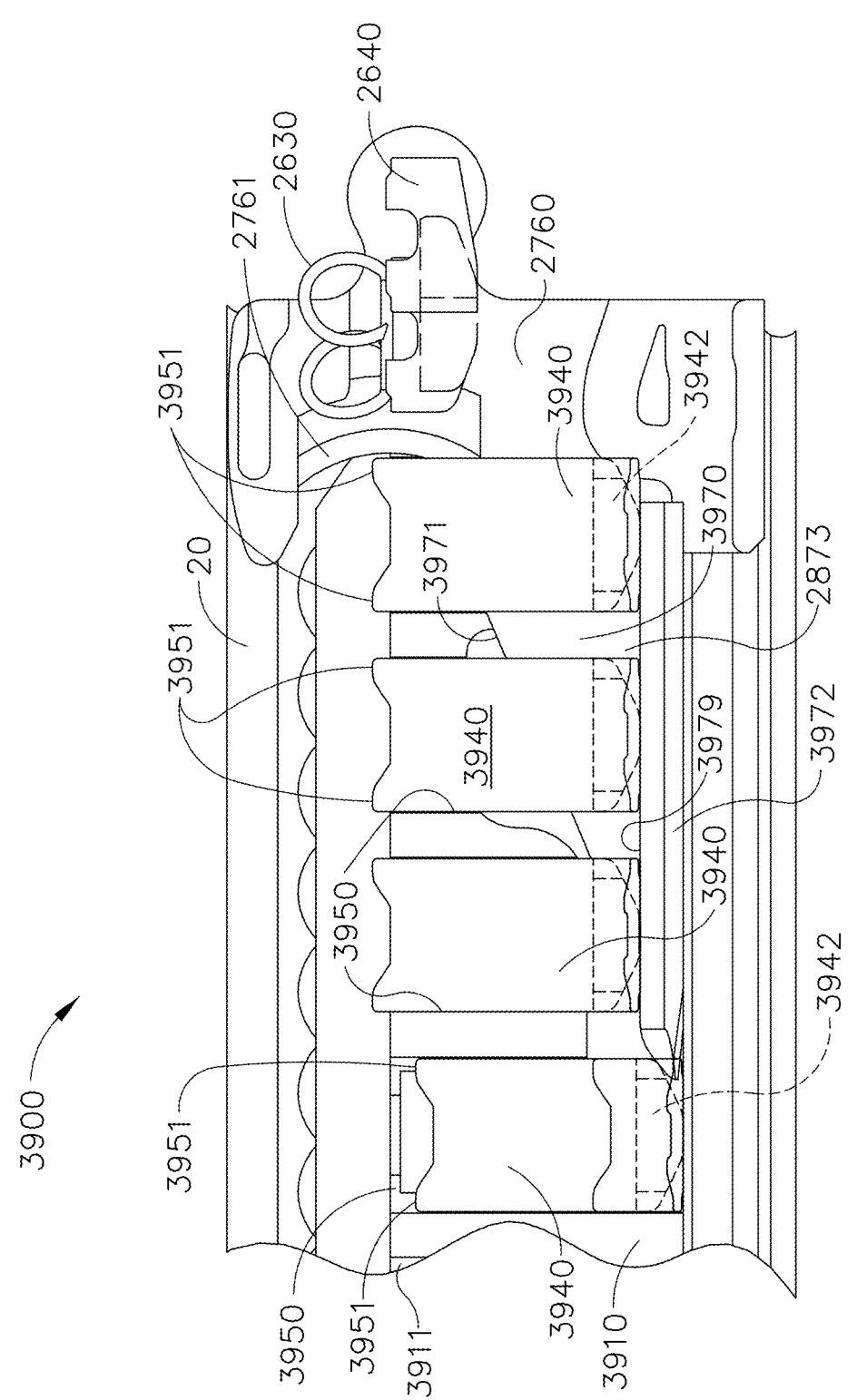
Figure 76:
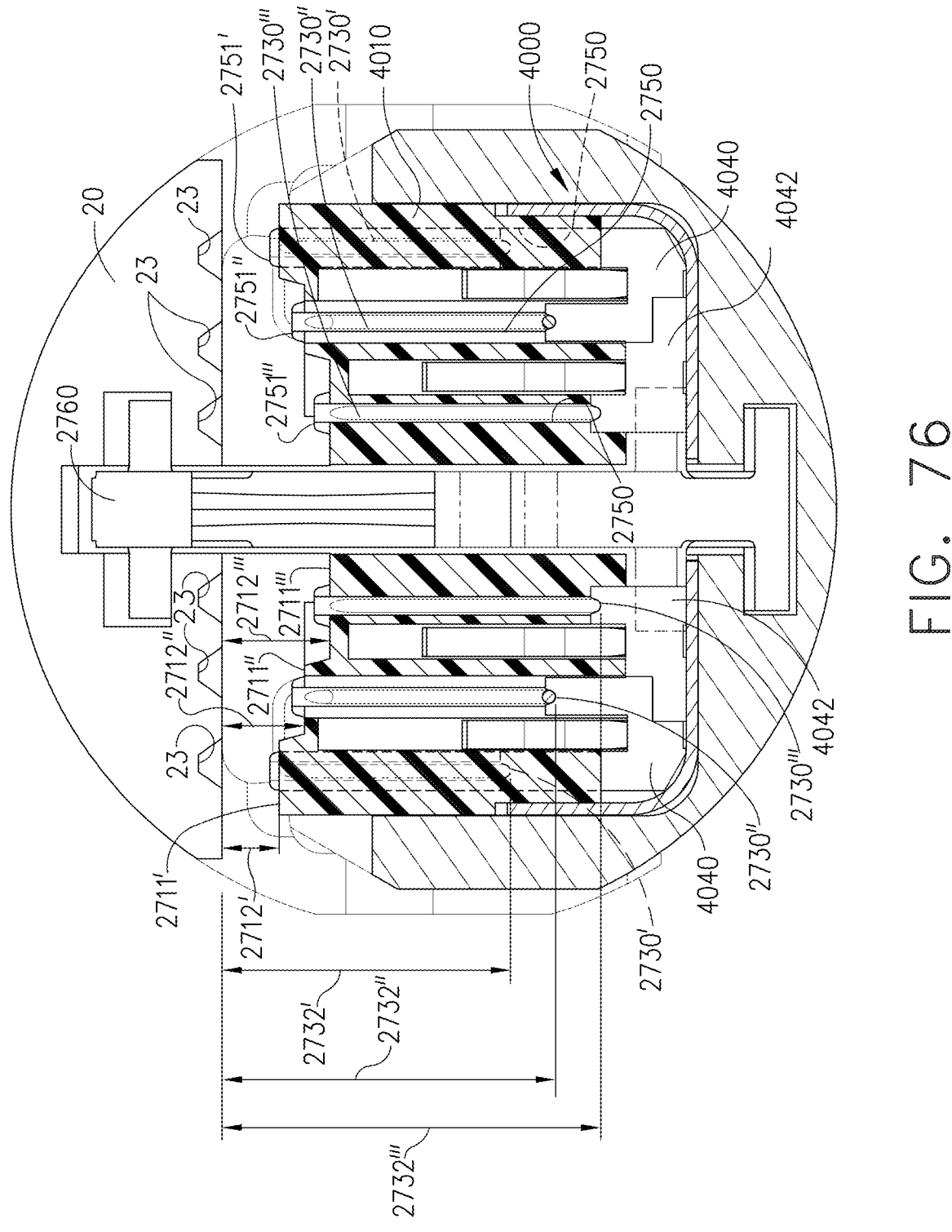
Figure 77:
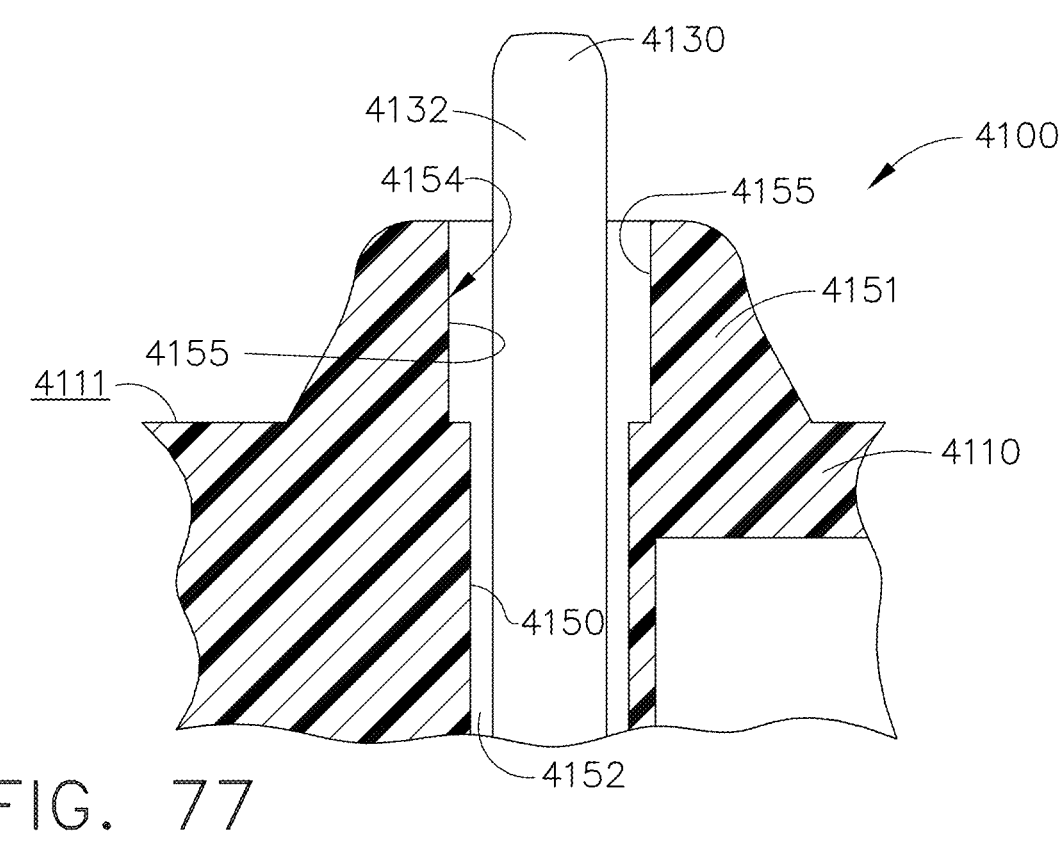
Figure 78:
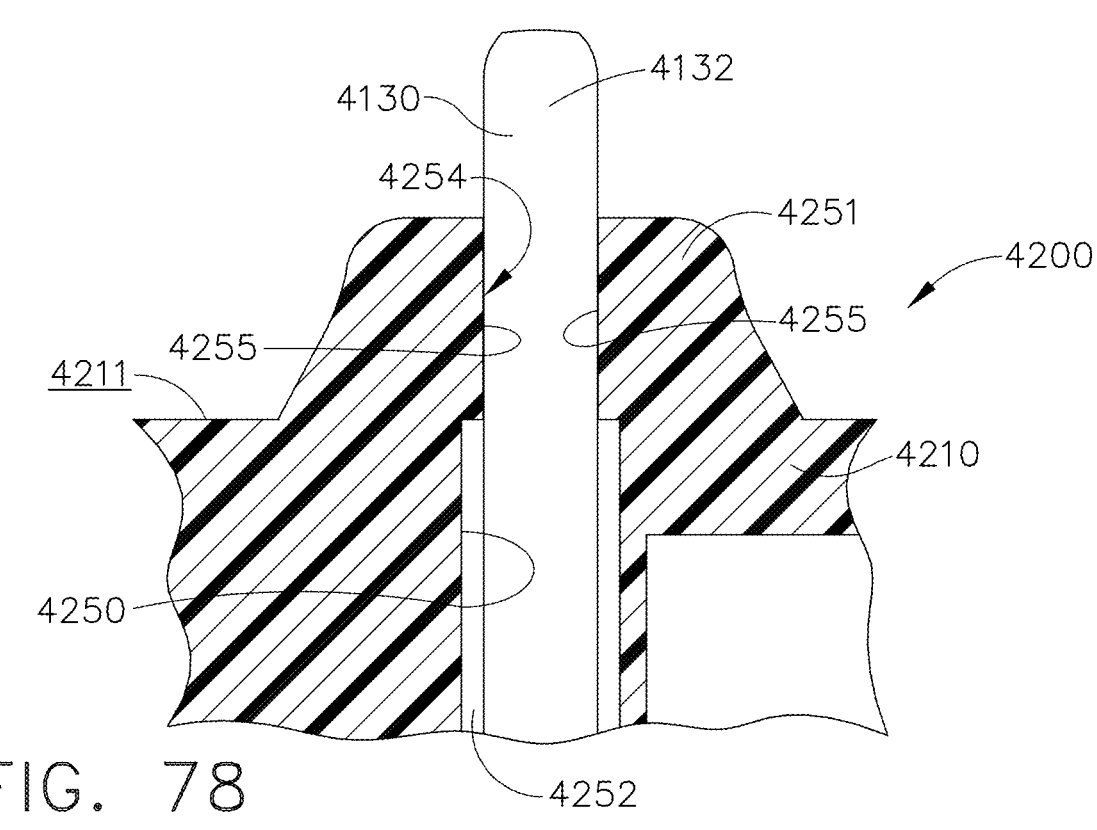
Figure 79:
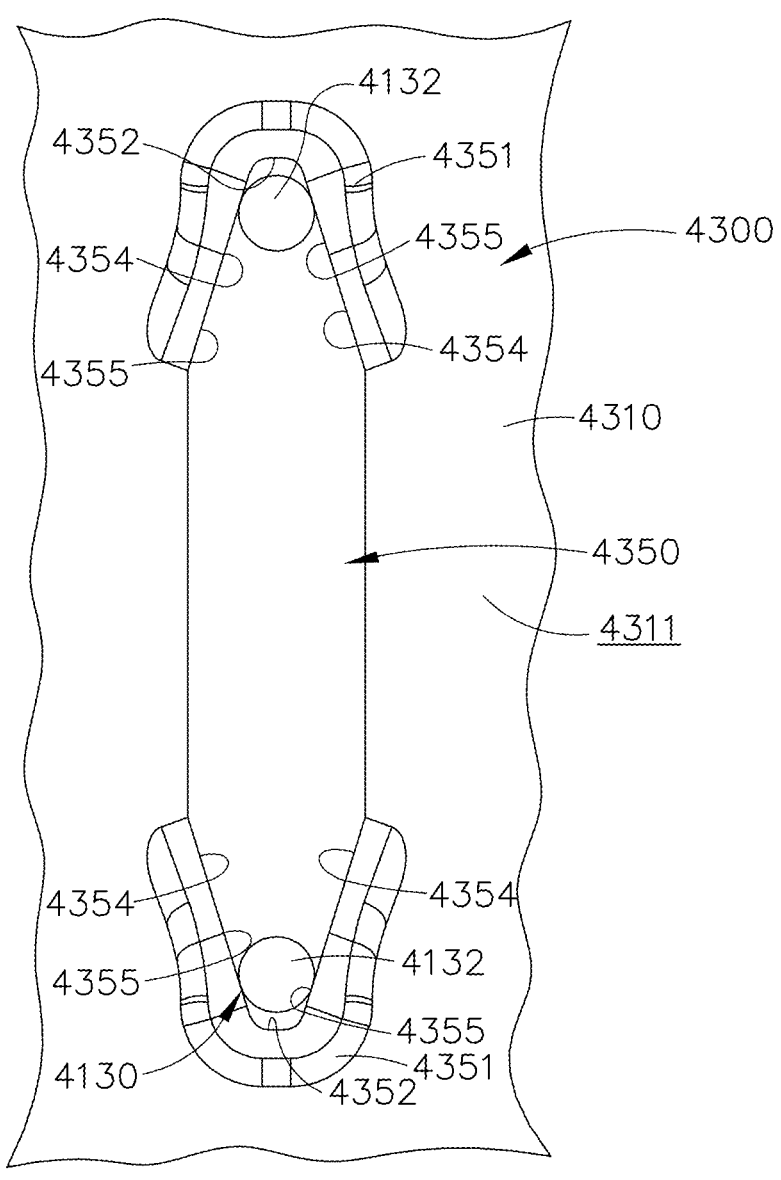
Figure 80:
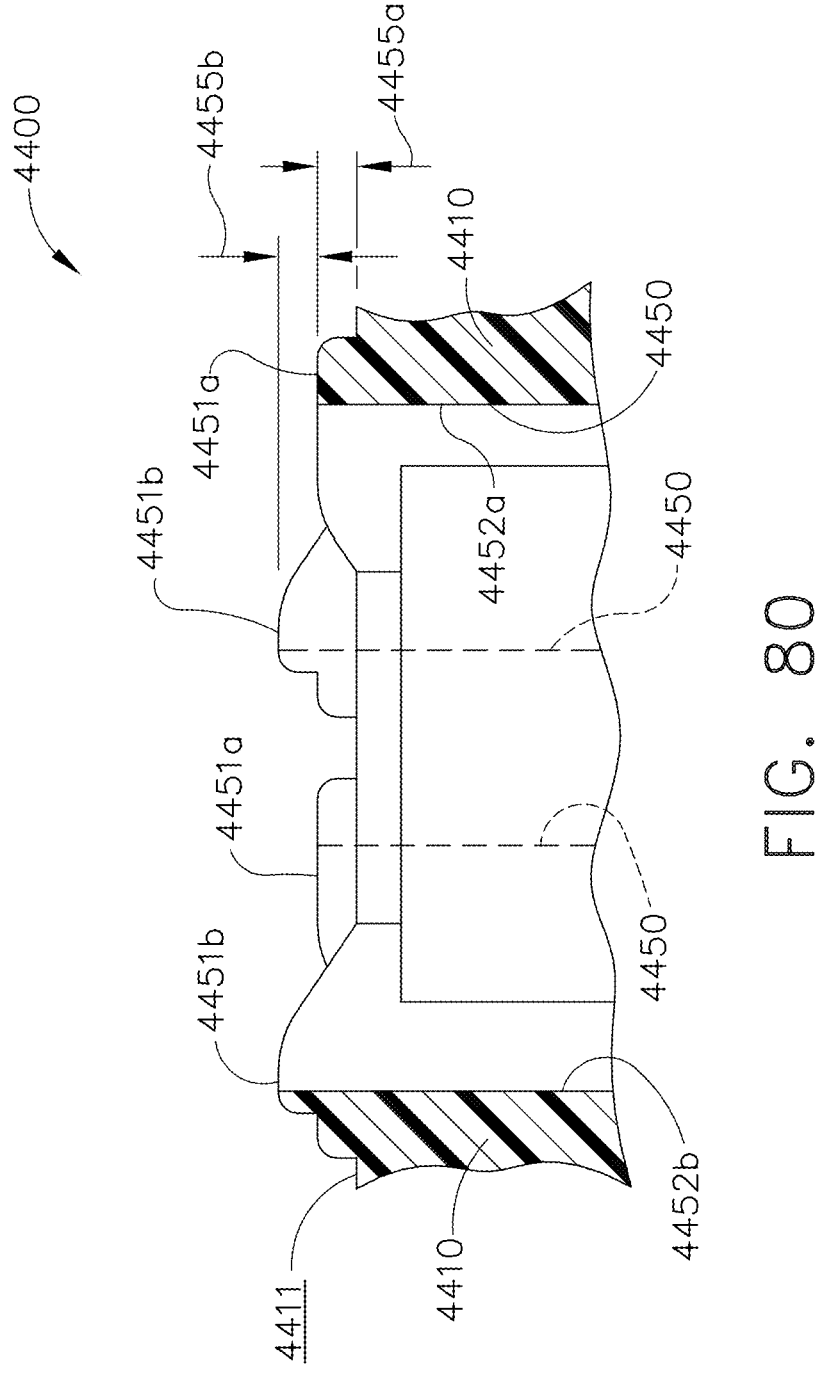
Figure 81:
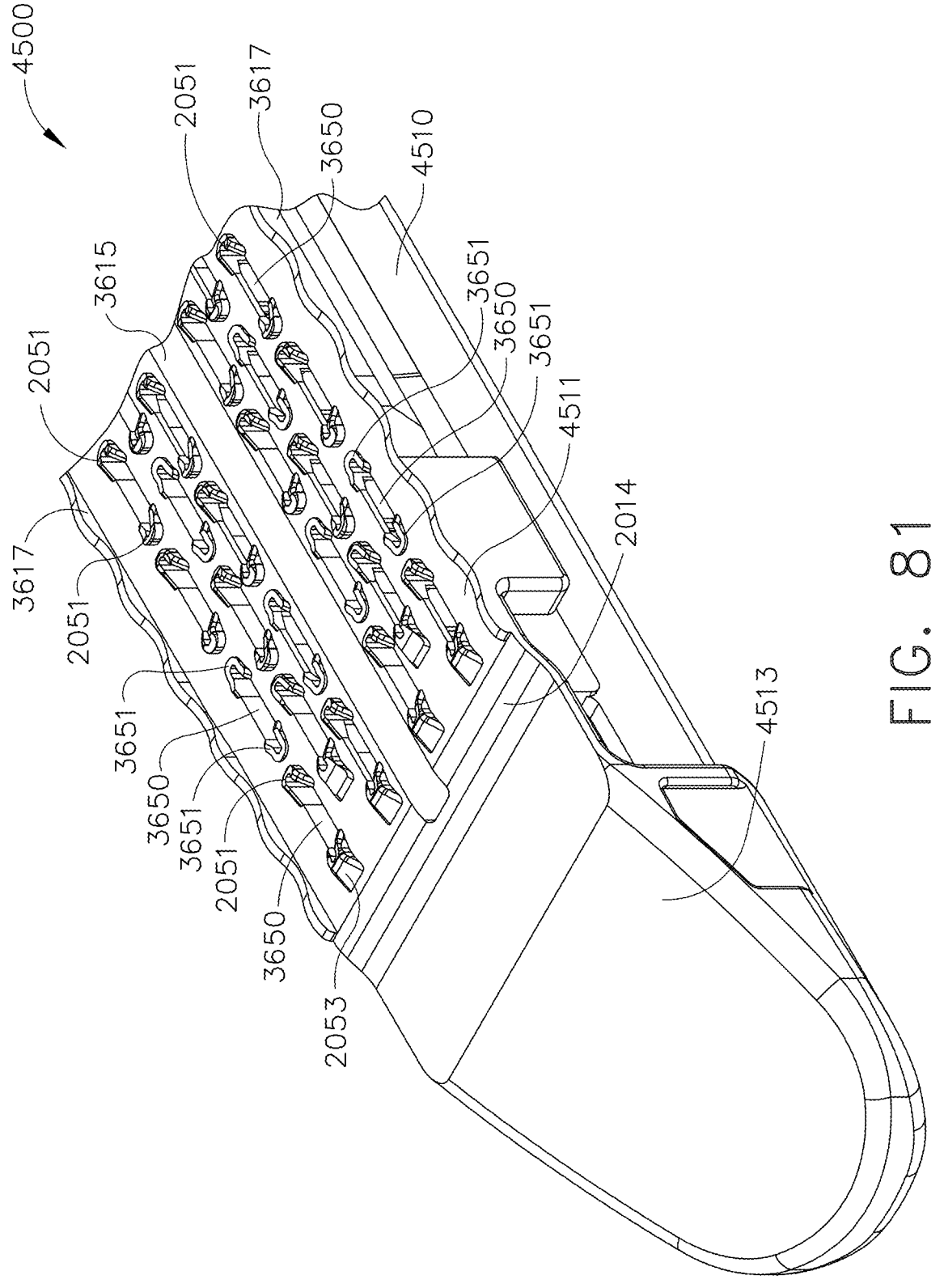
Figure 82:
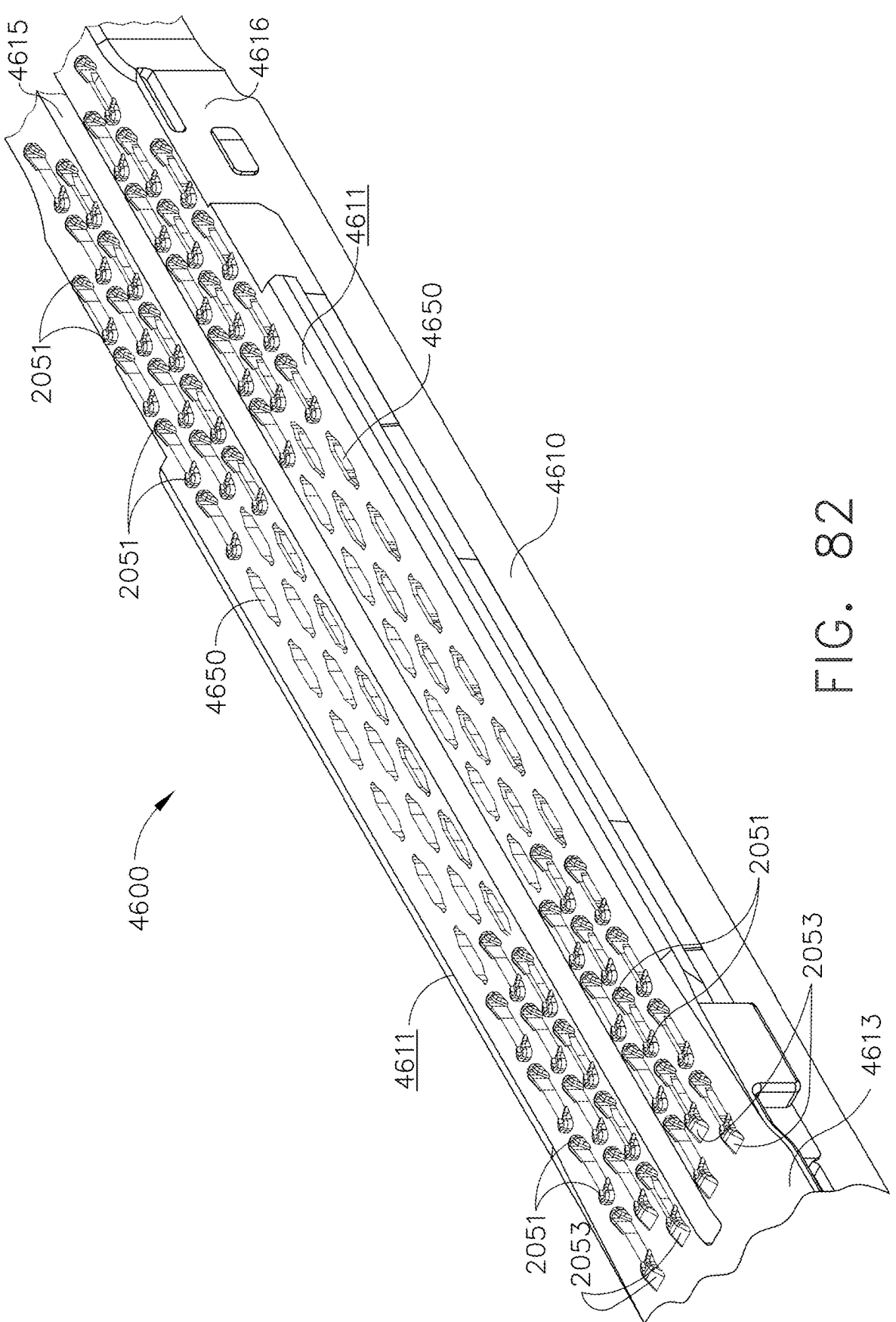
Figure 83:
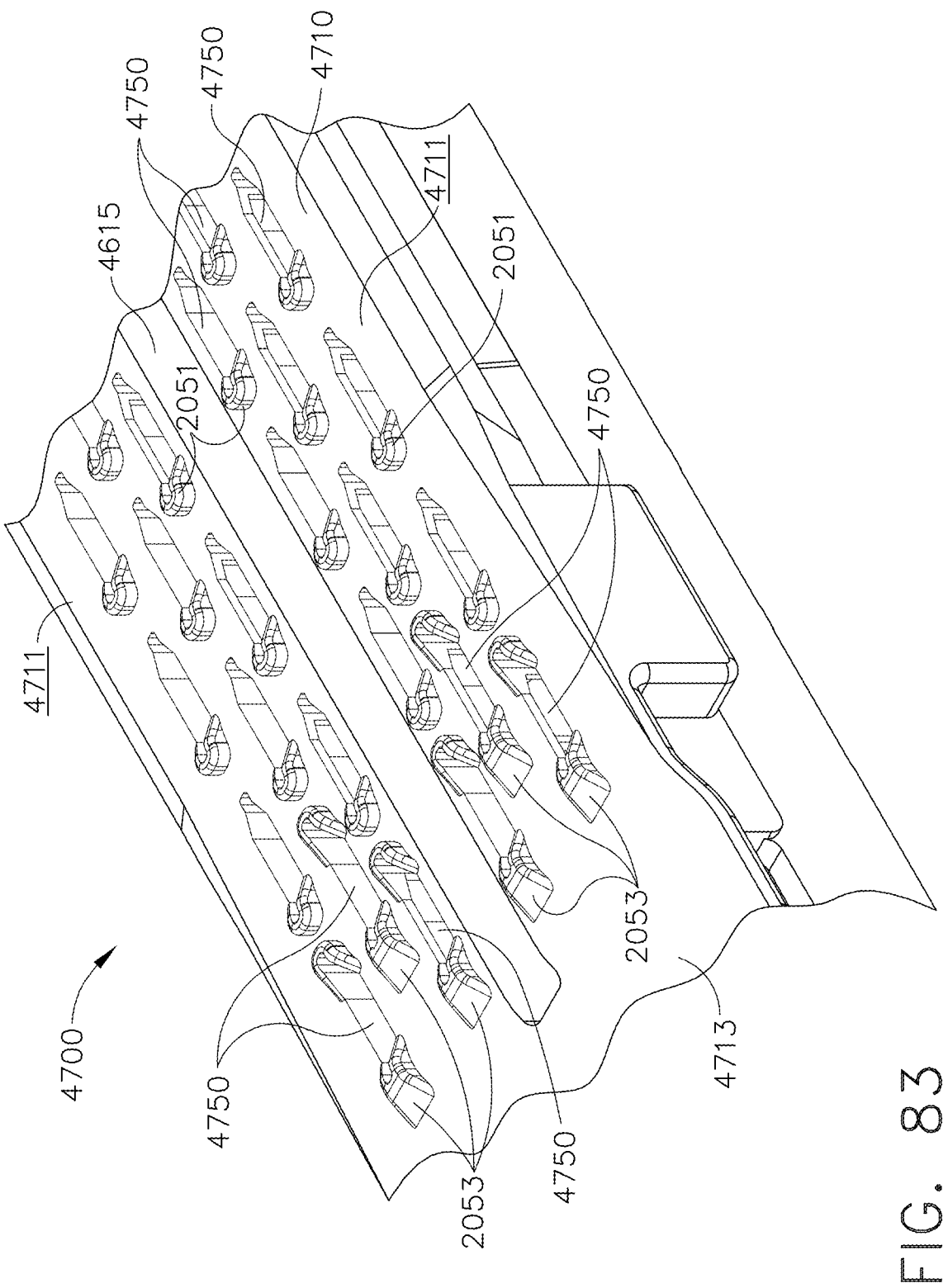
Figure 84:
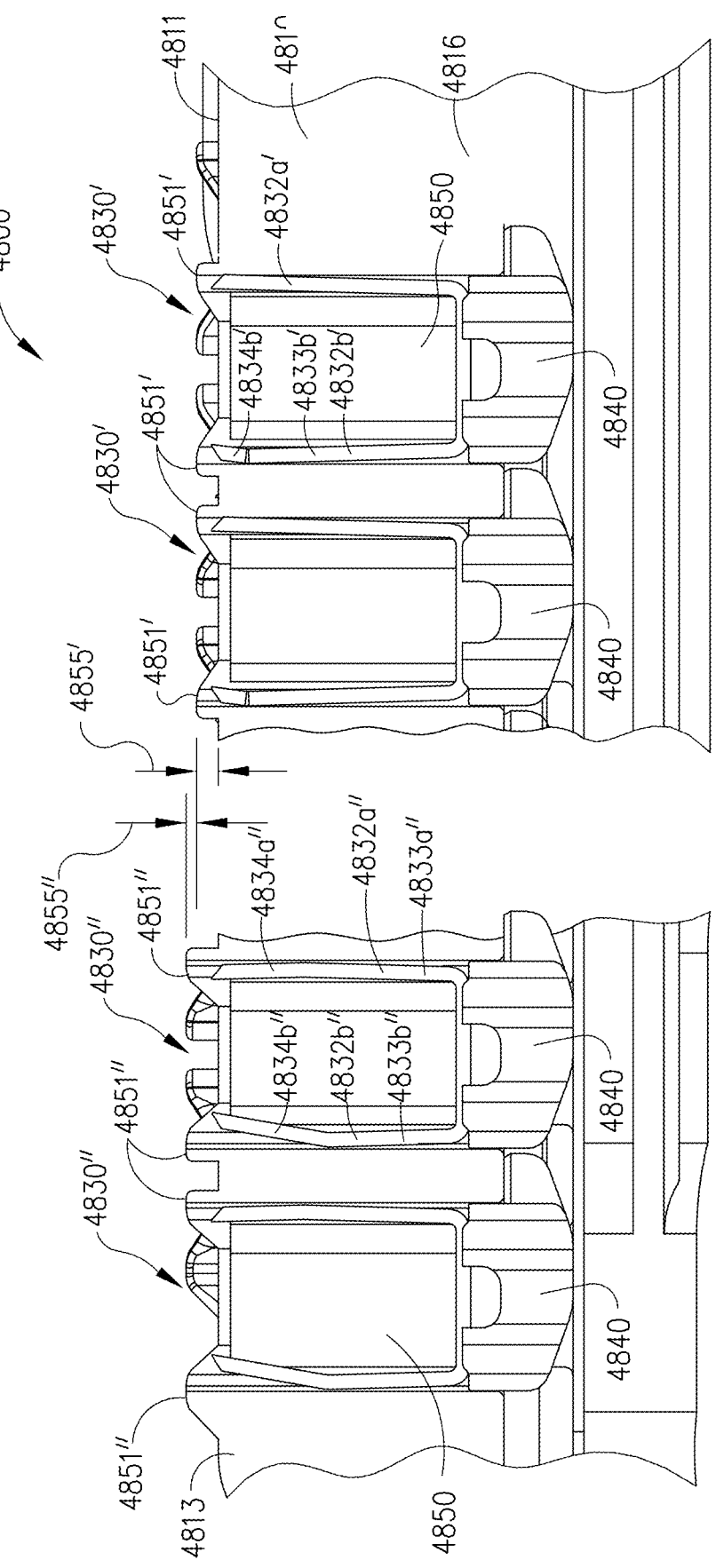
Figures 85A, 85B, 85C:
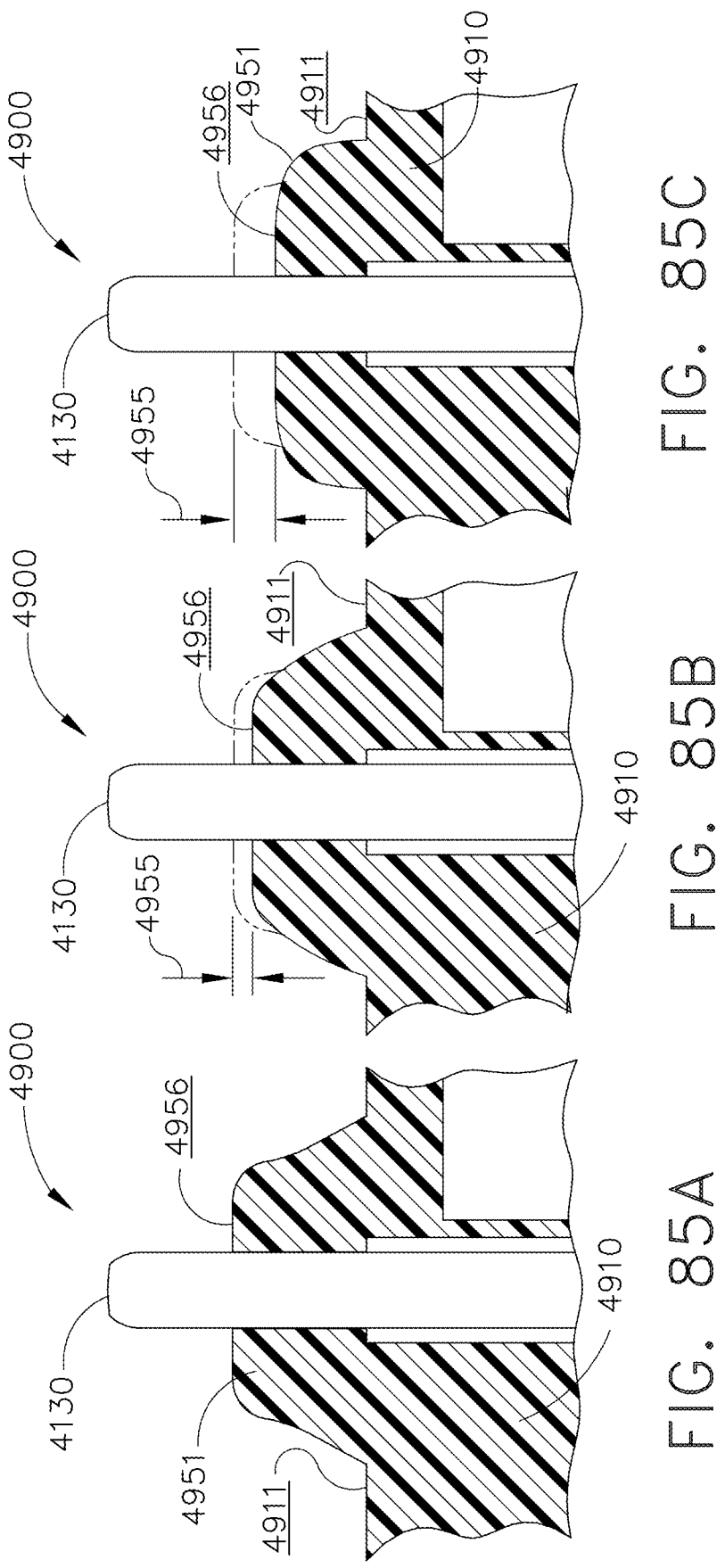
Figures 86A, 86B:
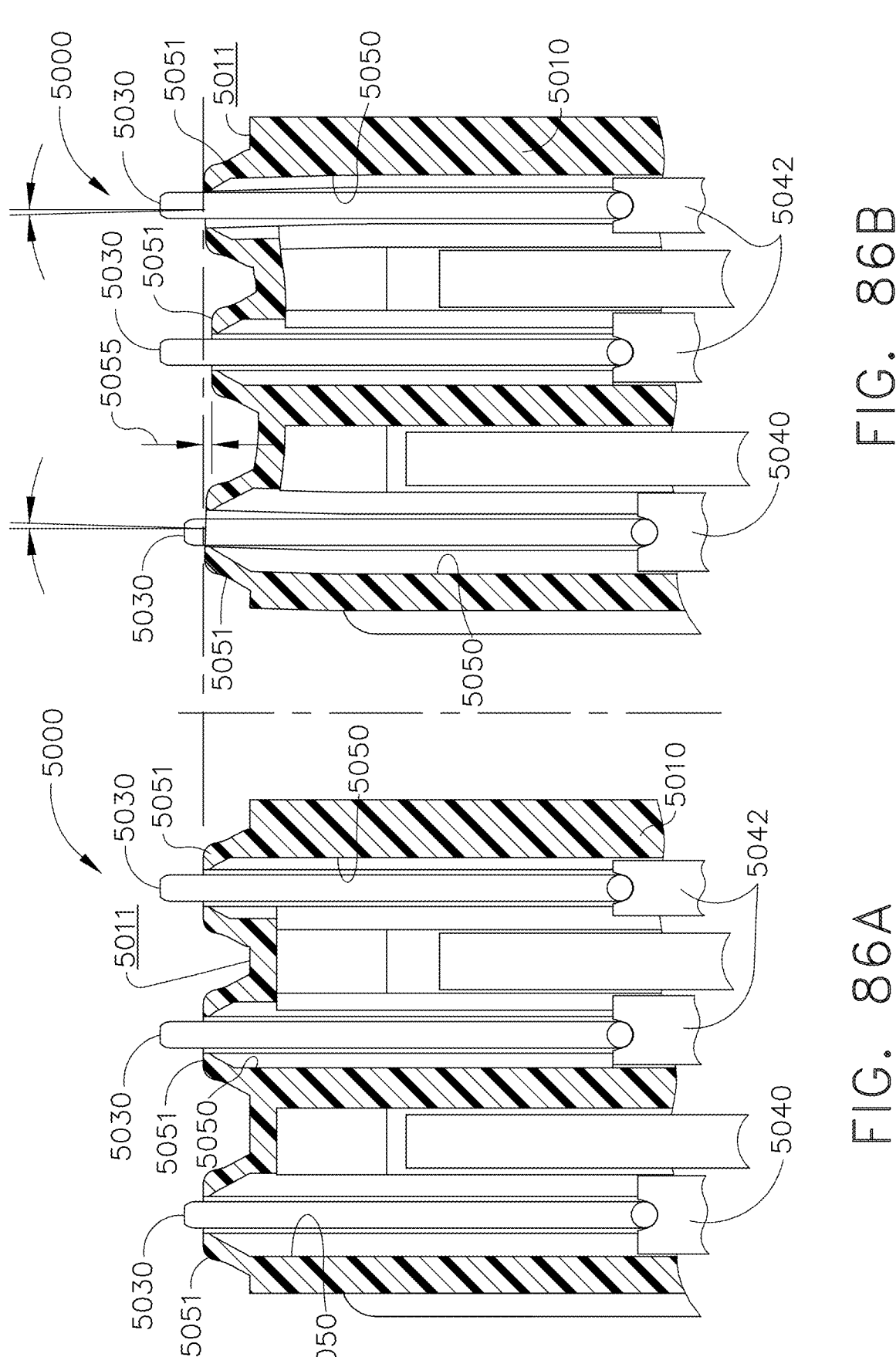
Figure 87:
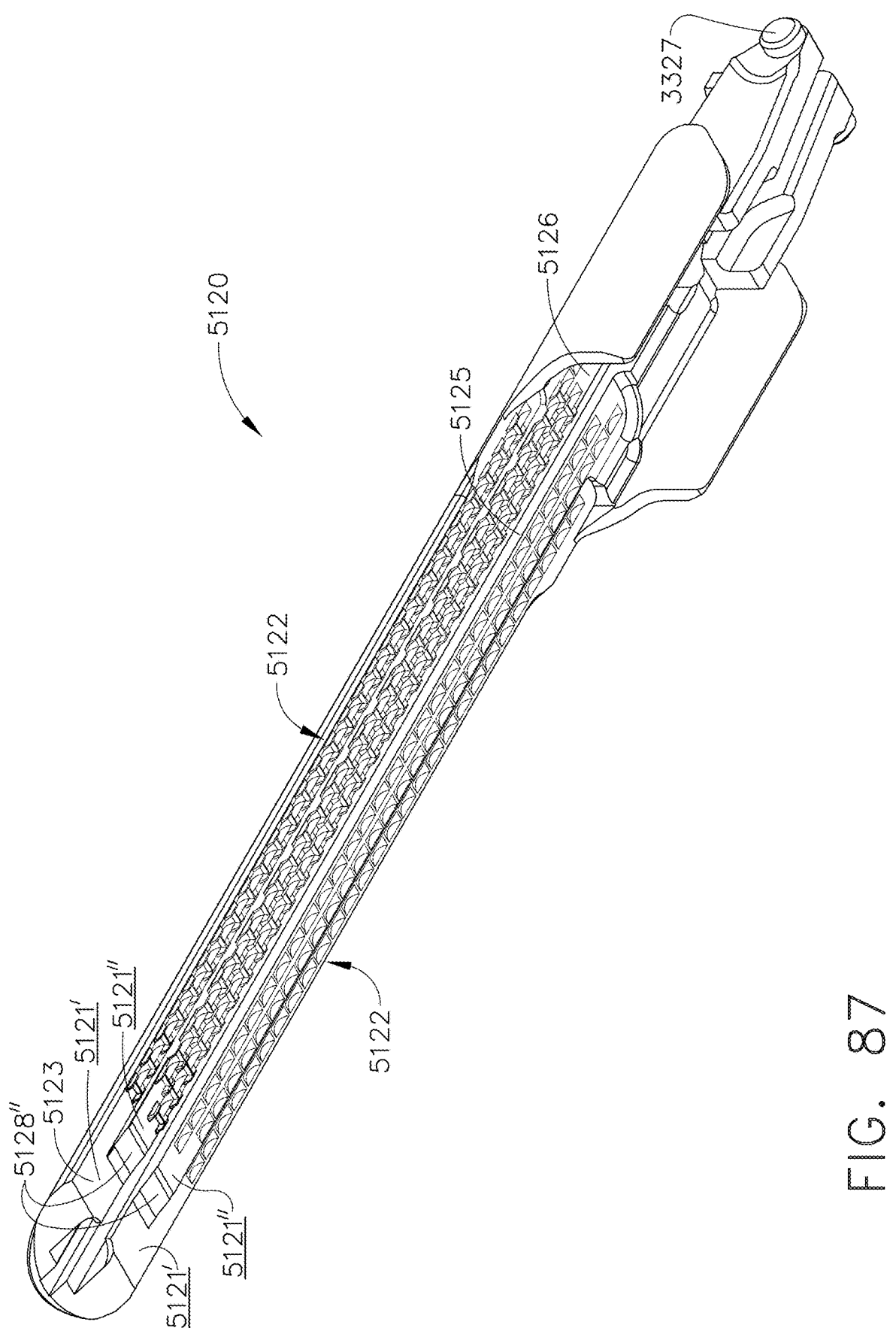
Figure 88:
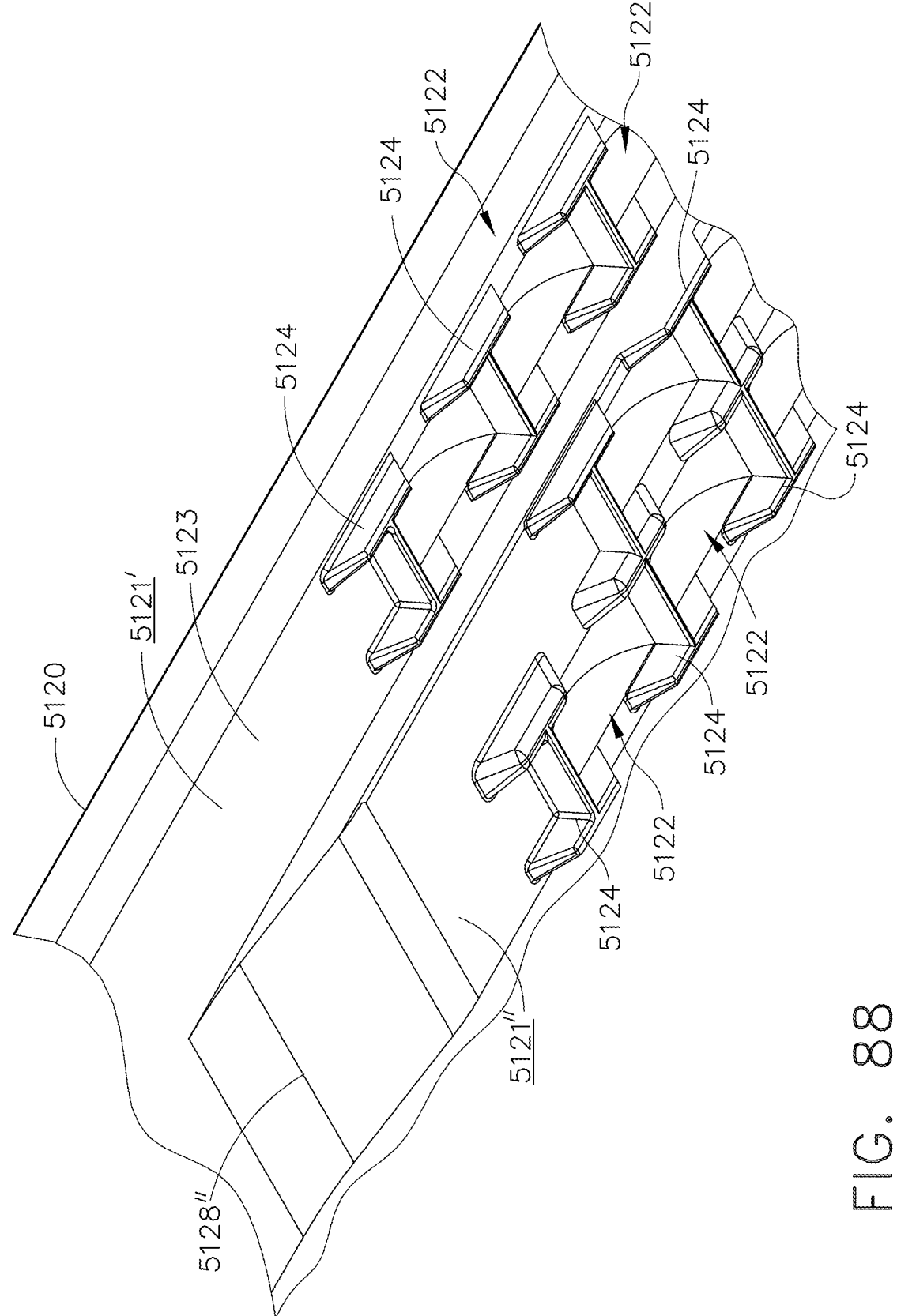
Figure 89:
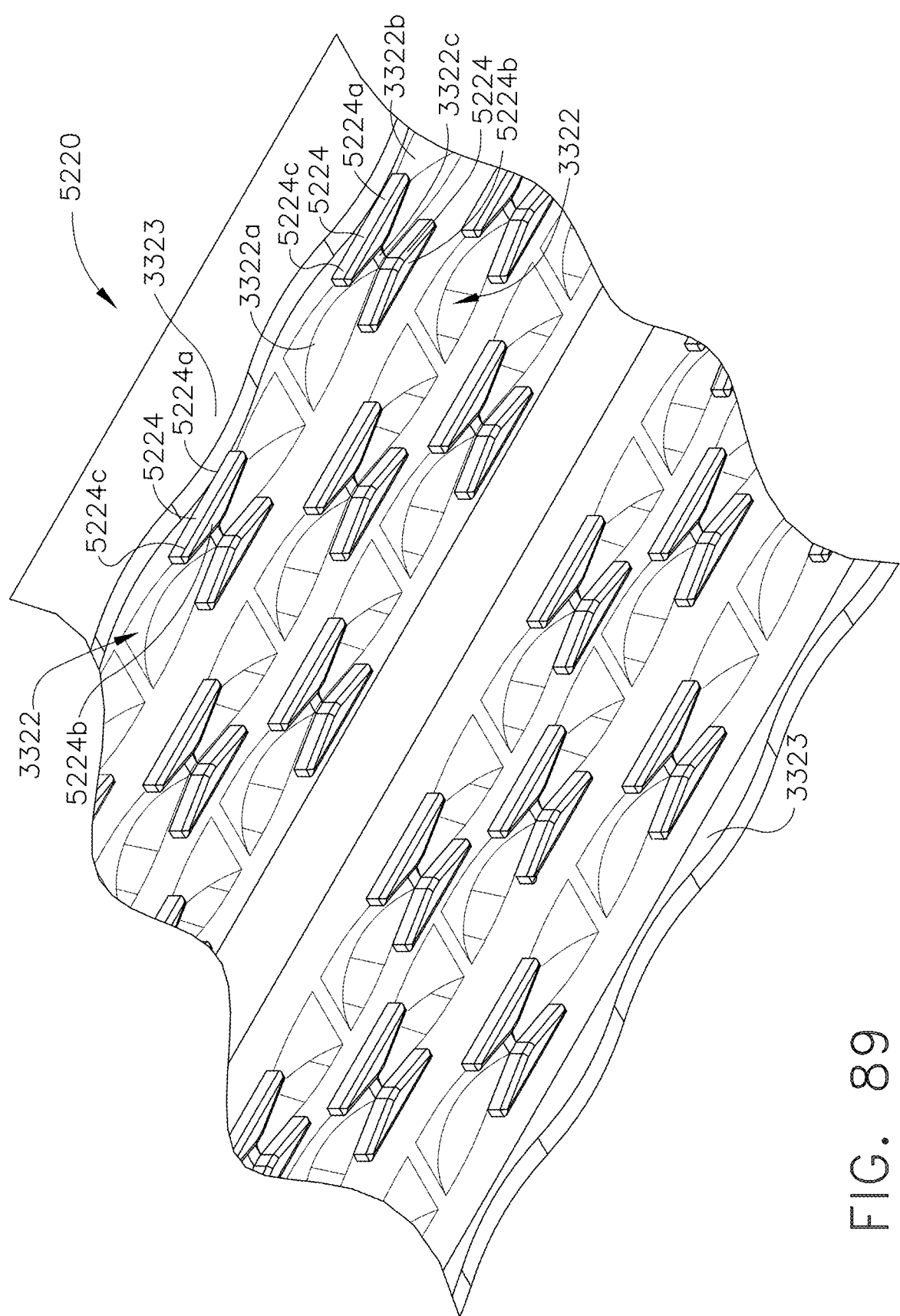
Figure 91:
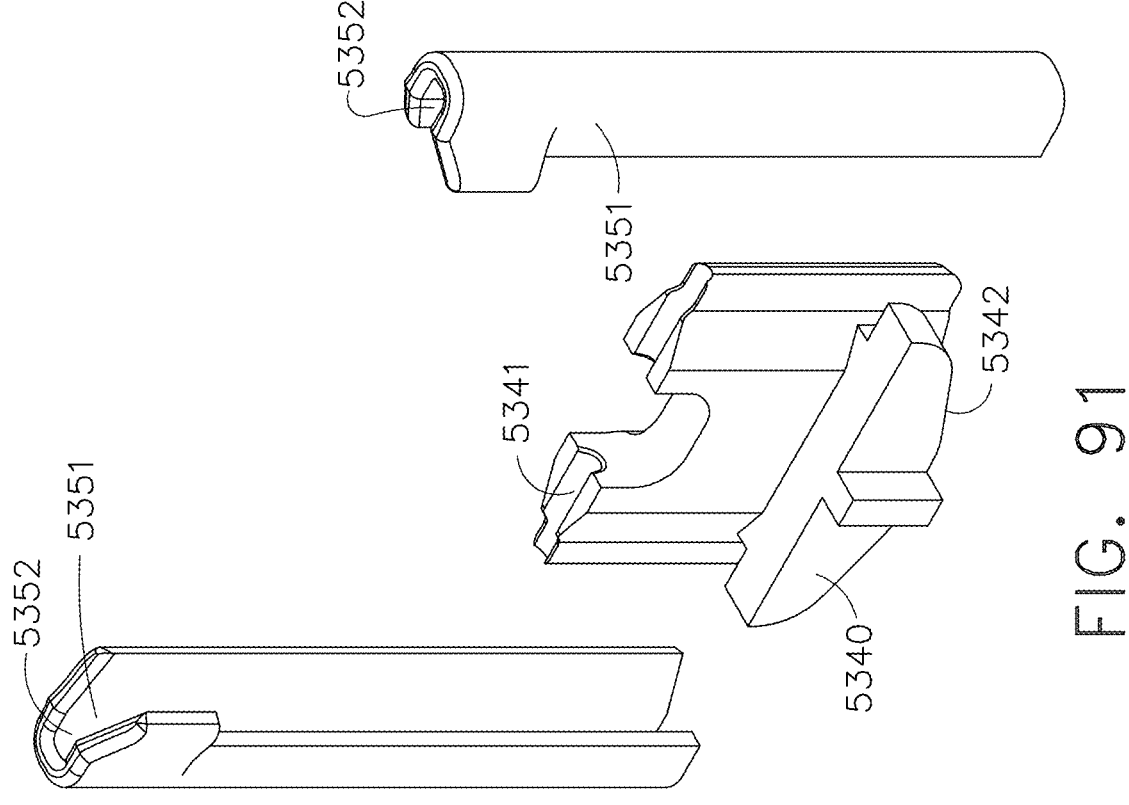
Figure 90:
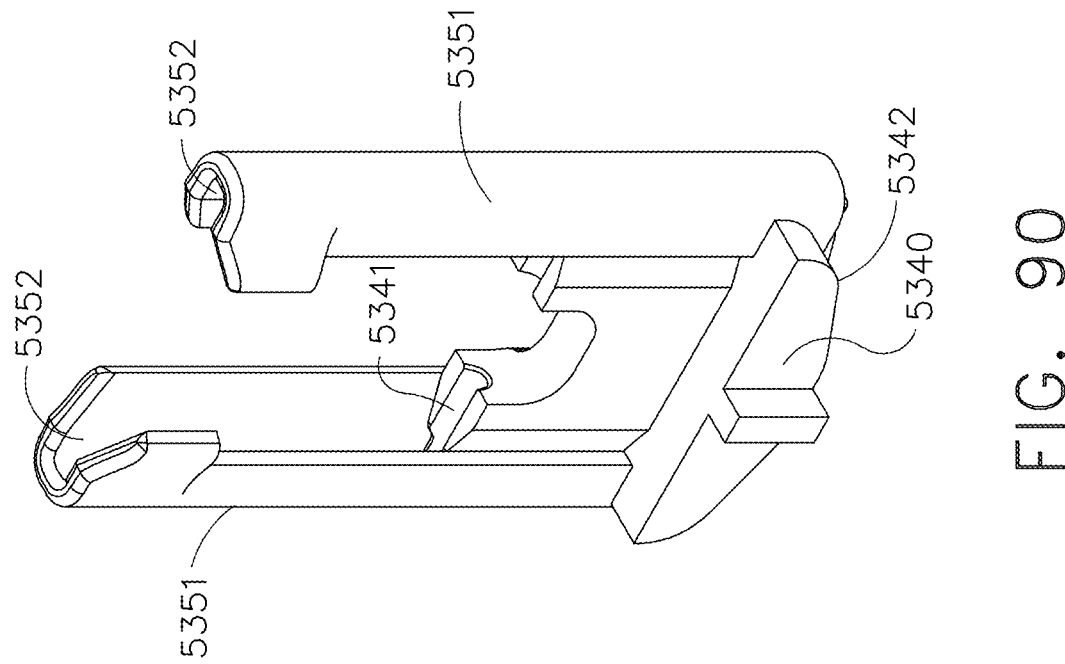
Figure 92:
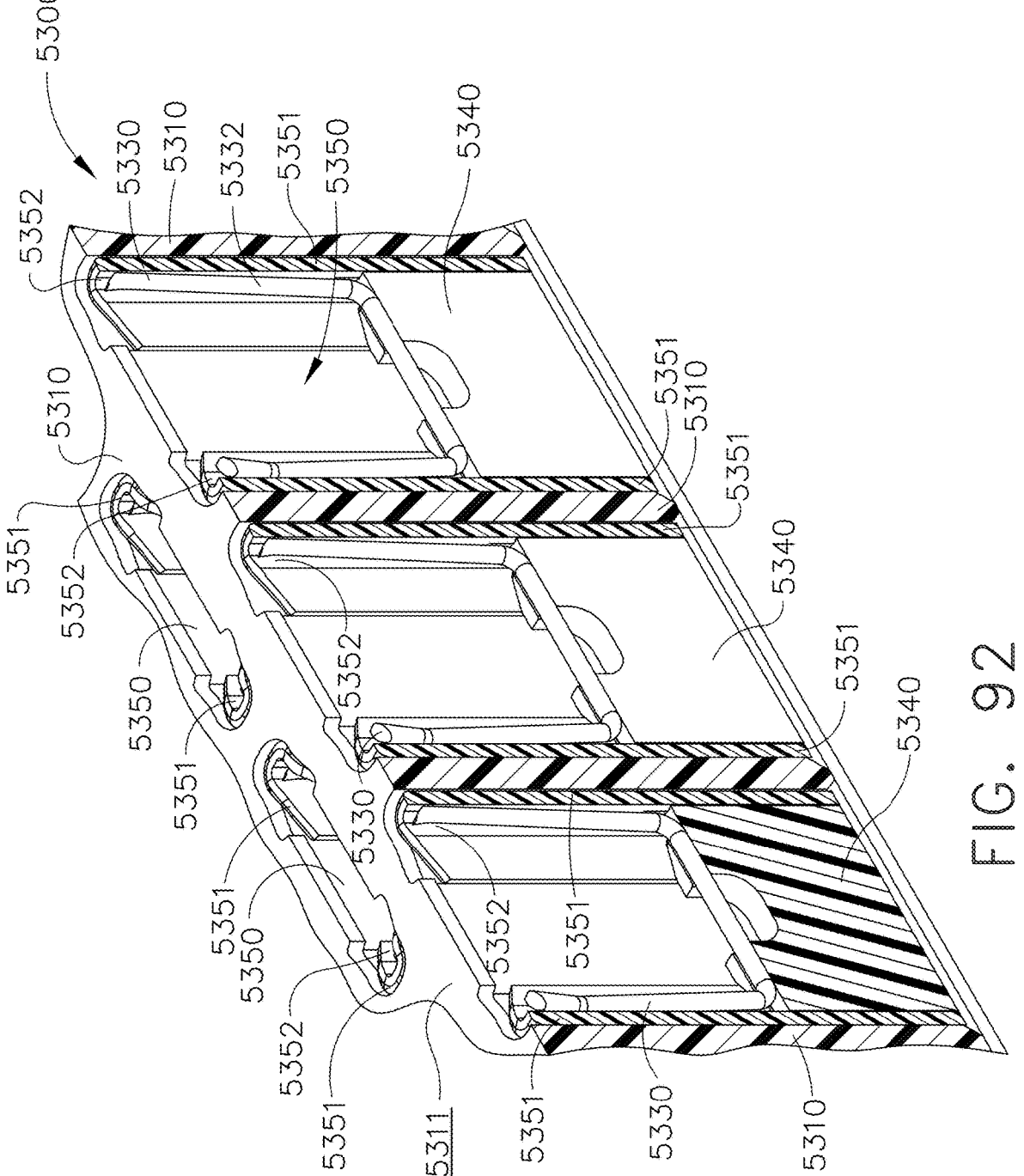
Figure 93:
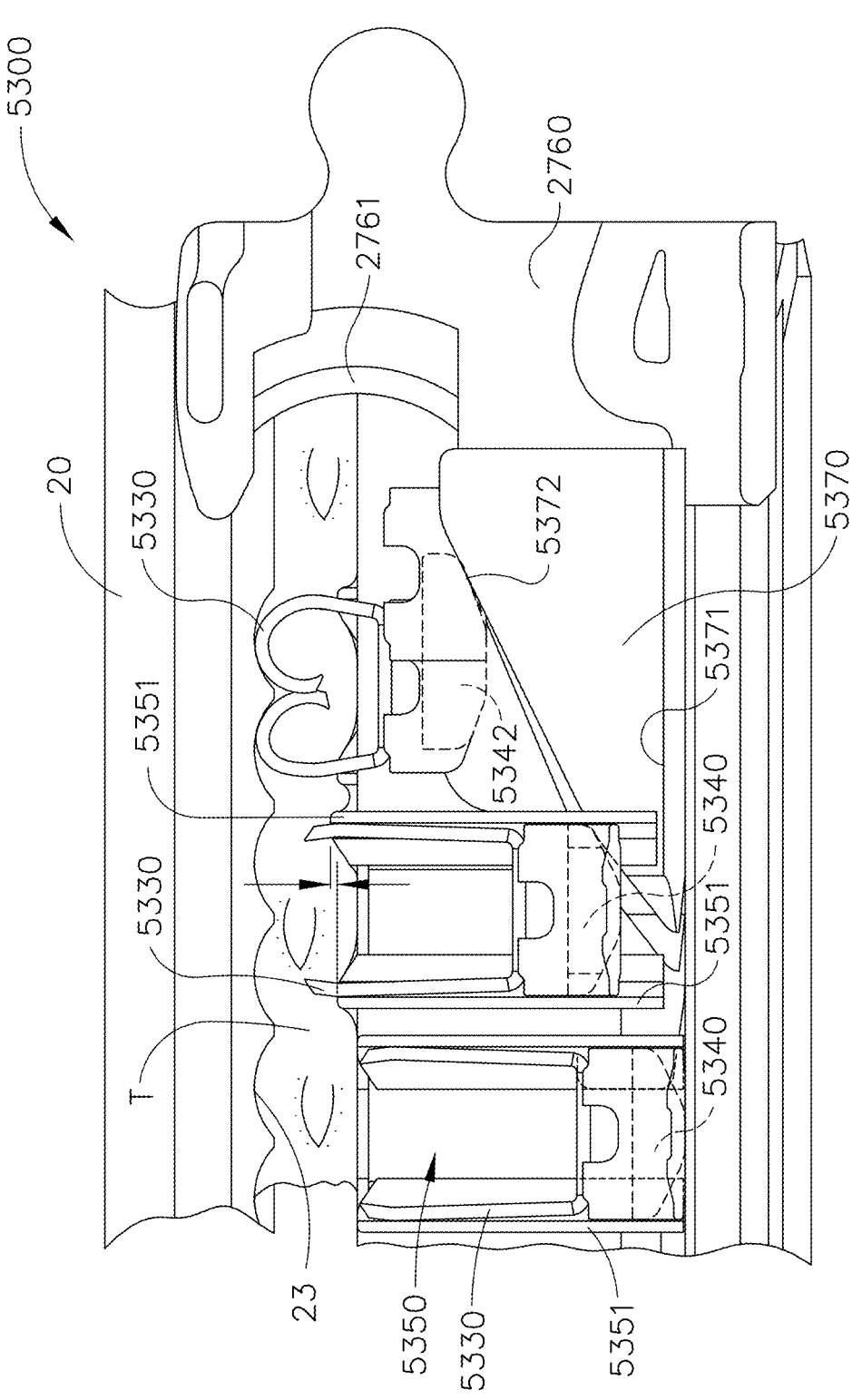
Figure 94:
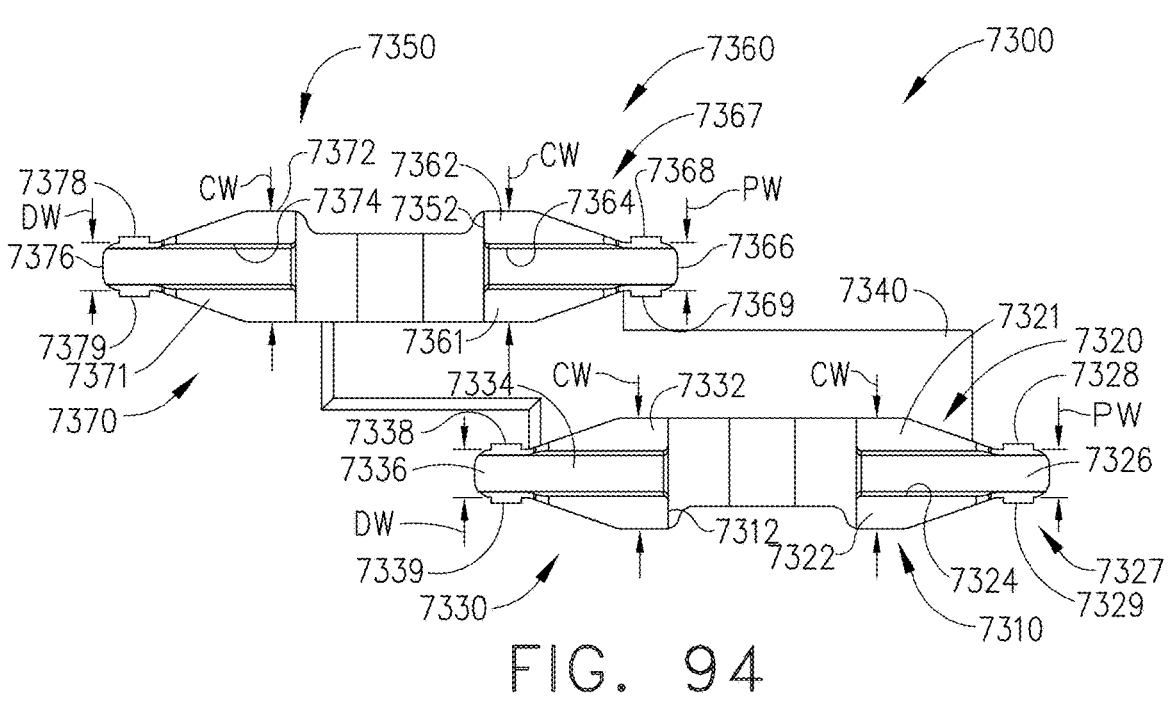
Figure 95:
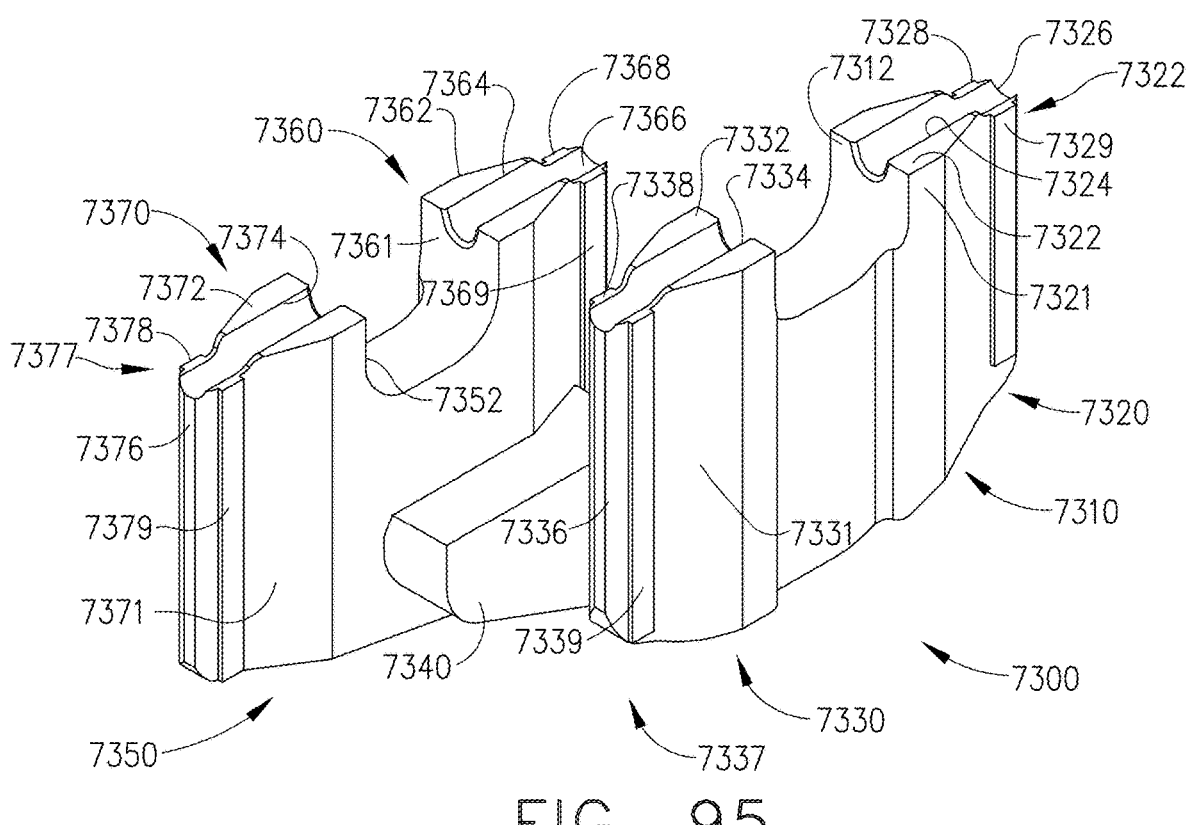
Figure 96:
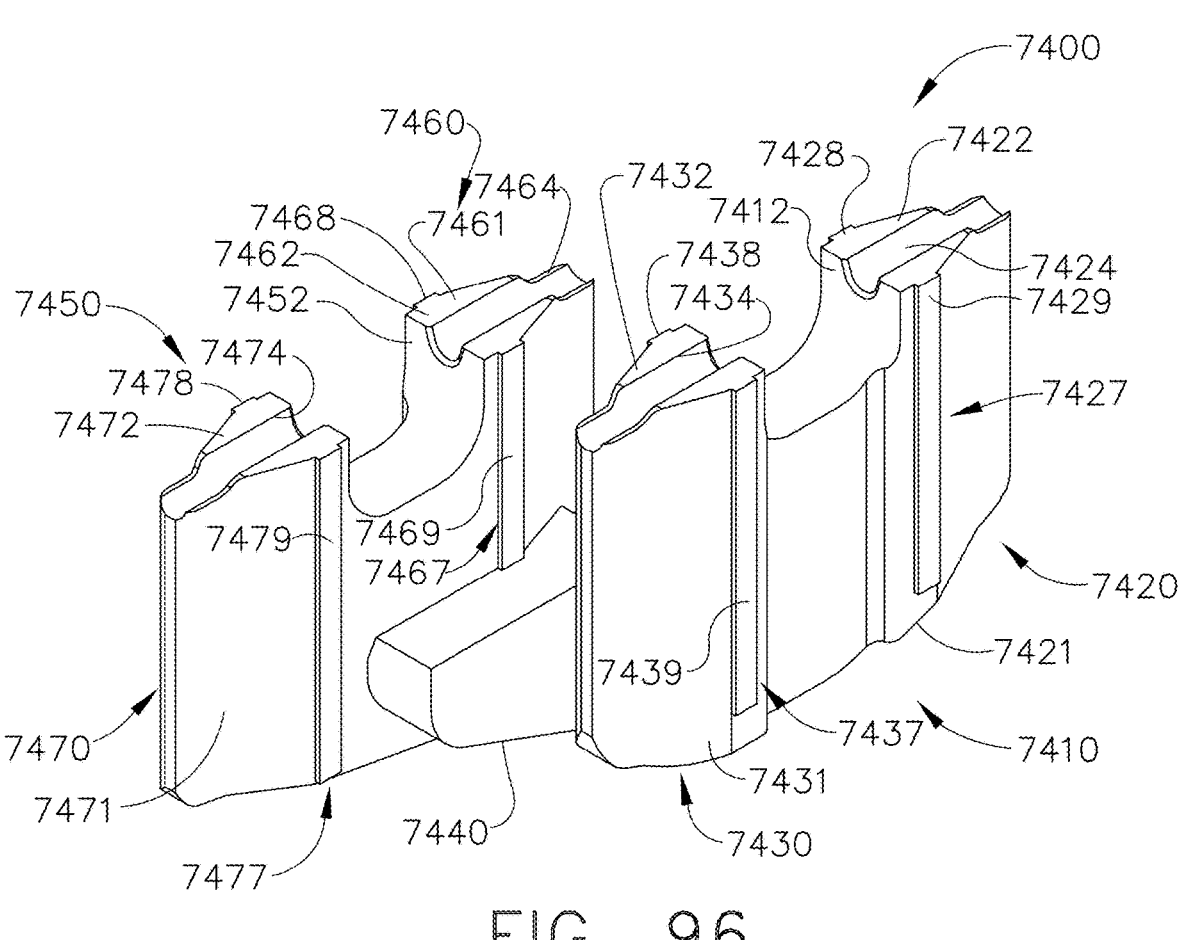
Figure 97:
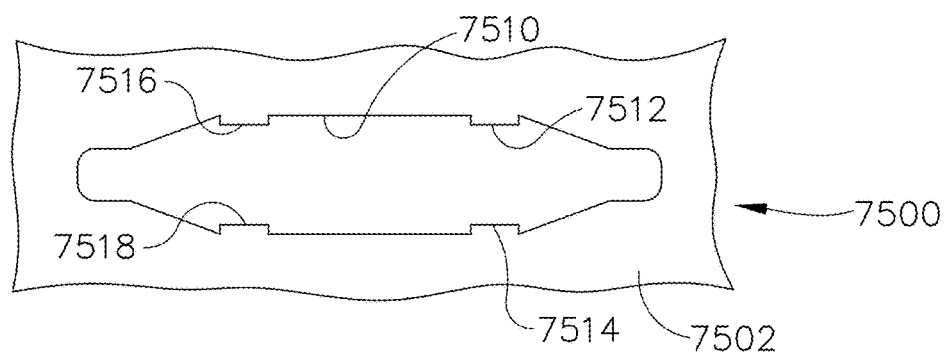
Figure 98:
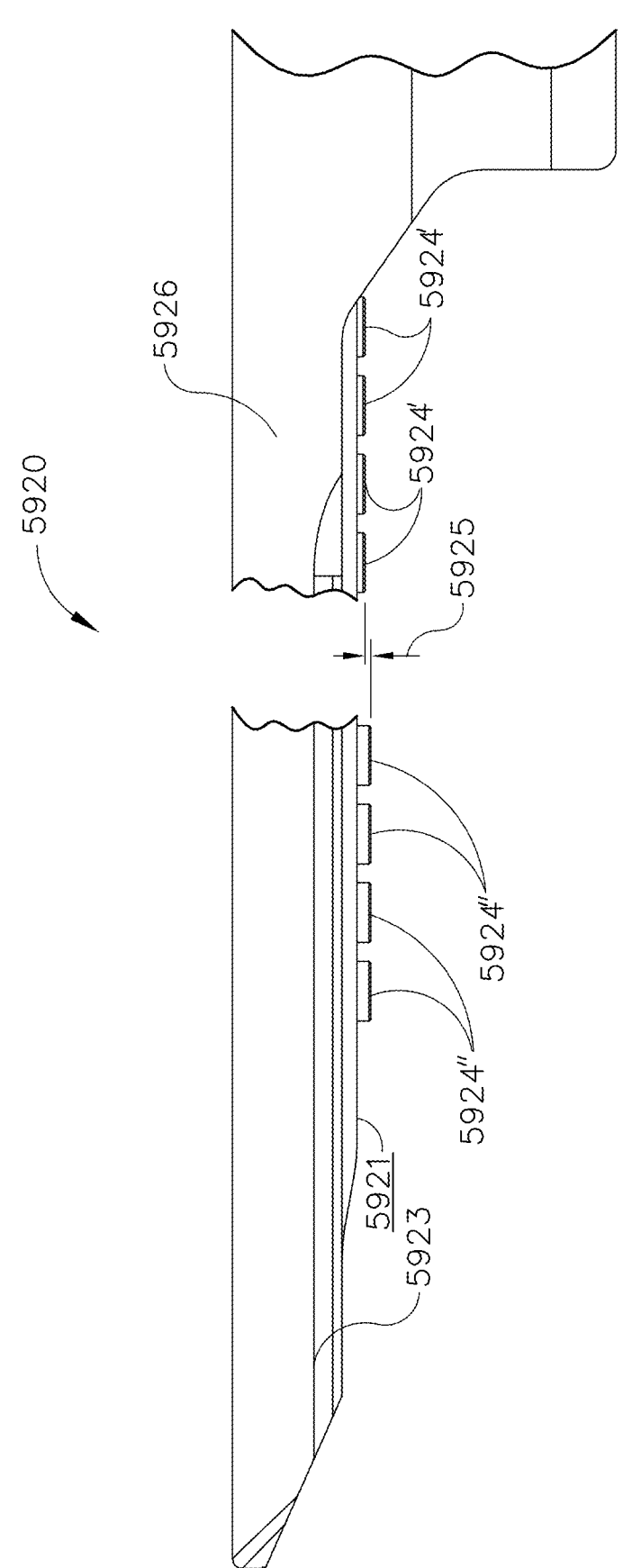
Figure 99:
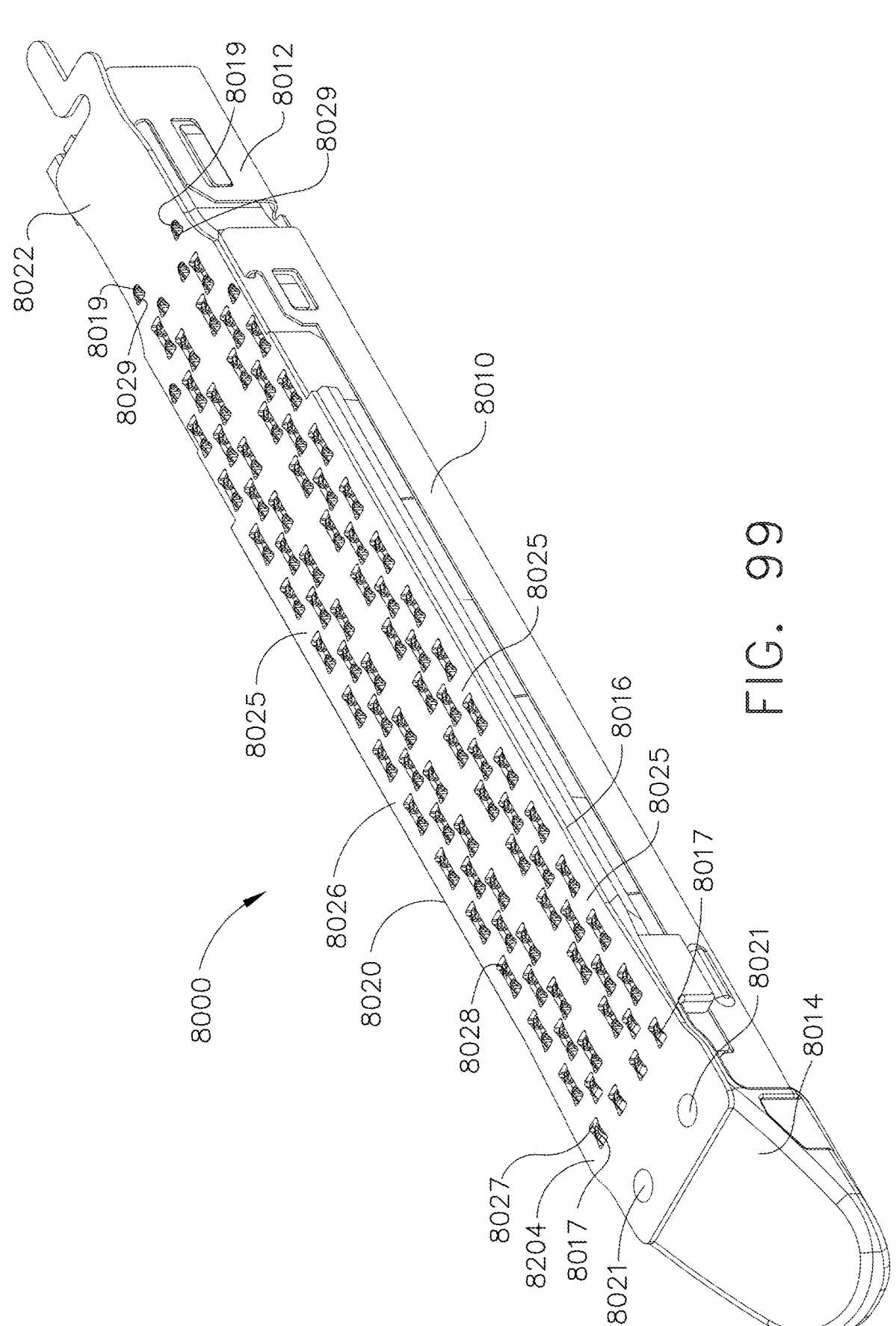
Figures 100, 101, 102:
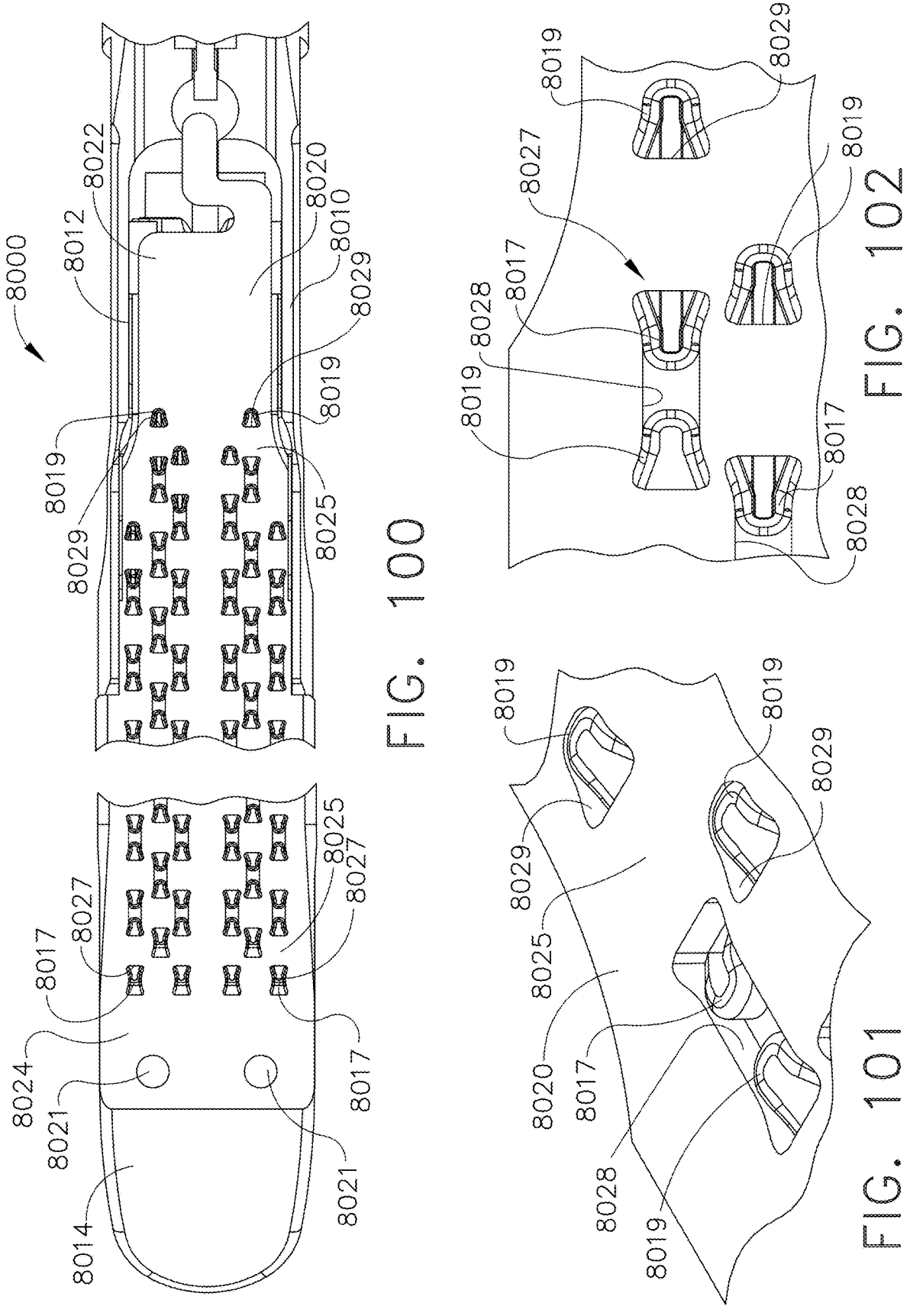

FIG. 42 is perspective view of a cutting head and firing bar embodiment;

FIG. 43 is a perspective view of another end effector and shaft arrangement;

FIG. 44 is another perspective view of the end effector and shaft arrangement of FIG. 43 with a portion of the outer shaft omitted for clarity;

FIG. 45 is a partial side view of another end effector and shaft arrangement;

FIG. 46 is a partial side elevational view of an end effector arrangement with the elongate channel omitted for clarity;

FIG. 47 is a top view of an anvil embodiment;

FIG. 48 is a top view of another anvil embodiment;

FIG. 49 is a cross-sectional view of an end effector of a surgical instrument in accordance with at least one embodiment comprising a staple cartridge including a stepped cartridge deck;

FIG. 49A is the same cross-sectional view depicted in FIG. 49 illustrating various gap heights between the stepped cartridge deck and an anvil positioned opposite thereto;

FIG. 50 is an elevational view of an asymmetrical staple in accordance with at least one embodiment;

FIG. 51 is an elevational view of another asymmetrical staple in accordance with at least one embodiment;

FIG. 52 is an elevational view of another asymmetrical staple in accordance with at least one embodiment;

FIG. 53 is a perspective view of a staple sled in accordance with at least one embodiment;

FIG. 54 is a top view of the staple sled of FIG. 53;

FIG. 54A is a partial top view of the staple cartridge of FIG. 23 illustrating the staple sled of FIG. 53 in a proximal, unfired position;

FIG. 54B is a partial, cross-sectional perspective view of the staple cartridge of FIG. 23;

FIG. 54C is partial rear perspective view of the staple cartridge of FIG. 23;

FIG. 54D is a perspective view of the staple sled of FIG. 53;

FIG. 55 is a perspective view of a distal end of the staple cartridge of FIG. 23;

FIG. 55A is a perspective view of a projection extending from the staple cartridge of FIG. 23;

FIG. 56 is a perspective view of a staple cartridge in accordance with at least one embodiment including a pattern of ridges extending from a deck of the staple cartridge;

FIG. 57 is a detail view of the pattern of ridges and the deck of the staple cartridge of FIG. 56;

FIG. 58 is a partial perspective view of a staple cartridge in accordance with at least one embodiment including a pattern of ridges extending from a deck of the staple cartridge;

FIG. 59 is a partial perspective view of a staple cartridge in accordance with at least one embodiment including a pattern of projections defined in a deck of the staple cartridge;

FIG. 60 is a detail view of a projection illustrated in FIG. 59;

FIG. 61 is a partial perspective view of a staple cartridge in accordance with at least one embodiment including a pattern of domes extending from a deck of a staple cartridge;

FIG. 62 is a detail view of a dome illustrated in FIG. 61;

FIG. 63 is a partial perspective view of projections extending from a deck of a staple cartridge in accordance with at least one embodiment;

FIG. 64 is an exploded perspective view of a surgical staple cartridge and a cartridge cover;

FIG. 65 is a cross-sectional view of the staple cartridge and cartridge cover of FIG. 64 with the cartridge cover installed on the staple cartridge;

FIG. 66 is a perspective view of an anvil of a surgical stapling instrument in accordance with at least one embodiment including projections extending therefrom;

FIG. 67 is a detail view of the projections illustrated in FIG. 66;

FIG. 68 is a partial perspective view of an anvil of a surgical stapling instrument in accordance with at least one embodiment including projections extending therefrom;

FIG. 69 is a cross-sectional view of an anvil of a surgical stapling instrument in accordance with at least one embodiment including a first array of projections having a first height adjacent a first row of staple pockets, a second array of projections having a second height adjacent a second row of staple pockets, and a third array of projections having a third height adjacent a third row of staple pockets;

FIG. 70 is a perspective view of a staple cartridge in accordance with at least one embodiment including projections extending from a stepped deck surface of the staple cartridge;

FIG. 71 is a detail view of a distal end of the stepped deck surface and the projections of FIG. 70;

FIG. 72 is a detail view of a proximal end of the stepped deck surface and the projections of FIG. 70;

FIG. 73 is a perspective view of a staple cartridge in accordance with at least one embodiment including projections extending from a stepped deck surface of the staple cartridge;

FIG. 74 is a partial perspective view of a staple cartridge in accordance with at least one embodiment;

FIG. 75 is a cross-sectional view of an end effector of a surgical stapling instrument in accordance with at least one embodiment comprising a plurality of deployable tissue engaging members;

FIG. 76 is a cross-sectional view of an end effector of a surgical stapling instrument in accordance with at least one embodiment comprising a plurality of projections extending from a stepped cartridge deck surface;

FIG. 77 is a cross-sectional view of a cartridge deck of a staple cartridge and a projection extending from the deck configured to support a staple as the staple is deployed from a staple cavity in accordance with at least one embodiment;

FIG. 78 is a cross-sectional view of another cartridge deck of a staple cartridge and a projection extending from the deck configured to support a staple as the staple is deployed from a staple cavity in accordance with at least one embodiment;

FIG. 79 is a partial plan view of a deck of a staple cartridge including projections extending from the deck configured to support a staple removably stored in a staple cavity defined in the staple cartridge in accordance with at least one embodiment;

FIG. 80 is a partial cross-sectional view of a staple cartridge including a first projection configured to support a first leg of a staple removably positioned within a staple cavity and a second projection configured to support a second leg of the staple in accordance with at least one embodiment;

FIG. 81 is a perspective view of a distal end of a staple cartridge including a deck, a plurality of staple cavities defined in the deck, and an assortment of projections extending from the deck in accordance with at least one embodiment;

FIG. 82 is a partial perspective view of a staple cartridge including a deck, a plurality of staple cavities defined in the deck, and a plurality of projections extending from the deck which surround the ends of some of the staple cavities, but not others, in accordance with at least one embodiment;

FIG. 83 is a partial perspective view of a staple cartridge including a deck, a plurality of staple cavities defined in the deck, and a plurality of projections extending from the deck which surround certain ends of the staple cavities, but not others, in accordance with at least one embodiment;

FIG. 84 is a partial cross-sectional view of a staple cartridge including a deck and a plurality of staple cavities defined in the deck, an array of staples positioned in the staple cavities extending between a proximal end and a distal end of the staple cartridge wherein the array of staples comprises an assortment of staples, and an array of projections extending from the deck extending between the proximal end and the distal end of the staple cartridge wherein the array of projections comprises an assortment of heights in accordance with at least one embodiment;

FIG. 85A is a partial cross-sectional view of a staple cartridge deck and a projection extending from the deck wherein the projection is comprised of a compliant material and is illustrated in an uncompressed state in accordance with at least one embodiment;

FIG. 85B is a partial cross-sectional view of the staple cartridge deck and projection of FIG. 85A illustrating the projection in a partially-compressed state;

FIG. 85C is a partial cross-sectional view of the staple cartridge deck and projection of FIG. 85A illustrating the projection in a compressed state;

FIG. 86A is partial cross-sectional view of a staple cartridge including a cartridge body comprised of a flexible material in accordance with at least one embodiment illustrated in an unflexed condition;

FIG. 86B is a partial cross-sectional view of the staple cartridge of FIG. 86A illustrated in a flexed condition;

FIG. 87 is a perspective view of an anvil including a plurality of projections extending from the anvil in accordance with at least one embodiment;

FIG. 88 is a detail view of a portion of the anvil of FIG. 87;

FIG. 89 is a partial perspective view of an anvil including a plurality of projections extending from the anvil in accordance with at least one embodiment;

FIG. 90 is a perspective view of an assembly including a staple driver and movable pocket extenders in accordance with at least one embodiment;

FIG. 91 is an exploded view of the assembly of FIG. 90;

FIG. 92 is a cross-sectional perspective view of a staple cartridge utilizing the assembly of FIG. 90 illustrated in an undeployed condition;

FIG. 93 is a cross-sectional elevational view of the staple cartridge of FIG. 92 illustrating an assembly of FIG. 90 in a deployed condition and an assembly of FIG. 90 in an undeployed condition;

FIG. 94 is a top view of a surgical staple driver;

FIG. 95 is a perspective view of the surgical staple driver of FIG. 94;

FIG. 96 is a perspective view of another surgical staple driver;

FIG. 97 is a top view of a staple driver pocket in a portion of a surgical staple cartridge;

FIG. 98 is an elevational view of an anvil in accordance with at least one embodiment comprising projections having different heights extending therefrom;

FIG. 99 is a perspective view of a fastener cartridge in accordance with at least one embodiment;

FIG. 100 is a plan view of the fastener cartridge of FIG. 99;

FIG. 101 is a partial perspective view of a proximal end of the fastener cartridge of FIG. 99; and FIG. 102 is a partial plan view of the proximal end of the fastener cartridge of FIG. 99.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Applicant of the present application owns the following patent applications that were filed on Jun. 30, 2014 and which are each herein incorporated by reference in their respective entireties:

U.S. patent application Ser. No. 14/318,996, entitled FASTENER CARTRIDGES INCLUDING EXTENSIONS HAVING DIFFERENT CONFIGURATIONS, now U.S. Patent Application Publication No. 2015/0297228;

U.S. patent application Ser. No. 14/319,006, entitled FASTENER CARTRIDGE COMPRISING FASTENER CAVITIES INCLUDING FASTENER CONTROL FEATURES, now U.S. Pat. No. 10,010,324;

U.S. patent application Ser. No. 14/319,014, entitled END EFFECTOR COMPRISING AN ANVIL INCLUDING PROJECTIONS EXTENDING THEREFROM, now U.S. Patent Application Publication No. 2015/0297234;

U.S. patent application Ser. No. 14/318,991, entitled SURGICAL FASTENER CARTRIDGES WITH DRIVER STABILIZING ARRANGEMENTS, now U.S. Pat. No. 9,833,241;

U.S. patent application Ser. No. 14/319,004, entitled SURGICAL END EFFECTORS WITH FIRING ELEMENT MONITORING ARRANGEMENTS, now U.S. Pat. No. 9,844,369;

U.S. patent application Ser. No. 14/318,997, entitled FASTENER CARTRIDGE COMPRISING DEPLOYABLE TISSUE ENGAGING MEMBERS, now U.S. Patent Application Publication No. 2015/0297229;

U.S. patent application Ser. No. 14/319,002, entitled FASTENER CARTRIDGE COMPRISING TISSUE CONTROL FEATURES, now U.S. Pat. No. 9,877,721;

U.S. patent application Ser. No. 14/319,013, entitled FASTENER CARTRIDGE ASSEMBLIES AND STAPLE RETAINER COVER ARRANGEMENTS, now U.S. Patent Application Publication No. 2015/0297233; and U.S. patent application Ser. No. 14/319,016, entitled FASTENER CARTRIDGE INCLUDING A LAYER ATTACHED THERETO, now U.S. Patent Application Publication No. 2015/0297235.

Applicant of the present application also owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION;

U.S. patent application Ser. No. 13/782,323, entitled ROTARY POWERED ARTICULATION JOINTS FOR SURGICAL INSTRUMENTS;

U.S. patent application Ser. No. 13/782,338, entitled THUMBWHEEL SWITCH ARRANGEMENTS FOR SURGICAL INSTRUMENTS;

U.S. patent application Ser. No. 13/782,499, entitled ELECTROMECHANICAL SURGICAL DEVICE WITH SIGNAL RELAY ARRANGEMENT;

U.S. patent application Ser. No. 13/782,460, entitled MULTIPLE PROCESSOR MOTOR CONTROL FOR MODULAR SURGICAL INSTRUMENTS;

U.S. patent application Ser. No. 13/782,358, entitled JOYSTICK SWITCH ASSEMBLIES FOR SURGICAL INSTRUMENTS;

U.S. patent application Ser. No. 13/782,481, entitled SENSOR STRAIGHTENED END EFFECTOR DURING REMOVAL THROUGH TROCAR;

U.S. patent application Ser. No. 13/782,518, entitled CONTROL METHODS FOR SURGICAL INSTRUMENTS WITH REMOVABLE IMPLEMENT PORTIONS;

U.S. patent application Ser. No. 13/782,375, entitled ROTARY POWERED SURGICAL INSTRUMENTS WITH MULTIPLEDEGREES OF FREEDOM; and U.S. patent application Ser. No. 13/782,536, entitled SURGICAL INSTRUMENT SOFT STOP.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE;

U.S. patent application Ser. No. 13/803,193, entitled CONTROL ARRANGEMENTS FOR A DRIVE MEMBER OF A SURGICAL INSTRUMENT;

U.S. patent application Ser. No. 13/803,053, entitled INTERCHANGEABLE SHAFT ASSEMBLIES FOR USE WITH A SURGICAL INSTRUMENT;

U.S. patent application Ser. No. 13/803,086, entitled ARTICULATABLE SURGICAL INSTRUMENT COMPRISING AN ARTICULATION LOCK;

U.S. patent application Ser. No. 13/803,210, entitled SENSOR ARRANGEMENTS FOR ABSOLUTE POSITIONING SYSTEM FOR SURGICAL INSTRUMENTS;

U.S. patent application Ser. No. 13/803,148, entitled MULTI-FUNCTION MOTOR FOR A SURGICAL INSTRUMENT;

U.S. patent application Ser. No. 13/803,066, entitled DRIVE SYSTEM LOCKOUT ARRANGEMENTS FOR MODULAR SURGICAL INSTRUMENTS; U.S. patent application Ser. No. 13/803,117, entitled ARTICULATION CONTROL SYSTEM FOR ARTICULATABLE SURGICAL INSTRUMENTS;

U.S. patent application Ser. No. 13/803,130, entitled DRIVE TRAIN CONTROL ARRANGEMENTS FOR MODULAR SURGICAL INSTRUMENTS; and U.S. patent application Ser. No. 13/803,159, entitled METHOD AND SYSTEM FOR OPERATING A SURGICAL INSTRUMENT.

Applicant of the present application also owns the following patent applications that were filed on Mar. 26, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS;

U.S. patent application Ser. No. 14/226,099, entitled STERILIZATION VERIFICATION CIRCUIT;

U.S. patent application Ser. No. 14/226,094, entitled VERIFICATION OF NUMBER OF BATTERY EXCHANGES/PROCEDURE COUNT;

U.S. patent application Ser. No. 14/226,117, entitled POWER MANAGEMENT THROUGH SLEEP OPTIONS OF SEGMENTED CIRCUIT AND WAKE UP CONTROL;

U.S. patent application Ser. No. 14/226,075, entitled MODULAR POWERED SURGICAL INSTRUMENT WITH DETACHABLE SHAFT ASSEMBLIES;

U.S. patent application Ser. No. 14/226,093, entitled FEEDBACK ALGORITHMS FOR MANUAL BAIL-OUT SYSTEMS FOR SURGICAL INSTRUMENTS;

U.S. patent application Ser. No. 14/226,116, entitled SURGICAL INSTRUMENT UTILIZING SENSOR ADAPTATION;

U.S. patent application Ser. No. 14/226,071, entitled SURGICAL INSTRUMENT CONTROL CIRCUIT HAVING A SAFETY PROCESSOR;

U.S. patent application Ser. No. 14/226,097, entitled SURGICAL INSTRUMENT COMPRISING INTER-ACTIVE SYSTEMS;

U.S. patent application Ser. No. 14/226,126, entitled INTERFACE SYSTEMS FOR USE WITH SURGI-CAL INSTRUMENTS;

U.S. patent application Ser. No. 14/226,133, entitled MODULAR SURGICAL INSTRUMENT SYSTEM;

U.S. patent application Ser. No. 14/226,081, entitled SYSTEMS AND METHODS FOR CONTROLLING A SEGMENTED CIRCUIT;

U.S. patent application Ser. No. 14/226,076, entitled POWER MANAGEMENT THROUGH SEG-MENTED CIRCUIT AND VARIABLE VOLTAGE PROTECTION;

U.S. patent application Ser. No. 14/226,111, entitled SURGICAL STAPLING INSTRUMENT SYSTEM; and U.S. patent application Ser. No. 14/226,125, entitled SURGICAL INSTRUMENT COMPRISING A ROTATABLE SHAFT.

The Applicant of the present application also owns the U.S. Patent Applications identified below which are each herein incorporated by reference in their respective entireties:

U.S. patent application Ser. No. 12/894,311, entitled SURGICAL INSTRUMENTS WITH RECONFIGUR-ABLE SHAFT SEGMENTS; now U.S. Patent Publi-cation No. 2012/0080496;

U.S. patent application Ser. No. 12/894,340, entitled SURGICAL STAPLE CARTRIDGES SUPPORTING NON-LINEARLY ARRANGED STAPLES AND SURGICAL STAPLING INSTRUMENTS WITH COMMON STAPLE-FORMING POCKETS; now U.S. Patent Publication No. 2012/0080482;

U.S. patent application Ser. No. 12/894,327, entitled JAW CLOSURE ARRANGEMENTS FOR SURGICAL INSTRUMENTS; now U.S. Patent Publication No. 2012/0080499;

U.S. patent application Ser. No. 12/894,351, entitled SURGICAL CUTTING AND FASTENING INSTRU-MENTS WITH SEPARATE AND DISTINCT FAS- TENER DEPLOYMENT AND TISSUE CUTTING SYSTEMS; now U.S. Patent Publication No. 2012/0080502;

U.S. patent application Ser. No. 12/894,338, entitled IMPLANTABLE FASTENER CARTRIDGE HAV-ING A NON-UNIFORM ARRANGEMENT; now U.S. Patent Publication No. 2012/0080481;

U.S. patent application Ser. No. 12/894,369, entitled IMPLANTABLE FASTENER CARTRIDGE COM-PRISING A SUPPORT RETAINER; now U.S. Patent Publication No. 2012/0080344;

U.S. patent application Ser. No. 12/894,312, entitled IMPLANTABLE FASTENER CARTRIDGE COM-PRISING MULTIPLE LAYERS; now U.S. Patent Pub-lication No. 2012/0080479;

U.S. patent application Ser. No. 12/894,377, entitled SELECTIVELY ORIENTABLE IMPLANTABLE FASTENER CARTRIDGE; now U.S. Pat. No. 8,393,514;

U.S. patent application Ser. No. 12/894,339, entitled SURGICAL STAPLING INSTRUMENT WITH COMPACT ARTICULATION CONTROL ARRANGEMENT; now U.S. Patent Publication No. 2012/0080500;

U.S. patent application Ser. No. 12/894,360, entitled SURGICAL STAPLING INSTRUMENT WITH A VARIABLE STAPLE FORMING SYSTEM; now U.S. Patent Publication No. 2012/0080484;

U.S. patent application Ser. No. 12/894,322, entitled SURGICAL STAPLING INSTRUMENT WITH INTERCHANGEABLE STAPLE CARTRIDGE ARRANGEMENTS; now U.S. Pat. No. 8,740,034;

U.S. patent application Ser. No. 12/894,350, entitled SURGICAL STAPLE CARTRIDGES WITH DETACHABLE SUPPORT STRUCTURES; now U.S. Patent Publication No. 2012/0080478;

U.S. patent application Ser. No. 12/894,383, entitled IMPLANTABLE FASTENER CARTRIDGE COM-PRISING BIOABSORBABLE LAYERS; now U.S. Pat. No. 8,752,699;

U.S. patent application Ser. No. 12/894,389, entitled COMPRESSIBLE FASTENER CARTRIDGE; now U.S. Pat. No. 8,740,037;

U.S. patent application Ser. No. 12/894,345, entitled FASTENERS SUPPORTED BY A FASTENER CAR-TRIDGE SUPPORT; now U.S. Patent Publication No. 2012/0080483;

U.S. patent application Ser. No. 12/894,306, entitled COLLAPSIBLE FASTENER CARTRIDGE; now U.S. Patent Publication No. 2012/0080332;

U.S. patent application Ser. No. 12/894,318, entitled FASTENER SYSTEM COMPRISING A PLURAL-ITY OF CONNECTED RETENTION MATRIX ELE-MENTS; now U.S. Patent Publication No. 2012/0080480;

U.S. patent application Ser. No. 12/894,330, entitled FASTENER SYSTEM COMPRISING A RETEN-TION MATRIX AND AN ALIGNMENT MATRIX; now U.S. Pat. No. 8,757,465;

U.S. patent application Ser. No. 12/894,361, entitled FASTENER SYSTEM COMPRISING A RETEN-TION MATRIX; now U.S. Pat. No. 8,529,600;

U.S. patent application Ser. No. 12/894,367, entitled FASTENING INSTRUMENT FOR DEPLOYING A FASTENER SYSTEM COMPRISING A RETEN-TION MATRIX; now U.S. Patent Publication No. 2012/0080485;

U.S. patent application Ser. No. 12/894,388, entitled FASTENER SYSTEM COMPRISING A RETENTION MATRIX AND A COVER; now U.S. Pat. No. 8,474,677;

U.S. patent application Ser. No. 12/894,376, entitled FASTENER SYSTEM COMPRISING A PLURALITY OF FASTENER CARTRIDGES; now U.S. Patent Publication No. 2012/0080486;

U.S. patent application Ser. No. 13/097,865, entitled SURGICAL STAPLER ANVIL COMPRISING A PLURALITY OF FORMING POCKETS; now U.S. Patent Publication No. 2012/0080488;

U.S. patent application Ser. No. 13/097,936, entitled TISSUE THICKNESS COMPENSATOR FOR A SURGICAL STAPLER; now U.S. Pat. No. 8,657,176;

U.S. patent application Ser. No. 13/097,954, entitled STAPLE CARTRIDGE COMPRISING A VARIABLE THICKNESS COMPRESSIBLE PORTION; now U.S. Patent Publication No. 2012/0080340;

U.S. patent application Ser. No. 13/097,856, entitled STAPLE CARTRIDGE COMPRISING STAPLES POSITIONED WITHIN A COMPRESSIBLE PORTION THEREOF; now U.S. Patent Publication No. 2012/0080336;

U.S. patent application Ser. No. 13/097,928, entitled TISSUE THICKNESS COMPENSATOR COMPRISING DETACHABLE PORTIONS; now U.S. Pat. No. 8,746,535;

U.S. patent application Ser. No. 13/097,891, entitled TISSUE THICKNESS COMPENSATOR FOR A SURGICAL STAPLER COMPRISING AN ADJUSTABLE ANVIL; now U.S. Patent Publication No. 2012/0080489;

U.S. patent application Ser. No. 13/097,948, entitled STAPLE CARTRIDGE COMPRISING AN ADJUSTABLE DISTAL PORTION; now U.S. Patent Publication No. 2012/0083836;

U.S. patent application Ser. No. 13/097,907, entitled COMPRESSIBLE STAPLE CARTRIDGE ASSEMBLY; now U.S. Patent Publication No. 2012/0080338;

U.S. patent application Ser. No. 13/097,861, entitled TISSUE THICKNESS COMPENSATOR COMPRISING PORTIONS HAVING DIFFERENT PROPERTIES; now U.S. Patent Publication No. 2012/0080337;

U.S. patent application Ser. No. 13/097,869, entitled STAPLE CARTRIDGE LOADING ASSEMBLY; now U.S. Patent Publication No. 2012/0160721;

U.S. patent application Ser. No. 13/097,917, entitled COMPRESSIBLE STAPLE CARTRIDGE COMPRISING ALIGNMENT MEMBERS; now U.S. Patent Publication No. 2012/0083834;

U.S. patent application Ser. No. 13/097,873, entitled STAPLE CARTRIDGE COMPRISING A RELEASABLE PORTION; now U.S. Pat. No. 8,740,038;

U.S. patent application Ser. No. 13/097,938, entitled STAPLE CARTRIDGE COMPRISING COMPRESSIBLE DISTORTION RESISTANT COMPONENTS; now U.S. Patent Publication No. 2012/0080491;

U.S. patent application Ser. No. 13/097,924, entitled STAPLE CARTRIDGE COMPRISING A TISSUE THICKNESS COMPENSATOR; now U.S. Patent Publication No. 2012/0083835;

U.S. patent application Ser. No. 13/242,029, entitled SURGICAL STAPLER WITH FLOATING ANVIL; now U.S. Patent Publication No. 2012/0080493;

U.S. patent application Ser. No. 13/242,066, entitled CURVED END EFFECTOR FOR A STAPLING INSTRUMENT; now U.S. Patent Publication No. 2012/0080498;

U.S. patent application Ser. No. 13/242,086, entitled STAPLE CARTRIDGE INCLUDING COLLAPSIBLE DECK; now U.S. Patent Publication No. 2013/0075450;

U.S. patent application Ser. No. 13/241,912, entitled STAPLE CARTRIDGE INCLUDING COLLAPSIBLE DECK ARRANGEMENT; now U.S. Patent Publication No. 2013/0075448;

U.S. patent application Ser. No. 13/241,922, entitled SURGICAL STAPLER WITH STATIONARY STAPLE DRIVERS; now U.S. Patent Publication No. 2013/0075449;

U.S. patent application Ser. No. 13/241,637, entitled SURGICAL INSTRUMENT WITH TRIGGER ASSEMBLY FOR GENERATING MULTIPLE ACTUATION MOTIONS; now U.S. Patent Publication No. 2012/0074201;

U.S. patent application Ser. No. 13/241,629, entitled SURGICAL INSTRUMENT WITH SELECTIVELY ARTICULATABLE END EFFECTOR; now U.S. Patent Publication No. 2012/0074200;

U.S. application Ser. No. 13/433,096, entitled TISSUE THICKNESS COMPENSATOR COMPRISING A PLURALITY OF CAPSULES; now U.S. Patent Publication No. 2012/0241496;

U.S. application Ser. No. 13/433,103, entitled TISSUE THICKNESS COMPENSATOR COMPRISING A PLURALITY OF LAYERS; now U.S. Patent Publication No. 2012/0241498;

U.S. application Ser. No. 13/433,098, entitled EXPANDABLE TISSUE THICKNESS COMPENSATOR; now U.S. Patent Publication No. 2012/0241491; U.S. application Ser. No. 13/433,102, entitled TISSUE THICKNESS COMPENSATOR COMPRISING A RESERVOIR; now U.S. Patent Publication No. 2012/0241497;

U.S. application Ser. No. 13/433,114, entitled RETAINER ASSEMBLY INCLUDING A TISSUE THICKNESS COMPENSATOR; now U.S. Patent Publication No. 2012/0241499;

U.S. application Ser. No. 13/433,136, entitled TISSUE THICKNESS COMPENSATOR COMPRISING AT LEAST ONE MEDICAMENT; now U.S. Patent Publication No. 2012/0241492;

U.S. application Ser. No. 13/433,141, entitled TISSUE THICKNESS COMPENSATOR COMPRISING CONTROLLED RELEASE AND EXPANSION; now U.S. Patent Publication No. 2012/0241493;

U.S. application Ser. No. 13/433,144, entitled TISSUE THICKNESS COMPENSATOR COMPRISING FIBERS TO PRODUCE A RESILIENT LOAD; now U.S. Patent Publication No. 2012/0241500;

U.S. application Ser. No. 13/433,148, entitled TISSUE THICKNESS COMPENSATOR COMPRISING STRUCTURE TO PRODUCE A RESILIENT LOAD; now U.S. Patent Publication No. 2012/0241501;

U.S. application Ser. No. 13/433,155, entitled TISSUE THICKNESS COMPENSATOR COMPRISING RESILIENT MEMBERS; now U.S. Patent Publication No. 2012/0241502;

U.S. application Ser. No. 13/433,163, entitled METHODS FOR FORMING TISSUE THICKNESS COM- PENSATOR ARRANGEMENTS FOR SURGICAL STAPLERS; now U.S. Patent Publication No. 2012/0248169;

U.S. application Ser. No. 13/433,167, entitled TISSUE THICKNESS COMPENSATORS; now U.S. Patent Publication No. 2012/0241503;

U.S. application Ser. No. 13/433,175, entitled LAYERED TISSUE THICKNESS COMPENSATOR; now U.S. Patent Publication No. 2012/0253298;

U.S. application Ser. No. 13/433,179, entitled TISSUE THICKNESS COMPENSATORS FOR CIRCULAR SURGICAL STAPLERS; now U.S. Patent Publication No. 2012/0241505;

U.S. application Ser. No. 13/763,028, entitled ADHESIVE FILM LAMINATE; now U.S. Patent Publication No. 2013/0146643;

U.S. application Ser. No. 13/433,115, entitled TISSUE THICKNESS COMPENSATOR COMPRISING CAPSULES DEFINING A LOW PRESSURE ENVIRONMENT; now U.S. Patent Publication No. 2013/0256372;

U.S. application Ser. No. 13/433,118, entitled TISSUE THICKNESS COMPENSATOR COMPRISED OF A PLURALITY OF MATERIALS; now U.S. Patent Publication No. 2013/0256365;

U.S. application Ser. No. 13/433,135, entitled MOVABLE MEMBER FOR USE WITH A TISSUE THICKNESS COMPENSATOR; now U.S. Patent Publication No. 2013/0256382;

U.S. application Ser. No. 13/433,140, entitled TISSUE THICKNESS COMPENSATOR AND METHOD FOR MAKING THE SAME; now U.S. Patent Publication No. 2013/0256368;

U.S. application Ser. No. 13/433,129, entitled TISSUE THICKNESS COMPENSATOR COMPRISING A PLURALITY OF MEDICAMENTS; now U.S. Patent Publication No. 2013/0256367;

U.S. application Ser. No. 11/216,562, entitled STAPLE CARTRIDGES FOR FORMING STAPLES HAVING DIFFERING FORMED STAPLE HEIGHTS, now U.S. Pat. No. 7,669,746;

U.S. application Ser. No. 11/714,049, entitled SURGICAL STAPLING DEVICE WITH ANVIL HAVING STAPLE FORMING POCKETS OF VARYING DEPTHS, now U.S. Patent Publication No. 2007/0194082;

U.S. application Ser. No. 11/711,979, entitled SURGICAL STAPLING DEVICES THAT PRODUCE FORMED STAPLES HAVING DIFFERENT LENGTHS, now U.S. Pat. No. 8,317,070;

U.S. application Ser. No. 11/711,975, entitled SURGICAL STAPLING DEVICE WITH STAPLE DRIVERS OF DIFFERENT HEIGHT, now U.S. Patent Publication No. 2007/0194079;

U.S. application Ser. No. 11/711,977, entitled SURGICAL STAPLING DEVICE WITH STAPLE DRIVER THAT SUPPORTS MULTIPLE WIRE DIAMETER STAPLES, now U.S. Pat. No. 7,673,781;

U.S. application Ser. No. 11/712,315, entitled SURGICAL STAPLING DEVICE WITH MULTIPLE STACKED ACTUATOR WEDGE CAMS FOR DRIVING STAPLE DRIVERS, now U.S. Pat. No. 7,500,979;

U.S. application Ser. No. 12/038,939, entitled STAPLE CARTRIDGES FOR FORMING STAPLES HAVING DIFFERING FORMED STAPLE HEIGHTS, now U.S. Pat. No. 7,934,630;

U.S. application Ser. No. 13/020,263, entitled SURGICAL STAPLING SYSTEMS THAT PRODUCE FORMED STAPLES HAVING DIFFERENT LENGTHS, now U.S. Pat. No. 8,636,187;

U.S. application Ser. No. 13/118,278, entitled ROBOTICALLY-CONTROLLED SURGICAL STAPLING DEVICES THAT PRODUCE FORMED STAPLES HAVING DIFFERENT LENGTHS, now U.S. Patent Publication No. 2011/0290851;

U.S. application Ser. No. 13/369,629, entitled ROBOTICALLY-CONTROLLED CABLE-BASED SURGICAL END EFFECTORS, now U.S. Patent Publication No. 2012/0138660;

U.S. application Ser. No. 12/695,359, entitled SURGICAL STAPLING DEVICES FOR FORMING STAPLES WITH DIFFERENT FORMED HEIGHTS, now U.S. Pat. No. 8,464,923;

U.S. application Ser. No. 13/072,923, entitled STAPLE CARTRIDGES FOR FORMING STAPLES HAVING DIFFERING FORMED STAPLE HEIGHTS, now U.S. Pat. No. 8,567,656;

U.S. application Ser. No. 13/766,325, entitled LAYER OF MATERIAL FOR A SURGICAL END EFFECTOR; now U.S. Patent Publication No. 2013/0256380;

U.S. application Ser. No. 13/763,078, entitled ANVIL LAYER ATTACHED TO A PROXIMAL END OF AN END EFFECTOR; now U.S. Patent Publication No. 2013/0256383;

U.S. application Ser. No. 13/763,094, entitled LAYER COMPRISING DEPLOYABLE ATTACHMENT MEMBERS; now U.S. Patent Publication No. 2013/0256377;

U.S. application Ser. No. 13/763,106, entitled END EFFECTOR COMPRISING A DISTAL TISSUE ABUTMENT MEMBER; now U.S. Patent Publication No. 2013/0256378;

U.S. application Ser. No. 13/433,147, entitled TISSUE THICKNESS COMPENSATOR COMPRISING CHANNELS; now U.S. Patent Publication No. 2013/0256369;

U.S. application Ser. No. 13/763,112, entitled SURGICAL STAPLING CARTRIDGE WITH LAYER RETENTION FEATURES; now U.S. Patent Publication No. 2013/0256379;

U.S. application Ser. No. 13/763,035, entitled ACTUATOR FOR RELEASING A TISSUE THICKNESS COMPENSATOR FROM A FASTENER CARTRIDGE; now U.S. Patent Publication No. 2013/0214030;

U.S. application Ser. No. 13/763,042, entitled RELEASABLE TISSUE THICKNESS COMPENSATOR AND FASTENER CARTRIDGE HAVING THE SAME; now U.S. Patent Publication No. 2013/0221063;

U.S. application Ser. No. 13/763,048, entitled FASTENER CARTRIDGE COMPRISING A RELEASABLE TISSUE THICKNESS COMPENSATOR; now U.S. Patent Publication No. 2013/0221064;

U.S. application Ser. No. 13/763,054, entitled FASTENER CARTRIDGE COMPRISING A CUTTING MEMBER FOR RELEASING A TISSUE THICKNESS COMPENSATOR; now U.S. Patent Publication No. 2014/0097227;

U.S. application Ser. No. 13/763,065, entitled FASTENER CARTRIDGE COMPRISING A RELEASABLY ATTACHED TISSUE THICKNESS COMPENSATOR; now U.S. Patent Publication No. 2013/0221065;

U.S. application Ser. No. 13/763,021, entitled STAPLE CARTRIDGE COMPRISING A RELEASABLE COVER;

U.S. application Ser. No. 13/763,078, entitled ANVIL LAYER ATTACHED TO A PROXIMAL END OF AN END EFFECTOR; now U.S. Patent Publication No. 2013/0256383;

U.S. application Ser. No. 13/763,095, entitled LAYER ARRANGEMENTS FOR SURGICAL STAPLE CARTRIDGES; now U.S. Patent Publication No. 2013/0161374;

U.S. application Ser. No. 13/763,147, entitled IMPLANT-ABLE ARRANGEMENTS FOR SURGICAL STAPLE CARTRIDGES; now U.S. Patent Publication No. 2013/0153636;

U.S. application Ser. No. 13/763,192, entitled MUL-TIPLE THICKNESS IMPLANTABLE LAYERS FOR SURGICAL STAPLING DEVICES; now U.S. Patent Publication No. 2013/0146642;

U.S. application Ser. No. 13/763,161, entitled RELEAS-ABLE LAYER OF MATERIAL AND SURGICAL END EFFECTOR HAVING THE SAME; now U.S. Patent Publication No. 2013/0153641;

U.S. application Ser. No. 13/763,177, entitled ACTUA-TOR FOR RELEASING A LAYER OF MATERIAL FROM A SURGICAL END EFFECTOR; now U.S. Patent Publication No. 2013/0146641;

U.S. application Ser. No. 13/763,037, entitled STAPLE CARTRIDGE COMPRISING A COMPRESSIBLE PORTION;

U.S. application Ser. No. 13/433,126, entitled TISSUE THICKNESS COMPENSATOR COMPRISING TIS-SUE INGROWTH FEATURES; now U.S. Patent Pub-lication No. 2013/0256366;

U.S. application Ser. No. 13/433,132, entitled DEVICES AND METHODS FOR ATTACHING TISSUE THICKNESS COMPENSATING MATERIALS TO SURGICAL STAPLING INSTRUMENTS; now U.S. Patent Publication No. 2013/0256373.

U.S. application Ser. No. 13/851,703, entitled FAS-TENER CARTRIDGE COMPRISING A TISSUE THICKNESS COMPENSATOR INCLUDING OPEN-INGS THEREIN;

U.S. application Ser. No. 13/851,676, entitled TISSUE THICKNESS COMPENSATOR COMPRISING A CUTTING MEMBER PATH;

U.S. application Ser. No. 13/851,693, entitled FAS-TENER CARTRIDGE ASSEMBLIES;

U.S. application Ser. No. 13/851,684, entitled FAS-TENER CARTRIDGE COMPRISING A TISSUE THICKNESS COMPENSATOR AND A GAP SET-TING ELEMENT;

U.S. patent application Ser. No. 14/187,387, entitled STAPLE CARTRIDGE INCLUDING A BARBED STAPLE; now U.S. Patent Publication No. 2014/0166724;

U.S. patent application Ser. No. 14/187,395, entitled STAPLE CARTRIDGE INCLUDING A BARBED STAPLE; now U.S. Patent Publication No. 2014/0166725;

U.S. patent application Ser. No. 14/187,400, entitled STAPLE CARTRIDGE INCLUDING A BARBED STAPLE; now U.S. Patent Publication No. 2014/0166726;

U.S. patent application Ser. No. 14/187,383, entitled IMPLANTABLE LAYERS AND METHODS FOR

ALTERING IMPLANTABLE LAYERS FOR USE WITH SURGICAL FASTENING INSTRUMENTS;

U.S. patent application Ser. No. 14/187,386, entitled IMPLANTABLE LAYERS AND METHODS FOR ALTERING ONE OR MORE PROPERTIES OF IMPLANTABLE LAYERS FOR USE WITH FAS-TENING INSTRUMENTS;

U.S. patent application Ser. No. 14/187,390, entitled IMPLANTABLE LAYERS AND METHODS FOR MODIFYING THE SHAPE OF THE IMPLANTABLE LAYERS FOR USE WITH A SURGICAL FASTEN-ING INSTRUMENT;

U.S. patent application Ser. No. 14/187,389, entitled IMPLANTABLE LAYER ASSEMBLIES;

U.S. patent application Ser. No. 14/187,385, entitled IMPLANTABLE LAYERS COMPRISING A PRESSED REGION; and U.S. patent application Ser. No. 14/187,384, entitled FASTENING SYSTEM COMPRISING A FIRING MEMBER LOCKOUT.

Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, compo-nents, and elements have not been described in detail so as not to obscure the embodiments described in the specifica-tion. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specifi-cation are not necessarily all referring to the same embodi-ment. Furthermore, the particular features, structures, or characteristics may be combined in any suitable manner in one or more embodiments. Thus, the particular features, structures, or characteristics illustrated or described in con-nection with one embodiment may be combined, in whole or in part, with the features structures, or characteristics of one or more other embodiments without limitation. Furthermore, it will be appreciated that for conciseness and clarity, spatial terms such as "vertical," "horizontal," "up," and "down", for example, may be used herein with respect to the illustrated embodiments. However, these terms are used to assist the reader and are not intended to be limiting and absolute.

Figures 1, 2:
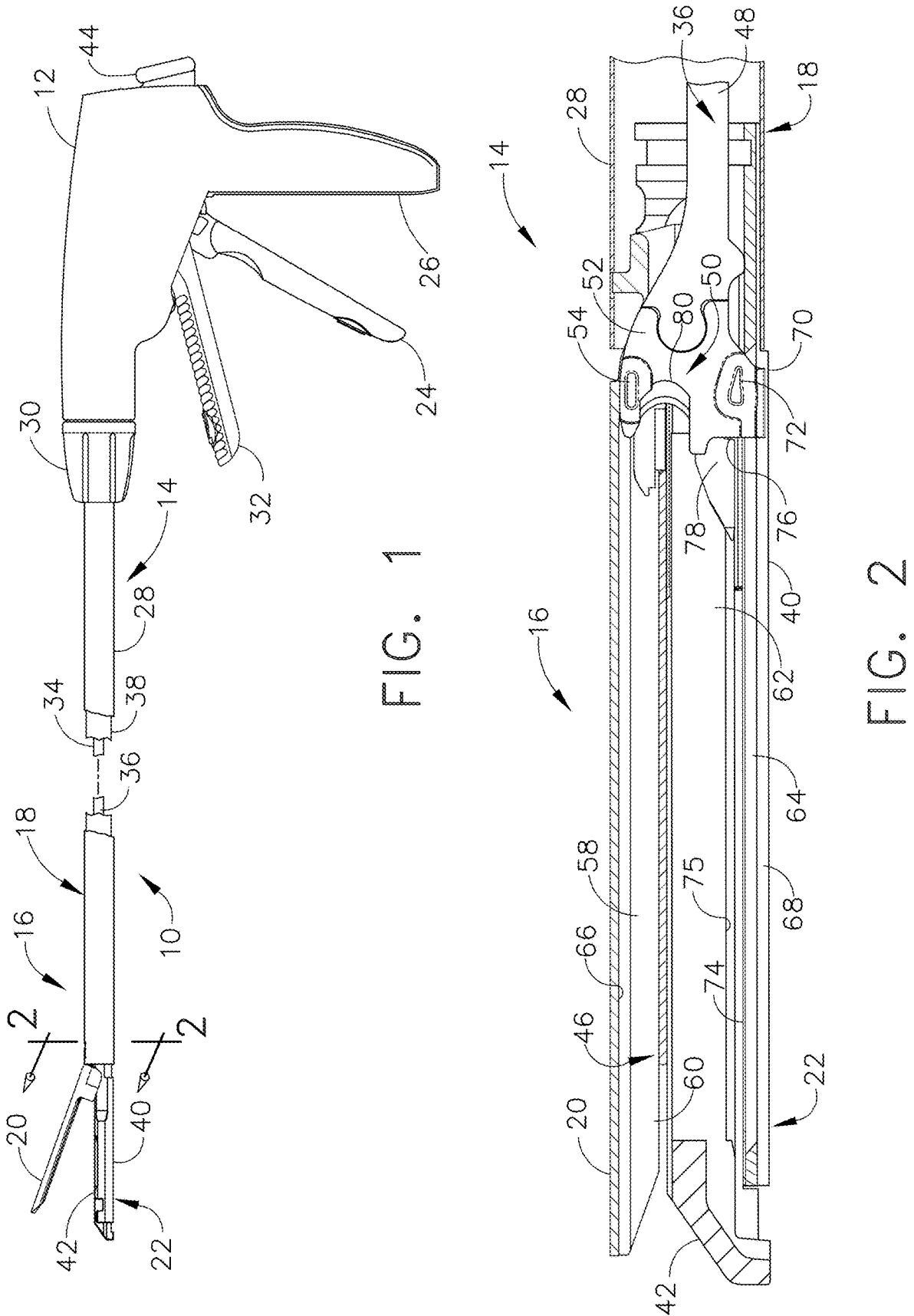
FIG. 1 is an elevational view of a surgical stapling instrument.
FIG. 2 is a cross-sectional view of an end effector of the surgical stapling instrument of FIG. 1 taken along line 2-2 in FIG. 1.

Turning to FIG. 1, a surgical stapling and severing instru-ment 10 can include a handle portion 12 that can be manipulated in order to position an implement portion 14 in a surgical site. In various embodiments, the implement portion 14 can include an end effector 16 attached to an elongate shaft 18. In various circumstances, the implement portion 14 can be sized and configured to be inserted through a cannula of a trocar (not shown) into the surgical site in order to perform an endoscopic or laparoscopic surgical procedure, for example. The end effector 16 can comprise an upper jaw, or anvil, 20 and a lower jaw 22, wherein the anvil 20 can be moved between an open position and a closed position when the closure trigger 24 of the handle portion 12 is moved, or depressed, toward a pistol grip 26 of the handle portion 12. In various embodiments, the depression of the closure trigger 24 can advance an outer closing sleeve 28 of the elongate shaft 18 wherein the outer closing sleeve 28 can contact the anvil 20 and pivot the anvil 20 into its closed position. In certain circumstances, the surgeon may rotate the implement portion 14 about its longitudinal axis by twisting a shaft rotation knob 30. In any event, once the end effector 16 has been inserted into an insufflated body cavity, for example, the closure trigger 24 may be released thereby allowing the anvil 20 to be biased open by a spring (not shown) and positioned relative to the targeted tissue. In various embodiments, the closure trigger 24 can be locked in its depressed condition and, in at least one embodiment, the handle portion 12 can further comprise a lock release actuator 44 which can be depressed to unlock the closure trigger 24. Once the anvil 20 and the lower jaw 22 have been suitably positioned relative to the tissue in the surgical site, the closure trigger 24 can be depressed once again in order to close the anvil 20 and compress the tissue against a staple cartridge 42 attached to the bottom jaw 22.

Figure 3:
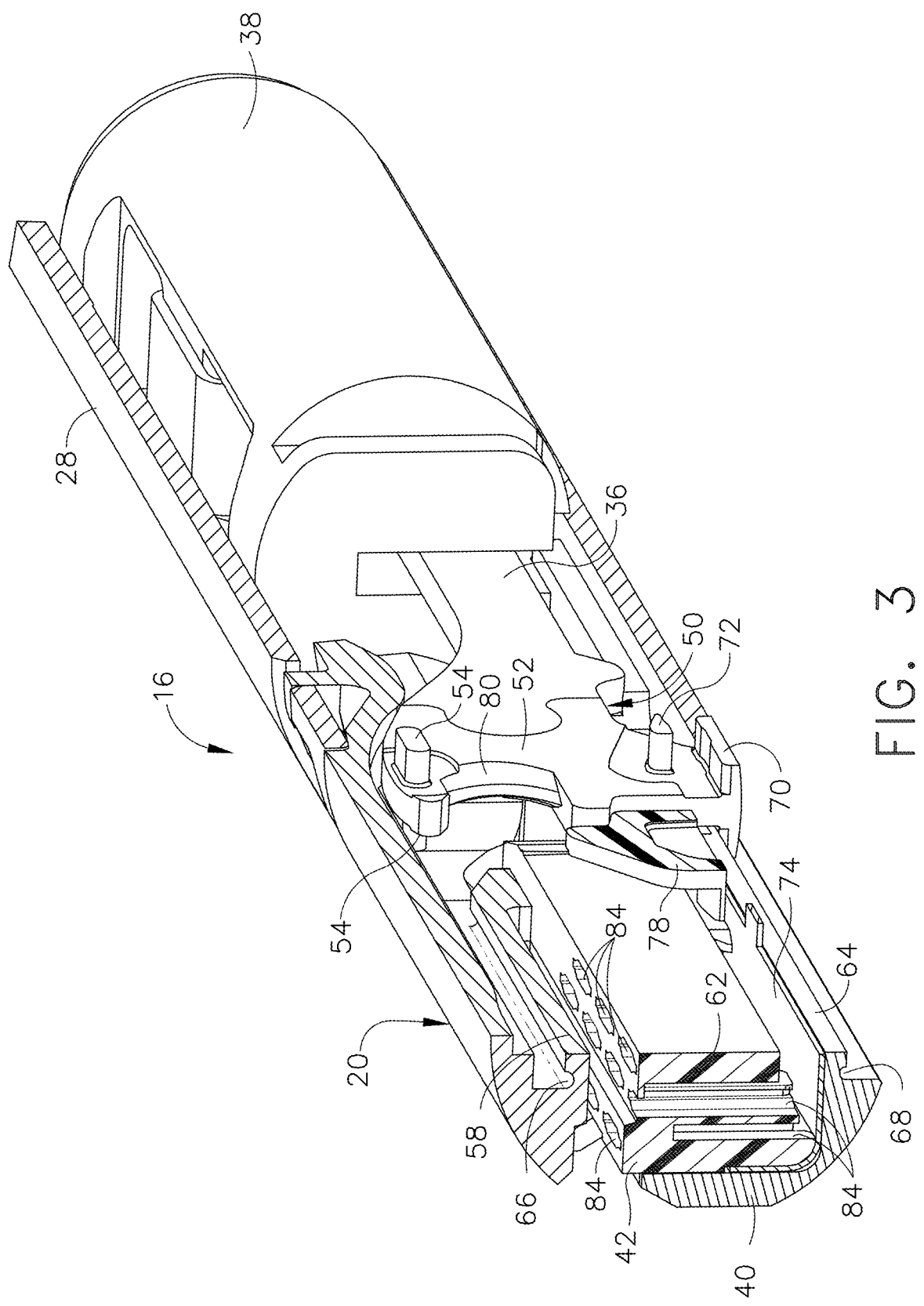
FIG. 3 is a cross-sectional perspective view of the end effector of FIG. 1.

Once the anvil 20 has been closed, a firing trigger 32 can be drawn, or depressed, toward the closure trigger 24 and the pistol grip 26 in order to apply a firing force or motion to a firing member and advance the firing member from an unfired position. In various embodiments, the firing member can comprise a proximal firing rod 34 which is attached to a distal firing bar 36. In at least one such embodiment, the firing rod 34 and/or the firing bar 36 can be supported within a frame 38 in shaft 18 which can extend between the handle portion 12 and the end effector 16. As a result of the firing motion applied to the firing member, the firing bar 36 can be advanced distally within a elongate staple cartridge channel 40 of the lower jaw 22 and a staple cartridge 42 positioned within the cartridge channel 40. In various embodiments, referring to FIG. 2, the firing bar 36 can comprise an attachment portion 48 that is attached to an E-beam 50 which can translate within the end effector 16. The E-beam 50 can comprise a vertical portion 52 which can pass through a narrow longitudinal anvil slot 58 extending through a tissue-contacting surface 60 in the anvil 20, a narrow vertical slot 62 in the staple cartridge 42, and a narrow longitudinal channel slot 64 in the elongate staple channel 40 when the E-beam 50 is advanced distally. Referring now to FIGS. 2 and 3, the anvil slot 58 can extend upwardly into the anvil 20 and can comprise an end which opens into a laterally-widened longitudinal channel 66 sized and configured to receive an upper pin 54 that extends laterally from the vertical portion 52. Similarly, the channel slot 64 can extend downwardly into the channel 40 and can comprise an end which opens into a laterally-widened longitudinal channel 68 sized and configured to receive one or more lower feet 70 extending laterally from the vertical portion 52.

In various embodiments, further to the above, the E-beam 50 can further comprise one or more middle pins 72 which can extend laterally from the vertical portion 52 and can be configured to slide along a top surface of a bottom tray 74 of the staple cartridge 42. In certain embodiments, the middle pins 72 can be configured to seat the staple cartridge 42, or assure that the staple cartridge 42 remains seated, in the channel 40. A longitudinal firing recess 75 formed in the staple cartridge 42 above the bottom tray 74 is sized to allow the middle pins 72 to translate through the staple cartridge

Figure 4:
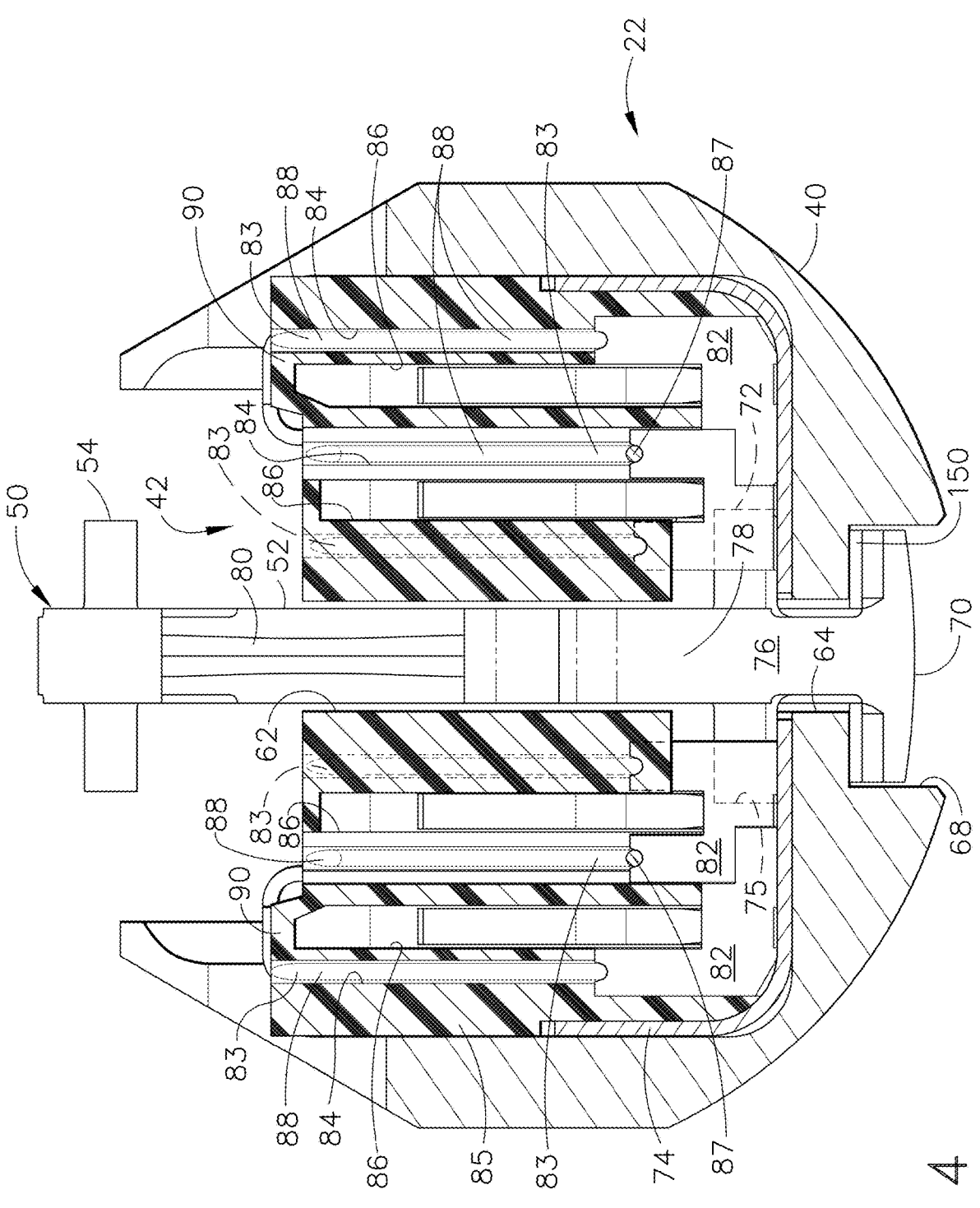
FIG. 4 is a cross-sectional view of the end effector of FIG. 1 illustrating staples contained therein in an unfired configuration.

42. In various embodiments, the E-beam 50 can further comprise a distal drive surface 76 which can be configured to translate through the vertical slot 62 in the staple cartridge 42 and drive a wedge sled 78 distally through the staple cartridge 42. In certain embodiments, the wedge sled 78 can be integrally-formed within the E-beam 50 while, in other embodiments, the wedge sled 78 can reside in the staple cartridge 42 and can be contacted by the drive surface 76 as the E-beam 50 is advanced distally. The vertical portion 52 of the E-beam 50 can further comprise a cutting surface 80 which extends along a distal edge above the distal drive surface 76 and below the upper pin 54 that severs the clamped tissue 46 as the tissue 46 is being stapled. Referring now to FIG. 4, the wedge sled 78 can be configured to engage one or more staple drivers 82 and drive the staple drivers 82 upwardly toward the anvil 20. In various embodiments, staples, such as staples 83, for example, can be seated on and/or otherwise supported by the staple drivers 82 such that, as the staple drivers 82 are lifted upwardly, the staples 83 can be lifted upwardly as well. In at least one such embodiment, the staples 83 can also be at least partially positioned within staple cavities, or pockets, 84 in a staple cartridge body 85 of the staple cartridge 42 wherein, as the staples 83 are lifted upwardly, the staples 83 can contact the anvil 20 and can be ejected from the staple cavities 84. In at least one embodiment, referring again to FIG. 4, the bottom tray 74 can be attached to the cartridge body 85 in order to retain the staple drivers 82 and the staples 83 within the staple cartridge 42 until the staples 83 are deployed therefrom as described above.

Figure 5:
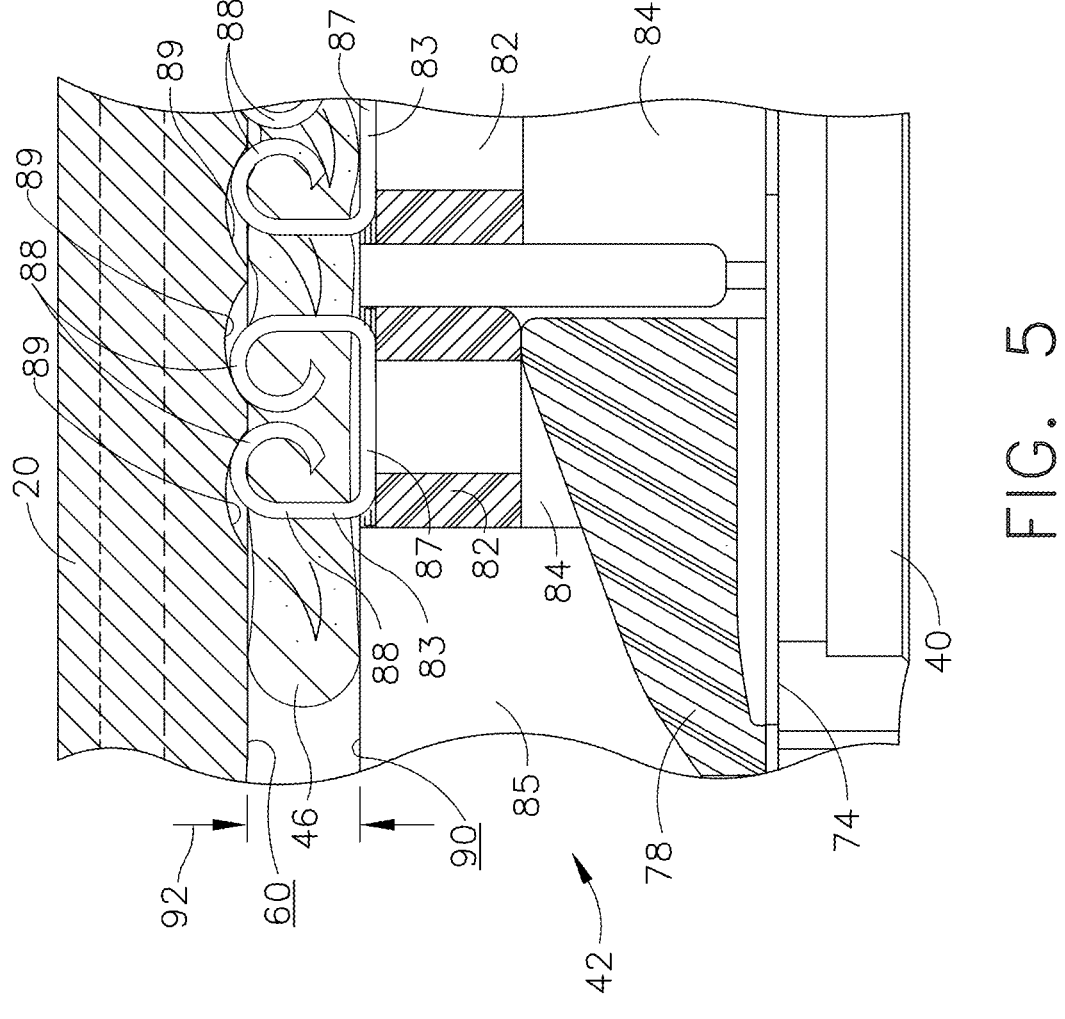
FIG. 5 is a diagram illustrating the staples of FIG. 4 in a fired configuration.
Figure 6:
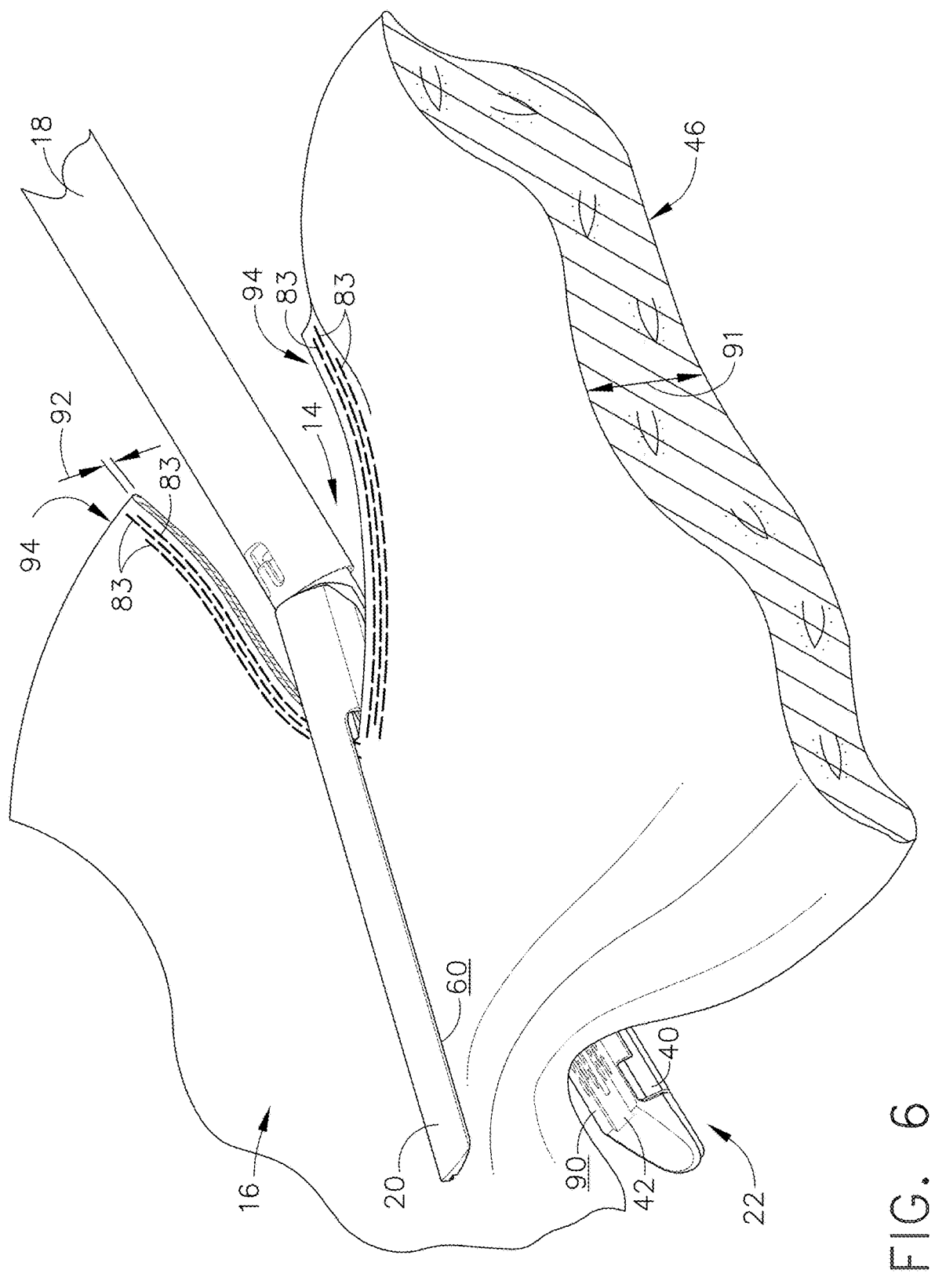
FIG. 6 is a diagram illustrating the end effector of FIG. 1 being used to staple and transect tissue.

In use, referring now to FIGS. 5 and 6, the anvil 20 can be positioned on one side of the tissue 46 and the bottom jaw 22 can be positioned on the opposite side of the tissue 46 such that, when the anvil 20 is closed onto the tissue, the tissue-contacting surface 60 of the anvil 20 and the tissue-contacting deck 90 of the staple cartridge 42 can compress the tissue 46 between an uncompressed thickness 91 and a compressed thickness 92. In order to staple and transect the tissue 46, as described above, the wedge sled 78 can be advanced distally within the staple cartridge 42 in order to lift the staple drivers 82 toward the anvil 20 and deform the staples 83. In various embodiments, each staple driver 82 can comprise one or more slots defined therein which can be configured to receive and releasably hold the bases 87 of the staples 83 in position. In at least one such embodiment, each staple 83 can comprise one or more staple legs 88 extending from the base 87, wherein the staple legs 88 can extend upwardly into the staple cavities 84. In various embodiments, the tips of the staple legs 88 can be recessed with respect to the deck, or tissue-contacting surface, 90 of the cartridge body 85 when the staples 83 are in their unfired position. As the staples 83 are being lifted upwardly by the drivers 82, the tips of the staple legs 88 can emerge from the staple cavities 84, penetrate the tissue 46, and contact the anvil forming pockets 89 positioned opposite the staple cavities 84. The anvil forming pockets 89 can be configured to deform the staples 83 into any suitable shape, such as the B-form shape depicted in FIG. 5, for example. As the staples 83 are deployed, referring now to FIG. 6, the cutting edge 80 can transect the tissue 46 into stapled portions 94.

As described above, the jaw members of an end effector can be configured to apply a compressive pressure, or force, to the tissue being stapled. In various circumstances, however, the tissue can be slippery, for example, and at least a portion of the tissue can slide relative to the jaw members. In certain circumstances, the tissue can slide out of the distal end of the end effector in a longitudinal direction and/or slide out of the sides of the end effector in a direction which is transverse to the longitudinal direction. In some circumstances, portions of the tissue can milk out of the distal end of the end effector and/or the sides of the end effector when the tissue is compressed. In various embodiments disclosed herein, a staple cartridge can comprise one or more tissue retention features which can be configured to prevent, or at least reduce the possibility of, tissue positioned within the end effector from moving relative to the end effector.

Figure 7:
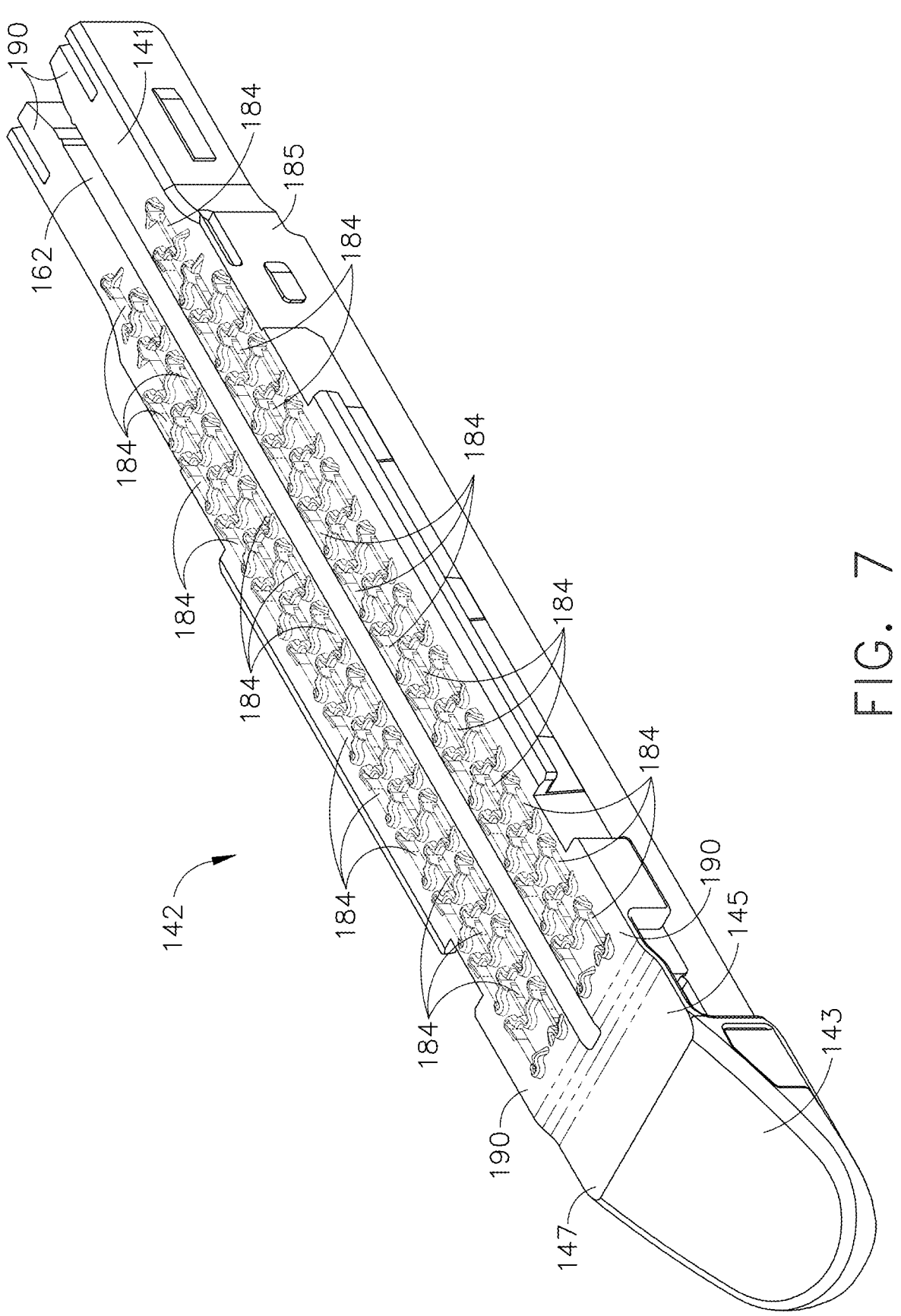
FIG. 7 is a perspective view of a staple cartridge in accordance with at least one embodiment comprising a plurality of ridges extending from a cartridge body.
Figure 8:
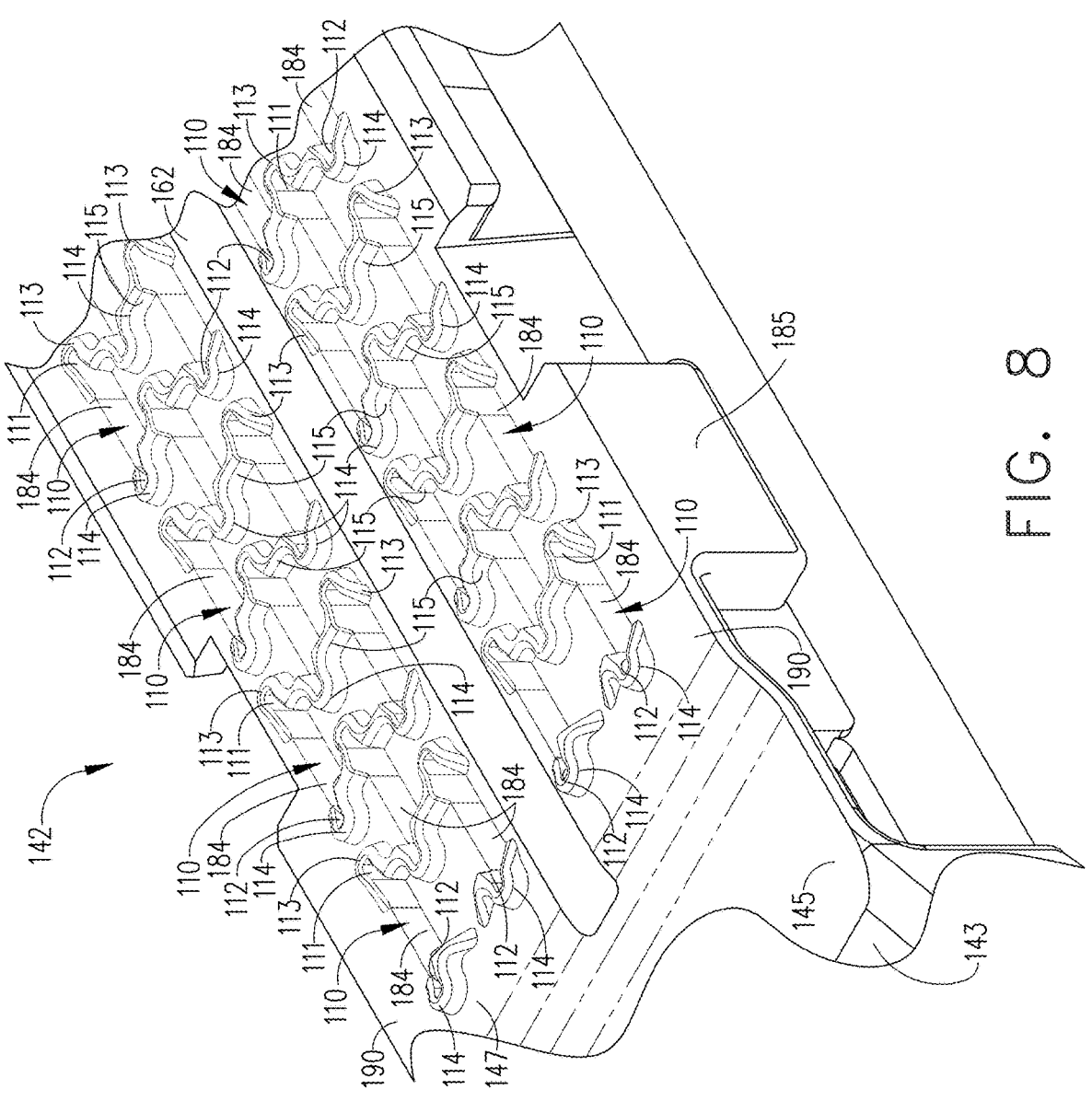
FIG. 8 is a detail view of the staple cartridge of FIG. 7.
Figure 9:
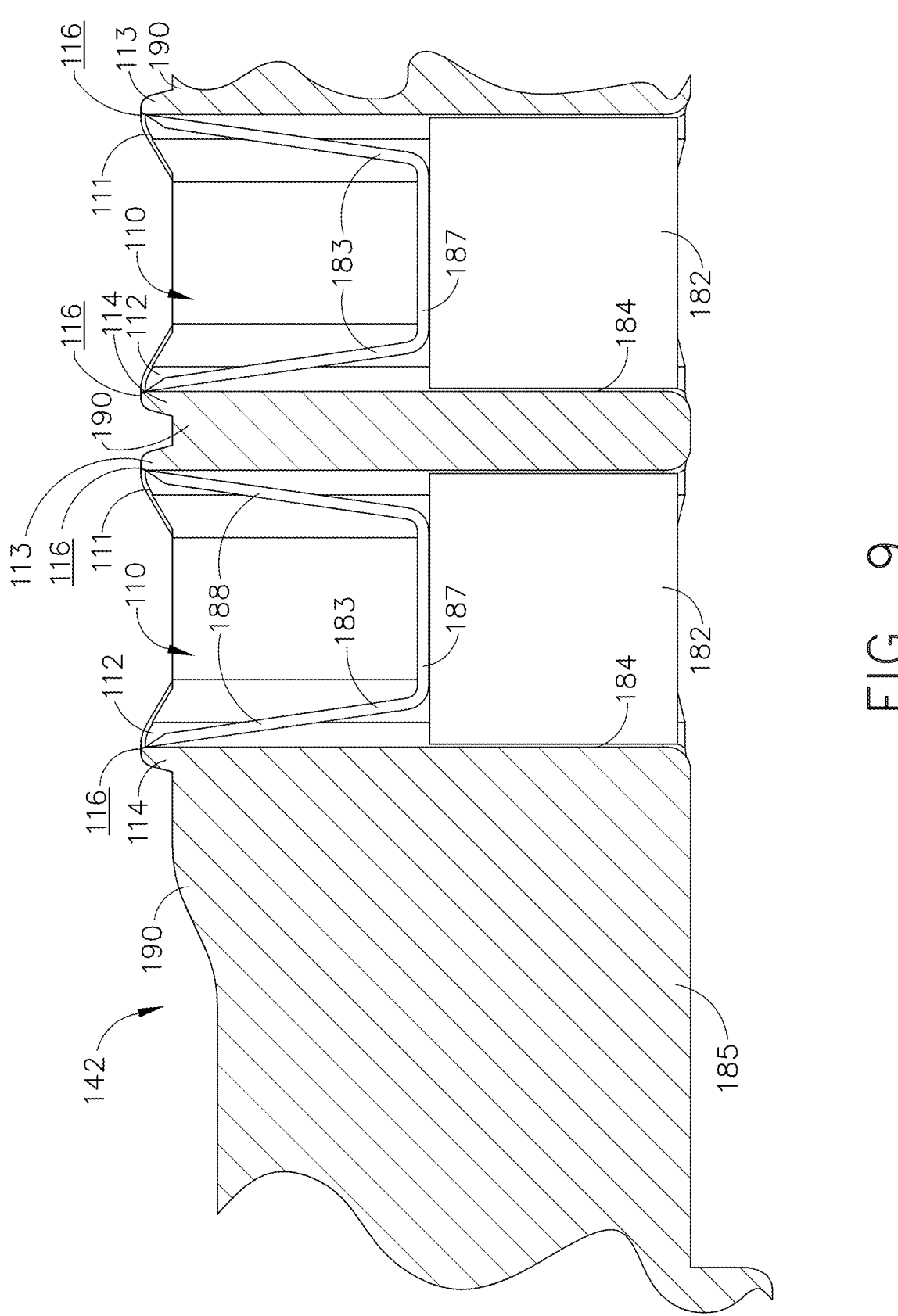
FIG. 9 is a detail view illustrating staples positioned within staple cavities defined in the staple cartridge of FIG. 7.

In various embodiments, referring now to FIGS. 7 and 8, a staple cartridge, such as staple cartridge 142, for example, can comprise a cartridge body 185 and a plurality of staples, such as staples 187 (FIG. 9), for example, positioned within the cartridge body 185. The cartridge body 185 can comprise a proximal end 141 and a distal end 143, wherein the proximal end 141 can be configured to be inserted into a proximal end of a staple cartridge channel and the distal end 143 can be configured to be inserted into a distal end of the staple cartridge channel. In at least one embodiment, the cartridge body 185 can comprise a plurality of staple cavities 184 which can each be configured to receive a staple 187 therein. In certain alternative embodiments, although not illustrated, a staple cavity can comprise more than one staple positioned therein. In any event, the staple cavities 184 can be arranged in a plurality of rows within the cartridge body 185. More particularly, in at least one embodiment, the staple cavities 184 can be arranged in three staple rows, for example, on a first side 145 of the cartridge body 185 and three staple rows, for example, on a second side 147 of the cartridge body 185. In at least one such embodiment, the first side 145 and the second side 147 of the cartridge body 185 can be separated by a knife slot 162 which can be configured to slidably receive a cutting member therein. In various other embodiments, a cartridge can comprise any other suitable number of staple rows, such as two staple rows or four staple rows, for example, on each side of the knife slot 162. Referring to FIG. 9, in various embodiments, the staple cartridge 142 can further comprise a plurality of staple drivers 182 configured to support the staples 187 and/or eject the staples 187 from the staple cavities 184. In certain embodiments, each staple cavity 184 can comprise an open end, or opening, 110 in the deck 190 of the cartridge body 185 through which the staples 187 can be ejected.

In various embodiments, referring primarily to FIG. 8, the staple cavities 184 can be arranged such that they are staggered longitudinally relative to one another. For example, the staple cavities 184 on the first side 145 of the cartridge body 185, for example, can be arranged in an innermost row of staple cavities 184, an intermediate row of staple cavities 184, and an outermost row of staple cavities 184, wherein the staple cavities 184 in one row may not be aligned transversely with the staple cavities 184 in one or both of the other rows. In at least one embodiment, each staple cavity 184 can comprise a proximal end 111 and a distal end 112, wherein the proximal end 111 of each staple cavity 184 can be positioned closer to the proximal end 141 of the cartridge body 185 than the distal end 112. Likewise, the distal end 112 of each cavity 184 can be positioned closer to the distal end 143 of the cartridge body 185 than the proximal end 111. In various embodiments, the innermost row of staple cavities 184 can be positioned such that the distal ends 112 of the staple cavities 184 within the innermost row are positioned distally with respect to the distal ends 112 of the staple cavities 184 in the intermediate row of staple cavities 184. Similarly, the outermost row of staple cavities 184 can be positioned such that the distal ends 112 of the staple cavities 184 within the outermost row are positioned distally with respect to the distal ends 112 of the staple cavities in the intermediate row of staple cavities 184. For example, the distal-most staple cavity 184 in the innermost row can be positioned distally with respect to the distal-most staple cavity 184 in the intermediate row and, similarly, the distal-most staple cavity 184 in the outermost row can be positioned distally with respect to the distal-most staple cavity 184 in the intermediate row. In certain embodiments, the staple cavities 184 of the innermost row and the staple cavities 184 of the outermost row can be aligned transversely with each other such that, one, the distal ends 112 of the innermost staple cavities 184 are aligned with the distal ends 112 of the outermost staple cavities 184 and, two, the proximal ends 111 of the innermost staple cavities 184 are aligned with the proximal ends 111 of the outermost staple cavities 184. In various embodiments, each staple cavity 184, and their openings 110, can have the same, or at least approximately the same, configuration and, in at least one embodiment, the staple cavities 184 can be spaced equidistantly, or at least substantially equidistantly, relative to one another within a staple row.

Figure 8A:
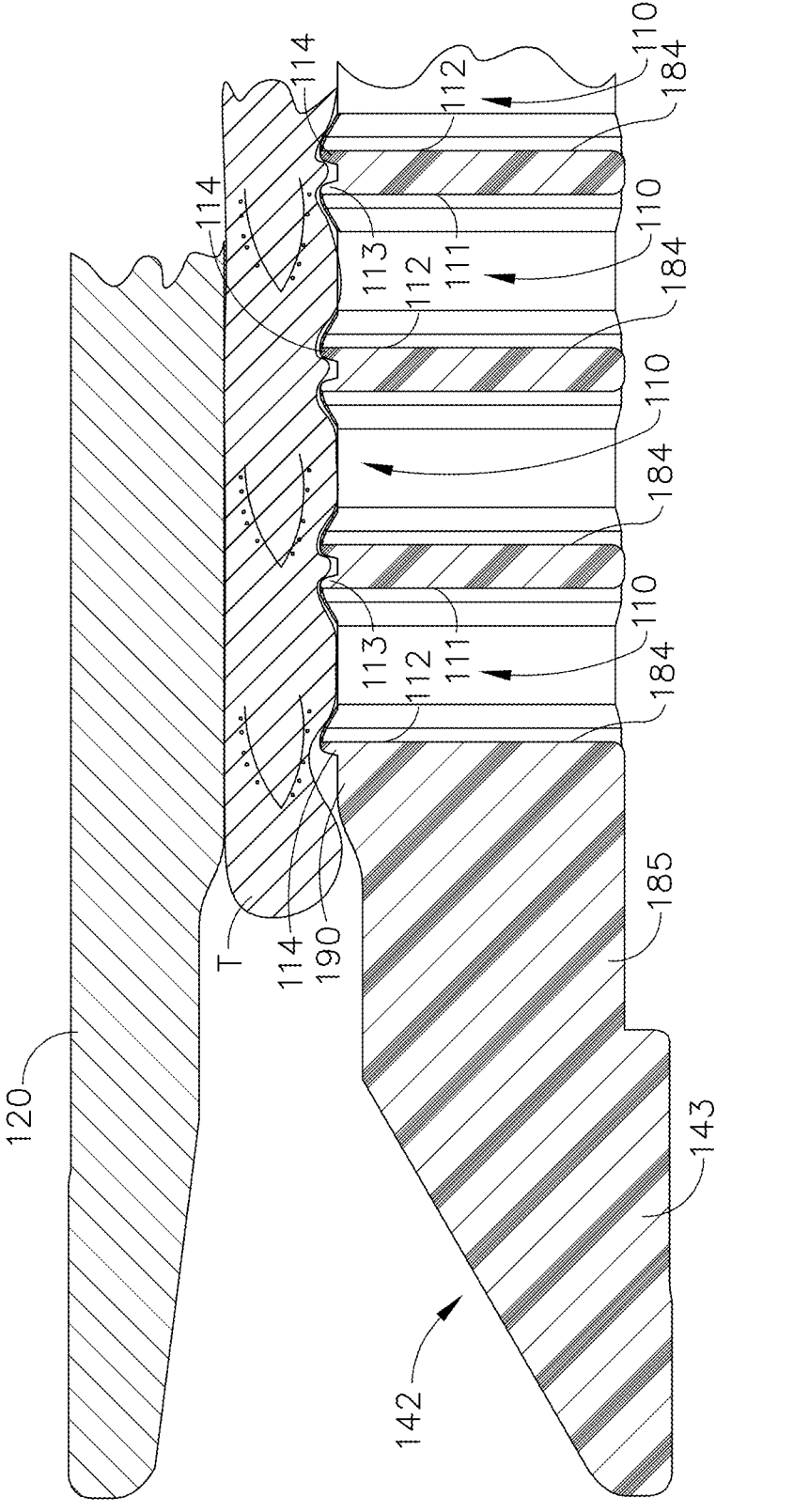
FIG. 8A is a cross-sectional view of the staple cartridge of FIG. 7.

In various embodiments, referring again to FIGS. 7 and 8, the cartridge body 185 of the staple cartridge 142 can further comprise one or more ridges, such as ridges 113, 114, and 115, for example, which can be configured to contact and compress the targeted tissue. More particularly, referring now to FIG. 8A, the anvil 120 of an end effector can be closed in order to compress the tissue T against the staple cartridge 142 wherein, in such circumstances, the tissue-contacting deck 190 and the ridges 113, 114, and 115 extending therefrom can engage the tissue. As the anvil 120 is closed, in certain circumstances, the anvil 120 can push the tissue toward the staple cartridge 142 such that the tissue first contacts the ridges 113, 114, and 115 and then contacts the cartridge deck 190. In other circumstances, the staple cartridge 142 can be positioned against the tissue such that the ridges 113, 114, and 115 contact the tissue before the tissue is contacted by the cartridge deck 190. In any event, the ridges 113, 114, and 115, once in contact in with the tissue, can prevent, or at least limit, relative movement between the tissue and the staple cartridge 142. In certain embodiments, the ridges 113, 114, and 115 can extend upwardly from a flat, or at least substantially flat, cartridge deck 190 and can define one or more pockets or channels, for example, which can be configured to receive a portion of the tissue therein and, as a result, inhibit the relative movement of the tissue in the longitudinal direction and/or the transverse direction of the end effector, especially when the tissue is at least partially compressed between the anvil 120 and the ridges 113, 114, and 115. In various embodiments, as the ridges 113, 114, and 115 extend above the cartridge deck 190, the tissue positioned intermediate the anvil 120 and the ridges 113, 114, and 115 can be compressed before the tissue positioned intermediate the anvil 120 and the cartridge deck 190 is compressed. In some such circumstances, as a result, the tissue positioned between the anvil 120 and the ridges 113, 114, and 115 can be pre-compressed, i.e., at least partially compressed before the other portions of the tissue positioned between the anvil 120 and the cartridge deck 190 are compressed. Owing to this pre-compression, in various circumstances, portions of the tissue can be controlled or prevented from slipping out of the end effector before the tissue is fully compressed as described in greater detail below.

In various embodiments, referring again to FIGS. 7 and 8, the ridges 113 extending from the cartridge deck 190 can extend around the proximal ends 111 of the staple cavity openings 110. Similarly, the ridges 114 extending from the cartridge deck 190 can extend around the distal ends 112 of the staple cavity openings 110. These proximal ridges 113 and distal ridges 114, in various embodiments, can be configured to engage the tissue positioned above and/or around the staple cavities 184 and hold these portions of the tissue in position as the tissue is being compressed and/or stapled. Stated another way, holding the tissue positioned above and/or surrounding the staple cavities 184 can provide localized control over the portions of the tissue that are going to be stapled and, as a result, prevent, or at least limit, the relative movement between these portions of the tissue and the staple cartridge 142. In various embodiments, the ridges 113 and 114 can be positioned around the openings 110 of all of the staple cavities 184 or only some of the staple cavities 184. In at least one embodiment, a cartridge body may comprise ridges 113 and 114 surrounding only the staple cavities 184 in the outermost rows of the first and second sides 145 and 147. In such embodiments, the ridges surrounding the outermost rows of staple cavities 184 may be sufficient to block the lateral movement of the tissue within the end effector. In certain embodiments, a cartridge body may only comprise proximal ridges 113 surrounding the proximal ends 111 of the proximal-most staple cavities 184 and/or distal ridges 114 surrounding the distal ends 112 of the distal-most staple cavities 184. In such embodiments, the ridges surrounding the proximal-most and distal-most staple cavities 184 may be sufficient to block the longitudinal movement of the tissue within the end effector.

In various embodiments, further to the above, each proximal ridge 113 can comprise an arcuate or curved profile, for example, which surrounds a proximal end 111 of an opening 110. The arcuate profile of each proximal ridge 113 can be defined by one radius of curvature or more than one radius of curvature. Similarly, each distal ridge 114 can comprise an arcuate or curved profile, for example, which surrounds a distal end 112 of an opening 110. The arcuate profile of each distal ridge 114 can be defined by one radius of curvature or more than one radius of curvature. In certain embodiments, further to the above, each ridge 113 and 114 can form a pocket which can receive a portion of tissue that is being compressed and prevent that portion of tissue from moving longitudinally and/or transversely relative to the staple cartridge 142. In various embodiments, the staple cartridge 142 can further comprise intermediate ridges 115 which can extend between and/or connect adjacent ridges 113 and 114 in adjacent rows of staple cavities 184. In at least one such embodiment, one or more ridges 113, 114, and 115 can co-operatively form an undulating ridge extending across the first side 145 or the second side 147 of the cartridge body 185 wherein, in at least one embodiment, the undulating ridge can extend between a center portion and a side portion of the cartridge body 142. In various embodiments, each undulating ridge can comprise a plurality of wave portions winding around the proximal and distal ends of the staple cavities 184, for example. In various embodiments, each ridge 113, 114, and 115 can comprise a height defined from the cartridge deck 190 wherein, in certain embodiments, the height of each ridge 113, 114, and 115 can be uniform, or at least substantially uniform, across the length thereof. In at least one embodiment, each ridge 113, 114, and 115 can have the same, or at least substantially the same, height.

In various embodiments, as described above, the staple cavities defined in a staple cartridge body can comprise a staple positioned therein wherein the entirety of the staple can be positioned below the top surface, or tissue-contacting surface, of the cartridge deck when the staple is in its unfired position. In certain other embodiments, at least a portion of the staple, such as the tips of the staple legs, for example, can extend above the top surface, or tissue-contacting surface, of the cartridge deck when the staples are in their unfired position. In some such embodiments, the tips of the staples can protrude from the deck and may snag on tissue as the staple cartridge is inserted into a surgical site. In at least one embodiment, referring now to FIG. 9, the ridges 113 and 114, for example, which extend above the tissue-contacting cartridge deck 190, can at least partially surround and protect the staple legs 183 of staples 187 when they extend above the cartridge deck 190 in their unfired position. Although the ridges 113 and 114 may not extend entirely around each opening 110, in various embodiments, the proximal ridge 113 may sufficiently surround one of the staple leg tips and the distal ridge 114 may sufficiently surround the other staple leg tip such that the staple leg tips do not contact the tissue prior to the tissue being compressed against the staple cartridge 142 and/or the staples 187 being ejected from the staple cartridge 142. In at least one embodiment, the staple leg tips can be positioned below the top surfaces 116 of the ridges 113 and 114. In certain embodiments, the staple leg tips can lie in a common plane with the top surfaces 116 of the ridges 113 and 114. In various embodiments, as a result of the protection afforded by the ridges 113 and 114, for example, staples having a taller staple height can be used without the staple tips protruding from the staple cartridge 142 in their unfired position. In certain embodiments, referring again to FIG. 9, the ridges 113 and 114 can extend or increase the length in which the staple legs 183 of the staples 187 can be controlled and/or supported. In at least one such embodiment, each ridge 113 and 114 can extend or increase the length in which the staple legs 183 are supported on three sides thereof. Such embodiments can prevent, or at least reduce the possibility of, the staple legs 183 from buckling when they are inserted through dense tissue, such as bronchus tissue, for example.

In various embodiments, referring again to FIG. 4, the cartridge body 85 can comprise cavities 84, slot 62, and channels 86, for example, defined therein which can reduce the strength of the cartridge body 85. In various circumstances, especially when the cartridge body 85 is compressed by the anvil 20, for example, the cartridge body 85 can deflect as a result of the load applied thereto. In at least one such embodiment, the portions of the cartridge deck 90 extending over the channels 86, for example, may be especially thin and may be especially subject to deflection and/or breakage. In certain embodiments, referring again to FIGS. 7 and 8, the ridges 113, 114, and/or 115 can be configured to strengthen and/or stiffen the cartridge body 185. In at least one such embodiment, the ridges 113 and 114, for example, can extend around the openings 110 in order to strengthen and/or stiffen the portions of the cartridge body 185 surrounding the staple cavities 184. In certain embodiments, the ridges 115, for example, can extend transversely over channels 86, or the like, defined within the cartridge body 185 such that the ridges 115 can strengthen and/or stiffen the cartridge body 185 surrounding the channels 86. In various other embodiments, the cartridge body 185 can comprise any suitable number and configuration of ridges extending therefrom in order to achieve the advantages described herein.

In various embodiments, a staple cartridge body 185 can be comprised of plastic materials, metallic materials, and/or ceramic materials, for example. Some such materials can comprise liquid crystal polymers, such as Vectra, for example, thermoplastic polymers, such as polycarbonate, ABS, Noryl, polyamides (nylons), polyethersulfones, polyetherimides, such as Ultem, for example, and/or polymer blends of two or more of the aforementioned thermoplastic polymers, for example, wherein, in various embodiments, the cartridge body 185 can be formed by an injection molding process, for example. Some such materials can comprise thermoset polymers, like thermoset polyesters, for example, investment cast stainless steels, such as 17-4 PH, for example, and/or metal Injection molded stainless steels, such as 17-4 PH, for example. In at least one such embodiment, the ridges 113, 114, and/or 115 can be integrally formed with the cartridge deck 190 of the cartridge body 185. In certain embodiments, the ridges 113, 114, and/or 115 can be attached to the cartridge deck 190 by at least one adhesive, for example.

Figure 12:
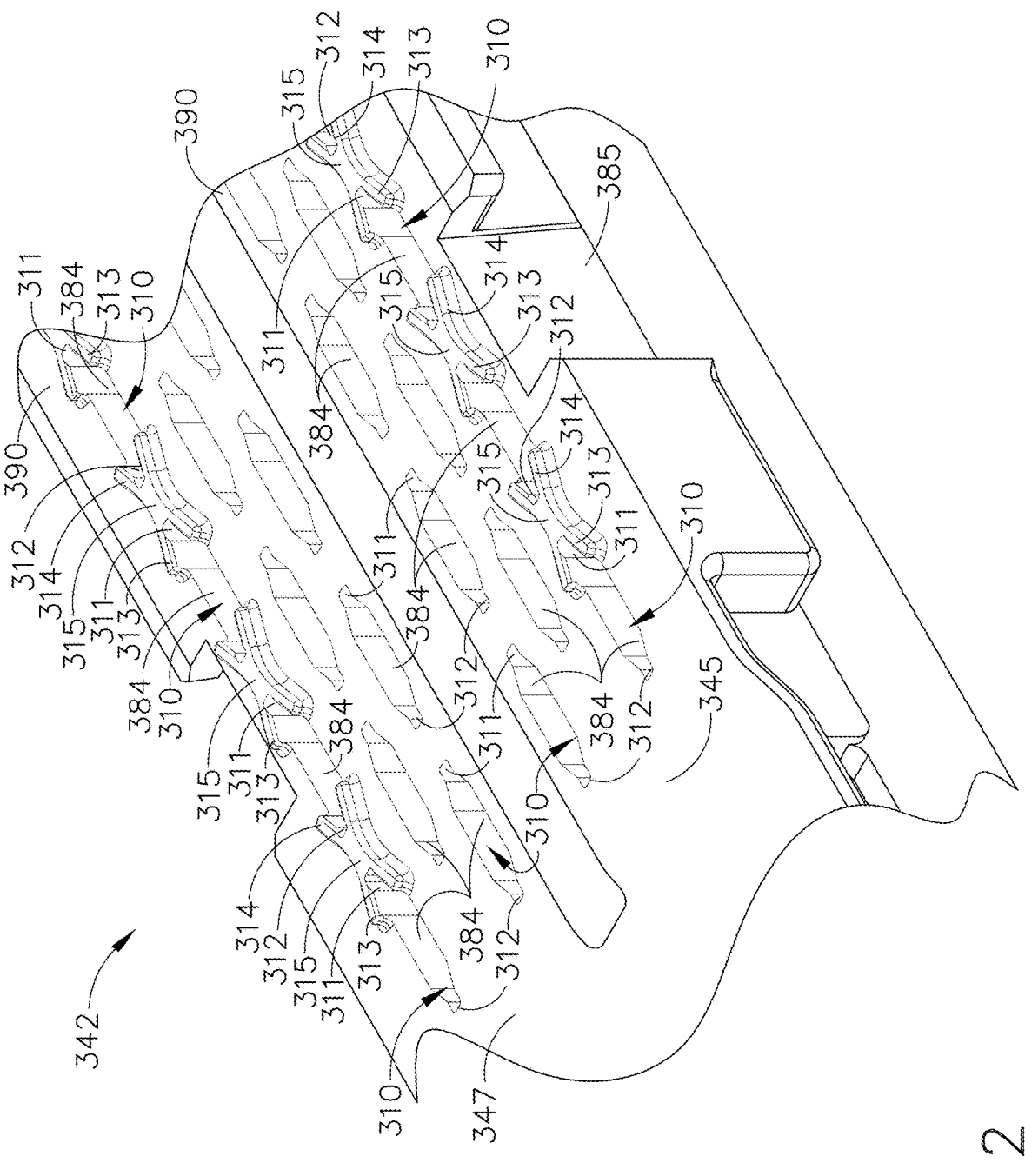
FIG. 12 is a partial perspective view of a staple cartridge in accordance with at least one alternative embodiment comprising a plurality of ridges surrounding the proximal and distal ends of staple cavity openings defined in a cartridge body.
Figure 13:
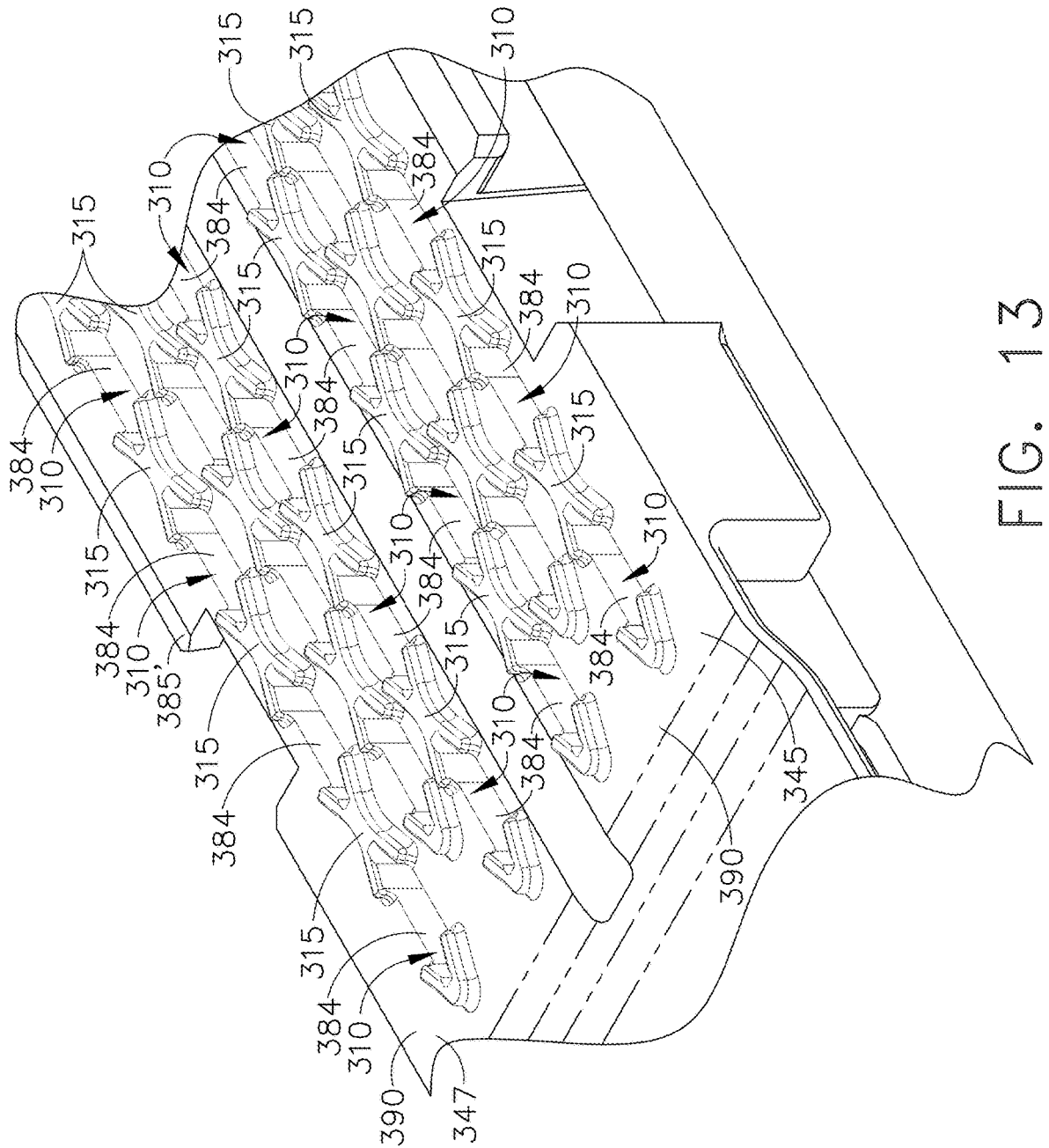
FIG. 13 is a partial perspective view of a staple cartridge in accordance with at least one alternative embodiment comprising a plurality of ridges surrounding the proximal and distal ends of staple cavity openings defined in a cartridge body.

In various embodiments, referring now to FIG. 12, a staple cartridge, such as staple cartridge 342, for example, can comprise a cartridge body 385, a plurality of staple cavities 384 defined in the cartridge body 385, and a staple positioned in each of the staple cavities 384. In certain embodiments, the cartridge body 385 can further comprise a first side 345 comprising a first group of staple cavities 384, a second side 347 comprising a second group of staple cavities 384, and a cartridge deck 390. In various embodiments, the cartridge body 385 can further comprise a plurality of ridges 315 extending from the cartridge deck 390 which can be positioned intermediate adjacent staple cavities 384 in a row of staple cavities 384. In at least one embodiment, each ridge 315 can comprise a cross-shaped or X-shaped configuration, for example. In at least one such embodiment, for example, each ridge 315 can comprise a V-shaped portion 313 which can at least partially surround a proximal end 311 of a staple cavity opening 310 and, in addition, a V-shaped portion 314 which can at least partially surround a distal end 312 of another staple cavity opening 310. In certain embodiments, only the outermost rows of staple cavities 384 in cartridge body 385 can be at least partially surrounded by ridges 315. In certain other embodiments, referring now to FIG. 13, a staple cartridge body 385' can comprise ridges 315 which at least partially surround the opening 310 of every staple cavity 384 in the cartridge body. In any event, in various embodiments, each ridge 315 can be configured to compress and control tissue positioned against the staple cartridge 342 as described above and/or surround the staple legs of the staples extending above the deck 390.

In various embodiments, referring now to FIG. 16, a staple cartridge, such as staple cartridge 542, for example, can comprise a cartridge body 585, a plurality of staple cavities 584 defined in the cartridge body 585, and a staple positioned in each of the staple cavities 584. In certain embodiments, the cartridge body 585 can further comprise a first side 545 comprising a first group of staple cavities 584, a second side 547 comprising a second group of staple cavities 584, and a cartridge deck 590. In various embodiments, the cartridge body 585 can further comprise a plurality of ridges 515 extending from the cartridge deck 590, wherein each ridge 515 can entirely surround or encompass a staple cavity opening 510. As illustrated in FIG. 16, some cavity openings 510 in the cartridge body 585 may not be surrounded by a ridge 515; whereas, in various alternative embodiments, referring now to FIG. 16A, every cavity opening 510 in a cartridge body 585' can be surrounded by a ridge 515. Various embodiments are contemplated where a cartridge body comprises a first group of staple cavities 584 which are surrounded by a ridge 515 and a second group of staple cavities 584 which are not surrounded by a ridge 515, wherein staples having a taller staple height can be positioned in the first group of staple cavities 584 and wherein staples having a shorter staple height can be positioned in the second group of staple cavities 584 such that neither the taller staples nor the shorter staples protrude from the staple cartridge 542. In at least one such embodiment, for example, the cartridge body can be configured to utilize taller staples in one row of staple cavities 584 and shorter staples in another row of staple cavities 584. In certain embodiments, ridges 515 can surround all of the staple cavities 584 in the outermost rows of staple cavities 584 in the cartridge body such that taller staples can be utilized in the outermost rows and shorter staples can be utilized in the innermost rows and/or intermediate rows of staple cavities 584, for example.

Figure 14:
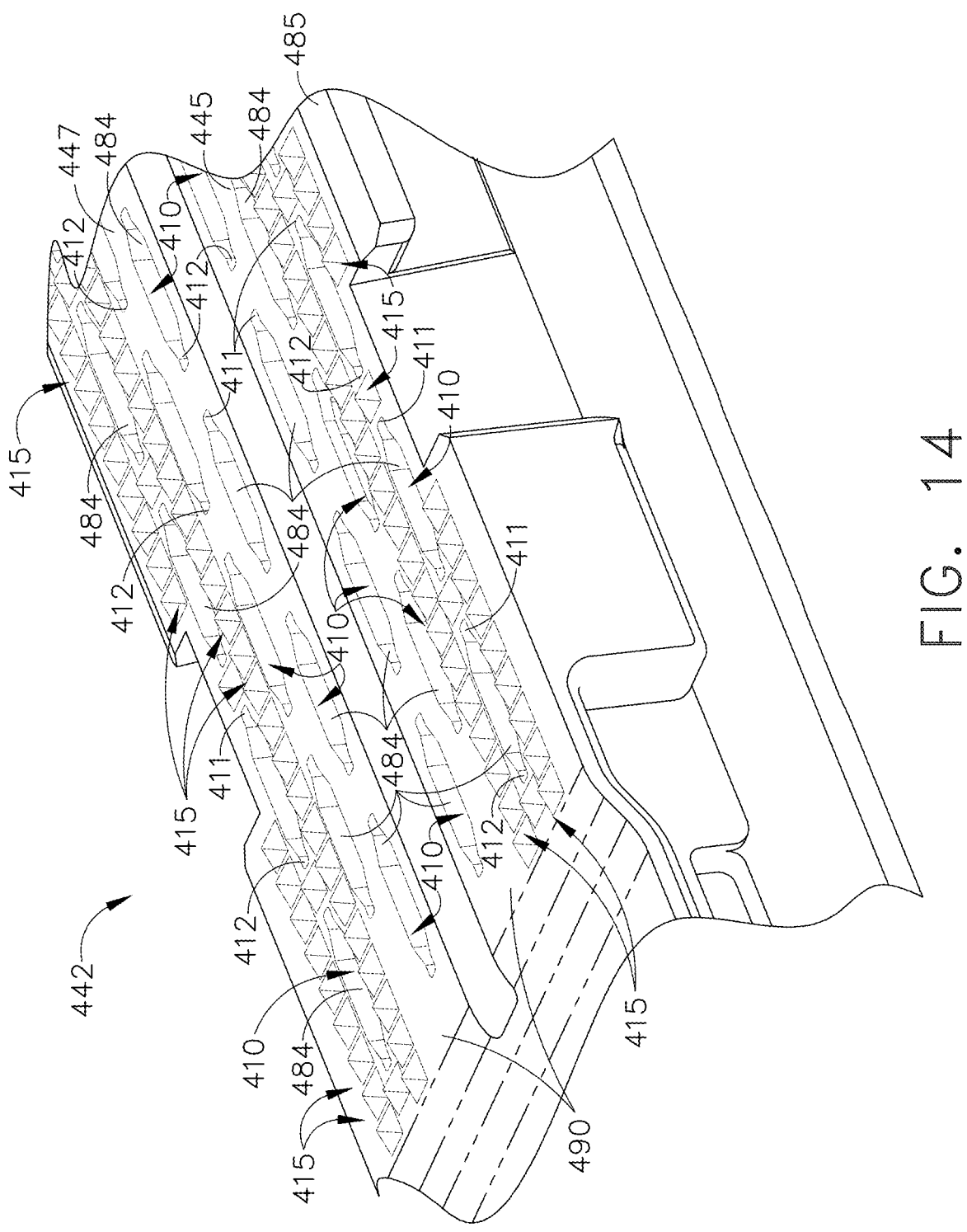
FIG. 14 is a partial perspective view of a staple cartridge in accordance with at least one alternative embodiment comprising a plurality of knurled ridges extending from a cartridge body.

In various embodiments, referring now to FIG. 14, a staple cartridge, such as staple cartridge 442, for example, can comprise a cartridge body 485, a plurality of staple cavities 484 defined in the cartridge body 485, and a staple positioned in each of the staple cavities 484. In certain embodiments, the cartridge body 485 can further comprise a first side 445 comprising a first group of staple cavities 484, a second side 447 comprising a second group of staple cavities 484, and a cartridge deck 490. In various embodiments, the cartridge body 445 can further comprise a plurality of ridges 415 extending from the cartridge deck 490, wherein each ridge 415 can comprise a plurality, or array, of knurls. In use, an anvil can be utilized to position tissue against the knurls such that the tissue conforms to the contour of the knurls. In various embodiments, each ridge 415 can comprise a plurality of pyramidal-shaped, or diamond-shaped, knurls, for example, at least partially surrounding one or more staple cavity openings 410 wherein, in at least one embodiment, the pyramidal-shaped knurls can point upwardly from the cartridge deck 490. In at least one embodiment, each pyramidal knurl can comprise four triangular sides which can converge together to form a sharp point. In certain embodiments, referring to FIG. 15A, the pyramidal knurls of ridges 415 can be truncated, wherein the top of each knurl can comprise a flat top surface surrounded by inclined sides. Although four-sided pyramidal knurls can be utilized, referring now to FIG. 15C, other pyramidal shapes are contemplated which have less than four sides or more than four sides, such as three sides, for example. In various embodiments, one or more ridges 415 can comprise a plurality of cone-shaped knurls, wherein each cone-shaped knurl can comprise a circular, or at least substantially circular, base which tapers upwardly to form a sharp point. In certain embodiments, referring now to FIG. 15B, the cone-shaped knurls can be truncated, wherein the top of each knurl can comprise a flat top surface surrounded by an annular side. In various embodiments, referring again to FIG. 14, the knurls of the ridges 415 can extend along the lateral sides of the staple cavity openings 410 and/or between adjacent staple cavity openings 410. In at least one embodiment, the knurls can extend around the proximal ends 411 and/or the distal ends 412 of the staple cavity openings 410. In certain embodiments, the knurls of ridges 415 may only surround some of the staple cavities 484 while, in certain other embodiments, referring to FIG. 15, the knurls of ridges 415 may cover the entirety, or at least the substantial entirety, of the cartridge deck 490, for example.

Figure 10:
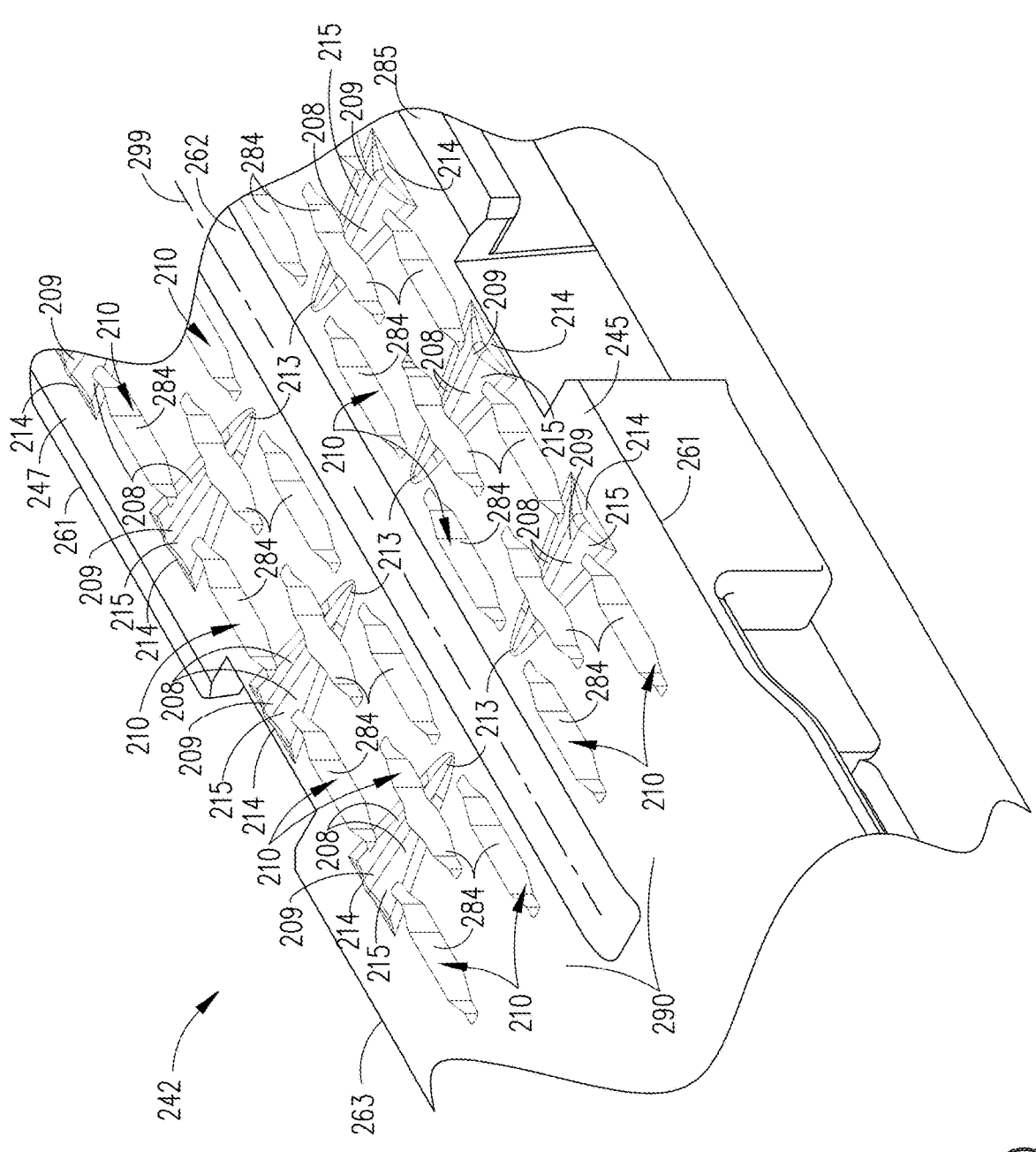
FIG. 10 is a partial perspective view of a staple cartridge in accordance with at least one alternative embodiment comprising a plurality of transverse ridges extending from a cartridge body.
Figure 11:
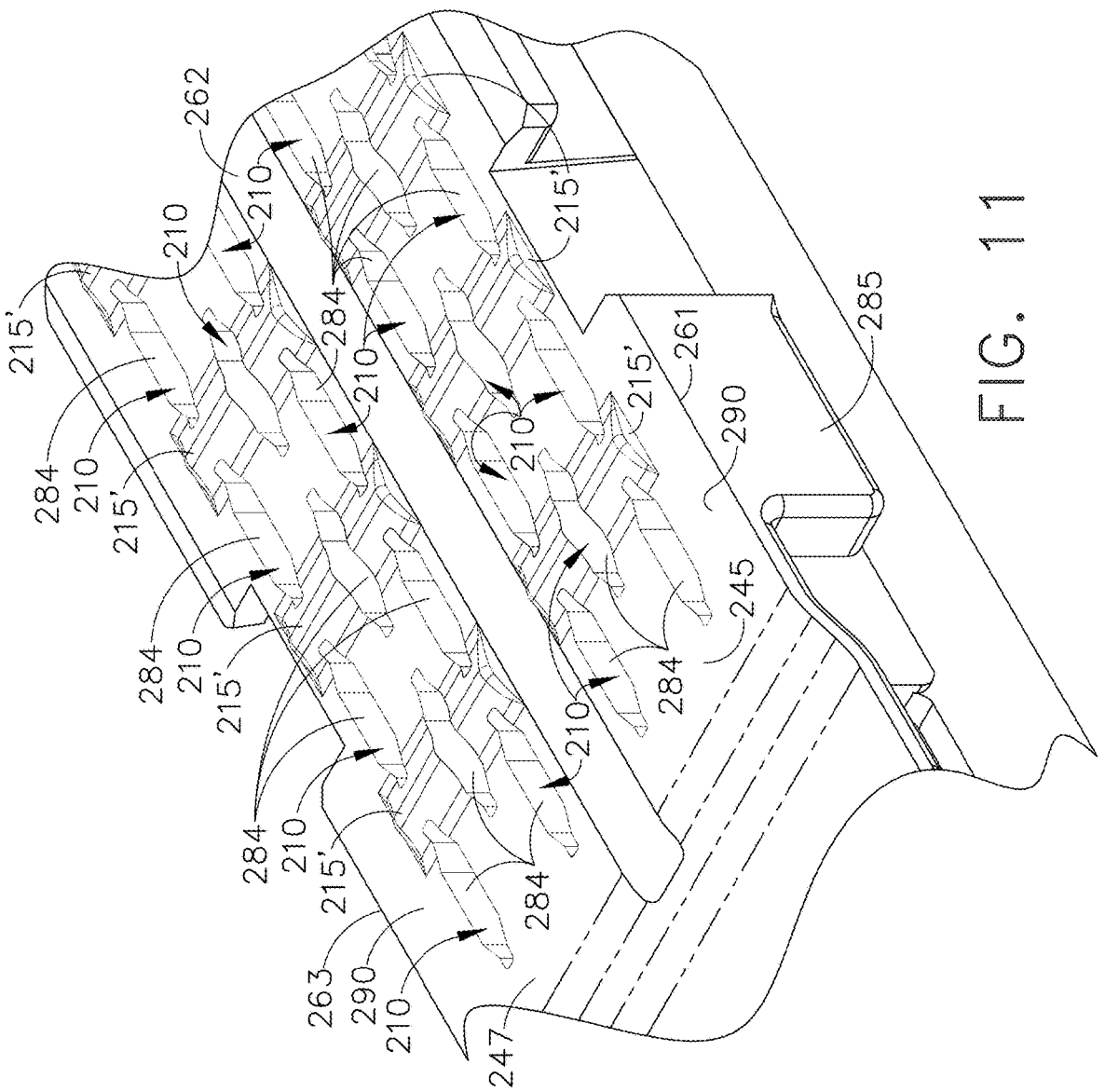
FIG. 11 is a partial perspective view of a staple cartridge in accordance with at least one alternative embodiment comprising a plurality of transverse ridges extending from a cartridge body.

In various embodiments, referring now to FIG. 10, a staple cartridge, such as staple cartridge 242, for example, can comprise a cartridge body 285, a plurality of staple cavities 284 defined in the cartridge body 285, and a staple positioned in each of the staple cavities 284. In certain embodiments, the cartridge body 285 can further comprise a first side 245 comprising a first group of staple cavities 284, a second side 247 comprising a second group of staple cavities 284, and a cartridge deck 290. In various embodiments, the cartridge body 285 can further comprise a plurality of ridges, or bumps, 215 extending from the cartridge deck 290. In at least one such embodiment, each ridge 215 can extend transversely between a center, or middle, portion of the cartridge body 245 positioned adjacent to a knife slot 262 and a lateral portion of the cartridge body 245. More particularly, referring specifically to the first side 245 of the cartridge body 285, each ridge 215 can comprise a first end 213 positioned adjacent to the knife slot 262 and a second end 214 positioned adjacent to the first side 261 of the cartridge body 285. Similarly, referring now to the second side 247 of the cartridge body 285, each ridge 215 can comprise a first end 213 positioned adjacent to the knife slot 262 and a second end 214 positioned adjacent to the second side 263 of the cartridge body 285. In at least one embodiment, each ridge 215 can comprise a height measured from the deck 290 wherein, in at least one such embodiment, the height of each ridge 215 can vary along the length thereof. In certain embodiments, the second end 214 can be taller than the first end 213 and the height of each ridge 215 can taper between the second end 214 and the first end 213. In certain alternative embodiments, although not illustrated, the first end 213 of the ridge 215 can be taller than the second end 214. In at least one embodiment, the height of each ridge 215 can taper linearly, or at least substantially linearly, between the ends 213 and 214. In at least one such embodiment, the height of each ridge 215 can taper between a maximum height at the second end 214 down to no height at all at the first end 213. In certain embodiments, the height of each ridge 215 can vary geometrically between the ends 213 and 214. In certain alternative embodiments, referring now to FIG. 11, each ridge 215' can comprise a uniform height across the length thereof.

As described above, the inner ends 213 of the ridges 215 can be shorter than the outer ends 214 of the ridges 215. In various circumstances, as a result, the inner ends 213 can apply less pressure to the tissue clamped between an anvil and the staple cartridge 242 as compared to the outer ends 214. In various embodiments, as described above, each ridge 215 can extend transversely across the cartridge deck 290. In certain embodiments, each ridge 215 can extend along a ridge axis which transects a longitudinal axis 299 of the cartridge body 285. In at least one such embodiment, the ridge axes can be perpendicular, or at least substantially perpendicular, to the longitudinal axis 299. In various embodiments, the staple cavities 284 can be arranged in a plurality of rows, wherein each row of staple cavities 284 can be defined along a longitudinal axis which can be parallel to, or at least substantially parallel to, the longitudinal axis 299. In at least one embodiment, the ridge axes of the ridges 215 can extend in a direction which transect the longitudinal axes of the staple cavities 284. In at least one such embodiment, the ridge axes of the ridges 215 can extend in a direction which is perpendicular, or at least substantially perpendicular, to the longitudinal axes of the staple cavities 284. In various embodiments, referring again to FIG. 10, each ridge 215 can comprise a crest 209 and, in addition, sloped surfaces 208 extending between the crest 209 and the cartridge deck 290. In certain embodiments, each sloped surface 208 can comprise one or more flat surfaces, curved surfaces, concave surfaces, and/or convex surfaces, for example. In various embodiments, each ridge 215 can extend along a path which extends across one or more openings 210 of the staple cavities 284. In at least one such embodiment, such openings 210 can extend upwardly through the ridges 215. As the ridges 215 extend transversely across the cartridge deck 290, the ridges 215, similar to the ridges 115, can increase the strength and/or stiffness of the cartridge body 285.

In various embodiments, referring now to FIGS. 17 and 18, a staple cartridge, such as staple cartridge 642, for example, can comprise a cartridge body 685, a plurality of staple cavities 684 defined in the cartridge body 685, and a staple positioned in each of the staple cavities 684. In certain embodiments, the cartridge body 685 can further comprise a first side 645 comprising a first group of staple cavities 684, a second side 647 comprising a second group of staple cavities 684, and a cartridge deck 690. In various embodiments, the cartridge body 685 can further comprise a plurality of ridges, or bumps, 615 extending from the cartridge deck 690. In at least one such embodiment, each ridge 615 can extend in a longitudinal direction, wherein each ridge 615 can comprise a distal end 613 and a proximal end 614, wherein the distal end 613 of the ridge 615 can positioned closer to the distal end 643 of the cartridge body 685, and wherein the proximal end 614 of the ridge 615 can be positioned closer to the proximal end 641. In at least one embodiment, each ridge 615 can comprise a height measured from the deck 690 wherein, in at least one such embodiment, the height of each ridge 615 can vary along the length thereof. In certain embodiments, the proximal end 614 can be taller than the distal end 613 and the height of each ridge 615 can taper between the proximal end 614 and the distal end 613. In certain alternative embodiments, although not illustrated, the distal end 613 of the ridge 615 can be taller than the proximal end 614. In at least one embodiment, the height of each ridge 615 can taper linearly, or at least substantially linearly, between the ends 613 and 614. In at least one such embodiment, the height of each ridge 615 can taper between a maximum height at the proximal end 614 down to no height at all at the distal end 613. In certain embodiments, the height of each ridge 615 can vary geometrically between the ends 613 and 614. In certain alternative embodiments, each ridge 615 can comprise a uniform height across the length thereof.

As described above, the distal ends 613 of the ridges 615 can be shorter than the proximal ends 614 of the ridges 615. In various circumstances, as a result, the distal ends 613 can apply less pressure to the tissue clamped between an anvil and the staple cartridge 642 as compared to the proximal ends 614. In various embodiments, as described above, each ridge 615 can extend longitudinally across the cartridge deck 690. In certain embodiments, each ridge 615 can extend along a ridge axis which is parallel to, or at least substantially parallel to, a longitudinal axis 699 of the cartridge body 685. In various embodiments, the staple cavities 684 can be arranged in a plurality of rows, wherein each row of staple cavities 684 can be defined along a longitudinal axis which can be parallel to, or at least substantially parallel to, the ridge axes of ridges 615. In at least one embodiment, referring again to FIG. 18, each ridge 615 can comprise a ramped surface which can comprise one or more flat surfaces, curved surfaces, concave surfaces, and/or convex surfaces, for example. In at least one such embodiment, the bottom of the ramped surface can face distally which can facilitate the sliding of tissue across the staple cartridge 642 when the tissue is positioned in the end effector. In various embodiments, each ridge 615 can extend along a path which extends across one or more openings 610 of the staple cavities 684. In at least one such embodiment, such openings 610 can extend upwardly through the ridges 615. As the ridges 615 extend transversely across the cartridge deck 690, the ridges 615 can increase the strength and/or stiffness of the cartridge body 685.

In various embodiments, further to the above, a surgical staple can be comprised of titanium, such as titanium wire, for example. In certain embodiments, a surgical staple can be comprised of an alloy comprising titanium, aluminum, and/or vanadium, for example. In at least one embodiment, the surgical staple can be comprised of surgical stainless steel and/or an alloy comprised of cobalt and chromium, for example. In any event, the surgical staple can be comprised of metal, such as titanium, and a metal oxide outer surface, such as titanium oxide, for example. In various embodiments, the metal oxide outer surface can be coated with a material. In certain embodiments, the coating material can be comprised of polytetrafluoroethylene (PTFE), such as Teflon®, and/or a tetrafluoroehtylene (TFE) such as ethylene-tetrafluoroehtylene (ETFE), perfluroralkoxyethylene-tetrafluoroehtylene (PFA), and/or Fluorinated Ethylene Propylene (FEP), for example. Certain coatings can comprise silicon. In various embodiments, such coating materials can prevent, or at least inhibit, further oxidation of the metal. In certain embodiments, the coating materials can provide one or more lubricious surfaces against which the anvil, or staple pockets, can contact the staples in order to reduce the friction force therebetween. In various circumstances, lower friction forces between the staples and the staple pockets can reduce the force required to deform the staples.

The disclosures of U.S. Patent Application Publication No. 2012/0074198, entitled STAPLE CARTRIDGE, which was filed on Sep. 29, 2010, now U.S. Pat. No. 8,733,613, and U.S. Patent Application Publication No. 2013/0161375, entitled STAPLE CARTRIDGE, which was filed on Feb. 21, 2013, are hereby incorporated by reference in their entirety.

An end effector of a surgical stapling instrument is illustrated in FIGS. 23 and 55. The end effector can include an anvil, such as anvil 20, for example, and a jaw, or staple cartridge channel, 22 configured to removably support a staple cartridge therein. A staple cartridge 2000, for example, is positioned in the cartridge channel 22. The staple cartridge 2000 can comprise a cartridge body 2010 including a plurality of staple cavities 2050 defined therein. Each staple cavity 2050 can be configured to removably store a staple therein. The cartridge body 2010 can include a deck surface 2011 and a longitudinal slot 2015 defined in the deck surface 2011 configured to removably receive a firing member and/or cutting edge therein. The cartridge body 2010 can further comprise a distal end 2013, a proximal end 2016, and opposing longitudinal sides 2012 extending between the distal end 2013 and the proximal end 2016. In various instances, each longitudinal side 2012 can comprise a contiguous or continuous edge without interruptions defined therein. Upon comparing FIGS. 7 and 23, for instance, the reader will appreciate that the longitudinal sides of the staple cartridge 142 depicted in FIG. 7 comprises at least one notch defined therein while the longitudinal sides 2012 comprise no such notches.

Referring primarily to FIG. 55, the cartridge body 2010 can further comprise a plurality of projections 2051 extending from the deck surface 2011. Projections 2051 can be configured to engage tissue positioned intermediate the anvil 20 and the cartridge 2000 and control the movement of the tissue relative to the cartridge 2000. Tissue can move relative to the cartridge 2000 in various instances. In at least one instance, tissue can flow relative to the cartridge 2000 when the anvil 20 is moved between an open position (FIG. 23) and a closed position in which the tissue is squeezed between the anvil 20 and the cartridge 2000. In such instances, the tissue may flow laterally toward the longitudinal sides 2012, distally toward the distal end 2013, and/or proximally toward the proximal end 2016. In at least one other instance, tissue can flow relative to the cartridge 2000 when the cutting edge is advanced distally through the tissue captured between the anvil 20 and the cartridge 2000. In such instances, tissue may flow laterally, distally, and/or proximally, but it primarily flows distally due to the distal movement of the cutting edge. In various instances, projections 2051 can be configured to limit or prevent the flow of the tissue relative to the staple cartridge. Projections 2051 can be positioned at the proximal end and/or the distal end of the staple cavities 2050. In various instances, each projection 2051 can comprise a cuff extending around an end of a staple cavity 2050. In certain instances, each projection 2051 can comprise an arcuate ridge extending around an end of a staple cavity 2050.

Referring primarily to FIG. 55, the cartridge body 2010 can comprise a sloped transition 2014 extending between the distal tip of the cartridge body 2010 and the deck surface 2011. The sloped transition 2014 can facilitate the movement of the cartridge 2000 relative to the tissue when positioning the cartridge 2000 and the anvil 20 within a surgical site. In such instances, the tissue can slide over the sloped surface 2014. In various instances, the sloped surface 2014 can comprise a radiused surface. In various instances, the sloped surface 2014 can comprise an angled surface. In certain instances, the sloped surface 2014 can comprise a concave surface and/or a convex surface. In at least one instance, as illustrated in FIG. 55, the sloped surface 2014 can comprise a distal concave surface which transitions into a flat, angled surface which transitions into a proximal convex surface, for example.

The staple cavities 2050 defined in the cartridge body 2010 can be arranged in longitudinal rows. For instance, three longitudinal rows of staple cavities 2050 can be arranged on a first side of the longitudinal slot 2015 and three longitudinal rows of staple cavities 2050 can be arranged on a second side of the longitudinal slot 2105. Each longitudinal row can include a distal-most staple cavity 2050 adjacent to the distal end 2013 and a proximal-most staple cavity 2050 adjacent to the proximal end 2016. In various instances, the cartridge body 2010 can further comprise projections 2053 extending from the deck surface 2011. The projections 2053 can be positioned at the distal ends of the distal-most staple cavities 2050. Each projection 2053 can comprise a distal sloped surface, for example, configured to facilitate the insertion of the tissue between the staple cartridge 2000 and the anvil 20. In various instances, the distal-most cavities 2050 can each include a projection 2053 positioned at the distal end thereof and a projection 2051 positioned at a proximal end thereof.

Each projection 2051 and/or projection 2053 can be configured to support at least a portion of a staple removably stored in a staple cavity 2050. In various instances, each projection 2051 can extend an endwall 2052 of the staple cavity 2050 above the deck 2011. In certain instances, referring generally to FIGS. 24 and 26-29, a staple positioned within the staple cavity 2050 can include a base, a first leg extending from the base at a first angle, and a second leg extending from the base at a second angle. The first leg can be in contact with a first endwall 2052 (FIG. 55) of a staple cavity 2050 and the second leg can be in contact with a second endwall 2052 of the staple cavity. In certain instances, the distance, or spread, between the first leg and the second leg of the staple can be wider than the distance between the endwalls 2052 such that, when the staple is positioned within the staple cavity 2050, the legs are biased inwardly by the endwalls 2052. When the staple is stored within the staple cavity 2050 in its unfired, or unlifted, position, the tips of the staple legs may be positioned within the projections 2051. In such instances, the projections 2051 can support and protect the tips of the staple legs above the deck 2011. In some instances, the tips of the staple legs may be positioned below the projections 2051 when the staple is in its unfired position and, thus, the projections 2051 may not support the staple legs when the staple is in its unfired position. When such a staple is fired, or lifted out of the staple cavity 2050, the staple legs may then come into contact with and be supported by the projections 2051. In any event, the projections 2051 can continue to support the staple legs as the staple is deployed until the staple has been sufficiently fired and/or lifted out of the staple cavity 2050 such that the staple legs are no longer in contact with the projections 2051. Projections 2053 can perform in a similar manner as that described in connection with projections 2051.

In various instances, further to the above, a projection 2051 can extend a staple cavity 2050 above the deck 2011 of the cartridge body 2010. In certain instances, the projection 2051 can be configured such that an endwall 2052 of the staple cavity 2050 extends seamlessly into the projection 2051. Stated another way, a seamless surface can be defined between the endwall 2052 and the projection 2051. Such a seamless surface can reduce the possibility of a staple leg which is biased against the endwall 2052 and the projection 2051 from contacting an edge or step defined within the staple cavity 2050 and/or digging into the sidewall of the staple cavity 2050. FIG. 55A illustrates a step 2056 defined between the projection 2051 and the endwall 2052. While the step 2056 comprises an outward step and not an inward step, the step 2056 can be eliminated to provide a seamless surface as discussed above. In embodiments where the cartridge body 2010 is formed during an injection molding process, the cartridge 2010 can be formed in a mold cavity defined between two halves of an injection mold. The two halves of the injection mold can contact one another to seal, or at least substantially seal, the mold cavity. The interface between the two mold halves is often referred to as the seal line, or parting line, and, oftentimes, a small ledge or lip is formed in the cartridge body along the seal line. This is especially true when the seal line is used to vent air from the mold cavity during the injection molding process. This ledge or lip is often referred to as 'flash'. The injection mold can be carefully designed such that the seal line does not produce a ledge or lip in the endwall 2052 and/or the inwardly-facing surface of the projection 2051. In at least one instance, the projection 2051 can comprise an end cuff portion 2057 and a transition portion 2058 extending from opposite ends of the cuff portion to the deck 2011. The seal line between the two mold halves can be selected such that it extends along the top surface of the projection 2051. An exemplary seal line 2059 is depicted in FIG. 55A, although other suitable seal lines could be selected.

A staple cartridge 2800 is illustrated in FIGS. 56 and 57. The staple cartridge 2800 can include a cartridge body 2810. The cartridge body 2810 can comprise a distal end 2813, a proximal end 2816, and opposing lateral sides 2812. Similar to the above, each lateral side 2812 may comprise a contiguous edge without notches defined therein. The cartridge body 2810 can further include a deck 2811, a plurality of staple cavities 2850 defined in the deck 2811, and a longitudinal slot 2815 configured to receive a knife edge of a firing member, for example. The cartridge body 2810 can further comprise ridges 2851 extending from the deck 2811. In various instances, the ridges 2851 can comprise a pattern. In at least one instance, each ridge 2851 can extend between a lateral side 2812 and the longitudinal slot 2815. Each ridge 2851 can comprise any suitable configuration, such as a plateau, for example. One or more staple cavities 2850 can extend through the ridge 2851. In some instances, at least a portion of a staple cavity 2850 in the inner row of staple cavities 2850, at least a portion of a staple cavity 2850 in the middle row of staple cavities 2850, and/or at least a portion of a staple cavity 2850 in an outer row of staple cavities 2850 can extend through the plateau of a ridge 2851. Each ridge 2851 can comprise an inner end 2858 positioned adjacent to the longitudinal slot 2815 and an outer end 2859 positioned adjacent to a lateral side 2812. In certain instances, the inner end 2858 can be positioned distally with respect to the outer end 2859. In other instances, although not illustrated, the outer end 2859 can be positioned distally with respect to the inner end 2858. The ridges 2851 can be parallel, for example. In certain instances, the ridges 2851 can comprise a tread pattern, for example. In at least one instance, the ridges 2851 extending from the deck 2811 on a first side of the longitudinal slot 2815 can comprise a mirror image of the ridges 2851 extending from the deck on a second side of the longitudinal slot 2815. In various instances, gaps can be defined between the ridges 2851. Tissue can flow into the gaps when the tissue is compressed against the cartridge deck 2811 by an anvil, for example. The gaps can be configured to direct the flow of tissue in a desired direction.

A staple cartridge 2900 is illustrated in FIG. 58. The staple cartridge 2900 can include a cartridge body 2910. The cartridge body 2910 can comprise a distal end 2913, a proximal end, and opposing lateral sides 2912. Similar to the above, each lateral side 2912 may comprise a contiguous edge without notches defined therein. The cartridge body 2910 can further include a deck 2911, a plurality of staple cavities 2950 defined in the deck 2911, and a longitudinal slot 2915 configured to receive a knife edge of a firing member, for example. The cartridge body 2910 can further comprise ridges 2951 extending from the deck 2911. In various instances, the ridges 2951 can comprise a pattern. Each ridge 2951 can extend between the distal end 2913 and the proximal end of the cartridge body 2910. In at least one instance, each ridge 2951 can extend toward a lateral side 2912 and toward the longitudinal slot 2915. In various instances, each ridge 2951 can comprise angled portions 2954 which extend inwardly and proximally, straight portions 2955 which extend longitudinally, and angled portions 2956 which extend inwardly and distally. The ridges 2951 can extend around and/or between the staple cavities 2950. In at least one instance, the angled portions 2954 and the angled portions 2956 can extend between staple cavities 2950 in a longitudinal row of staple cavities 2950. The ridges 2951 can be parallel to one another, for example. In certain instances, the ridges 2951 can comprise a tread pattern, for example. In at least one instance, the ridges 2951 extending from the deck 2911 on a first side of the longitudinal slot 2915 can comprise a mirror image of the ridges 2951 extending from the deck on a second side of the longitudinal slot 2915. In various instances, gaps can be defined between the ridges 2951. Tissue can flow into the gaps when the tissue is compressed against the cartridge deck 2911 by an anvil, for example. The gaps can be configured to direct the flow of tissue in a desired direction.

A staple cartridge can include a uniform array of projections extending therefrom. In other instances, the array may not be uniform. In certain instances, the projections in the array may not extend a staple cavity. In various instances, the projections in the array may not support a staple.

A staple cartridge 3000 is illustrated in FIGS. 59 and 60. The staple cartridge 3000 can include a cartridge body 3010. The cartridge body 3010 can comprise a distal end 3013, a proximal end, and opposing lateral sides 3012. Similar to the above, each lateral side 3012 may comprise a contiguous edge without notches defined therein. The cartridge body 3010 can further include a deck 3011, a plurality of staple cavities 3050 defined in the deck 3011, and a longitudinal slot 3015 configured to receive a knife edge of a firing member, for example. The cartridge body 3010 can further comprise projections 3051 extending from the deck 3011. In various instances, the projections 3051 can comprise a pattern. In at least one instance, each projection 3051 can comprise a pyramidal configuration. A pyramidal configuration can include four sides which culminate in a point, for example. Alternatively, the four sides could culminate in a flat surface, for example. Alternatively, a pyramidal configuration can include three sides which culminate in a point, for example. In any event, as illustrated in FIG. 59, an array of projections 3051 can extend across the deck 3011 between the longitudinal slot 3015 and the lateral sides 3012. The projections 3051 can be arranged around the staple cavities 3050. The staple cavities 3050 can be arranged in longitudinal rows and the projections 3051 can be positioned intermediate the staple cavities 3050 within a longitudinal row of staple cavities 3050. The projections 3051 can be positioned intermediate staple cavities 3050 in adjacent longitudinal rows of staple cavities 3050. The projections 3051 can be positioned intermediate the innermost rows of staple cavities 3050 and the longitudinal channel 3015. The projections 3051 can be positioned intermediate the outermost rows of staple cavities 3050 and the lateral edges 3012. The projections 3051 can be positioned distally with respect to the distal-most staple cavities 3050. The projections 3051 can be positioned proximally with respect to the proximal-most staple cavities 3050. The projections 3051 may be positioned distally with respect to the distal end of the longitudinal slot 3015. In other instances, the projections 3051 may not be positioned distally with respect to the distal end of the longitudinal slot 3015.

A staple cartridge 3100 is illustrated in FIGS. 61 and 62. The staple cartridge 3100 can include a cartridge body 3110. The cartridge body 3110 can comprise a distal end 3113, a proximal end, and opposing lateral sides 3112. Similar to the above, each lateral side 3112 may comprise a contiguous edge without notches defined therein. The cartridge body 3110 can further include a deck 3111, a plurality of staple cavities 3150 defined in the deck 3111, and a longitudinal slot 3115 configured to receive a knife edge of a firing member, for example. The cartridge body 3110 can further comprise projections 3151 extending from the deck 3111. In various instances, the projections 3151 can comprise a pattern. In at least one instance, each projection 3151 can comprise a dome configuration. A dome configuration can include a hemi-spherical protrusion, for example. In some instances, a dome could culminate in a flat surface. As illustrated in FIG. 61, an array of projections 3151 can extend across the deck 3111 between the longitudinal slot 3115 and the lateral sides 3112. The projections 3151 can be arranged around the staple cavities 3150. The staple cavities 3150 can be arranged in longitudinal rows and the projections 3151 can be positioned intermediate the staple cavities 3150 within a longitudinal row of staple cavities 3150. The projections 3151 can be positioned intermediate staple cavities 3150 in adjacent longitudinal rows of staple cavities 3150. The projections 3151 can be positioned intermediate the innermost rows of staple cavities 3150 and the longitudinal channel 3115. The projections 3151 can be positioned intermediate the outermost rows of staple cavities 3150 and the lateral edges 3112. The projections 3151 can be positioned distally with respect to the distal-most staple cavities 3150. The projections 3151 can be positioned proximally with respect to the proximal-most staple cavities 3150. The projections 3151 may be positioned distally with respect to the distal end of the longitudinal slot 3115. In other instances, the projections 3151 may not be positioned distally with respect to the distal end of the longitudinal slot 3115.

A staple cartridge 3200 is illustrated in FIG. 63. The staple cartridge 3200 can include a cartridge body 3210. The cartridge body 3210 can comprise a distal end 3213, a proximal end, and opposing lateral sides 3212. Similar to the above, each lateral side 3212 may comprise a contiguous edge without notches defined therein. The cartridge body 3210 can further include a deck 3211, a plurality of staple cavities 3250 defined in the deck 3211, and a longitudinal slot 3215 configured to receive a knife edge of a firing member, for example. The cartridge body 3210 can further comprise projections 3251 extending from the deck 3211. Similar to projections 2051, projections 3251 can be configured to engage tissue positioned intermediate an anvil and the cartridge 3200 and control the movement of the tissue relative to the cartridge 3200. In various instances, the projections 3251 can be configured to limit or prevent the flow of the tissue relative to the staple cartridge. Projections 3251 can be positioned at the proximal end and/or the distal end of the staple cavities 3250. In various instances, each projection 3251 can comprise a cuff extending around an end of a staple cavity 3250. In certain instances, each projection 3251 can comprise an arcuate ridge extending around an end of a staple cavity 3250. In various instances, each projection 3251 can include one or more protrusions 3254 defined thereon. The protrusions 3254 can provide a textured surface which improves the grip or hold that the projections 3251 can apply to the tissue positioned intermediate the anvil and the staple cartridge 3200. In various instances, each protrusion 3254 can comprise a nub, for example. In certain instances, each protrusion 3254 can comprise a dome. In at least one instance, the protrusions 3254 can be comprised of an elastomeric material, such as rubber, a thermoplastic elastomer, and/or Santoprene, for example, molded onto the projections 3251 which can be comprised of plastic material, for example. In various instances, the protrusions 3254 can be comprised of a pliable material and may not traumatize the tissue compressed by the protrusions 3254. The cartridge body 3210 can further comprise projections 3253. Similar to projections 2053, the projections 3253 can be positioned at the distal ends of the distal-most staple cavities 3250. Each projection 3253 can comprise a distal sloped surface, for example, configured to facilitate the insertion of the tissue between the staple cartridge 3200 and the anvil. In various instances, the distal-most cavities 3250 can each include a projection 3253 positioned at the distal end thereof and a projection 3251 positioned at a proximal end thereof. Also similar to the above, each projection 3251 and/or projection 3253 can be configured to support at least a portion of a staple removably stored in a staple cavity 3250.

A staple 2130 is illustrated in FIG. 24 which comprises a base 2131, a first staple leg 2132*a* extending from a first end of the base 2131, and a second staple leg 2132*b* extending from a second end of the base 2131. The distance between the first end of the base 2131 and the second end of the base 2131 can be referred to as the crown distance, and is indicated by dimension E. The first staple leg 2132*a* comprises a first portion 2133*a* extending from the base 2131 and a second portion 2134*a* extending from the first portion 2133*a*. The first portion 2133*a* can extend at a first angle from the base 2131. This first angle can be indicated by an angle F, which is measured from the vertical direction. The second portion 2134*a* can extend at a second angle from the first portion 2133*a*. This second angle can be indicated by an angle K, which is also measured from the vertical direction. The reader will appreciate that the first portion 2133*a* and the second portion 2134*a* are not collinear; rather, the first portion 2133*a* extends along a first axis 2137*a* and the second portion 2134*a* extends along a second axis 2138*a* which is different than the first axis 2137*a*. A joint 2135*a* interconnects the first portion 2133*a* and the second portion 2134*a* and is located a distance D measured from a support surface 2139 defined on the bottom of the base 2131. The second portion 2134*a* includes a leg tip 2136*a* which is located a distance C measured from the base support surface 2139. The first portion 2133*a* can comprise a first cantilever extending from the base 2131 and the second portion 2134*a* can comprise a second cantilever extending from the first portion 2133*a*. Distance D can define the first cantilever distance and the difference between distance C and distance D can define the second cantilever distance.

The second staple leg 2132*b* comprises a first portion 2133*b* extending from the base 2131 and a second portion 2134*b* extending from the first portion 2133*b*. The first portion 2133*b* can extend at a first angle from the base 2131. This first angle can be indicated by an angle G, which is measured from the vertical direction. Angle G may or may not be the same as angle F, described above. When the second staple leg 2132*b* is positioned distally with respect to the first staple leg 2132*a*, in at least one instance, angle G can be smaller than angle F, for example. Alternatively, when the first staple leg 2132*a* is positioned distally with respect to the second staple leg 2132*b*, in at least one instance, angle F can be smaller than angle G, for example. The second portion 2134*b* can extend at a second angle from the first portion 2133*b*. This second angle can be indicated by an angle H, which is also measured from the vertical direction. Angle H may or may not be the same as angle K, described above. When the second staple leg 2132*b* is positioned distally with respect to the first staple leg 2132*a*, in at least one instance, angle H can be smaller than angle K, for example. Alternatively, when the first staple leg 2132*a* is positioned distally with respect to the second staple leg 2132*b*, in at least one instance, angle K can be smaller than angle H, for example. The reader will appreciate that the first portion 2133*b* and the second portion 2134*b* are not collinear; rather, the first portion 2133*b* extends along a first axis 2137*b* and the second portion 2134*b* extends along a second axis 2138*b* which is different than the first axis 2137*b*. A joint 2135*b* interconnects the first portion 2133*b* and the second portion 2134*b* and is located a distance B measured from a support surface 2139 defined on the bottom of the base 2131. Distance B may or may not be the same as distance D, described above. The second portion 2134*b* includes a leg tip 2136*b* which is located a distance A measured from the base support surface 2139. Distance A may or may not be the same distance as distance C, described above. The first portion 2133*b* can comprise a first cantilever extending from the base 2131 and the second portion 2134*b* can comprise a second cantilever extending from the first portion 2133*b*. Distance B can define the first cantilever distance and the difference between distance A and distance B can define the second cantilever distance. The distance between the first tip 2136*a* of the first staple leg 2132*a* and the second tip 2136*b* of the second staple leg 2312 can define the spread distance between the staple legs 2132*a*, 2132*b* and is indicated by distance J. Distance J may or may not be wider than the crown distance E, described above.

FIG. 25 depicts the staple 2130 positioned within a staple cavity 2150 defined in a cartridge 2110 and supported by a staple driver 2040. The reader will appreciate that the legs 2132*a* and 2132*b* of the staple 2130 have been biased or flexed inwardly by the end walls of the staple cavity 2150. As a result, the distances A, B, C, D, E and J may have changed and are represented by A', B', C', D', E', and J', respectively. The staple 2130 can be comprised of a resilient material, such as stainless steel and/or titanium, for example, and the changes to these distances can be reversed, or at least partially reversed, when the staple 2130 is ejected from the staple cavity 2150. Similarly, the angles F, G, H, and K may have changed as a result of positioning the staple 2130 in the staple cavity 2150 and are represented by angles F', G', H', and K', respectively. As described above, the staple 2130 can be comprised of a resilient material and the changes to these angles can be reversed, or at least partially reversed, when the staple 2130 is ejected from the staple cavity 2150. FIG. 25 illustrates the staple 2130 and the driver 2040 in an unfired position. In this unfired position, the tip 2136*a* of the first staple leg 2132*a* may extend above a deck surface 2111 of the cartridge 2110 and may be positioned within and protected by a projection 2150*a* extending from the deck surface 2111 and, similarly, the tip 2136*b* of the second staple leg 2132*b* may extend above the deck surface 2111 and may be positioned within and protected by a projection 2150*b* extending from the deck surface 2111.

A staple 2230 is illustrated in FIG. 26. The staple 2230 can comprise a base 2231, a first leg 2232*a* extending from the base 2231, and a second leg 2232*b* extending from the base 2231. The first leg 2232*a* can comprise a first portion 2233*a* connected to the base 2231 and a second portion 2234*a* extending from the first portion 2233*a*. The second leg 2232*b* can comprise a first portion 2233*b* connected to the base 2231 and a second portion 2234*b* extending from the first portion 2233*b*. The base 2231, the first portion 2233*a*, and the first portion 2233*b* can comprise a generally V-shaped configuration. In various instances, the second portion 2234*a* can extend inwardly from the first portion 2233*a* at a joint 2235*a* and, similarly, the second portion 2234*b* can extend inwardly from the first portion 2233*b* at a joint 2235*b*. The base 2231, the first leg 2232*a*, and the second leg 2232*b* can be configured and arranged such that the staple 2230 is symmetrical in its unformed, or unfired, configuration illustrated in FIG. 26. In various instances, the first leg 2232*a* can be positioned distally with respect to the second leg 2232*b*. Alternatively, the first leg 2232*a* can be positioned proximally with respect to the second leg 2232*b*.

A staple 2330 is illustrated in FIG. 27. The staple 2330 can comprise a base 2331, a first leg 2332*a* extending from the base 2331, and a second leg 2332*b* extending from the base 2331. The first leg 2332*a* can comprise a straight portion 2333*a* connected to the base 2331 which extends along an axis. The second leg 2332*b* can comprise a first portion 2333*b* connected to the base 2331 and a second portion 2334*b* extending from the first portion 2333*b*. The base 2331, the straight portion 2333*a*, and the first portion 2333*b* can comprise a generally V-shaped configuration. In various instances, the second portion 2334*b* can extend inwardly from the first portion 2333*b* at a joint 2335*b*. The base 2331, the first leg 2332*a*, and the second leg 2332*b* can be configured and arranged such that the staple 2330 is asymmetrical in its unformed, or unfired, configuration illustrated in FIG. 27. In various instances, the first leg 2332*a* can be positioned distally with respect to the second leg 2332*b*. Alternatively, the first leg 2332*a* can be positioned proximally with respect to the second leg 2332*b*.

A staple 2430 is illustrated in FIG. 28. The staple 2430 can comprise a base 2431, a first leg 2432*a* extending from the base 2431, and a second leg 2432*b* extending from the base 2431. The first leg 2432*a* can comprise a first portion 2433*a* connected to the base 2431 and a second portion 2434*a* extending from the first portion 2433*a*. The second leg 2432*b* can comprise a first portion 2433*b* connected to the base 2431 and a second portion 2434*b* extending from the first portion 2433*b*. The base 2431, the first portion 2433*a*, and the first portion 2433*b* can comprise a generally V-shaped configuration. In various instances, the second portion 2434*a* can extend inwardly from the first portion 2433*a* at a first angle at a joint 2435*a* and, similarly, the second portion 2434*b* can extend inwardly from the first portion 2433*b* at a second angle at a joint 2435*b*. The first angle and the second angle can be different. The base 2431, the first leg 2432*a*, and the second leg 2432*b* can be configured and arranged such that the staple 2430 is asymmetrical in its unformed, or unfired, configuration illustrated in FIG. 28. In various instances, the first leg 2432*a* can be positioned distally with respect to the second leg 2432*b*. Alternatively, the first leg 2432*a* can be positioned proximally with respect to the second leg 2432*b*.

A staple 2530 is illustrated in FIG. 29. The staple 2530 can comprise a base 2531, a first leg 2532*a* extending from the base 2531, and a second leg 2532*b* extending from the base 2531. The first leg 2532*a* can comprise a first portion 2533*a* connected to the base 2531 and a second portion 2534*a* extending from the first portion 2533*a*. The second leg 2532*b* can comprise a first portion 2533*b* connected to the base 2531 and a second portion 2534*b* extending from the first portion 2533*b*. The base 2531, the first portion 2533*a*, and the first portion 2533*b* can comprise a generally V-shaped configuration. In various instances, the second portion 2534*a* can extend inwardly from the first portion 2533*a* at a first angle at a joint 2535*a* and, similarly, the second portion 2534*b* can extend inwardly from the first portion 2533*b* at a second angle at a joint 2535*b*. The first angle and the second angle can be different. The base 2531, the first leg 2532*a*, and the second leg 2532*b* can be configured and arranged such that the staple 2530 is asymmetrical in its unformed, or unfired, configuration illustrated in FIG. 29. The staple 2530 can be similar to the staple 2430 in many respects and, in at least one instance, can include a wider base 2531 than the base 2431, for example. In certain instances, a wider staple base can be accommodated within a given staple cavity when the staple leg 2532*a* and/or the staple leg 2532*b* extend in directions which are closer to the vertical direction. In various instances, the first leg 2532*a* can be positioned distally with respect to the second leg 2532*b*. Alternatively, the first leg 2532*a* can be positioned proximally with respect to the second leg 2532*b*.

As discussed above, the tissue captured between an anvil and a staple cartridge of a surgical end effector can move within or flow relative to the end effector during use. As also discussed above, this movement or flow can be generally distal as the firing member of the end effector is moved distally to fire the staples removably stored in the staple cartridge and incise the tissue. Were the firing member moved proximally, the movement or flow of the tissue would be generally proximal. Nonetheless, the distal flow of the tissue can shift the staples distally during the firing process. This phenomenon is depicted in FIG. 30. FIG. 30 illustrates a staple 2630 being ejected from a staple cavity 2650 defined in a cartridge body 2610. The staple 2630 is illustrated in at least partially fired position wherein a base 2631 of the staple 2630 is being moved upwardly toward the anvil 20 by a staple driver 2640 and wherein legs 2632*a*, 2632*b* of the staple 2630 have emerged from the staple cavity 2650 and have contacted the anvil 20. As the reader will appreciate, the staple cavity 2650 can include a first projection 2651*a* and a first endwall 2652*a* which are configured to support the first staple leg 2632*a* and, similarly, a second projection 2651*b* and a second sidewall 2652*b* which are configured to support the second staple leg 2632*b* as the staple 2630 is ejected from the staple cavity 2650 by the driver 2640. As illustrated in FIG. 30, however, the staple 2630 can be shifted distally during the firing process such that the staple leg 2632*a* is shifted away from the first endwall 2652*a* and the staple leg 2632*b* is shifted over the second projection 2651*b*. Although the staple 2630 has been shifted distally, the first leg 2632*a* has still been received within a first forming cup 22*a* of a staple pocket defined in the anvil 20 and the second leg 2632*b* has still been received within a second forming cup 22*b* of the staple pocket. Although the staple legs 2632*a*, 2632*b* may contact their respective forming cups 22*a*, 22*b*, the distal shifting of the staple 2630 may not result in a symmetrically formed staple, as illustrated in FIG. 31, for example. FIG. 31 illustrates the staple 2630 lifted into a position above a cartridge deck surface 2611 of the cartridge body 2610 by the staple driver 2640 and deformed into its fully fired configuration.

As discussed above, symmetrical staples may be deformed asymmetrically as a result of being shifted by the tissue captured within an end effector. In various instances, a staple cartridge can utilize asymmetrical staples, such as the asymmetrical staples illustrated in FIGS. 24 and 27-29, for example, which can compensate for this shifting. The staple legs of these asymmetrical staples can be configured in such a way that, when the asymmetrical staples are shifted distally, they may be shifted into an orientation which may cause them to be deformed into a symmetrical, or an at least more symmetrical, fired configuration. FIG. 84 depicts a staple cartridge 4800 which comprises a cartridge body 4810 including a plurality of staple cavities 4850 defined therein, asymmetrical staples positioned within the staple cavities 4850, and a plurality of drivers 4840 configured to eject the staples from the staple cavities 4850. The cartridge body 4810 can include a distal end 4813 and a proximal end 4816 wherein the staple cavities 4850 can be arranged in longitudinal rows defined in the cartridge body 4810. The cartridge body 4810 is cross-sectioned in FIG. 84 in such a manner so as to depict one such longitudinal row of staple cavities 4850. In some instances, the staples removably stored within a longitudinal row of staple cavities 4850 may have the same asymmetrical configuration while, in other instances, as illustrated in FIG. 84, the staples may have different asymmetrical configurations. For instance, staples 4830' are stored in the proximal end of the longitudinal row while staples 4830" are stored in distal end of the longitudinal row. Similar to the above, each staple 4830' may include a first staple leg 4832*a*' and a second staple leg 4832*b*' wherein one or both of the staple legs can include several segments, such as segments 4833*b*' and 4834*b*' of the second staple leg 4832*b*', for example. Also similar to the above, each staple 4830" may include a first staple leg 4832*a*" and a second staple leg 4832*b*" wherein one or both of the staple legs can include several segments, such as segments 4833*a*" and 4834*a*" of the first staple leg 4832*a*" and segments 4833*b*" and 4834*b*" of the second staple leg 4832*b*', for example. Upon comparing staples 4830' and staples 4830", the reader will appreciate that the angle between the segments 4833*b*" and 4834*b*" of the staples 4830" is more pronounced, or larger, than the angle between the segments 4833*b*' and 4834*b*' of the staples 4830'. Stated another way, the distal staples 4830" can be more asymmetrical than the proximal staples 4830'. In some instances, the tissue movement at the distal end 4813 of the staple cartridge 4800 can be larger than the tissue movement at the proximal end 4816 and, correspondingly, the shift in the staple orientations can be larger at the distal end 4813 of the staple cartridge 4800 than the proximal end 4816. The larger asymmetry of the distal staples 4830" can compensate for the larger staple shifts as compared to the smaller asymmetry of the proximal staples 4830' which are subjected to smaller staple shifts. This is but one example and any suitable assortment of staples could be utilized within a staple row to compensate for different staple shifts. It is contemplated, for example, that the staples located at the proximal end of a longitudinal row could have a larger asymmetry than the staples located at the distal end of the longitudinal row. It is also contemplated that a longitudinal row could utilize more than two groups of asymmetrical staples.

As mentioned above, the tissue movement or flow at the distal end of an end effector can be larger than the tissue movement or flow at the proximal end of the end effector, in various instances. Such instances can arise as a result of the distal movement of the firing member within the end effector. Although the firing member is configured to progressively staple and incise the tissue as it is moved distally, the firing member can also plow or push the tissue distally. This pushing or plowing effect may begin at the proximal end of the end effector and may compound as the firing member is moved distally such that the largest pushing or plowing effect is realized at the distal end of the end effector. Thus, further to the above, a gradient in staple asymmetries may be utilized within a longitudinal staple row to compensate for a gradient in tissue movement and staple shifting.

In addition to or in lieu of the above, a staple cartridge could utilize projections having different heights to control the movement of tissue within an end effector. In various instances, the projections disclosed herein which extend from a deck of a staple cartridge can reduce the gap between the staple cartridge and the anvil of the end effector. As a result, the projections can apply a larger localized pressure to the tissue positioned intermediate the anvil and the staple cartridge as compared to embodiments without projections. In various instances, projections having a taller height can apply a larger compressive force or pressure to the tissue while projections having a shorter height can apply a relatively smaller compressive force or pressure to the tissue. Along these lines, taller projections can provide greater control over tissue movement than shorter projections. As the reader will recall, the tissue movement at the proximal end of an end effector may be less than the tissue movement at the distal end of the end effector and, as a result, referring again to FIG. 84, the staple cartridge 4800 can utilize shorter projections 4851' at the proximal end 4816 of the cartridge body 4810 and taller projections 4851" at the distal end 4813. In at least one instance, the shorter projections 4851' can extend a distance 4855' from a deck surface 4811 of the cartridge body 4810 and the taller projections 4851" can extend a distance 4855" from the shorter projections 4851'. In certain instances, the projections extending from a cartridge body can comprise a gradient of heights extending between a proximal end and a distal end of the cartridge body. In at least one instance, as discussed above, the tallest projections of the gradient can be at the distal end of the cartridge body while the shortest projections of the gradient can be at the proximal end of the cartridge body. In other circumstances, the tallest projections of the gradient can be at the proximal end of the cartridge body while the shortest projections of the gradient can be at the distal end of the cartridge body.

As discussed above, tissue movement can shift staples as they are being deployed from a staple cartridge. In various instances, taller projections can provide greater control over such a shift than shorter projections. More particularly, referring again to FIG. 84, the taller distal projections 4851" can extend the staple pockets 4850 more than the shorter proximal projections 4851' such that the staples 4830" are controlled by the distal projections 4851" for a longer distance than the staples 4830' are controlled by the proximal projections 4851'. The taller projections 4851" may also increase the distance in which the staples 4830" are lifted upwardly before the legs of the staples 4830" emerge from the cavities 4850 as compared to the distance in which the staples 4830' are lifted upwardly before the legs of the staples 4830' emerge from the cavities 4850. Such an arrangement can reduce the distance and/or time in which the staples 4830" are exposed to the larger tissue movements at the distal end of the staple cartridge 4800, for example.

As discussed above, a staple cartridge can utilize more than one configuration of staple within a longitudinal staple row. In various instances, a staple cartridge can utilize staples having different configurations in different longitudinal staple rows. In at least one instance, a staple cartridge can include staples having a first configuration in a first longitudinal staple row and a second configuration in a second longitudinal staple row. Turning now to FIGS. 49 and 49A, a staple cartridge 2700, for example, can comprise a plurality of longitudinal rows of staple cavities 2750 defined therein wherein the staple cavities 2750 defined in a first row can each include a first staple 2730' (FIG. 50) removably stored therein, the staple cavities 2750 defined in a second row can each include a second staple 2730" (FIG. 51) removably stored therein, and the staple cavities 2750 defined in a third row can each include a third staple 2730" (FIG. 52) removably stored therein. The first staples 2730' can be positioned in the innermost longitudinal rows of staple cavities 2750, the second staples 2730" can be positioned in the intermediate rows of staple cavities 2750, and the third staples 2730" can be positioned in the outermost longitudinal rows of staple cavities 2750. When the first staples 2730', having a first height A' (FIG. 50), and the second staples 2730", having a second height A" (FIG. 51) are in their unfired configurations, the second staples 2730" can be taller than the first staples 2730'. Similarly, when the second staples 2730" and the third staples 2730", having a third height A" (FIG. 52), are in their unfired configurations, the third staples 2730"' can be taller than the second staples 2730".

In various instances, each longitudinal row of staples can be supported by a longitudinal row of staple drivers. For instance, a first longitudinal row of staple drivers can support a first row of first staples 2730', a second longitudinal row of staple drivers can support a second row of second staples 2730", and a third longitudinal row of staple drivers can support a third row of third staples 2730". In certain instances, referring to FIGS. 49 and 49A, a row of staple drivers 2742 can support a first row of first staples 2730' and a second row of staples 2730" such that each staple driver 2742 can support and fire at least one first staple 2730' and at least one second staple 2730", for example. A row of staple drivers 2740 can support a third row of third staples 2730'" such that each staple driver 2740 can support and fire at least one third staple 2730". The staple drivers 2742 can each include a first cradle 2741' configured to support a first staple 2730' and a second cradle 2741" configured to support a second staple 2730" and, similarly, the staple drivers 2740 can each include a third cradle 2741'" configured to support a third staple 2730". When the staple drivers 2740 and 2742 are in their unfired positions, as illustrated in FIG. 49A, the first cradles 2741' can be supported at a first distance 2732' from a first row of forming pockets 23 defined in the anvil 20, the second cradles 2741" can be supported at a second distance 2732" from a second row of forming pockets 23 defined in the anvil 20, and the third cradles 2741'" can be supported at a third distance 2732" from a third row of forming pockets 23 defined in the anvil 20. The first distance can be different than the second distance and/or the second distance can be different than third distance. As illustrated in FIG. 49, the first distance is shorter than the second distance and the second distance is shorter than the third distance. The first staples 2730', the second staples 2730", and/or the third staples 2730" can be deformed to different formed heights when the drivers 2740 and 2742 are lifted toward the anvil 20 by a firing member 2760, for example, to eject the staples 2730', 2730", and 2730" from the staple cavities 2750. For instance, the innermost row of staples, i.e., staples 2730', can be formed to a first formed height, the intermediate row of staples, i.e., staples 2730", can be formed to a second formed height, and the outer row of staples, i.e., staples 2730", can be formed to a third formed height. The first height can be shorter than the second height and the second height can be shorter than the third height. U.S. Pat. No. 8,317,070, entitled SURGICAL STAPLING DEVICES THAT PRODUCE FORMED STAPLES HAVING DIFFERENT LENGTHS, which issued on Nov. 27, 2012, is incorporated by reference in its entirety.

In various instances, a cartridge deck of a staple cartridge can be flat. In such instances, the projections described herein can extend from the flat deck surface. In other instances, a cartridge deck of a staple cartridge can comprise a stepped surface including at least two stepped surfaces, for example. Referring again to FIGS. 49 and 49A, the cartridge body 2710 of the staple cartridge 2700 can include a first deck side positioned on a first side of a longitudinal knife channel 2715 and a second deck side positioned on a second side of the longitudinal knife channel 2715. Each deck side comprises a first step 2711', a second step 2711", and a third step 2711", for example. The first longitudinal row of staple cavities 2750 can be defined in the first step 2711', the second longitudinal row of staple cavities 2750 can be defined in the second step 2711", and the third longitudinal row of staple cavities 2750 can be defined in the third step 2711'". When the anvil 20 is in its closed position, a tissue contacting surface 21 of the anvil 20 can be positioned adjacent to the deck surface of the cartridge body 2710. In such circumstances, the tissue contacting surface 21 can be positioned a first distance 2712' away from the first step 2711', a second distance 2712" away from the second step 2711", and a third distance 2712" away from the third step 2711". In various instances, the first distance, the second distance, and/or the third distance can be different. As illustrated in FIGS. 49 and 49A, the first distance 2712' is shorter than the second distance 2712" and the second distance 2712" is shorter than the third distance 2712". In various instances, the first distance 2712' can define a first tissue gap between the first step 2711' and the anvil 20, the second distance 2712" can define a second tissue gap between the second step 2711" and the anvil 20, and the third distance 2712'" can define a third tissue gap between the third step 2711'" and the anvil 20. The first tissue gap positioned over the innermost row of staple cavities 2750 can be smaller than the third tissue gap positioned over the outermost row of staple cavities 2750. The second tissue gap positioned over the intermediate row of staple cavities 2750 can be larger than the first tissue gap and smaller than the third tissue gap.

Further to the above, and referring again to FIGS. 49 and 49A, a first longitudinal row of projections 2751' can extend from the first step 2711', a second longitudinal row of projections 2751" can extend from the second step 2711", and a third longitudinal row of projections 2751" can extend from the third step 2711". The first projections 2751' can be defined by a first height 2755', the second projections 2751" can be defined by a second height 2755", and the third projections 2751" can be defined by a third height 2755". The first height, the second height, and/or the third height can be different. As illustrated in FIGS. 49 and 49A, the first height 2755' can be shorter than the second height 2755" and the second height 2755" can be shorter than the third height 2755". In various instances, the shortest longitudinal row of projections, i.e., projections 2751', can extend along the innermost row of staple cavities 2750, the tallest longitudinal row of projections, i.e., projections 2751" ", can extend along the outermost row of staple cavities 2750, and the projections having an intermediate height, i.e., projections 2751", can extend along the intermediate row of staple cavities 2750. FIG. 76 illustrates an alternative embodiment in which the tallest longitudinal row of projections, i.e., projections 2751", extends along the innermost row of staple cavities 2750, the shortest longitudinal row of projections, i.e., projections 2751', extends along the outermost row of staple cavities 2750, and the projections having an intermediate height, i.e., projections 2751" can extend along the intermediate row of staple cavities 2750.

Referring again to FIG. 76, a staple cartridge 4000 can be similar to the staple cartridge 2700, discussed above, in many respects. Similar to the staple cartridge 2700, the staple cartridge 4000 can include longitudinal rows of staple cavities 2750 comprising a first row of staple cavities 2750 including first staples 2730' removably stored therein, a second row of staple cavities 2750 including second staples 2730" removably stored therein, and a third row of staple cavities 2750 including third staples 2730'" removably stored therein. Contrary to the staple cartridge 2700, the first row of staples 2730' comprises the outermost row of staples and the third row of staples 2730'" comprises the innermost row of staples. The staple cartridge 4000 can include drivers 4040 and 4042 which are configured to support the third staples 2730" a third forming distance 2732'" from the anvil 20, the second staples 2730" a second forming distance 2732" from the anvil 20, and the first staples 2730' a first forming distance 2732' from the anvil 20 when the drivers 4040 and 4042 are in an unfired, or unlifted, position. The drivers 4040 and 4042 can deform the innermost row of staples, i.e., staples 2730", to a third formed height, the intermediate row of staples, i.e., staples 2730", to a second formed height, and the outermost row of staples, i.e., staples 2730' to a first formed height. The third formed height can be taller than the second formed height and the second formed height can be taller than the first formed height, for example. Similar to the staple cartridge 2700, the staple cartridge 4000 can include a stepped deck surface; however, the third step 2711''' can extend along the innermost row of staple cavities 2750 and the first step 2711' can extend along the outermost row of staple cavities 2750. The first tissue gap defined by the first gap distance 2712' can be positioned laterally outwardly with respect to the second tissue gap defined by the second gap distance 2712" which can be positioned laterally outwardly with respect to the third tissue gap defined by the third gap distance 2712'''.

A staple cartridge 3600 is illustrated in FIGS. 70-72. The staple cartridge 3600 can include a cartridge body 3610. The cartridge body 3610 can comprise a distal end 3613, a proximal end 3616, and opposing lateral sides 3612. The cartridge body 3610 can further include a deck 3611, a plurality of staple cavities 3650 defined in the deck 3611, and a longitudinal slot 3615 configured to receive a knife edge of a firing member, for example. The cartridge body 3610 can further comprise projections 2051 and 2053 extending from the deck 3611. The cartridge body 3610 can also comprise projections 3651 extending from the deck 3611. Similar to projections 2051, the projections 3651 can be configured to engage tissue positioned intermediate an anvil and the cartridge 3600 and control the movement of the tissue relative to the cartridge 3600. In various instances, the projections 3651 can be configured to limit or prevent the flow of the tissue relative to the staple cartridge. The projections 3651 can be positioned at the proximal end and/or the distal end of the staple cavities 3650. In various instances, each projection 3651 can comprise a cuff extending around an end of a staple cavity 3650. In certain instances, each projection 3651 can comprise an arcuate ridge extending around an end of a staple cavity 3650. In various instances, the projections 3651 may not be as tall as the projections 2051 and/or the projections 2053. The taller projections 2051 may apply a larger localized pressure to the tissue than the shorter projections 3651. In various instances, the projections 2051 may provide sufficient control over the tissue to hold the tissue in position during the firing process. In such instances, the projections 3651 may provide some additional control over the tissue in addition to protecting and guiding the staples positioned in the staple cavities 3650.

Further to the above, the deck 3611 can include steps 2711', 2711", and 2711''' which are configured to compress tissue positioned intermediate the cartridge body 3610 and an anvil. In various instances, the third step 2711''' can comprise a lowermost deck surface which extends along the outermost rows of staple cavities 3650 and around the distal end 3613 of the cartridge body 2610. The second step 2711" can extend upwardly from the lowermost deck surface 2711''' and the first step 2711' can extend upwardly from the second step 2711". When the cartridge body 3610 is slid relative to the tissue, the tissue can flow over the distal end 3613 of the cartridge body 3610 and onto the steps 2711', 2711", and 2711'''. The cartridge body 3610 can further include ramps 3614' and 3614" which are configured to assist the tissue in sliding onto the steps 2711' and 2711", respectively. As also discussed above, the steps 2711', 2711", and 2711''' can be utilized to control the flow of tissue relative to the staple cartridge 3600. Referring primarily to FIG. 71, the step 2711' can, in various instances, define a smaller tissue gap between the cartridge 3600 and an anvil positioned opposite the cartridge 3600 as compared to a tissue gap defined between the step 2711" and the anvil and/or a tissue gap defined between the step 2711" and the anvil. In the instances where the step 2711' and the smallest tissue gap are adjacent the longitudinal slot 3615, the tissue adjacent the longitudinal slot 3615 may be subjected to more compression, and more control, than the tissue positioned laterally with respect to the step 2711'. Such an embodiment could be advantageous for a variety of reasons. For instance, a cutting member passing through the longitudinal slot 3615 may attempt to displace the tissue captured between the staple cartridge 3600 and the anvil and, as a result of the compression applied by the innermost step 2711', the displacement of the tissue may be prevented, mitigated, or reduced.

As discussed above in connection with the embodiment depicted in FIG. 76, a staple cartridge can include a stepped deck surface in which the smallest tissue gap is co-extensive with the outermost longitudinal rows of staple cavities. In such instances, the smallest tissue gap may be adjacent the lateral sides of the cartridge and, as a result of the compression applied by the outermost steps, the displacement of the tissue, especially the lateral displacement of the tissue, may be prevented, mitigated, or reduced. In certain instances, referring again to FIGS. 70-72, the lateral displacement of the tissue captured between the staple cartridge 3600 and an anvil can be prevented, mitigated, or reduced by lateral sidewalls 3617. Each lateral sidewall 3617 can extend from a lateral side 3612 of the cartridge body 3610 and block the lateral movement of the tissue. The sidewalls 3617 can comprise any suitable configuration. In at least one instance, each sidewall 3617 can comprise a scalloped top surface, for example. Turning now to FIG. 73, a staple cartridge 3700 can include a cartridge body 3710 including lateral sidewalls 3717 extending from lateral sides 3712 of the cartridge body 3710. In at least one instance, each lateral sidewall 3717 can include a straight top surface, for example.

Turning now to FIG. 74, a staple cartridge 3800 can include a cartridge body 3810 comprising a distal end 3813 and staple cavities 3850. Similar to the above, the cartridge body 3810 can include projections 2053 at the distal ends of the distal-most staple cavities 3850. Also similar to the above, the cartridge body 3810 can include projections 2051 which can surround the proximal end and/or the distal end of at least some of the staple cavities 3850. In addition to or in lieu of the projections 2051 and 2053, the staple cartridge body 3810 can further include projections 3851 extending therefrom. Each projection 3851 can extend around an end of more than one staple cavity 3850. In at least one instance, each projection 3851 can extend around an end of a staple cavity 3850 in an innermost row of staple cavities 3850, an end of a staple cavity 3850 in an outermost row of staple cavities 3850, and/or an end of a staple cavity 3850 in an intermediate row of staple cavities, for example. In at least one such instance, a first portion of a projection 3851 could extend a first staple cavity 3850 above the cartridge deck surface, a second portion of the projection 3851 could extend a second staple cavity 3850 above the cartridge deck surface, and a third portion of the projection 3851 could extend a third staple cavity 3850 above the cartridge deck surface. The first portion of the projection 3851 can protect, guide, and/or hold a first staple, the second portion can protect, guide, and/or hold a second staple, and the third portion can protect, guide, and/or hold a third staple. In various instances, a projection 3851 can extend between the longitudinal slot 3615 defined in the cartridge body 3810 and a lateral sidewall 3717 extending from the cartridge body 3810. In at least one such instance, a projection 3851 can extend across a first step 2711', a second step 2711", and/or a third step 2711". Stated another way, a projection 3851 can extend across changes in elevation in the deck of the cartridge body 3810. In some instances, the top, or tissue-engaging, surface of the projection 3851 can be flat despite the change in elevation of the cartridge deck surface. In other instances, the top, or tissue-engaging, surface of the projection 3851 may also change in elevation. In at least one such instance, the top surface of the projection 3851 can increase in elevation when the deck surface increases in elevation and decrease in elevation when the deck surface decreases in elevation, for example. In other instances, the top surface of the projection 3851 can decrease in elevation when the deck surface increases in elevation and increase in elevation when the deck surface decreases in elevation, for example.

In various instances, referring again to FIG. 74, the cartridge body 3810 can include transverse projections, or ribs, 3817 extending therefrom. A transverse projection 3817 can extend transversely to the longitudinal slot 3615 and/or the lateral sidewalls 3717. In at least one instance, a transverse projection 3817 can extend in a direction which is perpendicular to the longitudinal slot 3615 and/or the lateral sidewalls 3717. In at least one instance, the transverse projections 3817 can extend between the projections 3851 and the sidewalls 3717. The transverse projections 3817 can also extend between the projections 2051 and the sidewalls 3717 and, similarly, between the projections 2053 and the sidewalls 3717. In some instances, the projections 3817 and the sidewalls 3717 can be the same height. In other instances, the projections 3817 and the sidewalls 3717 can be different heights. Referring to FIG. 74, the sidewalls 3717 are taller than the projections 3817, for example. In any event, the transverse projections 3817 can be configured to limit or prevent the flow of the tissue relative to the staple cartridge 3800, especially in the distal or longitudinal direction, for example.

Turning now to FIG. 81, a staple cartridge 4500 can include a cartridge body 4510 comprising a deck 4511, a proximal end, a distal end 4513, and a longitudinal knife slot 3615 extending between the proximal end and the distal end 4513. The cartridge body 4510 can include the sloped transition 2014, projections 2051, 2053, and 3651 at least partially surrounding staple cavities 3650, and lateral sidewalls 3617, among other features. In fact, various embodiments are envisioned in which the tissue control features of various embodiments disclosed herein can be combined with the tissue control features of other embodiments disclosed herein. Moreover, various embodiments are disclosed herein wherein all of the staple cavities defined in a staple cartridge can include projections at least partially surrounding the staple cavities. Other embodiments are envisioned wherein less than all of the staple cavities include projections at least partially surrounding the staple cavities. Turning now to FIG. 82, a staple cartridge 4600 can include a cartridge body 4610 comprising a deck 4611, a proximal end 4616, a distal end 4613, and a longitudinal knife slot 4615 extending between the proximal end 4616 and the distal end 4613. The cartridge body 4610 can include projections 2051 and 2053 extending from the deck 4611 and at least partially surrounding some of the staple cavities 4650. For instance, the proximal and/or distal ends of the staple cavities 4650 defined in the distal end 4613 of the staple cartridge 4600 can be at least partially surrounded by the projections 2051 and, similarly, the proximal and/or distal ends of the staple cavities 4650 defined in the proximal end 4616 of the staple cartridge 4600 can be at least partially surrounded by the projections 2051. In such an embodiment, the staple cavities 4650 defined in the middle of the cartridge body 4610, i.e., between the proximal end 4616 and the distal end 4613 of the staple cartridge may not be surrounded by the projections 2051 and/or any other projections, for example. Turning now to FIG. 83, a staple cartridge 4700 can include a cartridge body 4710 comprising a deck 4711, a proximal end, and a distal end 4713. The cartridge body 4710 can include a plurality of staple cavities 4750 defined therein. The distal-most staple cavities 4750 can comprise a distal end surrounded by a projection 2053 and a proximal end surrounded by a projection 2051. Other staple cavities 4750 can comprise a distal end surrounded by a projection 2051 and a proximal end that is not surrounded by a projection. Certain staple cavities 4750 could comprise a proximal end surrounded by a projection 2051 and a distal end that is not surrounded by a projection.

As discussed above, a projection extending from a deck surface can be configured to protect, support, and/or guide a staple positioned within a staple pocket. FIG. 77 depicts a staple cartridge 4100 including a cartridge body 4110 including a deck 4111, a staple cavity 4150 defined in the deck 4111, and a projection 4151 extending from the deck 4111. The staple cartridge 4100 can further comprise a staple 4130 removably positioned in the staple cavity 4150. The projection 4151 can include a slot 4154 defined therein which can be configured to support a leg 4132 of the staple 4130 when the staple 4130 is stored in the staple cavity 4150 and/or when the staple 4130 is being ejected from the staple cavity 4150. The slot 4154 can comprise an extension of a staple cavity end wall 4152. The staple cavity end wall 4152 and/or the slot 4154 can co-operate to support the staple leg 4132 when the staple 4130 is in an unfired position. As the staple 4130 is ejected from the cavity 4150, the leg 4132 can emerge from the projection 4151, as illustrated in FIG. 77. In such circumstances, the end wall 4152 and/or the slot 4154 can support the portion of the staple 4130 that has not yet emerged from the staple cavity 4150. In certain instances, the projection 4151 may not provide lateral support to the staple leg 4132. More particularly, referring to FIG. 77, the slot 4154 can comprise opposing lateral sides 4155 which can be spaced apart from, and not in contact with, the sides of the staple leg 4132. In various instances, the staple 4130 may be deformed into its fully deformed configuration while the staple 4130 is still at least partially positioned in the staple cavity 4150. In at least one such instance, the end wall 4152 and/or the slot 4154 may support the staple 4130 throughout the entire forming process of the staple 4130. In other instances, the staple 4130 may reach its fully deformed configuration after it has been lifted out of the slot 4154 and above the projection 4151. In such circumstances, the end wall 4152 and the slot 4154 may not support the staple 4130 during the entire forming process thereof.

FIG. 78 depicts a staple cartridge 4200 including a cartridge body 4210 including a deck 4211, a staple cavity 4250 defined in the deck 4211, and a projection 4251 extending from the deck 4211. The staple cartridge 4200 can further comprise a staple 4130 removably positioned in the staple cavity 4250. The projection 4251 can include a slot 4254 defined therein which can be configured to support a leg 4132 of the staple 4130 when the staple 4130 is stored in the staple cavity 4250 and/or when the staple 4130 is being ejected from the staple cavity 4250. The slot 4254 can comprise an extension of a staple cavity end wall 4252. The staple cavity end wall 4252 and/or the slot 4254 can cooperate to support the staple leg 4132 when the staple 4130 is in an unfired position. As the staple 4130 is ejected from the cavity 4250, the leg 4132 can emerge from the projection 4251, as illustrated in FIG. 78. In such circumstances, the end wall 4252 and/or the slot 4254 can support the portion of the staple 4130 that has not yet emerged from the staple cavity 4250. In certain instances, the projection 4251 may provide lateral support to the staple leg 4132. More particularly, referring to FIG. 78, the slot 4254 can comprise opposing lateral sides 4255 which can be in contact with the sides of the staple leg 4132. In various instances, the staple 4130 may be deformed into its fully deformed configuration while the staple 4130 is still at least partially positioned in the staple cavity 4250. In at least one such instance, the end wall 4252 and/or the slot 4254 may support the staple 4130 throughout the entire forming process of the staple 4130. In other instances, the staple 4130 may reach its fully deformed configuration after it has been lifted out of the slot 4254 and above the projection 4251. In such circumstances, the end wall 4252 and the slot 4254 may not support the staple 4130 during the entire forming process thereof.

FIG. 79 depicts a staple cartridge 4300 including a cartridge body 4310 including a deck 4311, a staple cavity 4350 defined in the deck 4311, and projections 4351 extending from the deck 4311. The staple cartridge 4300 can further comprise a staple 4130 removably positioned in the staple cavity 4350. Each projection 4351 can include a tapered slot 4354 defined therein which can be configured to support a leg 4132 of the staple 4130 when the staple 4130 is stored in the staple cavity 4350 and/or when the staple 4130 is being ejected from the staple cavity 4350. Each slot 4354 can comprise an extension of a staple cavity end wall 4352 and can include sidewalls 4355. The sidewalls 4355 of each slot 4354 can co-operate to support the staple leg 4132 when the staple 4130 is in an unfired position. As the reader will appreciate from FIG. 79, the staple leg 4132 may not be supported by the end wall 4352. As the staple 4130 is ejected from the cavity 4350, the legs 4132 can emerge from the projections 4351. In such circumstances, the sidewalls 4355 of the slots 4354 can support the portion of the staple 4130 that has not yet emerged from the staple cavity 4350. In certain instances, the sidewalls 4155 of the projections 4351 may provide lateral support to the staple legs 4132. In various instances, the staple 4130 may be deformed into its fully deformed configuration while the staple 4130 is still at least partially positioned in the staple cavity 4350. In at least one such instance, the slots 4354 may support the staple 4130 throughout the entire forming process of the staple 4130. In other instances, the staple 4130 may reach its fully deformed configuration after it has been lifted out of the slots 4354 and above the projections 4351. In such circumstances, the slots 4354 may not support the staple 4130 during the entire forming process thereof.

FIG. 80 depicts a staple cartridge 4400 including a cartridge body 4410 including a deck 4411, a staple cavity 4450 defined in the deck 4411, and projections 4451a and 4451b extending from the deck 4411. The staple cartridge 4400 can further comprise a staple 4130, for example, removably positioned in the staple cavity 4450. The staple cavity 4450 can comprise a first end wall 4452a configured to support and guide a first leg of the staple 4130 and a second end wall 4452b configured to support and guide a second leg of the staple 4130. The projection 4451a can extend from the deck 4411 a first distance 4455a and the projection 4451b can extend from the deck 4411 a second distance 4455b above the projection 4451a. In various instances, as a result, the projection 4451a can support and guide the first staple leg a first distance and the projection 4451b can support and guide the second staple leg a second distance, wherein the second distance can be longer than the first distance. In certain instances, the projection 4451b can be positioned at the distal end of the staple cavity 4450 and the projection 4451a can be positioned at the proximal end of the staple cavity 4450. Such an embodiment may be advantageous when the staple 4130 is pushed distally by the distal movement of the firing member and the tissue knife, as discussed above. Alternatively, the projection 4451b can be positioned at the proximal end of the staple cavity 4450 and the projection 4451a can be positioned at the distal end of the staple cavity 4450. In any event, a projection 4451b can comprise a stepped configuration, for example. In at least one instance, the projection 4451b can comprise a first portion defined by the height 4455a and a second portion defined by the height 4455b, for example.

FIGS. 85A-85C illustrate a staple cartridge 4900 comprising a cartridge body 4910 including a deck 4911. In various embodiments, the cartridge body 4910 can be comprised of a flexible material. In certain embodiments, the cartridge body 4910 can be comprised of a rigid material and a flexible material, wherein at least the deck 4911 can be comprised of the flexible material. A flexible material could include certain plastic materials, such as polypropylene, for example, and/or an elastomeric material, such as rubber, a thermoplastic elastomer, and/or Santoprene, for example. In various instances, the deck 4911 can be comprised of a pliable material. In any event, the deck 4911 can include a projection 4951 extending therefrom. Similar to the above, the projection 4951 can protect, support, and/or guide a staple 4130. Also similar to the above, the projection 4951 can prevent or at least limit the movement of tissue relative to the staple cartridge 4900. When an anvil is moved into a closed position opposite the staple cartridge 4900 or, alternatively, the staple cartridge 4900 is moved into a closed position relative to an anvil, the projection 4951 can be compressed by the tissue positioned intermediate the anvil and the staple cartridge 4900. FIGS. 85A-85C depict a sequence of events in which the projection 4951 is subjected in increasing compressive forces. FIG. 85A depicts the projection 4951 in an uncompressed configuration. In this configuration, a compressive or interference fit can be present between the projection 4951 and the staple leg of the staple 4130. FIG. 85B depicts the projection 4951 in a compressed configuration in response to a compressive force being applied thereto. Upon comparing FIGS. 85A and 85B, it can be appreciated that a top surface 4956 of the projection 4951 has been pushed downwardly toward the deck 4911 a distance 4955 and that the shape of the projection 4951 has become distorted. In this configuration, the projection 4951 can grip the staple leg of the staple 4130 and/or hold the staple leg in position. FIG. 85C depicts a larger compressive force being applied to the projection 4951. Upon comparing FIGS. 85B and 85C, it can be appreciated that the top surface 4956 of the projection 4951 has been pushed further downwardly toward the deck 4911 and that the shape of the projection 4951 has become further distorted. Moreover, in this configuration, the projection 4951 can increase the gripping force being applied to the staple leg.

FIGS. 86A and 86B illustrate a staple cartridge 5000 comprising a cartridge body 5010 including a deck 5011. The cartridge body 5010 can further comprise a plurality of staple cavities 5050 defined therein and a plurality of projections 5051 extending from the deck 5011 which are configured to protect, support, and/or guide staples 5030 removably positioned in the staple cavities 5050. Similar to the above, the staple cartridge 5000 can further include staple drivers 5040 and 5042 which are configured to support and lift the staples 5030 between an unfired position and a fired position. FIGS. 86A and 86B illustrated the staples 5030 in a partially-fired position wherein the tips of the staples 5030 have partially emerged from the projections 5051. Similar to the above, the cartridge body 5010 can be comprised of a flexible material. A flexible material could include certain plastic materials, such as polypropylene, for example, and/or an elastomeric material, such as rubber, a thermoplastic elastomer, and/or Santoprene, for example. In various instances, the cartridge body 5010 can be comprised of a pliable material. When a compressive force is applied to the cartridge body 5010, the cartridge body 5010 can flex, as illustrated in FIG. 86B. When the deck 5011 of the cartridge body 5010 is flexed downwardly, as illustrated in FIG. 86B, the projections 5051 can be deflected downwardly a distance 5055. In this way, the projections 5051 can be movable.

Various embodiments are envisioned in which projections extending from a staple cartridge deck can move relative to the deck. In at least one instance, a projection can move between a first position in which the projection extends a staple cavity above the deck and a second, or lowered, position in which the projection may or may not extend the staple cavity above the deck. In various instances, one or more projections extending from a deck can be collapsible. A collapsible projection can move between a first position in which the projection extends a staple cavity above the deck and a second, or collapsed, position in which the projection may or may not extend the staple cavity above the deck. In at least one instance, the collapsible projections may resiliently return to their uncollapsed configuration while, in certain instances, the projections may not completely return to their uncollapsed configuration. In various instances, one or more projections extending from a deck can be crushable. A crushable projection can move between a first position in which the projection extends a staple cavity above the deck and a second, or crushed, position in which the projection may or may not extend the staple cavity above the deck. The crushable projections may not return to their uncrushed configuration.

As discussed above, the staples of a staple cartridge can be supported by staple drivers when the staples are removably stored in the staple cartridge. As also discussed above, the staple drivers can be lifted upwardly by a firing member, such as firing member 2760, for example. In various instances, turning now to FIGS. 53 and 54, the firing member can be configured to advance a staple sled, such as staple sled 2870, for example, distally to lift the staple drivers and the staples toward the anvil. The staple sled 2870 can comprise a body 2871 and a shoulder 2876 which can be configured to be engaged by and support the firing member 2760. The sled 2870 can further comprise ramped or inclined surfaces 2872, 2873, 2874, and/or 2875, for example, which are configured to slide under the staple drivers and lift the staple drivers upwardly as the sled 2870 slides under the staple drivers. In various instances, further to the above, the first ramp surface 2872 can be configured to contact and lift staple drivers in a first row of staple drivers, the second ramp surface 2873 can be configured to contact and lift staple drivers in a second row of staple drivers, the third ramp surface 2874 can be configured to contact and lift staple drivers in a third row of staple drivers, and the fourth ramp surface 2875 can be configured to contact and lift staple drivers in a fourth row of staple drivers, for example.

In various instances, further to the above, the sled 2870 can be configured to simultaneously lift a staple driver in four rows of staple drivers. In some instances, the sled 2870 can synchronously lift the staple drivers in the four rows of staple drivers. In such instances, the distal ends of the four ramp surfaces 2872, 2873, 2874, and 2875 can be configured to contact the four staple drivers at the same time and lift them along four parallel lift surfaces such that the staple drivers reach the same height at the same time. Also, in such instances, the ramp surfaces 2872, 2873, 2874, and 2875 can all have the same length. In other instances, the sled 2870 can simultaneously lift a staple driver in each of the four rows of staple drivers, albeit in a staggered manner. Referring primarily to FIG. 54, the distal end 2872a of the first ramp 2872 can be aligned with the distal end 2875a of the fourth ramp 2875. In various instances, the first ramp 2872 can be parallel to the fourth ramp 2875. Moreover, the first ramp 2872 can define a first ramp length which is the same as a fourth ramp length defined by the fourth ramp 2875. The distal end 2873a of the second ramp 2873 can be positioned distally with respect to the distal end 2872a of the first ramp 2872 and the distal end 2875a of the fourth ramp 2875 by a distance indicated by distance 2879a. The second ramp 2873 may not be parallel to the first ramp 2872 and/or the fourth ramp 2875. Moreover, the second ramp 2873 can define a second ramp length which is longer than the first ramp length and/or the fourth ramp length. The distal end 2874a of the third ramp 2874 can be positioned distally with respect to the distal end 2873a of the second ramp 2873 by a distance indicated by distance 2878a. The third ramp 2874 may not be parallel to the first ramp 2872, the second ramp 2873, and/or the fourth ramp 2875. Moreover, the third ramp 2874 can define a third ramp length which is longer than the first ramp length, the second ramp length, and/or the fourth ramp length.

When a sled contacts a staple driver, further to the above, a reactionary force and/or torque can be created between the sled and the staple driver which can cause the sled and/or the staple driver to rotate in response to the reactionary force and/or torque. The arrangement of ramps depicted in FIGS. 53 and 54 can prevent, or at least limit, the rotation of the sled 2870 when the sled 2870 contacts and lifts the staple drivers. Moreover, the sled 2870 can include a stabilizing member 2877 which extends distally to stabilize the sled 2870 and prevent and/or inhibit the rocking or rotation of the sled 2870. The stabilizing member 2877 can extend distally with respect to the distal ends 2872a, 2873a, 2874a, and 2875a of the ramps 2872, 2873, 2874, and 2875, respectively.

Turning now to FIGS. 54A-54D, the sled 2870 can be configured to deploy staples from staple cartridge 2000, for example, when the sled 2870 is moved from the proximal end 2016 of the staple cartridge 2000 toward the distal end 2013 of the staple cartridge 2000. The staple cartridge 2000 and/or the sled 2870 can include features which can releasably hold the sled 2870 in the proximal end 2016 of the staple cartridge 2000. In various instances, the cartridge body 2010 of the staple cartridge 2000 can include detents 2019 configured to engage the sled 2870 and releasably hold the sled 2870 in its proximal, unfired position, as illustrated in FIG. 54A. In at least one instance, referring primarily to FIGS. 54B and 54C, each detent 2019 can comprise a rib, or ridge, which extends inwardly into the longitudinal slot 2015. The ridge can extend vertically within the longitudinal slot 2015, for example. Further to the above, the body 2871 of sled 2870 can be positioned within the longitudinal slot 2015 and can be engaged with the detents 2019 when the sled 2870 is in its proximal, unfired position, as illustrated in FIG. 54A. In various instances, the detents 2019 can define a gap therebetween which is smaller than the width of the body 2871. In such instances, an interference fit can be present between the detents 2019 and the body 2871 of the sled 2870 such that the detents 2019 can grip and retain the sled 2870 in position. When a firing member pushes the sled 2870 distally, the body 2871 can be pushed out of engagement with the detents 2019 and the sled 2870 can be advanced distally to fire the staples stored in the staple cartridge 2000. In various instances, referring now to FIG. 54D, the body 2871 of the sled 2870 can comprise grooves 2018 defined therein which can be configured to releasably receive the detents 2019. The grooves 2018 and the detents 2019, when aligned, can define the proximal, unfired position of the sled 2870. Although two sets of grooves 2018 and detents 2019 are present in the illustrated embodiment, a single set could be utilized to releasably hold the sled 2870 in position. In other instances, more than two sets of grooves 2018 and detents 2019 could be utilized. In some instances, the detents 2019 could extend from the body 2871 of the sled 2870 and the grooves 2018 could be defined in the cartridge body 2010.

As discussed above, a cartridge body can comprise a tissue-supporting deck and projections extending from the deck which can be configured to, one, control the flow of tissue relative to the cartridge body, two, extend the staple cavities defined in the cartridge body above the deck and/or, three, support, protect, and/or guide the staples in the staple cavities. In various instances, the cartridge body and the projections can be comprised of a unitary piece of material. In at least one instance, the projections can be integrally formed with the cartridge body. The cartridge body and the projections can be comprised of a plastic material and can be formed during an injection molding process, for example. In certain instances, the projections can be assembled to the cartridge body. In at least one instance, the projections can be adhered to the cartridge body, for example. The cartridge body and the projections can be comprised of the same material or different materials. In at least one instance, the cartridge body can be comprised of a plastic material and the projections can be formed from an elastomeric material, such as rubber, a thermoplastic elastomer, and/or Santoprene, for example. In various instances, the projections can be comprised of a pliable material and may not traumatize the tissue compressed by the projections. Projections 3051 (FIG. 60) and/or projections 3151 (FIG. 61), for example, can be comprised of an elastomeric material, such as rubber, a thermoplastic elastomer, and/or Santoprene, for example. In at least one instance, the cartridge body can be formed during a plastic injection molding process and the projections can be formed on the cartridge body during a second molding process using a material which is more pliable than the material comprising the cartridge body. In various instances, the projections 3051 and/or 3151, for example, can comprise a textured deck surface. In certain instances, the projections 3051 and/or 3151, for example, can be comprised of a material which has a higher coefficient of friction than the cartridge body. Such embodiments can improve the gripping force between the cartridge body and the tissue.

In various instances, the projections extending from a cartridge body can be static and they may not move relative to the cartridge body. In certain instances, as discussed above, the projections can be flexible and can deform relative to the cartridge body. In some instances, as also discussed above, the cartridge body can be flexible which can permit the projections to move when the cartridge body deflects. A staple cartridge can comprise projections which can be extended relative to the cartridge body. Turning now to FIG. 75, a staple cartridge 3900 can comprise a cartridge body 3910 comprising a plurality of cavities 3950 defined therein. In various instances, a cavity 3950 can comprise a deployable tissue-engaging member 3940 positioned therein. Each member 3940 can be moved from an undeployed position to a deployed position. When a member 3940 is in its undeployed position, the member 3940 may not extend above the deck 3911 and, when the member 3940 is in its deployed position, the member 3940 may extend above the deck 3911. Alternatively, a member 3940 can extend above the deck 3911 when it is in its undeployed position. In at least one such embodiment, the tissue-engaging member 3940 can engage the tissue in its undeployed position and its deployed position. In any event, the member 3940 can comprise projections 3951 extending therefrom which can be configured to engage, stabilize, and/or compress tissue positioned intermediate the anvil 20 and the cartridge 3900.

Referring again to FIG. 75, the members 3940 can be deployed by a sled 3970 which traverses the cartridge body 3910 longitudinally from a proximal end to a distal end thereof. The sled 3970 can comprise a ramp 3972 which is configured to sequentially engage the members 3940 and lift the members 3940 between their undeployed positions and their deployed positions. In at least one instance, each member 3940 can comprise a beveled or angled surface 3942 which can be contacted by the ramp 3972. The ramp 3972 can slide underneath the members 3940 and lift the members 3940 onto a surface 3979. The surface 3979 can hold the members 3940 in their deployed positions as the sled 3970 is advanced distally by a firing member, such as firing member 2760, for example. As illustrated in FIG. 75, the surface 3979 can be long enough to support several members 3940 thereon. Moreover, the surface 3979 can be long enough the support the members 3940 during the staple forming and tissue cutting processes performed by the firing member 2760. In at least one instance, the surface 3979 can lead, or be positioned distally with respect to, the knife edge 2761 of the firing member 2760. In such instances, the members 3940 can hold the tissue positioned distally with respect to the knife edge 2761 as the knife edge 2761 is moved distally through the tissue. Stated another way, the tissue-engaging members 3940 can be deployed to grip a portion of tissue in advance of the tissue portion being stapled and/or incised. The cavities 3950 can be configured to support and guide the members 3940 and inhibit the members 3940 from being translated laterally or rotated within the cavities 3950. The proximal end of the surface 3979 may be configured and arranged such that the sled 3970 can release a member 3940 once the knife edge 2761 has passed the member 3940. In at least one such instance, the surface 3979 may no longer support a member 3940 once the knife edge 2761 has slid by the member 3940.

Further to the above, referring again to FIG. 75, the cavities 3950 can be arranged in longitudinal rows. For instance, the cavities 3950 can be arranged in six longitudinal rows comprising two innermost rows, two outermost rows, and a row positioned intermediate each innermost row and outermost row. Other embodiments are envisioned in which the cavities 3950 are arranged in less than six rows or more than six rows. In any event, some of the cavities 3950 defined in the cartridge body 3910 can be configured to support and guide a member 3940, as discussed above, while some of the cavities 3950 can contain a staple, such as staple 2630, for example removably stored therein. The sled 3970 can be configured to deploy the members 3940 and, in addition, fire the staples. In at least one such instance, the sled 3970 can further comprise at least one ramp 2873 including a ramp surface 3971 configured to lift staple drivers 2640, for example, toward the anvil 20 which, as discussed above, can fire the staples 2630. In various instances, the ramp 3972 can lead the ramp 2873. In such instances, the ramp 3972 can deploy a member 3940 into its deployed position before the ramp 2873 lifts the staples adjacent the member 3940 into their fully-formed positions. Various embodiments are envisioned in which the outermost rows of cavities 3950 include tissue-engaging members 3940 stored therein and the innermost rows and the intermediate rows of cavities 3950 include staples removably stored therein. Such an embodiment could include two rows of staples and one row of tissue-engaging members 3940 on each side of the longitudinal knife slot defined in the cartridge body. Other embodiments are envisioned in which any suitable arrangement of members 3940 and staples could be utilized.

As discussed above, embodiments are envisioned in which a staple cartridge can include rows of staples and rows of deployable tissue-engaging members. In at least one embodiment, the deployable tissue-engaging members may not be interspersed within a staple row. Other embodiments are envisioned in which deployable tissue-engaging members are dispersed within a staple row. As also discussed above, embodiments are envisioned in which staple cavities are used to store deployable tissue-engaging members. Certain embodiments are envisioned in which the tissue-engaging members are not stored within staple cavities and can be stored within a row of cavities adjacent to the staple cavities.

FIGS. 90-93 illustrate another embodiment comprising deployable tissue-engaging projections. A staple cartridge 5300, for example, can comprise a cartridge body 5310 including a deck 5311 and a plurality of staple cavities 5350 defined therein. The staple cartridge 5310 can include staples 5330 removably stored within the staple cavities 5350 and a plurality of drivers 5340 configured to eject the staples 5330 from the staple cavities 5350. The staple cartridge 5310 can further include one or more deployable projections 5351 removably stored in the staple cavities 5350, as will be discussed in greater detail further below. Each driver 5340 can include a cradle 5341 configured to support a staple 5330 and, in addition, a drive surface 5342 configured to be engaged by a sled, such as sled 5370, for example. Similar to the above, the sled 5370 can be configured to lift the drivers 5340 between an undeployed position and a deployed position. FIG. 92 depicts the drivers 5340 and the staples 5330 in their undeployed positions. Referring primarily to FIG. 93, the drivers 5340 can be configured to lift the deployable projections 5351 between an undeployed position and a deployed position. In at least one such instance, referring primarily to FIGS. 90 and 91, each driver 5340 can be assembled between a first deployable projection 5351 positioned around a proximal end of the driver 5340 and a second deployable projection 5351 positioned around a distal end of the driver 5340 wherein the upward movement of the driver 5340 can be transferred to the deployable projections 5351 to move the projections 5351 to their deployed positions. In at least one instance, the projections 5351 can be frictionally engaged with the drivers 5340. When the drivers 5340 are lifted upwardly, the friction fit between the drivers 5340 and the projections 5351 can lift the projections 5351 upwardly. Each projection 5351 can comprise a tissue-engaging portion 5352 which can be configured to contact the tissue and apply a compressive force to the tissue. In various instances, a projection 5351 may apply a compressive force to the tissue until the compressive force exceeds the static friction force between the projection 5351 and the driver 5340 moving the projection 5351 upwardly. At such point, the driver 5340 can move or slip relative to the projection 5351. Stated another way, the driver 5340 can decouple from the projections 5341 associated therewith.

In various instances, referring again to FIG. 93, the tissue-engaging portions 5352 of the deployable projections 5351 may not extend above the deck 5311 when the projections 5351 are in their undeployed position. In other instances, the tissue-engaging portions 5352 of the deployable projections 5351 may extend above the deck 5311 when the projections 5351 are in their undeployed position. In either event, the tissue-engaging portions 5352 of the deployable projections 5351 may extend above the deck 5311 when the projections 5351 are in their deployed position. Further to the above, the friction fit between each projection 5351 and a driver 5340 can be the same such that the force in which the driver 5340 will slide relative to a projection 5351, i.e., the slip force, can be the same for each projection 5351. Other embodiments are envisioned in which the friction fit between certain projections 5351 and certain drivers 5340 can be different than other projections 5351 and other drivers 5340. In such embodiments, the slip force between the projections 5351 and the drivers 5340 can be different. In at least one embodiment, the first projection 5351 positioned at a distal end of a driver 5340 can begin to slip at a first slip force and the second projection 5351 positioned at a proximal end of a driver 5340 can begin to slip at a second slip force which is different than the first slip force. In various instances, as a result of the above, the compressive force in which a projection 5351 can apply to the tissue can be limited. Moreover, as a result of the above, the distance in which a projection 5351 can extend from the deck 5311 of the cartridge body 5310 can be limited. In various instances, the projections 5351 can comprise a variable response to the type of tissue and/or the thickness of tissue being stapled. For instance, the projections 5351 may be deployed further from the deck 5311 when the tissue is thinner and/or more pliable as compared to when the tissue is thicker and/or more rigid. In any event, the slip fit between the driver 5340 and the projections 5351 can prevent the tissue from being overcompressed by the projections 5351.

Further to the above, the projections 5351 can float relative to the cartridge deck 5311. In various instances, the projections 5351 can be dynamically responsive to the compressive pressure created within the tissue captured between the anvil 20 and the staple cartridge 5300. In at least one instance, the firing member 2760 can cam or move the anvil 20 toward the staple cartridge 5300 as the firing member 2760 is advanced distally. When the anvil 20 is moved toward the staple cartridge 5300, the tissue can be compressed by the anvil 20 wherein, in response thereto, the projections 5351 can move or retract downwardly into the cartridge body 5310, for example.

In various instances, a staple cartridge can comprise projections which extend rigidly from a deck of a cartridge body. In at least one instance, the deck and the projections may not move relative to one another. In other instances, the deck can move relative to the projections. In at least one such instance, the projections can extend rigidly from the cartridge body and the deck can comprise a movable surface. When tissue is compressed between an anvil and such a staple cartridge, the deck can move downwardly with respect to the projections. The deck can be movable between a first position and a second position. When the deck is in its first position, the projections may not extend above a top surface of the deck. In such instances, the projections can be recessed below the top surface of the deck when the deck is in its first position. When the deck is moved into its second position, the projections can be exposed and extend above the top surface of the deck. Alternatively, the projections can extend above the top deck surface when the deck is in its first position and its second position. In either event, the distance in which the deck is moved relative to the projections can be a function of the pressure applied to the tissue. For instance, the deck may move a larger distance when a larger compressive pressure is applied to the tissue and a smaller distance when a smaller compressive pressure is applied to the tissue. The top deck surface can float in response to the compressive pressure applied thereto. Certain embodiments are envisioned in which the deck comprises a unitary piece of material. Other embodiments are envisioned in which the deck comprises a plurality of portions. In at least one such embodiment, each portion can react independently of the other portions. In various instances, the deck can be comprised of a resilient material which can deflect in response to the compressive pressure applied thereto. In at least one instance, the deck can be comprised of foam, for example. In certain instances, the deck can be comprised of oxidized regenerated cellulose, for example. The deck may be comprised of an implantable material or an implantable material. The deck may or may not be implanted into the patient. In various instances, the deck can include apertures defined therein which can permit relative movement between the deck and the projections. In at least one such instance, the apertures can comprise through holes and the projections can be positioned within the through holes. In certain instances, an aperture can comprise a clearance slot which extends around a staple cavity and the projection, or projections, extending around the staple cavity. When the staples are ejected from the staple cavities, the staples can pass through the openings provided by the clearance slots. In some instances, at least a portion of the deck can be captured by the staples to implant the deck against the tissue being stapled.

In various instances, a staple cartridge disclosed herein can comprise an adjunct material. An adjunct material can comprise at least one layer of material which is positioned over the deck of the staple cartridge and is implanted into the patient by staples deployed from the staple cartridge, for example. In various instances, the at least one layer of material can comprise buttress material and/or a tissue thickness compensator, for example. The at least one layer of material can be comprised of Gore SeamGuard material, Synovis Peri-Strips material, and/or polyurethane, for example. Numerous references have already been incorporated by reference which disclose such layers. The entire disclosure of U.S. patent application Ser. No. 13/763,095, entitled LAYER ARRANGEMENTS FOR SURGICAL STAPLE CARTRIDGES, filed on Feb. 28, 2013, now U.S. Patent Publication No. 2013/0161374, is incorporated by reference herein. The entire disclosures of U.S. patent application Ser. No. 13/531,619, entitled TISSUE STAPLER HAVING A THICKNESS COMPENSATOR COMPRISING INCORPORATING A HEMOSTATIC AGENT, filed on Jun. 25, 2012, now U.S. Patent Publication No. 2012/0318842, U.S. patent application Ser. No. 13/531,623, entitled TISSUE STAPLER HAVING A THICKNESS COMPENSATOR INCORPORATING AN OXYGEN GENERATING AGENT, filed on Jun. 25, 2012, now U.S. Patent Publication No. 2012/0318843, U.S. patent application Ser. No. 13/531,627, entitled TISSUE STAPLER HAVING A THICKNESS COMPENSATOR INCORPORATING AN ANTI-MICROBIAL AGENT, filed on Jun. 25, 2012, now U.S. Patent Publication No. 2012/0312860, and U.S. patent application Ser. No. 13/531,630, entitled TISSUE STAPLER HAVING A THICKNESS COMPENSATOR INCORPORATING AN ANTI-INFLAMMATORY AGENT, filed on Jun. 25, 2012, now U.S. Patent Publication No. 2012/0318844, are incorporated by reference herein. A layer can be comprised of a bioabsorbable material and/or a non-bioabsorbable material. In some instances, a layer of material can be attached to the deck. In at least one instance, at least one adhesive can be utilized to releasably adhere the layer to the deck. In some instances, the layer of material can be releasably attached to the deck utilizing one or more sutures or straps, for example. In certain instances, the layer can comprise a solid piece of material. In some instances, the layer can include apertures defined therein. In at least one such instance, a layer could be utilized with the staple cartridge 2000, for example, and can include apertures, slits, and/or slots, for example, defined therein which are aligned with the projections 2051 and/or projections 2053 extending from the deck 2011 of the staple cartridge 2010. In certain instances, the apertures can comprise through holes or windows extending completely through the layer. The apertures, slits, and/or slots, for example, can be cut into a layer utilizing a bladed cutting member, for example. In some instances, the apertures, slits, and/or slots, for example, can be formed when the layer is molded, for example. In certain instances, the apertures, slits, and/or slots, for example, can be formed in the layer utilizing a laser cutting process, for example. In some instances, the apertures can comprise recesses defined in the layer which do not extend completely through the layer. In various instances, the projections can be closely received within the apertures such that relative movement between the cartridge body 2010 and the layer can be prevented or at least limited. In at least one such instance, an interference fit can be present between the projections and the sidewalls of the apertures.

Further to the above, an adjunct layer can be comprised of a woven layer and/or a non-woven layer, for example. A layer can be comprised of film, for example. In various instances, a layer can include a textured surface, projections, and/or protrusions, for example, extending therefrom which can be configured to prevent or at least limit the flow of tissue relative to the staple cartridge. A layer can comprise a first set of regions which are engaged by and/or captured within the staples ejected from the staple cartridge and a second set of regions which are not engaged by or captured within the staples. In various instances, the second set of regions can be modified. In at least one instance, a layer can be comprised of film and the second set of regions of the film can be modified to include apertures, slits, and/or slots, for example. In at least one instance, a perimeter of such a layer can comprise cuts defined therein which can soften the edges of the layer. In certain instances, a pattern of cuts can be made in the layer. In at least one such instance, the pattern of cuts can comprise cuts which extend at a 45 degree angle relative to one another, for example. In some instances, the depth, width, and/or spacing of the cuts can be random. The cuts described above can make a layer of film more flexible, stretchable, and/or compliant. The cuts described above could be made to a woven or a non-woven material, for example. The cuts described above can be made using any suitable process, such as by a mechanical blade system and/or a laser cutting system, for example. In various instances, the first set of regions of a layer may not be modified as discussed above.

As discussed above, a layer comprised of a solid piece of material can be modified to make the layer more flexible, stretchable, and/or compliant. A layer could be assembled from several pieces of material which are bonded together. In at least one instance, apertures, slits, and/or slots, for example, can be present between the bonded pieces of material. In certain instances, strips of a highly non-elastic absorbable polymer could be welded into a thinner, more flexible film to provide stretch in certain intended directions and limit stretch in others. Such strips could also be used to reinforce highly-stressed parts of the film while allowing the other parts of the film to remain soft and compliant. One way to accomplish this would be to make several thin strips comprised of a harder polymer, such as Vicryl, for example. These strips could be approximately 0.015" to 0.030" wide, for example, and extend the full length of a staple line, for example. Six strips could be arranged to correspond to the staple line lateral spread of six longitudinal staple rows. Then, a thin, continuous film layer approximately 0.003" to 0.005" thick, for example, comprised of a soft and elastic polymer, such as Monocryl or 36/64 PGA/PCL, for example, could be welded to the six strips. In some instances, a compression molding operation could be utilized. The result would be a highly-reinforced staple line with soft sides and the ability to readily stretch laterally, but not longitudinally. The strips extending from the film could even result in traction-like holding features that would minimize tissue flow over the film in the desired direction. In certain instances, a layer comprised of a woven and/or non-woven material can be modified so as to solidify certain regions of the layer, such as the first set of regions, for example. A flat extruded fiber could be woven into a strip and then, through the use of felting and/or another heat-based technique, the first set of regions, for example, could be fused together to solidify them. In some instances, the entirety of the layer could be fused together.

As discussed above, a staple cartridge can include projections extending from a cartridge body. In addition to or in lieu of these projections, an anvil can comprise projections extending therefrom which can be configured to, one, control the flow of tissue relative to the anvil and the cartridge body, two, extend the staple cavities from the opposite side of the tissue and/or, three, support and/or guide the staples as they are being ejected from the staple cavities.

An anvil 3320 is illustrated in FIGS. 66 and 67. The anvil 3320 can comprise a distal end 3323, a proximal end 3326, and a tissue-engaging surface 3321. The anvil 3320 can further comprise a pivot 3327 about which the anvil 3320 can be rotated between an open position and a closed position. The anvil 3320 can further comprise a longitudinal slot 3325 defined therein which is configured to receive a portion of a firing and/or cutting member therein. The anvil 3320 can also comprise lateral sides which can include a longitudinal projection, or wall, 3323 extending therefrom. In various instances, a longitudinal wall 3323 can comprise a scalloped surface, for example. In some instances, a longitudinal wall 3323 can comprise a flat surface, for example. Similar to the above, the walls 3323 can be configured to limit or block the flow of tissue laterally with respect to the anvil 3320, for example.

Further to the above, the anvil 3320 can include a plurality of staple forming pockets 3322 defined therein which can be arranged in longitudinal rows which are registerable with the staple cavities defined in a staple cartridge. For instance, the forming pockets 3322 can be arranged in innermost rows 3328a, outermost rows 3328c, and rows 3328b intermediate the innermost rows 3328a and the outermost rows 3328c. In at least one instance, each staple forming pocket 3322 can comprise a first, or distal, forming cup 3322a and a second, or proximal, forming cup 3322b. The first forming cup 3322a can be configured to receive and deform a first leg of a staple and the second forming cup 3322b can be configured to receive and deform a second leg of the staple. The first forming cup 3322a and the second forming cup 3322b can be separated by a flat 3322c. The anvil 3320 can further comprise tissue-engaging projections 3324. The projections 3324 can be positioned intermediate the first forming cup 3322a and the second forming cup 3322b. A first projection 3324 can be positioned on a first lateral side of the flat 3322c and a second projection 3324 can be positioned on a second lateral side of the flat 3322c. The projections 3324 extending from the anvil 3320 can co-operate with projections extending from a staple cartridge to guide and support the staples being ejected from the staple cartridge. In at least one instance, the anvil projections 3324 and the staple cartridge projections can interlock. In various instances, the cartridge projections can extend from the ends of a staple cavity while the anvil projections 3324 can be positioned intermediate the cartridge projections over the middle of the staple cavity, for example. The anvil projections 3324 and the cartridge projections can co-operate to extend a staple cavity and support and guide a staple while the staple is being formed against the anvil 3320. The cartridge projections extending from the ends of a staple cavity can support and guide the legs of the staple as the staple legs emerge from the staple cavity and contact the anvil 3320. As the staple legs are being deformed within the forming cups 3322a, 3322b, the staple legs can be supported and guided by the projections 3324 extending from the anvil. In various instances, the staple legs can be supported and guided by the cartridge projections and the anvil projections 3324 at the same time. In some instances, the staple legs may be supported and guided by the cartridge projections and the anvil projections 3324, but not at the same time.

In various instances, the forming cups 3322a, 3322b can be configured to receive at least a portion of the projections extending from the staple cartridge therein. In at least one such instance, each forming cup 3322a, 3322b can comprise a wide, outer end configured to receive a projection extending from a staple cartridge and a narrow, inner end. The wide, outer end of the forming cups 3322a, 3322b can also be configured to initially receive the staple legs. The forming cups 3322a, 3322b can further include curved surfaces configured to direct the staple legs toward the narrow, inner ends of the forming cups 3322a, 3322b. The staple legs can then exit the forming cups 3322a, 3322b from the narrow, inner ends, where the projections 3324 are situated to support and guide the staple legs. Each forming cup 3322a, 3322b can include angled surfaces intermediate the wide, outer end and the narrow, inner end. The angled surfaces can guide the staple legs within the forming cups 3322a, 3322b, limit the lateral movement of the staple legs, and improve the alignment of the staple legs with the narrow, inner ends.

Further to the above, the projections 3324 can be configured to engage tissue and hold the tissue in position while the tissue is being stapled and/or transected. In certain instances, each projection 3324 can comprise a plateau extending from the tissue-engaging surface 3321 which includes a flat surface. FIG. 89 depicts an alternative embodiment comprising an anvil 5220 including forming pockets 3322 defined therein and tissue-engaging projections 5224 extending therefrom. Similar to projections 3224, each projection 5224 can comprise a plateau portion 5224*a* and a flat surface 5224*b* configured to engage the tissue. In addition, each projection 5224 can comprise a transition surface 5224*c* intermediate the plateau portion 5224*a* and the flat surface 5224*c*. In various instances, the transition surface 5224*c* can comprise a radius, for example. In certain instances, the transition surface 5224*c* can comprise a bevel, for example.

An anvil 5120 is illustrated in FIGS. 87 and 88. The anvil 5120 can comprise a distal end 5123, a proximal end 5126, and a tissue-engaging surface. The tissue-engaging surface can comprise steps. For instance, the tissue-engaging surface can comprise a first step 5121' and a second step 5121", for example. The second step 5121" can be taller than the first step 5121' and can extend from the first step 5121'. The anvil 5120 can further comprise a pivot 3327 about which the anvil 3320 can be rotated between an open position and a closed position. The anvil 5120 can further comprise a longitudinal slot 5125 defined therein which is configured to receive a portion of a firing and/or cutting member therein. The anvil 5120 can also comprise lateral sides 5123 which may or may not include a longitudinal projection, or wall, extending therefrom. In various instances, the taller second step 5121" can be adjacent the longitudinal slot 5125 while the first step 5121' can be adjacent the lateral sides 5123. In various instances, the second step 5121" may apply a larger compressive force to the tissue than the first step 5121'. In various alternative embodiments, the taller second step 5121" can be adjacent the lateral sides 5123 while the first step 5121' can be adjacent the longitudinal slot 5125. While the anvil 5120 comprises two steps, the anvil 5120 could comprise more than two steps. In any event, the anvil 5120 can comprise a ramp surface 5128" extending between first step 5121' and the second step 5121" which can facilitate the positioning of the anvil 5120 relative to tissue.

Further to the above, the anvil 5120 can include a plurality of staple forming pockets 5122 defined therein which can be arranged in longitudinal rows which are registerable with the staple cavities defined in a staple cartridge. In various instances, the outermost rows of forming pockets 5122 can be defined in the first step 5121'. The innermost rows of forming pockets 5122 and the intermediate rows of forming pockets 5122 can be defined in the second step 5121", for example. Other embodiments are envisioned in which the intermediate rows of forming pockets 5122 are defined the first step 5121'. In any event, the anvil 5120 can comprise tissue-engaging projections 5124 extending therefrom. In various instances, each projection 5124 can comprise an H-shaped configuration, for example. A projection 5124 can extend between adjacent forming pockets 5122, for example. A projection 5124 can extend between adjacent forming cups within a forming pocket 5122, for example. In various instances, a projection 5124 can around an end of a forming cup to support and guide a staple leg being formed by the forming cup. A projection 5124 can extend along the lateral sides of a forming pocket 5122, for example. A projection 5124 can extend along the lateral sides of a first forming pocket 5122 and a second forming pocket 5122, for example. The lateral sides of the forming pockets 5122 can be parallel, for example. In various instances, the projections 5124 can guide the staple legs within the forming cups and limit the lateral movement of the staple legs. FIG. 88 depicts a projection 5124 on each side of a forming pocket 5122. FIG. 88 also depicts a projection 5124 on each side of a forming cup of a forming pocket 5122. In various other embodiments, a projection may be positioned adjacent only some of the forming pockets 5122 of the anvil 5120 and/or only some of the forming cups of the forming pockets 5122.

In various instances, the projections extending from an anvil may have the same height. In other instances, the projections extending from an anvil may have different heights. Turning now to FIG. 69, an anvil 3520 can include a tissue-engaging surface 3321 and a longitudinal slot 3325 defined therein which is configured to receive a portion of a firing and/or cutting member. The anvil 3520 can also comprise lateral sides which can include a longitudinal projection, or wall, 3323 extending therefrom. Similar to the above, the anvil 3520 can include forming pockets arranged in innermost rows 3328*a*, outermost rows 3328*c*, and rows 3328*b* intermediate the innermost rows 3328*a* and the outermost rows 3328*c*. In various instances, the anvil 3520 can comprise longitudinal rows of first projections 3551*a* adjacent the innermost rows 3328*a*, longitudinal rows of second projections 3551*b* adjacent the intermediate rows 3328*b*, and longitudinal rows of third projections 3551*c* adjacent the outermost rows 3228*c*, for example. The first projections 3551*a* can extend from the tissue-engaging surface 3221 a first distance and the second projections 3551*b* can extend from the tissue-engaging surface 3221 a second distance which is different than the first distance. The third projections 3551*c* can extend from the tissue-engaging surface 3221 a third distance which can be different than the first distance and/or the second distance. In various instances, the third projections 3551*c* can be taller than the second projections 3551*b* and the second projections 3551*b* can be taller than the first projections 3551*a*. In various alternative embodiments, the projections 3551*a* can be positioned adjacent to the intermediate rows 3328*b* and/or the outermost rows 3328*c*, for example, the projections 3551*b* can be positioned adjacent to the innermost rows 3328*a* and/or the outermost rows 3328*c*, for example, and/or the projections 3551*c* can be positioned adjacent to the innermost rows 3328*a* and/or the intermediate rows 3328*b*, for example.

An anvil 3420 is illustrated in FIG. 68. The anvil 3420 can comprise a distal end 3423, a proximal end, and a tissue-engaging surface 3321. The anvil 3420 can further comprise a pivot 3327 about which the anvil 3420 can be rotated between an open position and a closed position. The anvil 3420 can further comprise a longitudinal slot 3325 defined therein which is configured to receive a portion of a firing and/or cutting member therein. The anvil 3420 can also comprise lateral sides which can include a longitudinal projection, or wall, 3323 extending therefrom. The anvil 3420 can include a plurality of staple forming pockets 3322 defined therein which can be arranged in longitudinal rows which are registerable with the staple cavities defined in a staple cartridge. In various instances, further to the above, the anvil 3420 can comprise projections extending therefrom. For example, the anvil 3420 can include pyramidal projections 3051 and/or domed-shaped projections 3151 extending therefrom. The projections 3051 and/or the projections 3151 can improve the gripping force that can be applied to the tissue.

In various instances, an anvil and the projections extending from the anvil can be comprised of a unitary piece of material. In at least one instance, the projections can be integrally formed with the anvil. The anvil and projections can be comprised of a metallic material, such as stainless steel, for example, and can be formed during a machining and/or stamping process, for example. In certain instances, the projections can be assembled to the anvil. In at least one instance, the projections can be adhered to the anvil, for example. The anvil and the projections can be comprised of the same material or different materials. In at least one instance, the anvil can be comprised of a metallic material and the projections can be formed from an elastomeric material, such as rubber, a thermoplastic elastomer, and/or Santoprene, for example. In various instances, the projections can be comprised of a pliable material and may not traumatize the tissue compressed by the projections. Projections 3051 and/or projections 3151, for example, can be comprised of an elastomeric material, such as rubber, a thermoplastic elastomer, and/or Santoprene, for example. In at least one instance, the anvil can be formed during a machining and/or stamping process and the projections can be formed on the anvil during a molding process using a material which is more pliable than the material comprising the anvil. In various instances, the projections 3051 and/or 3151, for example, can comprise a textured anvil surface. In certain instances, the projections 3051 and/or 3151, for example, can be comprised of a material which has a higher coefficient of friction than the anvil. Such embodiments can improve the gripping force between the anvil and the tissue.

Further to the above, an anvil can include a uniform array of projections extending therefrom. In other instances, the array may not be uniform. Referring again to FIG. 68, projections 3051 can extend from the anvil surface 3321 on a first side of the longitudinal slot 3325 and the projections 3151 can extend from the anvil surface 3321 on a second side of the longitudinal slot 3325. In various instances, the projections can be positioned distally with respect to the forming pockets 3322, for example. In certain instances, the projections can interspersed among the forming pockets 3322. The projections can extend from a surface 3429*a* defined intermediate the innermost forming pockets 3322 and the slot 3325, a surface 3429*b* defined intermediate the innermost forming pockets 3322 and the intermediate forming pockets 3322, a surface 3429*c* defined intermediate the intermediate forming pockets 3322 and the outermost forming pockets 3322, and/or a surface 3429*d* defined intermediate the outermost forming pockets 3322 and the lateral walls 3323, for example.

FIG. 98 depicts an anvil 5920. The anvil 5920 can include a distal end 5923, a proximal end 5926, and a tissue-engaging surface 5921. The anvil 5920 can further comprise tissue-engaging members extending from the surface 5921 which are configured to prevent or limit the flow of tissue relative to the anvil 5920. In at least one instance, the anvil 5920 can include projections 5924' and projections 5924", for example. The projections 5924" can be taller than the projections 5924'. This difference in height is indicated by dimension 5925. As illustrated in FIG. 98, the projections 5924" can be positioned distally with respect to the projections 5924'. In various instances, the projections 5924" and the projections 5924' can be part of a longitudinal row of projections. In some instances, the projections 5924" and the projections 5924' can be part of different longitudinal rows of projections. In certain instances, although not illustrated, the projections 5924' can be positioned distally with respect to the projections 5924".

In various instances, an anvil disclosed herein can comprise an adjunct material. An adjunct material can comprise at least one layer of material which is positioned over the tissue-engaging surface of the anvil and is implanted into the patient by staples deployed from a staple cartridge, for example. In various instances, the at least one layer of material can comprise buttress material and/or a tissue thickness compensator, for example. The at least one layer of material can be comprised of Gore SeamGuard material, Synovis Peri-Strips material, and/or polyurethane, for example. Numerous references have already been incorporated by reference which disclose such layers. The entire disclosure of U.S. patent application Ser. No. 13/763,095, entitled LAYER ARRANGEMENTS FOR SURGICAL STAPLE CARTRIDGES, filed on Feb. 28, 2013, now U.S. Patent Publication No. 2013/0161374, is incorporated by reference herein. The entire disclosures of U.S. patent application Ser. No. 13/531,619, entitled TISSUE STAPLER HAVING A THICKNESS COMPENSATOR COMPRISING INCORPORATING A HEMOSTATIC AGENT, filed on Jun. 25, 2012, now U.S. Patent Publication No. 2012/0318842, U.S. patent application Ser. No. 13/531,623, entitled TISSUE STAPLER HAVING A THICKNESS COMPENSATOR INCORPORATING AN OXYGEN GENERATING AGENT, filed on Jun. 25, 2012, now U.S. Patent Publication No. 2012/0318843, U.S. patent application Ser. No. 13/531,627, entitled TISSUE STAPLER HAVING A THICKNESS COMPENSATOR INCORPORATING AN ANTI-MICROBIAL AGENT, filed on Jun. 25, 2012, now U.S. Patent Publication No. 2012/0312860, and U.S. patent application Ser. No. 13/531,630, entitled TISSUE STAPLER HAVING A THICKNESS COMPENSATOR INCORPORATING AN ANTI-INFLAMMATORY AGENT, filed on Jun. 25, 2012, now U.S. Patent Publication No. 2012/0318844, are incorporated by reference herein. A layer can be comprised of a bioabsorbable material and/or a non-bioabsorbable material. In some instances, a layer of material can be attached to the anvil. In at least one instance, at least one adhesive can be utilized to releasably adhere the layer to the anvil. In some instances, the layer of material can be releasably attached to the anvil utilizing one or more sutures or straps, for example. In various instances, a layer can comprise projections extending therefrom which can extend into the forming pockets defined in the anvil. The projections can be arranged in an array, or pattern, which is aligned with the array, or pattern, of forming pockets in the anvil. In at least one instance, the projections can fit snugly within the forming pockets. The projections can be configured to limit the lateral and/or longitudinal movement of the layer relative to the anvil.

In certain instances, a layer can comprise a solid piece of material. In some instances, the layer can include apertures defined therein. In at least one such instance, a layer could be utilized with the anvil 3320, for example, and can include apertures, slits, and/or slots, for example, defined therein which are aligned with the projections extending from the tissue-engaging surface 3321 of the anvil 3320. In certain instances, the apertures can comprise through holes or windows extending completely through the layer. The apertures, slits, and/or slots, for example, can be cut into a layer utilizing a bladed cutting member, for example. In some instances, the apertures, slits, and/or slots, for example, can be formed when the layer is molded, for example. In certain instances, the apertures, slits, and/or slots, for example, can be formed in the layer utilizing a laser cutting process, for example. In some instances, the apertures can comprise recesses defined in the layer which do not extend completely through the layer. In various instances, the projections can be closely received within the apertures such that relative movement between the anvil 3320 and the layer can be prevented or at least limited. In at least one such instance, an interference fit can be present between the projections and the sidewalls of the apertures.

Further to the above, an adjunct layer can be comprised of a woven layer and/or a non-woven layer, for example. A layer can be comprised of film, for example. In various instances, a layer can include a textured surface, projections, and/or protrusions, for example, extending therefrom which can be configured to prevent or at least limit the flow of tissue relative to the anvil. A layer can comprise a first set of regions which are engaged by and/or captured within staples ejected from a staple cartridge and a second set of regions which are not engaged by or captured within the staples. In various instances, the second set of regions can be modified. In at least one instance, a layer can be comprised of film and the second set of regions of the film can be modified to include apertures, slits, and/or slots, for example. In at least one instance, a perimeter of such a layer can comprise cuts defined therein which can soften the edges of the layer. In certain instances, a pattern of cuts can be made in the layer. In at least one such instance, the pattern of cuts can comprise cuts which extend at a 45 degree angle relative to one another, for example. In some instances, the depth, width, and/or spacing of the cuts can be random. The cuts described above can make a layer of film more flexible, stretchable, and/or compliant. The cuts described above could be made to a woven or a non-woven material, for example. The cuts described above can be made using any suitable process, such as by a mechanical blade system and/or a laser cutting system, for example. In various instances, the first set of regions of a layer may not be modified as discussed above.

As discussed above, a layer comprised of a solid piece of material can be modified to make the layer more flexible, stretchable, and/or compliant. A layer could be assembled from several pieces of material which are bonded together. In at least one instance, apertures, slits, and/or slots, for example, can be present between the bonded pieces of material. In certain instances, strips of a highly non-elastic absorbable polymer could be welded into a thinner, more flexible film to provide stretch in certain intended directions and limit stretch in others. Such strips could also be used to reinforce highly-stressed parts of the film while allowing the other parts of the film to remain soft and compliant. One way to accomplish this would be to make several thin strips comprised of a harder polymer, such as Vicryl, for example. These strips could be approximately 0.015" to 0.030" wide, for example, and extend the full length of a staple forming pocket line, for example. Six strips could be arranged to correspond to the staple line lateral spread of six longitudinal staple rows. Then, a thin, continuous film layer approximately 0.003" to 0.005" thick, for example, comprised of a soft and elastic polymer, such as Monocryl or 36/64 PGA/PCL, for example, could be welded to the six strips. In some instances, a compression molding operation could be utilized. The result would be a highly-reinforced staple line with soft sides and the ability to readily stretch laterally, but not longitudinally. The strips extending from the film could even result in traction-like holding features that would minimize tissue flow over the film in the desired direction. In certain instances, a layer comprised of a woven and/or non-woven material can be modified so as to solidify certain regions of the layer, such as the first set of regions, for example. A flat extruded fiber could be woven into a strip and then, through the use of felting and/or another heat-based technique, the first set of regions, for example, could be fused together to solidify them. In some instances, the entirety of the layer could be fused together.

Various embodiments are disclosed herein comprising staples removably stored within a staple cartridge in an end-to-end arrangement within one or more longitudinal rows. Similarly, various embodiments are disclosed herein comprising an anvil including staple forming pockets arranged in a corresponding end-to-end arrangement. Other staple and staple forming pocket arrangements are envisioned and are adaptable to the embodiments disclosed herein. Such arrangements may or may not comprise an end-to-end arrangement. The entire disclosure of U.S. Pat. No. 8,186,560, entitled SURGICAL STAPLING SYSTEMS AND STAPLE CARTRIDGES FOR DEPLOYING SURGICAL STAPLES WITH TISSUE COMPRESSION FEATURES, which issued on May 29, 2012, is incorporated by reference herein. The entire disclosure of U.S. Pat. No. 8,365,976, entitled SURGICAL STAPLES HAVING DISSOLVABLE, BIOABSORBABLE OR BIOFRAGMENTABLE PORTIONS AND STAPLING INSTRUMENTS FOR DEPLOYING THE SAME, which issued on Feb. 5, 2013, is incorporated by reference herein.

FIGS. 19-22 depict a motor-driven surgical cutting and fastening instrument 1010 that may or may not be reused. In the illustrated embodiment, the instrument 1010 includes a housing 1012 that comprises a handle 1014 that is configured to be grasped, manipulated and actuated by the clinician. The housing 1012 is configured for operable attachment to an interchangeable shaft assembly 1200 that has a surgical end effector 1300 operably coupled thereto that is configured to perform one or more surgical tasks or procedures. As the present Detailed Description proceeds, it will be understood that the various unique and novel arrangements of the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. US 2012/0298719. U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. US 2012/0298719, is incorporated by reference herein in its entirety.

The housing 1012 depicted in FIGS. 19-21 is shown in connection with an interchangeable shaft assembly 1200 that includes an end effector 1300 that comprises a surgical cutting and fastening device that is configured to operably support a surgical staple cartridge 1304 therein. The housing 1012 may be configured for use in connection with interchangeable shaft assemblies that include end effectors that are adapted to support different sizes and types of staple cartridges, have different shaft lengths, sizes, and types, etc. In addition, the housing 1012 may also be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

FIG. 19 illustrates the surgical instrument 1010 with an interchangeable shaft assembly 1200 operably coupled thereto. FIGS. 20 and 21 illustrate attachment of the interchangeable shaft assembly 1200 to the housing 1012 or handle 1014. As can be seen in FIG. 21, the handle 1014 may comprise a pair of interconnectable handle housing segments 1016 and 1018 that may be interconnected by screws, snap features, adhesive, etc. In the illustrated arrangement, the handle housing segments 1016, 1018 cooperate to form a pistol grip portion 1019 that can be gripped and manipulated by the clinician. As will be discussed in further detail below, the handle 1014 operably supports a plurality of drive systems therein that are configured to generate and apply various control motions to corresponding portions of the interchangeable shaft assembly that is operably attached thereto.

Referring now to FIG. 21, the handle 1014 may further include a frame 1020 that operably supports a plurality of drive systems. For example, the frame 1020 can operably support a "first" or closure drive system, generally designated as 1030, which may be employed to apply closing and opening motions to the interchangeable shaft assembly 1200 that is operably attached or coupled thereto. In at least one form, the closure drive system 1030 may include an actuator in the form of a closure trigger 1032 that is pivotally supported by the frame 1020. More specifically, as illustrated in FIG. 21, the closure trigger 1032 is pivotally coupled to the housing 1014 by a pin 1033. Such arrangement enables the closure trigger 1032 to be manipulated by a clinician such that when the clinician grips the pistol grip portion 1019 of the handle 1014, the closure trigger 1032 may be easily pivoted from a starting or "unactuated" position to an "actuated" position and more particularly to a fully compressed or fully actuated position. The closure trigger 1032 may be biased into the unactuated position by spring or other biasing arrangement (not shown). In various forms, the closure drive system 1030 further includes a closure linkage assembly 1034 that is pivotally coupled to the closure trigger 1032. As can be seen in FIG. 21, the closure linkage assembly 1034 may include a first closure link 1036 and a second closure link 1038 that are pivotally coupled to the closure trigger 1032 by a pin 1035. The second closure link 1038 may also be referred to herein as an "attachment member" and include a transverse attachment pin 1037.

Still referring to FIG. 21, it can be observed that the first closure link 1036 may have a locking wall or end 1039 thereon that is configured to cooperate with a closure release assembly 1060 that is pivotally coupled to the frame 1020. In at least one form, the closure release assembly 1060 may comprise a release button assembly 1062 that has a distally protruding locking pawl 1064 formed thereon. The release button assembly 1062 may be pivoted in a counterclockwise direction by a release spring (not shown). As the clinician depresses the closure trigger 1032 from its unactuated position towards the pistol grip portion 1019 of the handle 1014, the first closure link 1036 pivots upward to a point wherein the locking pawl 1064 drops into retaining engagement with the locking wall 1039 on the first closure link 1036 thereby preventing the closure trigger 1032 from returning to the unactuated position. Thus, the closure release assembly 1060 serves to lock the closure trigger 1032 in the fully actuated position. When the clinician desires to unlock the closure trigger 1032 to permit it to be biased to the unactuated position, the clinician simply pivots the closure release button assembly 1062 such that the locking pawl 1064 is moved out of engagement with the locking wall 1039 on the first closure link 1036. When the locking pawl 1064 has been moved out of engagement with the first closure link 1036, the closure trigger 1032 may pivot back to the unactuated position. Other closure trigger locking and release arrangements may also be employed.

An arm 1061 may extend from the closure release button 1062. A magnetic element 1063, such as a permanent magnet, for example, may be mounted to the arm 1061. When the closure release button 1062 is rotated from its first position to its second position, the magnetic element 1063 can move toward a circuit board 1100. The circuit board 1100 can include at least one sensor that is configured to detect the movement of the magnetic element 1063. In at least one embodiment, for example, a "Hall Effect" sensor (not shown) can be mounted to the bottom surface of the circuit board 1100. The Hall Effect sensor can be configured to detect changes in a magnetic field surrounding the Hall Effect sensor caused by the movement of the magnetic element 1063. The Hall Effect sensor can be in signal communication with a microcontroller, for example, which can determine whether the closure release button 1062 is in its first position, which is associated with the unactuated position of the closure trigger 1032 and the open configuration of the end effector, its second position, which is associated with the actuated position of the closure trigger 1032 and the closed configuration of the end effector, and/or any position between the first position and the second position.

In at least one form, the handle 1014 and the frame 1020 may operably support another drive system referred to herein as a firing drive system 1080 that is configured to apply firing motions to corresponding portions of the interchangeable shaft assembly attached thereto. The firing drive system may 1080 also be referred to herein as a "second drive system". The firing drive system 1080 may employ an electric motor 1082 that is located in the pistol grip portion 1019 of the handle 1014. In various forms, the motor 1082 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 1082 may be powered by a power source 1090 that in one form may comprise a removable power pack 1092. As can be seen in FIG. 21, for example, the power pack 1092 may comprise a proximal housing portion 1094 that is configured for attachment to a distal housing portion 1096. The proximal housing portion 1094 and the distal housing portion 1096 are configured to operably support a plurality of batteries 1098 therein. Batteries 1098 may each comprise, for example, a Lithium Ion ("LI") or other suitable battery. The distal housing portion 1096 is configured for removable operable attachment to the circuit board assembly 1100 which is also operably coupled to the motor 1082. A number of batteries 1098 may be connected in series may be used as the power source for the surgical instrument 1010. In addition, the power source 1090 may be replaceable and/or rechargeable.

As outlined above with respect to other various forms, the electric motor 1082 can include a rotatable shaft (not shown) that operably interfaces with a gear reducer assembly 1084 that is mounted in meshing engagement with a with a set, or rack, of drive teeth 1122 on a longitudinally-movable drive member 1120. In use, a voltage polarity provided by the power source 1090 can operate the electric motor 1082 in a clockwise direction wherein the voltage polarity applied to the electric motor by the battery can be reversed in order to operate the electric motor 1082 in a counterclockwise direction. When the electric motor 1082 is rotated in one direction, the drive member 1120 will be axially driven in the distal direction "DD". When the motor 82 is driven in the opposite rotary direction, the drive member 1120 will be axially driven in a proximal direction "PD". The handle 1014 can include a switch which can be configured to reverse the polarity applied to the electric motor 1082 by the power source 1090. As with the other forms described herein, the handle 1014 can also include a sensor that is configured to detect the position of the drive member 1120 and/or the direction in which the drive member 1120 is being moved.

Actuation of the motor 1082 can be controlled by a firing trigger 1130 that is pivotally supported on the handle 1014. The firing trigger 1130 may be pivoted between an unactuated position and an actuated position. The firing trigger 1130 may be biased into the unactuated position by a spring 1132 or other biasing arrangement such that when the clinician releases the firing trigger 1130, it may be pivoted or otherwise returned to the unactuated position by the spring 1132 or biasing arrangement. In at least one form, the firing trigger 1130 can be positioned "outboard" of the closure trigger 132 as was discussed above. In at least one form, a firing trigger safety button 1134 may be pivotally mounted to the closure trigger 1032 by pin 1035. The safety button 1134 may be positioned between the firing trigger 1130 and the closure trigger 1032 and have a pivot arm 1136 protruding therefrom. See FIG. 21. When the closure trigger 1032 is in the unactuated position, the safety button 1134 is contained in the handle 1014 where the clinician cannot readily access it and move it between a safety position preventing actuation of the firing trigger 1130 and a firing position wherein the firing trigger 1130 may be fired. As the clinician depresses the closure trigger 1032, the safety button 1134 and the firing trigger 1130 pivot down wherein they can then be manipulated by the clinician.

As indicated above, in at least one form, the longitudinally movable drive member 1120 has a rack of teeth 1122 formed thereon for meshing engagement with a corresponding drive gear 1086 of the gear reducer assembly 1084. At least one form also includes a manually-actuatable "bailout" assembly 1140 that is configured to enable the clinician to manually retract the longitudinally movable drive member 1120 should the motor 1082 become disabled. The bailout assembly 1140 may include a lever or bailout handle assembly 1142 that is configured to be manually pivoted into ratcheting engagement with teeth 1124 also provided in the drive member 1120. Thus, the clinician can manually retract the drive member 1120 by using the bailout handle assembly 1142 to ratchet the drive member 1120 in the proximal direction "PD". U.S. Patent Application Publication No. US 2010/0089970, now U.S. Pat. No. 8,608,045, discloses bailout arrangements and other components, arrangements and systems that may also be employed with the various instruments disclosed herein. U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045, is hereby incorporated by reference herein in its entirety.

Turning now to FIGS. 20 and 22, the interchangeable shaft assembly 1200 includes a surgical end effector 1300 that comprises an elongate channel 1302 that is configured to operably support a staple cartridge 1304 therein. The end effector 1300 may further include an anvil 1306 that is pivotally supported relative to the elongate channel 1302. The interchangeable shaft assembly 1200 may further include an articulation joint 1270 and an articulation lock which can be configured to releasably hold the end effector 1300 in a desired position relative to a shaft axis SA-SA. Details regarding the construction and operation of the end effector 1300, the articulation joint 1270 and the articulation lock are set forth in U.S. patent application Ser. No. 13/803,086, filed Mar. 14, 2013, entitled ARTICULATABLE SURGICAL INSTRUMENT COMPRISING AN ARTICULATION LOCK. The entire disclosure of U.S. patent application Ser. No. 13/803,086, filed Mar. 14, 2013, entitled ARTICULATABLE SURGICAL INSTRUMENT COMPRISING AN ARTICULATION LOCK is hereby incorporated by reference herein. As can be seen in FIG. 22, the interchangeable shaft assembly 1200 can further include a proximal housing or nozzle 1201 comprised of nozzle portions 1202 and 1203. The interchangeable shaft assembly 1200 can further include a closure tube 1260 which can be utilized to close and/or open the anvil 1306 of the end effector 1300. The shaft assembly 1200 can include a spine 1210 that is configured to, one, slidably support a firing member therein and, two, slidably support the closure tube 1260 which extends around the spine 210. The spine 210 can also be configured to slidably support a proximal articulation driver. The articulation driver has a distal end that is configured to operably engage the articulation lock. The articulation lock interfaces with an articulation frame that is adapted to operably engage a drive pin on the end effector frame. As indicated above, further details regarding the operation of the articulation lock and the articulation frame may be found in U.S. patent application Ser. No. 13/803,086. In various circumstances, the spine 1210 can comprise a proximal end 1211 which is rotatably supported in a chassis 1240. In one arrangement, for example, the proximal end 1211 of the spine 1210 has a thread 1214 formed thereon for threaded attachment to a spine bearing 1216 configured to be supported within the chassis 1240. See FIG. 22. Such an arrangement facilitates rotatable attachment of the spine 1210 to the chassis 1240 such that the spine 1210 may be selectively rotated about a shaft axis SA relative to the chassis 1240.

Referring primarily to FIG. 22, the interchangeable shaft assembly 1200 includes a closure shuttle 1250 that is slidably supported within the chassis 1240 such that it may be axially moved relative thereto. The closure shuttle 1250 includes a pair of proximally-protruding hooks 1252 that are configured for attachment to the attachment pin 1037 (FIGS. 20 and 21) that is attached to the second closure link 1038 as will be discussed in further detail below. A proximal end 1261 of the closure tube 1260 is coupled to the closure shuttle 1250 for relative rotation thereto. For example, a U shaped connector 1263 is inserted into an annular slot 1262 in the proximal end 1261 of the closure tube 1260 and is retained within vertical slots 1253 in the closure shuttle 1250. Such an arrangement serves to attach the closure tube 1260 to the closure shuttle 1250 for axial travel therewith while enabling the closure tube 1260 to rotate relative to the closure shuttle 1250 about the shaft axis SA. A closure spring 1268 is journaled on the closure tube 1260 and serves to bias the closure tube 1260 in the proximal direction "PD"

which can serve to pivot the closure trigger into the unactuated position when the shaft assembly is operably coupled to the handle 1014.

In at least one form, the interchangeable shaft assembly 1200 may further include an articulation joint 1270. Other interchangeable shaft assemblies, however, may not be capable of articulation. As can be seen in FIG. 22, for example, the articulation joint 1270 includes a double pivot closure sleeve assembly 1271. According to various forms, the double pivot closure sleeve assembly 1271 includes an end effector closure sleeve assembly 1272 having upper and lower distally projecting tangs 1273, 1274. An end effector closure sleeve assembly 1272 includes a horseshoe aperture 1275 and a tab 1276 for engaging an opening tab on the anvil 1306 in the various manners described in U.S. patent application Ser. No. 13/803,086, filed Mar. 14, 2013, entitled, ARTICULATABLE SURGICAL INSTRUMENT COMPRISING AN ARTICULATION LOCK which has been incorporated by reference herein. As described in further detail therein, the horseshoe aperture 1275 and tab 1276 engage a tab on the anvil when the anvil 1306 is opened. An upper double pivot link 1277 includes upwardly projecting distal and proximal pivot pins that engage respectively an upper distal pin hole in the upper proximally projecting tang 1273 and an upper proximal pin hole in an upper distally projecting tang 1264 on the closure tube 1260. A lower double pivot link 1278 includes upwardly projecting distal and proximal pivot pins that engage respectively a lower distal pin hole in the lower proximally projecting tang 1274 and a lower proximal pin hole in the lower distally projecting tang 1265. See also FIG. 22.

In use, the closure tube 1260 is translated distally (direction "DD") to close the anvil 1306, for example, in response to the actuation of the closure trigger 1032. The anvil 1306 is closed by distally translating the closure tube 1260 and thus the shaft closure sleeve assembly 1272, causing it to strike a proximal surface on the anvil 1360 in the manner described in the aforementioned referenced U.S. patent application Ser. No. 13/803,086. As was also described in detail in that reference, the anvil 1306 is opened by proximally translating the closure tube 1260 and the shaft closure sleeve assembly 1272, causing tab 1276 and the horseshoe aperture 1275 to contact and push against the anvil tab to lift the anvil 1306. In the anvil-open position, the shaft closure tube 1260 is moved to its proximal position.

As was also indicated above, the interchangeable shaft assembly 1200 further includes a firing member that is supported for axial travel within the shaft spine 1210. The firing member includes an intermediate firing shaft portion 1222 that is configured for attachment to a distal cutting portion or knife bar. The intermediate firing shaft portion 1222 may include a longitudinal slot in the distal end thereof which can be configured to receive a tab on the proximal end of the distal knife bar. The longitudinal slot and the proximal end can be sized and configured to permit relative movement therebetween and can comprise a slip joint. The slip joint can permit the intermediate firing shaft portion 1222 of the firing drive to be moved to articulate the end effector 1300 without moving, or at least substantially moving, the knife bar. Once the end effector 1300 has been suitably oriented, the intermediate firing shaft portion 1222 can be advanced distally until a proximal sidewall of the longitudinal slot comes into contact with the tab in order to advance the knife bar and fire the staple cartridge positioned within the channel 1302. Further description of the operation of the firing member may be found in U.S. patent application Ser. No. 13/803,086.

As can be seen in FIG. 22, the shaft assembly 1200 further includes a switch drum 1500 that is rotatably received on the closure tube 1260. The switch drum 1500 comprises a hollow shaft segment 1502 that has a shaft boss formed thereon for receive an outwardly protruding actuation pin therein. In various circumstances, the actuation pin extends through a longitudinal slot provided in the lock sleeve to facilitate axial movement of the lock sleeve when it is engaged with the articulation driver. A rotary torsion spring 1420 is configured to engage the boss on the switch drum 1500 and a portion of the nozzle housing 1203 to apply a biasing force to the switch drum 1500. The switch drum 1500 can further comprise at least partially circumferential openings 1506 defined therein which can be configured to receive circumferential mounts extending from the nozzle halves 1202, 1203 and permit relative rotation, but not translation, between the switch drum 1500 and the proximal nozzle 1201. The mounts also extend through openings 1266 in the closure tube 1260 to be seated in recesses in the shaft spine 1210. However, rotation of the nozzle 1201 to a point where the mounts reach the end of their respective slots 1506 in the switch drum 1500 will result in rotation of the switch drum 1500 about the shaft axis SA. Rotation of the switch drum 1500 will ultimately result in the rotation of the actuation pin and the lock sleeve between its engaged and disengaged positions. Thus, in essence, the nozzle 1201 may be employed to operably engage and disengage the articulation drive system with the firing drive system in the various manners described in further detail in U.S. patent application Ser. No. 13/803,086 and U.S. patent application Ser. No. 14/226,142, entitled SURGICAL INSTRUMENT COMPRISING A SENSOR SYSTEM, filed Mar. 26, 2014, the entitle disclosures of each being hereby incorporated by reference herein.

As also illustrated in FIG. 22, the shaft assembly 1200 can comprise a slip ring assembly 1600 which can be configured to conduct electrical power to and/or from the end effector 1300 and/or communicate signals to and/or from the end effector 1300, for example. The slip ring assembly 1600 can comprise a proximal connector flange 1604 that is mounted to a chassis flange 1242 that extends from the chassis 1240 and a distal connector flange that is positioned within a slot defined in the shaft housings. The proximal connector flange 1604 can comprise a first face and the distal connector flange can comprise a second face which is positioned adjacent to and movable relative to the first face. The distal connector flange can rotate relative to the proximal connector flange 1604 about the shaft axis SA. The proximal connector flange 1604 can comprise a plurality of concentric, or at least substantially concentric, conductors defined in the first face thereof. A connector can be mounted on the proximal side of the connector flange and may have a plurality of contacts wherein each contact corresponds to and is in electrical contact with one of the conductors. Such an arrangement permits relative rotation between the proximal connector flange 1604 and the distal connector flange while maintaining electrical contact therebetween. The proximal connector flange 1604 can include an electrical connector 1606 which can place the conductors in signal communication with a shaft circuit board 1610 mounted to the shaft chassis 1240, for example. In at least one instance, a wiring harness comprising a plurality of conductors can extend between the electrical connector 1606 and the shaft circuit board 1610. The electrical connector 1606 may extend proximally through a connector opening 1243 defined in the chassis mounting flange 1242. See FIG. 22. U.S. patent application Ser. No. 13/800,067, entitled STAPLE CARTRIDGE TIS- SUE THICKNESS SENSOR SYSTEM, filed on Mar. 13, 2013, is incorporated by reference herein in its entirety. U.S. patent application Ser. No. 13/800,025, entitled STAPLE CARTRIDGE TISSUE THICKNESS SENSOR SYSTEM, filed on Mar. 13, 2013, is incorporated by reference herein in its entirety. Further details regarding slip ring assembly 1600 may be found in U.S. patent application Ser. No. 13/803,086.

As discussed above, the shaft assembly 1200 can include a proximal portion which is fixably mounted to the handle 1014 and a distal portion which is rotatable about a longitudinal axis. The rotatable distal shaft portion can be rotated relative to the proximal portion about the slip ring assembly 1600, as discussed above. The distal connector flange of the slip ring assembly 1600 can be positioned within the rotatable distal shaft portion. Moreover, further to the above, the switch drum 1500 can also be positioned within the rotatable distal shaft portion. When the rotatable distal shaft portion is rotated, the distal connector flange and the switch drum 1500 can be rotated synchronously with one another. In addition, the switch drum 1500 can be rotated between a first position and a second position relative to the distal connector flange. When the switch drum 1500 is in its first position, the articulation drive system may be operably disengaged from the firing drive system and, thus, the operation of the firing drive system may not articulate the end effector 1300 of the shaft assembly 1200. When the switch drum 1500 is in its second position, the articulation drive system may be operably engaged with the firing drive system and, thus, the operation of the firing drive system may articulate the end effector 1300 of the shaft assembly 1200. When the switch drum 1500 is moved between its first position and its second position, the switch drum 1500 is moved relative to distal connector flange. In various instances, the shaft assembly 1200 can comprise at least one sensor configured to detect the position of the switch drum 1500.

Referring again to FIG. 22, the chassis 1240 includes at least one, and preferably two, tapered attachment portions 1244 formed thereon that are adapted to be received within corresponding dovetail slots 1702 formed within a distal attachment flange portion 1700 of the frame 1020. See FIG. 21. Each dovetail slot 1702 may be tapered or, stated another way, be somewhat V-shaped to seatingly receive the attachment portions 1244 therein. As can be further seen in FIG. 22, a shaft attachment lug 1226 is formed on the proximal end of the intermediate firing shaft 1222. As will be discussed in further detail below, when the interchangeable shaft assembly 1200 is coupled to the handle 1014, the shaft attachment lug 1226 is received in a firing shaft attachment cradle 1126 formed in the distal end 1125 of the longitudinal drive member 1120. See FIG. 21.

Various shaft assembly embodiments employ a latch system 1710 for removably coupling the shaft assembly 1200 to the housing 1012 and more specifically to the frame 1020. As can be seen in FIG. 22, for example, in at least one form, the latch system 1710 includes a lock member or lock yoke 1712 that is movably coupled to the chassis 1240. In the illustrated embodiment, for example, the lock yoke 1712 has a U-shape with two spaced downwardly extending legs 1714. The legs 1714 each have a pivot lug 1715 formed thereon that are adapted to be received in corresponding holes 1245 formed in the chassis 1240. Such arrangement facilitates pivotal attachment of the lock yoke 1712 to the chassis 1240. The lock yoke 1712 may include two proximally protruding lock lugs 1716 that are configured for releasable engagement with corresponding lock detents or grooves 1704 in the distal attachment flange 1700 of the frame 1020. See FIG. 21. In various forms, the lock yoke 1712 is biased in the proximal direction by spring or biasing member (not shown). Actuation of the lock yoke 1712 may be accomplished by a latch button 1722 that is slidably mounted on a latch actuator assembly 1720 that is mounted to the chassis 1240. The latch button 1722 may be biased in a proximal direction relative to the lock yoke 1712. As will be discussed in further detail below, the lock yoke 1712 may be moved to an unlocked position by biasing the latch button the in distal direction which also causes the lock yoke 1712 to pivot out of retaining engagement with the distal attachment flange 1700 of the frame 1020. When the lock yoke 1712 is in "retaining engagement" with the distal attachment flange 1700 of the frame 1020, the lock lugs 1716 are retainingly seated within the corresponding lock detents or grooves 1704 in the distal attachment flange 1700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 32 to grasp and manipulate the target tissue into a desired position. Once the target tissue is positioned within the end effector 1300 in a desired orientation, the clinician may then fully actuate the closure trigger 1032 to close the anvil 1306 and clamp the target tissue in position for cutting and stapling. In that instance, the first drive system 1030 has been fully actuated. After the target tissue has been clamped in the end effector 1300, it may be desirable to prevent the inadvertent detachment of the shaft assembly 1200 from the housing 1012. One form of the latch system 1710 is configured to prevent such inadvertent detachment.

As can be most particularly seen in FIG. 22, the lock yoke 1712 includes at least one and preferably two lock hooks 1718 that are adapted to contact corresponding lock lug portions 1256 that are formed on the closure shuttle 1250. When the closure shuttle 1250 is in an unactuated position (i.e., the first drive system 1030 is unactuated and the anvil 1306 is open), the lock yoke 1712 may be pivoted in a distal direction to unlock the interchangeable shaft assembly 1200 from the housing 1012. When in that position, the lock hooks 1718 do not contact the lock lug portions 1256 on the closure shuttle 1250. However, when the closure shuttle 1250 is moved to an actuated position (i.e., the first drive system 1030 is actuated and the anvil 1306 is in the closed position), the lock yoke 1712 is prevented from being pivoted to an unlocked position. Stated another way, if the clinician were to attempt to pivot the lock yoke 1712 to an unlocked position or, for example, the lock yoke 1712 was in advertently bumped or contacted in a manner that might otherwise cause it to pivot distally, the lock hooks 1718 on the lock yoke 1712 will contact the lock lugs 1256 on the closure shuttle 1250 and prevent movement of the lock yoke 1712 to an unlocked position.

Attachment of the interchangeable shaft assembly 1200 to the handle 1014 will now be described. To commence the coupling process, the clinician may position the chassis 1240 of the interchangeable shaft assembly 1200 above or adjacent to the distal attachment flange 1700 of the frame 1020 such that the tapered attachment portions 1244 formed on the chassis 1240 are aligned with the dovetail slots 1702 in the frame 1020. The clinician may then move the shaft assembly 1200 along an installation axis that is perpendicular to the shaft axis SA to seat the attachment portions 1244 in "operable engagement" with the corresponding dovetail receiving slots 1702. In doing so, the shaft attachment lug 1226 on the intermediate firing shaft 1222 will also be seated in the cradle 1126 in the longitudinally movable drive member 1120 and the portions of pin 1037 on the second closure link 1038 will be seated in the corresponding hooks 1252 in the closure yoke 1250. As used herein, the term "operable engagement" in the context of two components means that the two components are sufficiently engaged with each other so that upon application of an actuation motion thereto, the components may carry out their intended action, function and/or procedure.

At least five systems of the interchangeable shaft assembly 1200 can be operably coupled with at least five corresponding systems of the handle 1014. A first system can comprise a frame system which couples and/or aligns the frame or spine of the shaft assembly 1200 with the frame 1020 of the handle 1014. Another system can comprise a closure drive system 1030 which can operably connect the closure trigger 1032 of the handle 1014 and the closure tube 1260 and the anvil 1306 of the shaft assembly 1200. As outlined above, the closure tube attachment yoke 1250 of the shaft assembly 1200 can be engaged with the pin 1037 on the second closure link 1038. Another system can comprise the firing drive system 1080 which can operably connect the firing trigger 1130 of the handle 1014 with the intermediate firing shaft 1222 of the shaft assembly 1200. As outlined above, the shaft attachment lug 1226 can be operably connected with the cradle 1126 of the longitudinal drive member 1120. Another system can comprise an electrical system which can signal to a controller in the handle 1014, such as microcontroller, for example, that a shaft assembly, such as shaft assembly 1200, for example, has been operably engaged with the handle 1014 and/or, two, conduct power and/or communication signals between the shaft assembly 1200 and the handle 1014. For instance, the shaft assembly 1200 can include an electrical connector 1810 that is operably mounted to the shaft circuit board 1610. The electrical connector 1810 is configured for mating engagement with a corresponding electrical connector 1800 on the handle control board 1100. Further details regaining the circuitry and control systems may be found in U.S. patent application Ser. No. 13/803,086, and U.S. patent application Ser. No. 14/226, 142, the entire disclosures of each which were previously incorporated by reference herein. The fifth system may consist of the latching system for releasably locking the shaft assembly 1200 to the handle 1014.

Surgical staplers have been used in the prior art to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

The simultaneous severing of tissue while forming rows of staples on each side of the cut reduces bleeding and simplifies the surgical procedure. Increasingly, endoscopic and laparoscopic procedures are preferred over open procedures due to their reduced post-operative recovery times and other advantages. Endoscopic stapling and severing instruments use a long slender jaw member that tends to deflect upwardly when clamped onto thick tissues. On thick tissue, this upward deflection of the free (distal) end of the jaw can cause differences in height of the formed staples as the distal gap between the anvil and cartridge is larger than the proximal gap. To ensure more uniform proximal to distal staple formation, the anvil is frequently cambered or bent inwardly toward the staple cartridge. This camber is better for thick tissue and can cause tighter staple forms at the distal end when used on thin tissue. To overcome this tight distal closure, pins or bumps have been added to the clamping surface of the cartridge adjacent to the distal end of the cartridge. The closure of the anvil onto the pin ensures a minimum gap at the distal end. However, surgeons were concerned about the pins or bumps causing tissue trauma.

Various arrangements have been developed to address such challenges. One arrangement, for example, comprises an "E-beam" cutting head or firing bar that is configured to affirmatively space the anvil from the elongate channel that supports the staple cartridge. Such E-beam cutting head and firing bar arrangements are disclosed in, for example, U.S. Pat. No. 6,978,921, entitled SURGICAL STAPLING INSTRUMENT INCORPORATING AN E-BEAM FIRING MECHANISM, the entire disclosure of which is hereby incorporated by reference herein.

For example, as illustrated in FIGS. 2 and 3 herein the tissue-cutting head comprises an E-beam 50 which can translate within the end effector 16. As described above, the E-beam 50 can comprise a vertical portion 52 which can pass through a narrow longitudinal anvil slot 58 extending through a tissue-contacting surface 60 in the anvil 20, a narrow vertical slot 62 in the staple cartridge 42, and a narrow longitudinal channel slot 64 in the elongate staple channel 40 when the E-beam 50 is advanced distally. The anvil slot 58 can extend upwardly into the anvil 20 and can comprise an end which opens into a laterally-widened longitudinal channel 66 sized and configured to receive an upper pin 54 that extends laterally from the vertical portion 52. Similarly, the channel slot 64 can extend downwardly into the channel 40 and can comprise an end which opens into a laterally-widened longitudinal channel 68 sized and configured to receive one or more lower feet 70 extending laterally from the vertical portion 52. The E-beam 50 can further comprise one or more middle pins 72 which can extend laterally from the vertical portion 52 and can be configured to slide along a top surface of a bottom tray 74 of the staple cartridge 42. In certain embodiments, the middle pins 72 can be configured to seat the staple cartridge 42, or assure that the staple cartridge 42 remains seated, in the channel 40. A longitudinal firing recess 75 formed in the staple cartridge 42 above the bottom tray 74 is sized to allow the middle pins 72 to translate through the staple cartridge 42.

Various elongate channel arrangements include an elongate or longitudinal slot that extends between a starting position of the E-beam cutting head in a proximal portion of the elongate channel and an ending position adjacent the distal end of the elongate channel. The vertical portion of the E-beam cutting head extends through that longitudinal slot and the lower foot portion of the E-beam rides along the bottom surface of the elongate channel. The foot portion may help affirmatively space the anvil relative to the elongate channel and can also serve as convenient means for the clinician to ascertain the position of the cutting head in the elongate channel. By observing the position of the cutting head foot as the cutting head is advanced distally through the cartridge, the clinician will know exactly where the cutting head is located within the cartridge. While providing an effective means for spacing the anvil and for monitoring the location of the cutting head, such arrangement does employ a longitudinal slot in the elongate channel which may reduce the channel stiffness as well as the channel's resistance to twisting and spreading.

To avoid such spreading of the elongate channel, it may be desirable to eliminate the longitudinal slot to increase the resistance to twisting and spreading when stapling thick tissue. However, such arrangement may eliminate the ability of the surgeon to see how far the stapling has progressed by observing the position of the knife foot. FIG. 32 illustrates an elongate channel 6022 that may be similar to various elongate channels disclosed herein including, for example, elongate channels 22 and 302 except for the following differences. Elongate channel 6022 may be molded, and/or machined and/or otherwise formed from a suitable polymer material and include a substantially solid bottom surface portion 6024. The elongate channel 6022 is configured to operably support a surgical staple cartridge (not shown) therein. The elongate channel 6022 may include an elongate internal slot 6026 that is defined by two inwardly extending ledge portions 6028. The inwardly extending ledge portions 6028 also define an elongate internal passageway 6030 between the ledge portions 6028 and the solid bottom portion 6024. While the elongate internal slot 6026 extends for most of the length of the elongate channel 6022, it does not extend through the bottom surface 6024 of the elongate channel 6022. The internal passageway 6030 is sized to slidably accommodate the foot or feet that are formed on or otherwise attached to the cutting head.

FIG. 42 illustrates, for example, an E-beam cutting head 6050 that may be used in connection with the elongate channel 6022. However, as will become apparent, the elongate channel 6022 may also be used in connection with a variety of different cutting head arrangements that employ a single foot or a plurality of feet on the bottom of the cutting head. Referring to FIG. 42, the cutting head 6050 includes a vertical portion 6052 that terminates with two laterally extending lower feet 6070. The vertical portion 6052 is configured to pass through the elongate slot 6026 such that the lower feet 6070 are received under the corresponding ledge portions 6028.

Referring again to FIG. 32, the elongate channel 6022 may further include a proximal channel opening 6040 that is provided in the proximal end of the bottom portion 6024 of the elongate channel 6022. The proximal channel opening 6040 may afford the clinician with a view of at least one of the feet 6070 or other portion(s) of the cutting head 6050 when the cutting head 6050 is in a starting or unfired position. This "starting position" may also correspond to a position that the cutting head 6050 is in when cutting head 6050 is in a locked out position as will be discussed in further detail below. Similarly a distal channel opening 6042 is provided in the distal end of the bottom portion 6024 which affords the clinician with a view of at least one of the feet 6070 or other portion(s) of the cutting head 6050 when the cutting head 6050 is in its "fully-fired" or "ending position". Such arrangement affords the clinician with a method for ascertaining whether the cutting head is in its starting or ending position while providing a relatively stiffer elongate channel when compared to other channels that have a longitudinal slot that extends longitudinally through the bottom of the elongate channel. The proximal channel opening 6040 and the distal channel opening 6042 may be shaped in the manners illustrated in FIG. 32 to facilitate easy installation of the cutting head 6050 into the elongate channel 6022 (through proximal channel opening 6040) and removal of the cutting head 6050 from the elongate channel 6022 (through the distal channel opening 6042) for example. Thus, the elongate channel 6022 has a closed bottom with openings 6040, 6042 corresponding to the beginning and end, respectively of the cutting head firing stroke. Such arrangement allows for the visibility of the beginning and ending of firing as well as permitting the downward movement of the cutting head to a locked position as will be discussed in further detail below.

The elongate channel 6022 may be effectively employed with a cutting head assembly that is manually advanced or one that is advanced by means of a motor-powered firing system. For example, the surgical instrument 10 described above includes a cutting head 50 that is manually advanced by actuating the trigger 32. In various arrangements, the cutting head 50 may be advanced from its starting to ending position by actuating the firing trigger 32 three times. Thus, for example, activating the trigger 32 one time may move the cutting head distally in the elongate channel one third of the distance between the starting position and the ending position ("first firing position"). Activating the trigger a second time may result in the cutting head 50 travelling two-thirds of the way between the starting and end position ("second firing position") and activating the trigger 32 a third time may result in the advancement of the cutting head 50 from the second firing position to the ending position. Thus, when the cutting head 6050 is viewable through the distal channel opening 6042, the clinician will know that the cutting head 6050 has been fully fired. Such elongate channel 6022 may also be employed in connection with the powered surgical instrument 1010 (FIGS. 19-22).

FIGS. 33-35 illustrate another elongate channel arrangement 6122 that is similar to the elongate channel 6022 except for the noted differences. Those portions of the elongate channel arrangement 6122 that are identical to portions of elongate channel arrangement 6022 will share the same element numbers. In particular, as can be seen in FIG. 33, a series of spaced indicator openings 6144 are provided in the bottom portion 6124. The indicator openings 6144 may vary in number, size and spacing, but in at least one arrangement, the indicator openings 6144 have the same size and are equally spaced in a line such that they open into the elongate internal passageway 6030. As can be seen in those Figures, the indicator openings 6144 are round in shape. As can also be seen in FIG. 33, a light source 6160 may be mounted within a proximal end of the elongate channel 6122 such that the light source 6160 projects light into the internal passageway 6030 (represented by the broken line "L" in FIGS. 33 and 34). The light source 6160 may comprise, for example, one or more light emitting diodes ("LED's) or other light source arrangement that may receive power through a conductor 6164 that is coupled to the handle of the surgical instrument or robotic system, etc. to which the elongate channel 6122 is operably attached. When the light source 6160 is powered, the light will be projected into the internal passageway 6030. When the cutting head 6050 is in the starting position, the cutting head 6050 may block any light "L" from being visible through any of the indicator openings 6144. Thus, when no light "L" is visible through any of the indicator openings 6144, the clinician will know that the cutting head 6050 is in the starting position. As the cutting head 6050 is advanced distally past indicator openings 6144, the light "L" will strike the cutting head 6050—and be visible at least through the unobstructed indicator opening 6144 that is immediately proximal to the cutting head 6050 as shown in FIG. 34. Thus, such arrangement enables the clinician to monitor the progress of the cutting head 6050 as it moves distally in the elongate channel 6122 from its starting position to its ending position. Such elongate channel arrangement is also more stiff and rigid than those elongate channel arrangements that have an elongate slot that extends completely through most of the bottom surface of the elongate channel. In one arrangement the clinician can determine the position of the cutting head because there will be no light shining through the indicator opening where the cutting head is located. All of the other indicator openings will have light shining through them. Thus in one arrangement, the "black" or unlit indicator opening is where the cutting head is located. In other embodiments, the light source may be omitted. The clinician can still monitor the position of the cutting head 6050 in the elongate channel 6122 by viewing the location of the feet 6070 through the indicator openings 6144.

FIG. 36 illustrates another elongate channel arrangement 6222 that is similar to the elongate channel 6122 except for the noted differences. Those portions of the elongate channel arrangement 6222 that are identical to portions of elongate channel arrangement 6122 will share the same element numbers. As can be seen in that Figure, a series of spaced indicator openings 6144 are provided through the bottom surface 6224. In the illustrated arrangement, the indicator openings 6144 have the same size and shape but are provided through the bottom surface 6224 at different spacing intervals. For example, the proximal-most indicator opening 6144P may be spaced from the proximal opening 6040 a first spacing distance "FSD" that enables, for example, at least one of the feet 6070 or other portion of the cutting head 6050 to be viewed therethrough when the cutting head 6050 is in the starting position. Likewise, the distal-most indicator opening 6144D may be spaced from the adjacent indicator opening 6144 a second spacing distance "SSD" that is different from the first spacing distance FSD. As can be seen in FIG. 36 for example, the SSD is greater than the FSD. The distal-most indicator opening 6144D may correspond to the position of the cutting head 6050 in its ending position. Thus, the elongate channel arrangement 6222 illustrates variable spaced indicator openings wherein the number of openings decrease as you move proximal to distal.

FIG. 37 illustrates another elongate channel arrangement 6322 that is similar to the elongate channel 6122 except for the noted differences. Those portions of the elongate channel arrangement 6322 that are identical to portions of elongate channel arrangement 6122 will share the same element numbers. As can be seen in that Figure, the elongate channel arrangement 6322 includes a series of elongate discrete indicator openings 6144'. In the illustrated arrangement, the indicator openings 6144' have the same size and shape and are arranged at equally spaced intervals.

FIG. 38 illustrates another elongate channel arrangement 6422 that is similar to the elongate channel 6222 except for the noted differences. Those portions of the elongate channel arrangement 6422 that are identical to portions of elongate channel arrangement 6222 will share the same element numbers. As can be seen in that Figure, only two spaced "discrete" indicator openings 6144" are provided through the bottom surface 6424. In the illustrated arrangement, the indicator openings 6144" have the same size and shape but are provided through the bottom surface 6424 at different spacing intervals. For example, the proximal-most indicator opening 6144P" may be spaced from the proximal opening 6040 a first spacing distance "FSD" and the distal-most indicator opening 6144D" may be spaced from the proximal-most indicator opening 6144" a second spacing distance "SSD" that is different from the first spacing distance FSD. In at least one arrangement for example, when the elongate channel 6422 is employed with a cutting head assembly that is manually advanced by actuating the firing trigger, at least one foot or other portion of the cutting head assembly is viewable through the proximal indicator opening 6144P" when the cutting head assembly is being advanced through the "first stroke" or first actuation of the firing trigger. Likewise, at least one foot or other portion of the cutting head assembly is viewable through the distal most indication opening 6144D" during the second stroke or second actuation sequence of the firing trigger. Thus, the elongate channel 6422 includes elongate slot-shaped indicator openings as well as circular shaped indicator openings that provide more closure/less openings as you move proximal to distal.

FIG. 39 illustrates another elongate channel arrangement 6522 that is similar to the elongate channel 6422 except for the noted differences. Those portions of the elongate channel arrangement 6522 that are identical to portions of elongate channel arrangement 6422 will share the same element numbers. As can be seen in that Figure, the elongate channel 6522 includes a combination of a proximal most elongate indicator opening 6144P" that enables the clinician to view at least one foot or other portion of the cutting head assembly during the first stroke or actuation sequence of the firing trigger along with a combination of the round, equally-spaced indicator openings 6144. Thus, the elongate channel 6522 employs a combination of slotted and elongate slots. Any one of the above-described elongate channel arrangements may incorporate the light source 6160 that was specifically described herein in connection with the embodiment depicted in FIG. 33 or they may be employed without a light source.

Other cutting head monitoring arrangements may comprise, for example, one or more light source arrangements or light emitting diode ("LED") arrangements that cast light down the openings in the channel or down the slot inside of the channel. This would vastly increase the user's ability to locate where the cutting head is in its travels and determine whether the overall stroke is complete. In some arrangements, for example, the LED's could comprise multi-colored LED's that change from green to blue (or other color arrangements) with the advancement of the cutting head down the channel further differentiating cutting head advancement.

In various end effector arrangements, it may be desirable to employ system for preventing the advancement or firing of the cutting head unless an unspent staple cartridge has been operably mounted in the elongate channel. For example, U.S. Pat. No. 6,988,649, entitled SURGICAL STAPLING INSTRUMENT HAVING A SPENT CARTRIDGE LOCKOUT and U.S. Pat. No. 7,044,352, entitled SURGICAL STAPLING INSTRUMENT HAVING A SINGLE LOCKOUT MECHANISM FOR PREVENTION OF FIRING, the entire disclosures of each being hereby incorporated by reference herein disclose various lockout systems. In such lockout arrangements, the cutting head or "firing bar" is normally biased into a locked position by a spring arrangement. Until an unspent cartridge has been installed in the elongate channel, the cutting head cannot otherwise be advanced by the firing drive system of the surgical instrument.

Referring to FIGS. 40-42, there is shown a cutting head 6050 that is attached to a firing bar 6080. As shown, the firing bar 6080 is of laminate construction. However the firing bar 6080 may be of solid construction. In either case, the firing bar 6080 operably interfaces with the firing drive system of the surgical instrument as described herein or as is otherwise known. Actuation of the firing drive system axially advances the firing bar 6080 and cutting head 6050 attached thereto through the surgical staple cartridge that is mounted within the elongate channel 6122. The vertical portion 6052 of the cutting head 6050 includes a tissue cutting surface 6053 that is located between an upper end portion 6054 and a central hook portion 6056. See FIG. 42. An upper pin or upper tab 6058 extends laterally from each side of the upper end portion 6054. The upper tabs 6058 are configured to be slidably received within an upper passageway within an anvil that is operably mounted to the elongate channel as will be further discussed below.

FIG. 41 illustrates the position of the cutting head 6050 and firing bar 6080 when a surgical staple cartridge is not present within the elongate channel 6122. When in that position, the firing bar 6080 and cutting head 6050 are biased in a downward direction "D" by a spring arm 6090 is supported by the shaft spine (not shown) that is coupled to the elongate channel 6122. As can be seen in that Figure, the spring arm 6090 is in sliding engagement with a spring tail 6082 that is formed in the distal end of the firing bar 6080. The bottom portion of the spring tail 6082 is biased into a sloped surface 6123 formed on the elongate channel 6122 when the cutting head 6050 is in that locked position as shown in FIG. 41. As can be further seen in FIG. 41, when the cutting head 6050 is in the locked position, if the clinician were to inadvertently try to advance or "fire" the cutting head 6050 distally through the elongate channel 6122, the lower feet or foot 6070 would contact the bottom of the elongate channel 6122. Stated another way, when the cutting head 6050 is in the locked position, the feet 6070 are not aligned with the internal passageway 6030 in the elongate channel 6122 and therefore the cutting head assembly 6050 could not be axially advanced therein. The clinician will know that the cutting head is locked by observing the position of the feet 6070 within the proximal opening 6040.

FIG. 40 illustrates the position of the cutting head 6050 and firing bar 6080 when an unspent surgical staple cartridge has been operably supported within the elongate channel 6122. Although the body of the surgical staple cartridge is not shown in FIG. 40, a wedge sled assembly 6078 is shown. It will be understood that the wedge sled assembly 6078 will be in the position shown in FIG. 40 in an unfired or unspent staple cartridge. When in that position, the wedge sled assembly 6078 engages with the hook portion 6056 on the cutting head 6050 to raise the cutting head 6050 in an upward direction (arrow "U" in FIG. 40) to a point wherein, when the cutting head 6050 is advanced distally, the feet 6070 thereon will enter the internal passage 6030 in the elongate channel 6122. When employing the elongate channels that have closed bottoms or substantially closed bottoms such as those described herein, a dimensional stack situation could conceivably occur wherein interference between the channel bottom and the knife foot or feet could occur when the end effector is used to cut and staple extremely thin tissue. If the tissue is too thin, for example, the tissue compression resistance may not be enough to push the anvil away from the elongate channel and load those two components against the cutting head tabs. If this situation occurs, the knife foot or feet could extend below the bottom of the elongate channel far enough so that the cutting head could not be distally advanced. The cutting head assembly 6050 and elongate channel arrangement 6122 depicted in FIGS. 40 and 41 may prevent this from happening.

As can be seen in FIGS. 40 and 41, for example, the distal end of each foot 6070 may have a chamfer 6072 formed thereon. The chamfer 6072 is configured to engage corresponding portions of the elongate channel 6122 as the cutting head 6050 is advanced distally to cause the feet 6070 to enter the internal passage 6030. Thus the chamfers 6072 form small "lead-in" ramps which help to guide the feet 6070 into the passage 6030. As can also be seen in FIGS. 40 and 41, the portion of the elongate channel 6122 defining the proximal end 6131 of the internal passage 6030 may have a chamfer 6133 thereon or otherwise be sloped as shown. In alternative arrangements, the feet 6070 (or single foot) may be provided with the chamfer 6072 or the proximal end portion 6131 of the internal passage 6030 may be provided with the chamfer 6133 or both chamfer arrangements may be provided as shown in FIGS. 40 and 41.

FIGS. 43 and 44 illustrate an end effector 7016 that may be similar, for example to end effector 16 or 300 or other end effectors disclosed herein. In this arrangement, the closure tube or sleeve 7028 has a series of indicator openings 7144 therein that enable the clinician to view the firing bar 6080 therethrough. The firing bar 6080 may be provided with a status mark 6084 thereon that may be viewed by the clinician through the indicator openings 7144 as the firing bar 6080 is advanced distally. The status mark 6084 may simply comprise a painted mark or other feature that would serve as a reference mark. In one arrangement, the status mark 6084 comprises one or more light emitting diodes (LED's) or other light source that is powered by a source of power in the surgical instrument or surgical system to which the end effector 7016 is attached.

FIG. 45 illustrates another end effector 7016 wherein a closure sleeve segment 7030 includes an indicator window 7032 that enables the clinician to determine whether cutting head is in its locked position. In this arrangement, if the clinician can see the spring tail 6082 through the indicator window 7032, the cutting head is not in its locked position. If the clinician cannot see the spring tail 6082 through the indicator window 7032, the cutting head is in the locked position. In alternative arrangements, the indicator window 7032 may be provided in such a location (e.g.; lower in the closure sleeve segment) such that if the spring tail 6082 is visible through the indicator window 7032, the cutting head is in its locked position and if the spring tail 6082 is not visible through the indicator opening, the cutting head is not in the locked position. To assist the clinician in determining the position of the cutting head, the cutting head may be provided in a particular bright or florescent color. These color arrangements may, for example, be Radium based. Furthermore, the color of the cutting head may vary along its length to enable the clinician to easily ascertain its position.

FIG. 47 illustrates an anvil 7020 that includes a plurality or series of indicator openings 7044 that provide viewing into a passage 7022 into which the upper end portion 6054 on the cutting head 6050 axially passes. In the embodiment depicted in FIG. 47, the indicator openings 7044 have a circular shape and are equally spaced along the length of the anvil 7020. In the embodiment depicted in FIG. 48, the indicator openings 7044 are spaced closer together at the proximal end of the anvil 7020. The spacing between the indicator openings 7044 gradually increases moving distally in the anvil 7020. The size, shape and spacing of the indicator openings 7044 may vary, however. Referring to FIG. 42, an indicator member 6059 may be provided in the top end portion 6054 of the cutting head 6050. In one embodiment, the indicator member 6059 comprises one or more light emitting diodes or other light sources that may obtain power from the surgical instrument through a conductor 6081 that passes through the firing bar 6080. Such arrangement enables the clinician to view the position of the indicator member 6059 through the indicator openings 7044 in the anvil 7020 as the cutting head 6050 is advanced through the end effector. In other arrangements, no indicator member (led, light) may be provided in the cutting head. However, the top end portion of the cutting head may be provided in a color or florescent marking that would make increase its visibility through the indicator openings in the anvil. For example, the color may be radium-based. The cutting head may alternatively be provided with laser scribed numbers to provide a means for determining the position of the cutting head within the channel or anvil.

The anvil 7020 depicted in FIG. 46 employs an indicator system generally designated as 7200. In this embodiment, the indicator system 7200 includes a flexible strip or wave spring 7202 that is journaled at least at its proximal end 7204 in a slot 7021 provided in the anvil 7020. The wave spring 7202 extends the length of the anvil 7020 and is at least coextensive with the portion of the anvil 7020 that has the indicator openings 7044 therethrough. As can be seen in FIG. 46, a series of indicator members 7206 is attached to the flexible strip 7202 such that each indicator member 7206 is slidably supported in a corresponding indicator opening 7044. Each indicator member 7206 is initially supported in its corresponding indicator opening 7044 such that it does not protrude therefrom. Stated another way, the wave spring 7202 is configured such that the indicator members 7206 are biased into the initial position wherein they do not protrude out of their respective indicator opening 7044. However, as the cutting head 6050 is advanced distally through the end effector, the top portion 6054 of the cutting head 6050 slides along the bottom of the wave spring 7202 and serves to bias the wave spring 7202 upward such that, as the cutting head slides under a portion of the wave spring 7202 to which an indicator member 7206 is attached, the indicator member 7206 is caused to protrude out of the indicator opening 7044 as shown in FIG. 46. Thus, the clinician may monitor the position of the cutting head 6050 within the end effector by noting which indicator member 7206 is protruding out of its indicator opening 7044.

Thus, several of the elongate channel arrangements disclosed herein offer vast improvements over prior elongate channel arrangements. For example, at least some of the elongate channel arrangements do not employ an elongate slot that extends through the bottom surface of the channel. Thus, such elongate channel arrangements tend to be stiffer and resist spreading during operation. These advantages are also achieved while providing the clinician with a means for monitoring the progress of the cutting head. For example, some elongate channel arrangements provide periodic visibility along the length of the channel to inform the clinician of where the cutting head is in the firing cycle. At least some of the elongate channel arrangement also enables the clinician to see at least a portion of the cutting head when it is in the fully deployed position and a well as when the cutting head is in the fully retracted position. Furthermore at least some of the channel and/or anvil arrangements provide visibility of at least a portion of the cutting head from the side or top of the end effector or otherwise provide means for ascertaining the position of the cutting head from the side or top of the end effector.

As described above, a surgical staple cartridge operably supports a series of staple drivers therein that each support one or more surgical staples thereon. The staple drivers are supported in correspondingly-shaped staple pockets arranged in a linear orientation within the cartridge body. The surgical staples are movably supported on the drivers such that when the drivers are driven upward in the cartridge, the staples are driven through the tissue that is clamped between the cartridge and the anvil into forming contact with the underside of the anvil. When the anvil is opened, the staples remain with the stapled tissue. Because the staples are 'loosely" supported in their respective pockets on their staple drivers, they could conceivably fall out of the staple cartridge should the staple cartridge be inadvertently turned upside down prior to use. To avoid that from happening, cartridge covers are typically removably attached to the staple cartridge prior to use. When attached to the cartridge, the cartridge cover covers the staple pockets to retain the staples therein regardless of the position of the cartridge. When the clinician desires to install the cartridge into an end effector, the cover may be removed prior to installation.

As was further discussed above, the staple drivers are sequentially driven upward within the cartridge by a wedge sled that is driven distally with the cutting head assembly. In at least some arrangements, the wedge sled is therefore oriented in a proximal-most "starting" position in an unspent cartridge prior to firing. Indeed as was also discussed above, at least some arrangements require interaction between the wedge sled (when in its starting position) and the cutting head (when in its locked position) in order to move the cutting head out of the locked position to ready it for firing. In at least some prior arrangements, however, the cartridge lacked means or structure for ensuring that the wedge sled remained in its starting position prior to use. The cartridge cover 7250 depicted in FIGS. 64 and 65 may address such problem.

FIG. 64 illustrates a surgical staple cartridge 7220 that has a cartridge body 7222 that operably supports a plurality of staple drivers therein (not shown) on each lateral side of a longitudinally-extending slot 7224. The longitudinally-extending slot 7224 is configured to facilitate the longitudinal travel of a cutting head through the cartridge. As can be seen in FIG. 65, the cartridge 7220 also supports a wedge sled 7230 in a starting position adjacent the proximal end of the cartridge body 7222. FIGS. 64 and 65 also illustrate a cartridge cover 7250 that includes a top portion 7252 that is configured to cover the cartridge deck 7226 when the cartridge cover 7250 is installed on the cartridge 7220. More specifically, the top portion 7252 is configured to cover all of the fastener cavity openings in the deck 7226 of the cartridge body 7222 when the top portion 7252 is in a "covering position". The cartridge cover 7250 may be removably affixed to the staple cartridge 7220 by a pair of flexible attachment arms 7254 that are configured to retainingly engage the cartridge body 7222. The clinician may easily remove the cartridge cover 7250 by prying the flexible attachment arms 7254 out of retaining engagement with the cartridge body 7222. The cartridge cover 7250 may further include a pair of downwardly extending lateral side plates 7255 that serve to locate the cartridge cover 7250 in a desired position on the cartridge 7220. For example, the lateral side plates 7255 may be positioned to engage a laterally extending lip 7227 formed on each side of the cartridge deck 7226. The cartridge cover 7250 may also include a centrally-disposed locating fin 7256 that is orientated to be received within the longitudinally-extending slot 7224 when the cartridge cover 7250 is attached to the cartridge 7220 as shown in FIG. 65. The locating fin 7256 includes an engagement notch 7258 or other formation(s) that are configured to retainingly engage a portion of the wedge sled 7230 and retain the wedge sled 7230 in its starting position. Thus, when the cartridge cover 7250 is installed onto the staple cartridge 7220, the staples are retained within their respective pockets regardless of the orientation of the cartridge 7220. In addition, the wedge sled 7230 is retained in its starting position. In various arrangements, the locating fin may be sized relative to the longitudinally-extending slot 7224 to establish a frictional fit therewith. In such arrangements, the frictional fit may be employed to retain the cover 7250 in position on the cartridge 7220 without the need for the attachment arms 7254. In other arrangements, the frictional fit established between the locating fin 7256 and the cartridge body 7222 as well as the attachment arms 7254 may be employed to retain the cover 7250 on the cartridge body 7222 in the covering position. In addition, retention ribs 7257 may be formed on the locating fin 7256 to further establish a frictional fit with the cartridge body 7222. Also, as can be seen in FIG. 65, the distal end 7221 of the surgical staple cartridge 7220 may have a nose surface 7223 that is angularly oriented relative to the cartridge deck 7226. In various arrangements, the cartridge cover 7250 may also include a nose portion 7251 that is configured to retainingly engage the distal end 7221 of the surgical staple cartridge 7220. For example, the nose portion 7251 may be configured to cover the nose surface 7223 of the cartridge 7220 and include a distal retention tab 7253 that is arranged to hookingly engage the distal end 7221 of the cartridge 7220. In addition, a detachment tab or protrusion 7259 may be formed on the nose portion 7251 to facilitate detachment of the retention tab 7253 from the cartridge 7220. As such, in certain arrangements, the distal end of the cartridge cover 7250 is configured to allow it to absorb the full force of a nose-down drop and transmit that force directly to the cartridge 7220 with as little longitudinal movement of the cover 7250 with respect to the cartridge body 7222. Such arrangement serves to prevent the cover 7250 from moving the sled 7230 proximally under such conditions. When the clinician desires to use the cartridge 7220, the cartridge cover 7250 is removed. In at least some arrangements, the cartridge cover 7250 may be provided in a particular color that corresponds to a size of staples that are received within the staple cartridge 7220.

As discussed in detail above, in various embodiments the surgical staples are supported on "drivers" that are operably supported in pockets that are formed into the body of the staple cartridge. Various forms of drivers may be employed. For example, a driver may be configured to support a single surgical staple, while other drivers may support multiple surgical staples. The drivers are supported in the cartridge body in longitudinally extending rows that are provided on each lateral side of the centrally-disposed elongate slot that accommodates passage of the cutting member or cutting head therethrough. As was previously discussed herein, the cutting head includes or cooperates with a wedge sled that is configured to sequentially contact the drivers to drive them upward in their respective pockets. As the driver moves upwardly in the staple cartridge, the surgical staple(s) supported thereon are driven upward through the tissue clamped between the cartridge and the anvil and into forming contact with the underside of the anvil.

As is known, the underside of the anvil includes a "staple-forming" surface that typically comprises a series of staple forming pockets that are arranged to be contacted by the ends of the staple legs. The pockets are situated and shaped such that when contacted by the staple legs, the legs are urged to bend around in the pocket to ultimately form a closed staple that roughly resembles a "B-shape". Misalignment of the staple legs during the forming process may cause the staple to become malformed which in severe cases may cause undesirable leakage. The staple driver configuration depicted in FIGS. 94 and 95 may help to maintain staple alignment during the firing process. Furthermore, if during the firing process, the driver is not maintained in proper alignment within its respective pocket, higher firing forces must be generated to fire the staples supported thereon.

FIGS. 94 and 95 depict a "double" staple driver 7300. As can be seen in those Figures, the staple driver 7300 includes a first driver portion 7310 and a second driver portion 7350 that are separated in a "staggered" orientation by a centrally disposed separator portion 7340. The staple driver 7300 may be of one-piece construction and, for example, be molded from a suitable polymer material. The first driver portion 7310 includes a centrally disposed first cavity 7312 that divides the first driver 7310 into a first proximal upstanding support portion 7320 and a first distal upstanding support portion 7330. The first proximal upstanding support portion 7320 has a first proximal body portion 7321 that has an upper end 7322 that has a first proximal cradle section 7324 formed therein. Similarly, the first distal upstanding support portion 7330 has a first distal body portion 7331 that has a first distal end 7332 that has a first distal cradle section 7334 formed therein. The first proximal cradle section 7324 and first distal cradle section 7334 are aligned and configured to support the base of surgical staple therein. As can be further seen in FIG. 94, the first proximal upstanding support portion 7320 has a somewhat tapered shape when viewed from above. Stated another way, the first proximal upstanding support portion 7320 has a first proximal end 7326 that has a width "PW" that is less than a central width "CW" of the first proximal body portion 7321. Likewise, the first distal upstanding support portion 7330 has a first distal end 7336 that has a distal width "DW" that is less than a central width "CW" of the first distal body portion 7331. In at least one arrangement, the distal width "DW" is equal to the proximal width "PW".

Still referring to FIG. 94, the second driver portion 7350 includes a centrally disposed second cavity 7352 that divides the second driver portion 7310 into a second proximal upstanding support portion 7360 and a second distal upstanding support portion 7370. The second proximal upstanding support portion 7360 has a second proximal body portion 7361 that has an upper end 7362 that has a second proximal cradle section 7364 formed therein. Similarly, the second distal upstanding support portion 7370 has a second distal body portion 7371 that has a second distal end 7372 that has a second distal cradle section 7374 formed therein. The second proximal cradle section 7364 and second distal cradle section 7374 are aligned and configured to support the base of another surgical staple therein. As can be further seen in FIG. 94, the second proximal upstanding support portion 7360 has a somewhat tapered shape when viewed from above. Stated another way, the second proximal upstanding support portion 7360 has a proximal end 7366 that has a width "PW" that is less than a central width "CW" of the second proximal body portion 7361. Likewise, the second distal upstanding support portion 7370 has a distal end 7376 that has a distal width "DW" that is less than a central width "CW" of the second distal body portion 7371. Thus, the first driver portion 7310 and the second driver portion 7350 have similar shapes.

To provide the staple driver 7300 with more stability during the firing process, the first and second driver portions 7310, 7350 may be further provided with stabilizer arrangements that cooperate with complementary-shaped staple pockets in the staple cartridge body. For example, the first staple driver portion 7310 may have a first proximal set 7327 of laterally-protruding support columns 7328, 7329 formed on the first proximal end 7326 thereof. A first distal set 7337 of laterally-protruding support columns 7338, 7339 may also be provided on the first distal end 7336 of the first distal upstanding support portion 7330 as shown. Likewise, the second staple driver portion 7350 may have a second proximal set 7367 of laterally-protruding support columns 7368, 7369 formed on the second proximal end 7366 thereof. A second distal set 7377 of laterally-protruding support columns 7378, 7379 may also be provided on the second distal end 7376 of the second distal upstanding support portion 7370 as shown.

As indicated above, the staple driver 7300 is movably supported with a complimentary shaped staple pocket in the staple cartridge. As the wedge sled is driven distally, a corresponding portion thereof drivingly contacts the centrally disposed separator portion 7340 and drives the driver 7300 upward. Each of the laterally-protruding support columns 7328, 7329, 7338, 7339, 7368, 7369, 7378 and 7379 are received in correspondingly-shaped grooves in the staple cartridge body and serve to maintain the alignment of the driver 7300 and prevent twisting thereof during its advancement toward the anvil. In one arrangement, the driver 7300 is molded or otherwise formed from solid material. In other arrangements, however, the first driver portion 7310 and the second driver portion 7350 may be hollow to enable those portions of the driver 7300 to be somewhat flexible and compliant to further maintain the alignment of the driver in its respective pocket and thereby further reduce the driving force required. In either arrangement, by providing the alignment columns on both ends of both driver portions, alignment of the driver within its respective pocket is further enhanced.

FIG. 96 depicts another "double" staple driver 7400 that is configured to be received in a complementary-shaped staple pocket formed in the body of a surgical staple cartridge. As can be seen in FIG. 96, the staple driver 7400 includes a first driver portion 7410 and a second driver portion 7450 that are separated in a "staggered" orientation by a centrally disposed separator portion 7440. The staple driver 7400 may be of one-piece construction and, for example, be molded from a suitable polymer material. The first driver portion 7410 includes a centrally disposed first cavity 7412 that divides the first driver 7410 into a first proximal upstanding support portion 7420 and a first distal upstanding support portion 7430. The first proximal upstanding support portion 7420 has a first proximal body portion 7421 that has an upper end 7422 that has a first proximal cradle section 7424 formed therein. Similarly, the first distal upstanding support portion 7430 has a first distal body portion 7431 that has a first distal end 7432 that has a first distal cradle section 7434 formed therein. The first proximal cradle section 7424 and first distal cradle section 7434 are aligned and configured to support the base of surgical staple therein. As can be further seen in FIG. 96, the first proximal upstanding support portion 7420 and the first distal upstanding support portion each have has a somewhat tapered shape.

Still referring to FIG. 96, the second driver portion 7450 includes a centrally disposed second cavity 7452 that divides the second driver portion 7450 into a second proximal upstanding support portion 7460 and a second distal upstanding support portion 7470. The second proximal upstanding support portion 7460 has a second proximal body portion 7461 that has an upper end 7462 that has a second proximal cradle section 7464 formed therein. Similarly, the second distal upstanding support portion 7470 has a second distal body portion 7471 that has a second distal end 7472 that has a second distal cradle section 7474 formed therein. The second proximal cradle section 7464 and second distal cradle section 7474 are aligned and configured to support the base of another surgical staple therein.

To provide the staple driver 7400 with more stability during the firing process, the first and second driver portions 7410, 7450 may be further provided with stabilizer arrangements that cooperate with complementary-shaped staple pockets in the staple cartridge body. For example, the first staple driver portion 7410 may have a first proximal set 7427 of laterally-protruding support columns 7428, 7429 formed on the first proximal body portion 7421. A first distal set 7437 of laterally-protruding support columns 7438, 7439 may also be provided on the first distal body portion 7431 of the first distal upstanding support portion 7430 as shown. Likewise, the second staple driver portion 7450 may have a second proximal set 7467 of laterally-protruding support columns 7468, 7469 formed on the second proximal body portion 7461. A second distal set 7477 of laterally-protruding support columns 7478, 7479 may also be provided on the second distal body portion 7471 of the second distal upstanding support portion 7470 as shown.

As indicated above, the staple driver 7400 is movably supported with a complimentary-shaped staple pocket in the staple cartridge. As the wedge sled is driven distally, a corresponding portion thereof drivingly contacts the centrally disposed separator portion 7440 and drives the driver 7400 upward. Each of the laterally-protruding support columns 7428, 7429, 7438, 7439, 7468, 7469, 7478 and 7479 are received in correspondingly-shaped grooves in the staple cartridge body and serve to maintain the alignment of the driver 7400 and prevent twisting thereof driving its advancement toward the anvil. In one arrangement, the driver 7400 is molded or otherwise formed from solid material. In other arrangements, however, the first driver portion 7410 and the second driver portion 7450 may be hollow to enable those portions of the driver 7400 to be somewhat flexible and compliant to further maintain the alignment of the driver in its respective pocket and thereby further reduce the driving force required. In either arrangement, by providing the alignment columns on both ends of both driver portions, alignment of the driver within its respective pocket is further enhanced.

FIG. 97 illustrates a staple or driver pocket 7510 that is formed in a body portion 7502 of a staple cartridge 7500. This staple or driver pocket 7510 is configured to operably support a complementary-shaped "single" staple driver therein. As can be seen in that Figure, the staple pocket 7510 is formed with two inwardly-extending proximal column members 7512, 7514 and two inwardly extending distal columns 7516, 7518. The columns 7512, 7514, 7516 and 7518 are configured to slidably extend into corresponding lateral grooves provided in the staple driver. Such driver pocket configurations serve to provide further stabilization and alignment of the driver as it is driven from the pocket. Although FIG. 97 illustrates a staple or driver pocket that is configured to operably support a single staple driver therein, the same concept may be applied to those driver pockets that are configured to support drivers that are constructed to support multiple surgical staples. For example, the support columns employed in the driver embodiments illustrated in FIGS. 94-96 may be replaced with grooves that are configured to slidably receive corresponding columns formed in the sides of the staple pockets in the cartridge body.

As illustrated in FIGS. 94-96, various driver arrangements essentially may include a driver body or driver body portion that includes an outer surface as well as a leading and trailing end. In various arrangements, the outer surface may be sized and shaped to avoid contact with any portions of the inner wall of the staple pocket in which is it movably supported-except for the laterally extending features/support columns formed thereon. For example, the double staple driver 7400 depicted in FIG. 96 includes a first driver portion 7410 and a second driver portion 7450. The first driver portion 7410 and the second driver portion 7450 may be sized relative to a staple pocket such that the only portions that are in contact with the inner wall of the staple pocket are the laterally extending features formed thereon such as elements 7428, 7429, 7438, 7439, 7468, 7469. The proximal-most end of the first driver portion 7410 may comprise the "leading end" and the distal-most end of the second driver portion 7450 may comprise the "trailing end". In still another arrangement, for example, the leading end and the trailing end may be sized relative to the corresponding portions of the staple pocket in which they are received such that the clearance between those ends and their corresponding pocket portions is less than the clearance between the other driver portions and the other portions of the staple pocket. Such amounts of clearance may be sized to improve lateral stability of the driver during actuation without establishing a frictional fit between the outer surface of the driver and the inner wall of the staple pocket. In another arrangement, the driver may be configured (e.g., sized and shaped) relative to the staple pocket such that the only portion(s) of the driver that contact the inner wall portions of the staple pocket consist of one or more formations (support columns) on the leading and/or the trailing ends of the driver. Conversely, one or more grooves may be provided in the leading and/or trailing ends that are configured to receive corresponding formations on the inner wall portions of the staple pocket—with those formations being the only point(s) of contact between the driver and the inner walls of the staple pocket during actuation of the driver. As indicated above, the drivers may generally be supported in the cartridge body in longitudinally extending rows of staple pockets that are provided on each lateral side of the centrally-disposed elongate slot that accommodates passage of the cutting member or cutting head therethrough. In certain arrangements, the various drivers disclosed herein that employ one or more support columns/laterally extending features may be employed in one or more longitudinal rows of staple pockets (or portions of longitudinal rows) on one or both sides of the elongate slot. For example, the row of staple pockets on each side of the elongate slot that is the closest to the edge of the cartridge body may include drivers that employ the support column/laterally extending formations, but the other rows of staple pockets may employ conventional drivers. This arrangement may also be employed with staple pockets 7510. That is, the staple pockets 7510 may only be employed in certain longitudinal rows of staple pockets (or portions of longitudinal lines) on one or both sides of the elongate slot.

Tissue flow can be one of the contributing issues to staple malformations. During stapling, the tissue flows both distally and laterally, with the lateral motion being more detrimental that the longitudinal. With tissue flow and high compressive forces, the staples are directed laterally and distally from their respective pockets. By tightening up the fit between the driver and the portions of the cartridge adjacent to it, the staple has less ability to rock to the side or front during firing because the driver also has less ability to rock. The various driver and staple pocket arrangements disclosed herein serve to minimize such rocking. The support columns/laterally extending features disclosed herein may be provided on all of the drivers or simply to drivers in specific regions (e.g., the drivers in the outer rows within the cartridge). Such support columns/laterally extending features may be on the sides of the driver, the ends of the driver or both, for example. The term "support column" as used to describe the driver stabilization arrangements disclosed herein encompasses the various laterally extending, vertically-elongate formations as shown in the present Figures. The term "support column" may also encompass a variety of differently-shaped laterally extending features that are configured to be movably received in correspondingly shaped grooves provided in the inner wall of the staple pocket (in arrangements wherein the support columns/laterally extending features are on the driver) or in the various driver portions (in arrangements wherein the support columns/laterally extending features protrude from the inner walls of the staple pocket), whichever the case may be. A support column may, for example, comprise a single laterally extending feature or it may comprise a plurality of aligned laterally extending features. For example, a support column may consist of column segments or aligned portions/formations. In still other arrangements, other protrusion shapes may be employed.

With regard to the various embodiments disclosed herein, a fastener cartridge can include a layer of material which is implantable into a patient. Such a layer can comprise one or more pieces of buttress material and/or one or more tissue thickness compensators, for example. U.S. patent application Ser. No. 13/097,856, entitled STAPLE CARTRIDGE COMPRISING STAPLES POSITIONED WITHIN A COMPRESSIBLE PORTION THEREOF, which was filed on Apr. 29, 2011, is incorporated by reference herein. Turning now to FIGS. 99-102, a staple cartridge 8000 includes a cartridge body 8010 and an implantable layer 8020. The cartridge body 8010 includes a proximal end 8012, a distal end 8014, and a deck 8016 extending between the proximal end 8012 and the distal end 8014. The deck 8016 is configured to support tissue when the tissue is clamped between the staple cartridge 8000 and an anvil. The cartridge body 8010 further includes fastener cavities defined therein which are each configured to store a fastener, such as a staple, for example, therein. Each fastener cavity includes a proximal end and a distal end. The proximal end of each fastener cavity is closer to the proximal end 8012 of the cartridge body 8010 than the distal end of each fastener cavity and, correspondingly, the distal end of each fastener cavity is closer to the distal end 8014 of the cartridge body 8010.

Further to the above, the cartridge body 8010 comprises projections extending from the deck 8016. In various instances, the projections can be arranged in any suitable arrangement. For instance, distal projections 8017 can be positioned adjacent the distal ends of the fastener cavities while proximal projections 8019 can be positioned adjacent the proximal ends of the fastener cavities. Similar to the above, the distal projections 8017 and/or the proximal projections 8019 can be configured to guide the fasteners stored in the fastener cavities as the fasteners are ejected from the fastener cavities. In such instances, the distal projections 8017 and/or the proximal projections 8019 can extend the fastener cavities above the deck 8016. Some fastener cavities may have an adjacent distal projection 8017 and a proximal projection 8019 while other fastener cavities may only have one or the other. Some fastener cavities may have neither a distal projection 8017 nor a proximal projection 8019 associated therewith.

Layer 8020 comprises a layer body 8026 which includes a proximal end 8022 and a distal end 8024. The proximal end 8022 of the layer body 8026 is positioned adjacent or relative to the proximal end 8012 of the cartridge body 8010 and the distal end 8024 is positioned adjacent or relative to the distal end 8014. In certain instances, the layer 8026 can comprise a solid sheet of material. In various instances, the layer body 8026 can extend over one or more fastener cavities defined in the cartridge body 8010. In at least one such instance, the layer body 8026 includes portions 8025 which extend over the fastener cavities. When the fasteners are ejected from the fastener cavities, the fasteners can capture the portions 8025 therein thereby retaining the layer 8020 to the tissue. In some instances, the layer body 8026 can comprise openings aligned with some of the fastener cavities in the cartridge body 8010.

The layer body 8026 can comprise apertures defined therein which are aligned with the projections extending from the deck 8016. For instance, the layer body 8026 can comprise distal apertures 8027 which are aligned with at least some of the distal projections 8017 and/or proximal apertures 8029 which are aligned with at least some of the distal projections 8019. In various instances, the distal apertures 8027 and the distal projections 8017 can be sized and configured such that there is clearance therebetween. Similarly, the proximal apertures 8029 and the proximal projections 8019 can be sized and configured such that there is clearance therebetween. In some instances, the distal apertures 8027 and the distal projections 8017 can be sized and configured such that there is an interference fit therebetween. Also, similarly, the proximal apertures 8029 and the proximal projections 8019 can be sized and configured such that there is an interference fit therebetween. In at least one such instance, the interference fit between the projections and the apertures can releasably retain the layer 8020 to the cartridge body 8010. In use, the fasteners stored in the cartridge body 8010 can contact the portions 8025 of the layer 8020 as the fasteners are ejected from the cartridge body 8010 and lift the layer 8020 away from the deck 8016 and disengage the apertures from the projections.

The layer body 8026 can include apertures 8028 which are each configured to receive a distal projection 8017 and a proximal projection 8019 therein. Each aperture 8028 can comprise an elongate slot having a proximal end configured to receive a distal projection 8017 and a distal end configured to receive a proximal projection 8019. In some instances, a clearance fit may be present between the apertures 8028 and the projections 8017 and 8019. In certain instances, an interference fit may be present between the apertures 8028 and the projections 8017 and 8019 to releasably retain the layer 8020 to the cartridge body 8010. In at least one instance, the apertures 8028 can be sized and configured to stretch to accommodate a distal projection 8017 and a proximal projection 8019 therein.

The layer 8020 can be removably affixed to the cartridge body 8010. In certain instances, the distal end 8024 of the layer 8020 can be removably attached to the distal end 8014 of the cartridge body 8010. In some instances, the proximal end 8022 of the layer 8020 can be removably attached to the proximal end 8012 of the cartridge body 8010. In at least one example, attachment portions 8021 can be utilized to releasably hold the layer 8020 to the cartridge body 8010.

A layer, such as buttress material, for example, may be made from any biocompatible material. Buttress material may be formed from a natural material and/or a synthetic material. Buttress material may be bioabsorbable and/or non-bioabsorbable. It should be understood that any combination of natural, synthetic, bioabsorbable and non-bioabsorbable materials may be used to form buttress material. Some non-limiting examples of materials from which the buttress material may be made include, but are not limited to, poly(lactic acid), poly(glycolic acid), poly(hydroxybutyrate), poly(phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and copolymers, block copolymers, homopolymers, blends and/or combinations thereof, for example.

Natural biological polymers can be used in forming the buttress material. Suitable natural biological polymers include, but are not limited to, collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethyl cellulose, chitan, chitosan, and/or combinations thereof, for example. Natural biological polymers may be combined with any of the other polymeric materials described herein to produce the buttress material. Collagen of human and/or animal origin, e.g., type I porcine or bovine collagen, type I human collagen or type III human collagen may be used to form the buttress material. The buttress material may be made from denatured collagen or collagen which has at least partially lost its helical structure through heating or any other method, consisting mainly of non-hydrated a chains, of molecular weight close to 100 kDa, for example. The term "denatured collagen" means collagen which has lost its helical structure. The collagen used for the porous layer as described herein may be native collagen or atellocollagen, notably as obtained through pepsin digestion and/or after moderate heating as defined previously, for example. The collagen may have been previously chemically modified by oxidation, methylation, succinylation, ethylation and/or any other known process.

Where the buttress material is fibrous, the fibers may be filaments or threads suitable for knitting or weaving or may be staple fibers, such as those frequently used for preparing non-woven materials. The fibers may be made from any biocompatible material. The fibers may be formed from a natural material or a synthetic material. The material from which the fibers are formed may be bioabsorbable or non-bioabsorbable. It should be understood that any combination of natural, synthetic, bioabsorbable and non-bioabsorbable materials may be used to form the fibers. Some non-limiting examples of materials from which the fibers may be made include, but are not limited to, poly(lactic acid), poly(glycolic acid), poly(hydroxybutyrate), poly(phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and copolymers, block copolymers, homopolymers, blends and/or combinations thereof. Where the buttress material is fibrous, the buttress material may be formed using any method suitable to forming fibrous structures including, but not limited to, knitting, weaving, non-woven techniques and the like, for example. Where the buttress material is a foam, the porous layer may be formed using any method suitable to forming a foam or sponge including, but not limited to the lyophilization or freeze-drying of a composition, for example.

The buttress material may possesses haemostatic properties. Illustrative examples of materials which may be used in providing the buttress material with the capacity to assist in stopping bleeding or hemorrhage include, but are not limited to, poly(lactic acid), poly(glycolic acid), poly(hydroxybutyrate), poly(caprolactone), poly(dioxanone), polyalkylene-oxides, copoly(ether-esters), collagen, gelatin, thrombin, fibrin, fibrinogen, fibronectin, elastin, albumin, hemoglobin, ovalbumin, polysaccharides, hyaluronic acid, chondroitin sulfate, hydroxyethyl starch, hydroxyethyl cellulose, cellulose, oxidized cellulose, hydroxypropyl cellulose, carboxyethyl cellulose, carboxymethyl cellulose, chitan, chitosan, agarose, maltose, maltodextrin, alginate, clotting factors, methacrylate, polyurethanes, cyanoacrylates, platelet agonists, vasoconstrictors, alum, calcium, RGD peptides, proteins, protamine sulfate, epsilon amino caproic acid, ferric sulfate, ferric subsulfates, ferric chloride, zinc, zinc chloride, aluminum chloride, aluminum sulfates, aluminum acetates, permanganates, tannins, bone wax, polyethylene glycols, fucans and/or combinations thereof, for example. The use of natural biological polymers, and in particular proteins, may be useful in forming buttress material having haemostatic properties. Suitable natural biological polymers include, but are not limited to, collagen, gelatin, fibrin, fibrinogen, elastin, keratin, albumin and/or combinations thereof, for example. Natural biological polymers may be combined with any other haemostatic agent to produce the porous layer of the buttress. The entire disclosure of U.S. Pat. No. 8,496,683, entitled BUTTRESS AND SURGICAL STAPLING APPARATUS, which issued on Jul. 30, 2013, is incorporated by reference herein.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES; now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009; now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719;

U.S. patent application Ser. No. 13/524,049, entitled ARTICULATABLE SURGICAL INSTRUMENT COMPRISING A FIRING DRIVE, filed on Jun. 15, 2012; now U.S. Patent Application Publication No. 2013/0334278;

U.S. patent application Ser. No. 13/800,025, entitled STAPLE CARTRIDGE TISSUE THICKNESS SENSOR SYSTEM, filed on Mar. 13, 2013;

U.S. patent application Ser. No. 13/800,067, entitled STAPLE CARTRIDGE TISSUE THICKNESS SENSOR SYSTEM, filed on Mar. 13, 2013;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical staple cartridge, comprising:
a cartridge body, comprising:
    a tissue-facing deck comprising a first step and a second step, wherein a first staple cavity is defined in the cartridge body at the first step and a second staple cavity is defined in the cartridge body at the second step;
    a first projection extending from the first step and bordering at least a portion of the first staple cavity; and
    a second projection extending from the second step and bordering at least a portion of the second staple cavity;
    a first staple removably stored in the first staple cavity; and
    a second staple removably stored in the second staple cavity.

2. The surgical staple cartridge of claim 1, wherein a longitudinal slot is defined in the tissue-facing deck, wherein the tissue-facing deck includes a first deck side on a first side of the longitudinal slot and a second deck side on a second side of the longitudinal slot, and wherein the first step and the second step are on the first deck side.

3. The surgical staple cartridge of claim 2, wherein the first step is laterally offset from the second step.

4. The surgical staple cartridge of claim 3, wherein the first step is higher than the second step.

5. The surgical staple cartridge of claim 4, wherein the second step is closer than the first step to the longitudinal slot.

6. The surgical staple cartridge of claim 5, wherein the first projection extends a first height from a first surface of the first step, wherein the second projection extends a second height from a second surface the second step, and wherein the first height and second height are different.

7. The surgical staple cartridge of claim 6, wherein the second height is greater than the first height.

8. The surgical staple cartridge of claim 7, wherein the tissue-facing deck further comprises:
    a distal end surface; and
    a ramp connecting the first surface of the first step to the distal end surface.

9. The surgical staple cartridge of claim 8, wherein the cartridge body comprises a first row of staple cavities defined in the first step and a second row of staple cavities defined in the second step, wherein the first row of staple cavities comprises the first staple cavity, and wherein the second row of staple cavities comprises the second staple cavity.

10. The surgical staple cartridge of claim 9, wherein the first staple cavity is a most distal staple cavity of the first row of staple cavities, and wherein the first projection borders at least a portion of a distal end of the first staple cavity.

11. The surgical staple cartridge of claim 10, wherein the first projection comprises a first distal portion sloping downwardly from the first height toward the ramp.

12. The surgical staple cartridge of claim 11, wherein the second staple cavity is a most distal staple cavity of the second row of staple cavities, and wherein the second projection borders at least a portion of a distal end of the second staple cavity.

13. The surgical staple cartridge of claim 12, wherein the second projection comprises a second distal portion sloping downwardly from the second height toward the distal end surface.

14. The surgical staple cartridge of claim 1, wherein the first staple and the second staple are ejectable from the first staple cavity and the second staple during a staple firing stroke, wherein the first projection is structured to support the first staple across a first distance as the first staple is ejected during the staple firing stroke, wherein the second projection is structured to support the second staple across a second distance as the second staple is ejected during the staple firing stroke, and wherein the first distance is different from the second distance.

15. The surgical staple cartridge of claim 1, wherein the first staple cavity forms a first opening in the tissue-facing deck, wherein the second staple cavity forms a second opening in the tissue-facing deck, wherein the first projection forms a rim around at least a portion of the first opening, and wherein the second projection forms a rim around at least a portion of the second opening.

16. A surgical staple cartridge, comprising:
a cartridge body, comprising:
    a deck comprising a first surface and a second surface, wherein a longitudinal slot is defined in the second surface, wherein the first surface is raised relative to second surface, wherein a first staple cavity defined in the first surface, and wherein a second staple cavity defined in the second surface;

a first cavity extension of the first staple cavity extending a first height from the first surface; and a second cavity extension of the first staple cavity extending a second height from the second surface;

a first staple removably stored in the first staple cavity; and a second staple removably stored in the second staple cavity.

17. The surgical staple cartridge of claim 16, wherein the first height and the second height are different.

18. The surgical staple cartridge of claim 17, wherein the deck comprises a distal end surface, wherein a portion of the first surface slopes downwardly to meet the distal end surface, wherein the first cavity extension of the first staple cavity extends from at least a portion of a distal end of the first staple cavity, and wherein the first cavity extension slopes downwardly and distally from the first height to meet the first surface.

19. The surgical staple cartridge of claim 18, wherein the first staple cavity is a distal most staple cavity of multiple staple cavities formed in the first surface.

20. A surgical staple cartridge, comprising:

a cartridge body, comprising:

a stepped deck comprising a base surface and a step surface;

a first staple cavity defined in the step surface, the first staple cavity comprising a first perimeter;

a second staple cavity defined in the base surface, the second staple cavity comprising a second perimeter;

a first projection extending from the step surface and abutting at least a portion of first perimeter of the first staple cavity; and a second projection extending from the base surface and abutting at least a portion of the second perimeter of the second staple cavity;

a first staple removably stored in the first staple cavity; and a second staple removably stored in the second staple cavity.

* * * * *